US012514326B2

(12) United States Patent
Amos et al.

(10) Patent No.: US 12,514,326 B2
(45) Date of Patent: Jan. 6, 2026

(54) FOOTWEAR HAVING SENSOR SYSTEM

(71) Applicant: NIKE, Inc., Beaverton, OR (US)

(72) Inventors: Michael S. Amos, Beaverton, OR (US); Andrew A. Owings, Portland, OR (US); Jordan M. Rice, Portland, OR (US); Allan M. Schrock, Portland, OR (US); Steven H. Walker, Camas, WA (US); Jeffrey J. Hebert, Seattle, WA (US); Martine W. Stillman, Seattle, WA (US); Mark A. Tempel, Seattle, WA (US); Dane Weitmann, Seattle, WA (US); Andreas Heinrich Steier, Luxembourg (LU); Ndikum Protus Atang, Rochester, MI (US)

(73) Assignee: NIKE, Inc., Beaverton, OR (US)

( * ) Notice: Subject to any disclaimer, the term of this patent is extended or adjusted under 35 U.S.C. 154(b) by 196 days.

(21) Appl. No.: 18/370,011

(22) Filed: Sep. 19, 2023

(65) Prior Publication Data

US 2024/0074529 A1 Mar. 7, 2024

Related U.S. Application Data

(63) Continuation of application No. 17/300,505, filed on Jul. 26, 2021, now Pat. No. 11,793,264, which is a
(Continued)

(51) Int. Cl.
*G01L 1/00* (2006.01)
*A43B 3/34* (2022.01)
(Continued)

(52) U.S. Cl.
CPC .................. *A43B 3/44* (2022.01); *A43B 3/34* (2022.01); *A43B 7/084* (2013.01); *A43B 7/088* (2013.01);
(Continued)

(58) Field of Classification Search
CPC ........ A43B 3/44; A61B 5/1036; A61B 5/1038
See application file for complete search history.

(56) References Cited

U.S. PATENT DOCUMENTS

| | | | |
|---|---|---|---|
| 3,270,564 A | 9/1966 | Evans | |
| 4,372,558 A | 2/1983 | Shimamoto et al. | |

(Continued)

FOREIGN PATENT DOCUMENTS

| | | | |
|---|---|---|---|
| CA | 2668946 A1 | 5/2008 | |
| CN | 1101757 A | 4/1995 | |

(Continued)

OTHER PUBLICATIONS

Aug. 21, 2012—(WO) ISR & WO—App. No. PCT/US2012/025717.

(Continued)

*Primary Examiner* — Herbert K Roberts
(74) *Attorney, Agent, or Firm* — Banner & Witcoff, Ltd.

(57) ABSTRACT

An insert for an article of footwear includes an insert member having top and bottom sides, and an opening extending therethrough, and a housing connected to the insert member to receive an electronic module. The housing includes a tub positioned at least partially on the bottom side of the insert member to receive the module, a flange connected to the tub and extending outward around at least a portion thereof to cover at least a portion of the top side of the insert member, and a peg extending from the flange downward through the opening to the tub. A port is connected to the insert and has an interface accessible within the housing for communication with the module within the housing. A plurality of force sensors are connected to the insert member, and a plurality of conductive leads on the insert connect the sensors to the interface.

25 Claims, 71 Drawing Sheets

Related U.S. Application Data continuation of application No. 16/513,057, filed on Jul. 16, 2019, now Pat. No. 11,071,345, which is a continuation of application No. 15/677,709, filed on Aug. 15, 2017, now Pat. No. 10,357,078, which is a continuation of application No. 14/559,680, filed on Dec. 3, 2014, now Pat. No. 9,756,895, which is a continuation of application No. 13/401,918, filed on Feb. 22, 2012, now abandoned.

(51) Int. Cl.

| | |
|---|---|
| ***A43B 3/44*** | (2022.01) |
| ***A43B 7/08*** | (2022.01) |
| ***A43B 13/12*** | (2006.01) |
| ***A43B 13/14*** | (2006.01) |
| ***A43B 13/20*** | (2006.01) |
| ***A43B 13/38*** | (2006.01) |
| ***A43B 17/00*** | (2006.01) |
| ***A61B 5/00*** | (2006.01) |
| ***G01L 1/20*** | (2006.01) |
| *A61B 5/11* | (2006.01) |

(52) U.S. Cl.

CPC .............. *A43B 13/12* (2013.01); *A43B 13/14* (2013.01); *A43B 13/203* (2013.01); *A43B 13/386* (2013.01); *A61B 5/6807* (2013.01); *G01L 1/20* (2013.01); *G01L 1/205* (2013.01); *A61B 5/0022* (2013.01); *A61B 5/1114* (2013.01); *A61B 5/112* (2013.01); *A61B 5/1121* (2013.01); *A61B 5/1124* (2013.01); *A61B 2503/10* (2013.01); *A61B 2560/045* (2013.01); *A61B 2562/0247* (2013.01); *A61B 2562/0252* (2013.01); *A61B 2562/046* (2013.01); *A61B 2562/164* (2013.01); *A61B 2562/166* (2013.01); *A61B 2562/168* (2013.01); *A61B 2562/222* (2013.01); *A61B 2562/227* (2013.01)

(56) References Cited

U.S. PATENT DOCUMENTS

| | | | |
|---|---|---|---|
| 4,373,651 | A | 2/1983 | Fanslow |
| 4,518,267 | A | 5/1985 | Hepp |
| 4,578,969 | A | 4/1986 | Larson |
| 4,647,918 | A | 3/1987 | Goforth |
| 4,703,445 | A | 10/1987 | Dassler |
| 4,745,930 | A | 5/1988 | Confer |
| 4,771,555 | A | 9/1988 | Ohashi |
| 4,814,661 | A | 3/1989 | Ratzlaff et al. |
| 4,862,743 | A | 9/1989 | Seitz |
| 4,866,412 | A | 9/1989 | Rzepczynski |
| 4,991,317 | A | 2/1991 | Lakic |
| 5,010,774 | A | 4/1991 | Kikuo et al. |
| 5,033,291 | A | 7/1991 | Podoloff et al. |
| 5,047,952 | A | 9/1991 | Kramer et al. |
| 5,050,962 | A | 9/1991 | Monnier et al. |
| 5,150,536 | A | 9/1992 | Strong |
| 5,154,960 | A | 10/1992 | Mucci et al. |
| 5,249,967 | A | 10/1993 | O'Leary et al. |
| 5,253,656 | A | 10/1993 | Rincoe et al. |
| 5,303,131 | A | 4/1994 | Wu |
| 5,323,650 | A | 6/1994 | Fullen et al. |
| 5,357,696 | A | 10/1994 | Gray et al. |
| 5,373,651 | A | 12/1994 | Wood |
| 5,374,821 | A | 12/1994 | Muhs et al. |
| 5,393,651 | A | 2/1995 | Hoshi |
| 5,408,873 | A | 4/1995 | Schmidt et al. |
| 5,419,562 | A | 5/1995 | Cromarty |
| 5,422,521 | A | 6/1995 | Neer et al. |
| 5,444,462 | A | 8/1995 | Wambach |
| 5,471,405 | A | 11/1995 | Marsh |
| 5,500,635 | A | 3/1996 | Mott |
| 5,588,227 | A | 12/1996 | Goldston et al. |
| 5,636,146 | A | 6/1997 | Flentov et al. |
| 5,636,378 | A | 6/1997 | Griffith |
| 5,638,300 | A | 6/1997 | Johnson |
| 5,644,858 | A | 7/1997 | Bemis |
| 5,655,316 | A | 8/1997 | Huang |
| 5,678,448 | A | 10/1997 | Fullen et al. |
| 5,697,791 | A | 12/1997 | Nashner et al. |
| 5,702,323 | A | 12/1997 | Poulton |
| 5,714,706 | A | 2/1998 | Nakada et al. |
| 5,720,200 | A | 2/1998 | Anderson et al. |
| 5,724,265 | A | 3/1998 | Hutchings |
| 5,764,786 | A | 6/1998 | Kuwashima et al. |
| 5,785,666 | A | 7/1998 | Costello et al. |
| 5,812,142 | A | 9/1998 | Small et al. |
| 5,813,142 | A | 9/1998 | Demon |
| 5,813,406 | A | 9/1998 | Kramer et al. |
| 5,815,954 | A | 10/1998 | Huang |
| 5,844,861 | A | 12/1998 | Maurer |
| 5,889,464 | A | 3/1999 | Huang |
| 5,903,454 | A | 5/1999 | Hoffberg et al. |
| 5,907,819 | A | 5/1999 | Johnson |
| 5,913,727 | A | 6/1999 | Ahdoot |
| 5,929,332 | A | 7/1999 | Brown |
| 5,960,380 | A | 9/1999 | Flentov et al. |
| 5,963,891 | A | 10/1999 | Walker et al. |
| 5,983,433 | A | 11/1999 | Chapman |
| 6,017,128 | A | 1/2000 | Goldston et al. |
| 6,018,705 | A | 1/2000 | Gaudet et al. |
| 6,050,962 | A | 4/2000 | Kramer et al. |
| 6,066,075 | A | 5/2000 | Poulton |
| 6,081,750 | A | 6/2000 | Hoffberg et al. |
| 6,122,340 | A | 9/2000 | Darley et al. |
| 6,122,846 | A | 9/2000 | Gray et al. |
| 6,148,280 | A | 11/2000 | Kramer |
| 6,155,120 | A | 12/2000 | Taylor |
| 6,174,294 | B1 | 1/2001 | Crabb et al. |
| 6,195,921 | B1 | 3/2001 | Truong |
| 6,198,394 | B1 | 3/2001 | Jacobsen et al. |
| 6,226,577 | B1 | 5/2001 | Yeo |
| 6,266,623 | B1 | 7/2001 | Vock et al. |
| 6,287,200 | B1 | 9/2001 | Sharma |
| 6,298,314 | B1 | 10/2001 | Blackadar et al. |
| 6,330,757 | B1 | 12/2001 | Russell |
| 6,336,365 | B1 | 1/2002 | Blackadar et al. |
| 6,356,856 | B1 | 3/2002 | Damen et al. |
| 6,357,147 | B1 | 3/2002 | Darley et al. |
| 6,360,597 | B1 | 3/2002 | Hubbard, Jr. |
| 6,426,490 | B1 | 7/2002 | Storz |
| 6,428,490 | B1 | 8/2002 | Kramer et al. |
| 6,430,843 | B1 | 8/2002 | Potter et al. |
| 6,496,787 | B1 | 12/2002 | Flentov et al. |
| 6,496,952 | B1 | 12/2002 | Osada et al. |
| 6,498,994 | B2 | 12/2002 | Vock et al. |
| 6,515,284 | B1 | 2/2003 | Walle et al. |
| 6,516,284 | B2 | 2/2003 | Flentov et al. |
| 6,536,139 | B2 | 3/2003 | Darley et al. |
| 6,539,336 | B1 | 3/2003 | Vock et al. |
| 6,544,858 | B1 | 4/2003 | Beekman et al. |
| 6,560,903 | B1 | 5/2003 | Darley |
| 6,578,291 | B2 | 6/2003 | Hirsch et al. |
| 6,611,789 | B1 | 8/2003 | Darley |
| 6,640,144 | B1 | 10/2003 | Huang et al. |
| 6,656,042 | B2 | 12/2003 | Reiss et al. |
| 6,718,200 | B2 | 4/2004 | Marmaropoulos et al. |
| 6,739,200 | B1 | 5/2004 | Norton |
| 6,748,462 | B2 | 6/2004 | Dubil et al. |
| 6,778,973 | B2 | 8/2004 | Harlan |
| 6,785,579 | B2 | 8/2004 | Huang et al. |
| 6,785,805 | B1 | 8/2004 | House et al. |
| 6,808,462 | B2 | 10/2004 | Snyder et al. |
| 6,829,512 | B2 | 12/2004 | Huang et al. |
| 6,836,744 | B1 | 12/2004 | Asphahani et al. |
| 6,876,947 | B1 | 4/2005 | Darley et al. |
| 6,882,897 | B1 | 4/2005 | Fernandez |
| 6,885,971 | B2 | 4/2005 | Vock et al. |
| 6,889,282 | B2 | 5/2005 | Schollenberger |
| 6,892,216 | B2 | 5/2005 | Coburn, II et al. |

(56) References Cited

U.S. PATENT DOCUMENTS

| | | | |
|---|---|---|---|
| 6,909,420 | B1 | 6/2005 | Nicolas et al. |
| 6,922,664 | B1 | 7/2005 | Fernandez et al. |
| 6,932,698 | B2 | 8/2005 | Sprogis |
| 6,959,259 | B2 | 10/2005 | Vock et al. |
| 6,963,818 | B2 | 11/2005 | Flentov et al. |
| 6,978,320 | B2 | 12/2005 | Nonaka |
| 7,030,861 | B1 | 4/2006 | Westerman et al. |
| 7,045,151 | B2 | 5/2006 | Trant |
| 7,046,151 | B2 | 5/2006 | Dundon |
| 7,054,784 | B2 | 5/2006 | Flentov et al. |
| 7,057,551 | B1 | 6/2006 | Vogt |
| 7,070,571 | B2 | 7/2006 | Kramer et al. |
| 7,072,789 | B2 | 7/2006 | Vock et al. |
| 7,092,846 | B2 | 8/2006 | Vock et al. |
| 7,152,343 | B2 | 12/2006 | Whatley |
| 7,162,392 | B2 | 1/2007 | Vock et al. |
| 7,171,331 | B2 | 1/2007 | Vock et al. |
| 7,200,517 | B2 | 4/2007 | Darley et al. |
| 7,219,449 | B1 | 5/2007 | Hoffberg et al. |
| 7,245,898 | B2 | 7/2007 | Van Bosch et al. |
| 7,277,021 | B2 | 10/2007 | Beebe et al. |
| 7,283,647 | B2 | 10/2007 | McNitt |
| 7,304,580 | B2 | 12/2007 | Sullivan et al. |
| 7,310,895 | B2 | 12/2007 | Whittlesey et al. |
| 7,383,728 | B2 | 6/2008 | Noble et al. |
| RE40,474 | E | 9/2008 | Quellais et al. |
| 7,426,873 | B1 | 9/2008 | Kholwadwala et al. |
| 7,428,471 | B2 | 9/2008 | Darley et al. |
| 7,433,805 | B2 | 10/2008 | Vock et al. |
| 7,457,724 | B2 | 11/2008 | Vock et al. |
| 7,497,037 | B2 | 3/2009 | Vick et al. |
| 7,498,856 | B2 | 3/2009 | Lin et al. |
| 7,498,956 | B2 | 3/2009 | Baier et al. |
| 7,522,970 | B2 | 4/2009 | Fernandez |
| 7,552,549 | B2 | 6/2009 | Whittlesey et al. |
| 7,579,946 | B2 | 8/2009 | Case, Jr. |
| 7,596,891 | B2 | 10/2009 | Carnes et al. |
| 7,602,301 | B1 | 10/2009 | Stirling et al. |
| 7,607,243 | B2 | 10/2009 | Berner, Jr. et al. |
| 7,617,068 | B2 | 11/2009 | Tadin et al. |
| 7,623,987 | B2 | 11/2009 | Vock et al. |
| 7,625,314 | B2 | 12/2009 | Ungari et al. |
| 7,651,442 | B2 | 1/2010 | Carlson |
| 7,658,694 | B2 | 2/2010 | Ungari |
| 7,670,263 | B2 | 3/2010 | Ellis et al. |
| 7,726,206 | B2 | 6/2010 | Terrafranca, Jr. et al. |
| 7,739,076 | B1 | 6/2010 | Vock et al. |
| 7,758,523 | B2 | 7/2010 | Collings et al. |
| 7,771,320 | B2 | 8/2010 | Riley et al. |
| 7,805,150 | B2 | 9/2010 | Graham et al. |
| 7,816,632 | B2 | 10/2010 | Bourke, III et al. |
| 7,840,378 | B2 | 11/2010 | Vock et al. |
| 7,901,325 | B2 | 3/2011 | Henderson |
| 7,905,815 | B2 | 3/2011 | Ellis et al. |
| 7,909,737 | B2 | 3/2011 | Ellis et al. |
| 7,921,716 | B2 | 4/2011 | Morris Bamberg et al. |
| 7,934,983 | B1 | 5/2011 | Eisner |
| 7,969,315 | B1 | 6/2011 | Ross et al. |
| 7,997,007 | B2 | 8/2011 | Sanabria-Hernandez |
| 8,056,268 | B2 | 11/2011 | DiBenedetto et al. |
| 8,061,061 | B1 | 11/2011 | Rivas |
| 8,099,258 | B2 | 1/2012 | Alten et al. |
| 8,131,498 | B1 | 3/2012 | McCauley |
| 8,142,267 | B2 | 3/2012 | Adams |
| 8,155,525 | B2 | 4/2012 | Cox |
| 8,172,722 | B2 | 5/2012 | Molyneux et al. |
| 8,212,158 | B2 | 7/2012 | Wiest |
| 8,216,081 | B2 | 7/2012 | Snyder et al. |
| 8,230,619 | B2 | 7/2012 | Salvatelli et al. |
| 8,251,930 | B2 | 8/2012 | Ido |
| 8,253,586 | B1 | 8/2012 | Matak |
| 8,291,618 | B2 | 10/2012 | Ellis |
| 8,333,643 | B2 | 12/2012 | Eisner |
| 8,467,979 | B2 | 6/2013 | Sobolewski |
| 8,474,153 | B2 | 7/2013 | Brie et al. |
| 8,479,416 | B2 | 7/2013 | Auger et al. |
| 8,484,654 | B2 | 7/2013 | Graham et al. |
| 8,676,541 | B2 | 3/2014 | Schrock et al. |
| 8,739,639 | B2 | 6/2014 | Owings et al. |
| 9,002,680 | B2 | 4/2015 | Nurse et al. |
| 9,089,182 | B2 | 7/2015 | Schrock et al. |
| 9,445,646 | B2 | 9/2016 | Cook et al. |
| 9,462,844 | B2 | 10/2016 | Schrock et al. |
| 9,642,415 | B2 | 5/2017 | Pease et al. |
| 10,314,361 | B2 | 6/2019 | Amos et al. |
| 2001/0003665 | A1 | 6/2001 | Kim |
| 2001/0054043 | A1 | 12/2001 | Harlan |
| 2002/0035184 | A1 | 3/2002 | Plaver et al. |
| 2002/0133069 | A1 | 9/2002 | Roberts |
| 2002/0134153 | A1 | 9/2002 | Grenlund |
| 2003/0009308 | A1 | 1/2003 | Kirtley |
| 2003/0054327 | A1 | 3/2003 | Evensen |
| 2003/0097878 | A1 | 5/2003 | Farringdon et al. |
| 2003/0130183 | A1 | 7/2003 | Southard et al. |
| 2003/0163287 | A1 | 8/2003 | Vock et al. |
| 2003/0207718 | A1 | 11/2003 | Perlmutter |
| 2004/0078091 | A1 | 4/2004 | Elkins |
| 2004/0148799 | A1 | 8/2004 | Lussier et al. |
| 2004/0154190 | A1 | 8/2004 | Munster |
| 2004/0162702 | A1 | 8/2004 | Pandipati et al. |
| 2004/0177531 | A1 | 9/2004 | DiBenedetto et al. |
| 2004/0215413 | A1 | 10/2004 | Weldum et al. |
| 2004/0218317 | A1 | 11/2004 | Kawazu et al. |
| 2004/0225467 | A1 | 11/2004 | Vock et al. |
| 2004/0226192 | A1 | 11/2004 | Geer et al. |
| 2005/0011085 | A1 | 1/2005 | Swigart et al. |
| 2005/0032582 | A1 | 2/2005 | Mahajan et al. |
| 2005/0046576 | A1 | 3/2005 | Julian et al. |
| 2005/0106977 | A1 | 5/2005 | Coulston |
| 2005/0183292 | A1 | 8/2005 | DiBenedetto et al. |
| 2005/0184848 | A1 | 8/2005 | Yoshida et al. |
| 2005/0188566 | A1 | 9/2005 | Whittlesey et al. |
| 2005/0221403 | A1 | 10/2005 | Gazenko |
| 2005/0231379 | A1 | 10/2005 | Sprecher et al. |
| 2005/0261609 | A1 | 11/2005 | Collings et al. |
| 2005/0282633 | A1 | 12/2005 | Nicolas et al. |
| 2006/0000420 | A1 | 1/2006 | Martin Davies |
| 2006/0010174 | A1 | 1/2006 | Nguyen et al. |
| 2006/0017692 | A1 | 1/2006 | Wehrenberg et al. |
| 2006/0025229 | A1 | 2/2006 | Mahajan et al. |
| 2006/0026120 | A1 | 2/2006 | Carolan et al. |
| 2006/0053656 | A1 | 3/2006 | Kumle |
| 2006/0082977 | A1 | 4/2006 | Kim |
| 2006/0091715 | A1 | 5/2006 | Schmitz et al. |
| 2006/0143645 | A1 | 6/2006 | Vock et al. |
| 2006/0144152 | A1 | 7/2006 | Cabuz et al. |
| 2006/0217231 | A1 | 9/2006 | Parks et al. |
| 2006/0226843 | A1 | 10/2006 | Al-Anbuky et al. |
| 2006/0248749 | A1 | 11/2006 | Ellis |
| 2006/0262120 | A1 | 11/2006 | Rosenberg |
| 2006/0270951 | A1 | 11/2006 | Ikeuchi |
| 2006/0282017 | A1 | 12/2006 | Avni et al. |
| 2006/0283050 | A1 | 12/2006 | Carnes et al. |
| 2007/0000154 | A1 | 1/2007 | DiBenedetto et al. |
| 2007/0006489 | A1 | 1/2007 | Case et al. |
| 2007/0016091 | A1 | 1/2007 | Butt et al. |
| 2007/0026421 | A1 | 2/2007 | Sundberg et al. |
| 2007/0032748 | A1 | 2/2007 | McNeil et al. |
| 2007/0033838 | A1 | 2/2007 | Luce et al. |
| 2007/0039289 | A1 | 2/2007 | LeCompte |
| 2007/0060408 | A1 | 3/2007 | Schultz et al. |
| 2007/0063849 | A1 | 3/2007 | Rosella et al. |
| 2007/0063850 | A1 | 3/2007 | Devaul et al. |
| 2007/0067885 | A1 | 3/2007 | Fernandez |
| 2007/0068244 | A1 | 3/2007 | Billing et al. |
| 2007/0073178 | A1 | 3/2007 | Browning et al. |
| 2007/0078324 | A1 | 4/2007 | Wijisiriwardana |
| 2007/0082389 | A1 | 4/2007 | Clark et al. |
| 2007/0094890 | A1 | 5/2007 | Cho et al. |
| 2007/0118328 | A1 | 5/2007 | Vock et al. |
| 2007/0143452 | A1 | 6/2007 | Suenbuel et al. |
| 2007/0152812 | A1 | 7/2007 | Wong et al. |
| 2007/0173705 | A1 | 7/2007 | Teller et al. |

(56) References Cited

U.S. PATENT DOCUMENTS

| | | | | |
|---|---|---|---|---|
| 2007/0193070 | A1* | 8/2007 | Bertagna | A43B 3/46 36/132 |
| 2007/0208544 | A1 | 9/2007 | Kulach et al. | |
| 2007/0232455 | A1 | 10/2007 | Hanoun | |
| 2007/0250286 | A1 | 10/2007 | Duncan et al. | |
| 2007/0260421 | A1 | 11/2007 | Berner et al. | |
| 2007/0261271 | A1 | 11/2007 | Krouse | |
| 2007/0283599 | A1 | 12/2007 | Talbott | |
| 2008/0027679 | A1 | 1/2008 | Shklarski | |
| 2008/0028783 | A1 | 2/2008 | Immel et al. | |
| 2008/0039203 | A1 | 2/2008 | Ackley et al. | |
| 2008/0048616 | A1 | 2/2008 | Paul et al. | |
| 2008/0056508 | A1 | 3/2008 | Pierce et al. | |
| 2008/0060224 | A1 | 3/2008 | Whittlesey et al. | |
| 2008/0061023 | A1 | 3/2008 | Moor | |
| 2008/0066343 | A1 | 3/2008 | Sanabria-Hernandez | |
| 2008/0066560 | A1 | 3/2008 | Yu et al. | |
| 2008/0127527 | A1 | 6/2008 | Chen | |
| 2008/0134583 | A1 | 6/2008 | Polus | |
| 2008/0165140 | A1 | 7/2008 | Christie et al. | |
| 2008/0172498 | A1 | 7/2008 | Boucard | |
| 2008/0177507 | A1 | 7/2008 | Mian et al. | |
| 2008/0186143 | A1 | 8/2008 | George et al. | |
| 2008/0188353 | A1 | 8/2008 | Vitolo et al. | |
| 2008/0200312 | A1 | 8/2008 | Tagliabue | |
| 2008/0203144 | A1 | 8/2008 | Kim | |
| 2008/0218310 | A1 | 9/2008 | Alten et al. | |
| 2008/0221403 | A1 | 9/2008 | Fernandez | |
| 2008/0246629 | A1 | 10/2008 | Tsui et al. | |
| 2008/0255794 | A1 | 10/2008 | Levine | |
| 2008/0258921 | A1 | 10/2008 | Woo et al. | |
| 2008/0259028 | A1 | 10/2008 | Teepell et al. | |
| 2008/0269644 | A1 | 10/2008 | Ray | |
| 2008/0287832 | A1 | 11/2008 | Collins et al. | |
| 2008/0289217 | A1 | 11/2008 | Horvath | |
| 2008/0293023 | A1 | 11/2008 | Diehl et al. | |
| 2008/0297832 | A1 | 12/2008 | Otsuka | |
| 2008/0306410 | A1 | 12/2008 | Kalpaxis et al. | |
| 2008/0307899 | A1 | 12/2008 | Von Lilienfeld-Toal et al. | |
| 2008/0318679 | A1 | 12/2008 | Tran et al. | |
| 2009/0018691 | A1 | 1/2009 | Fernandez | |
| 2009/0027917 | A1 | 1/2009 | Chen et al. | |
| 2009/0048538 | A1 | 2/2009 | Levine et al. | |
| 2009/0061837 | A1 | 3/2009 | Chaudhri et al. | |
| 2009/0075347 | A1 | 3/2009 | Cervin et al. | |
| 2009/0075781 | A1 | 3/2009 | Schwarzberg et al. | |
| 2009/0076341 | A1 | 3/2009 | James et al. | |
| 2009/0100705 | A1 | 4/2009 | Cook et al. | |
| 2009/0105047 | A1 | 4/2009 | Guidi et al. | |
| 2009/0107009 | A1 | 4/2009 | Bishop et al. | |
| 2009/0135001 | A1 | 5/2009 | Yuk | |
| 2009/0137933 | A1 | 5/2009 | Lieberman et al. | |
| 2009/0149299 | A1 | 6/2009 | Tchao et al. | |
| 2009/0150178 | A1 | 6/2009 | Sutton et al. | |
| 2009/0152456 | A1 | 6/2009 | Waid et al. | |
| 2009/0153369 | A1 | 6/2009 | Baier et al. | |
| 2009/0153477 | A1 | 6/2009 | Saenz | |
| 2009/0163287 | A1 | 6/2009 | Vald'Via et al. | |
| 2009/0167677 | A1 | 7/2009 | Kruse et al. | |
| 2009/0171614 | A1 | 7/2009 | Damen | |
| 2009/0235739 | A1 | 9/2009 | Morris Bamberg et al. | |
| 2009/0259566 | A1 | 10/2009 | White, III et al. | |
| 2009/0262088 | A1 | 10/2009 | Moll-Carrillo et al. | |
| 2009/0293319 | A1 | 12/2009 | Avni | |
| 2009/0297832 | A1 | 12/2009 | Hatta et al. | |
| 2010/0000121 | A1 | 1/2010 | Brodie et al. | |
| 2010/0004566 | A1 | 1/2010 | Son et al. | |
| 2010/0009810 | A1 | 1/2010 | Trzecieski | |
| 2010/0023231 | A1 | 1/2010 | Allgaier et al. | |
| 2010/0023531 | A1 | 1/2010 | Brisebois et al. | |
| 2010/0035688 | A1 | 2/2010 | Picunko | |
| 2010/0053867 | A1 | 3/2010 | Ellis et al. | |
| 2010/0054746 | A1 | 3/2010 | Logan | |
| 2010/0056340 | A1 | 3/2010 | Ellis et al. | |
| 2010/0057951 | A1 | 3/2010 | Ellis et al. | |
| 2010/0059561 | A1 | 3/2010 | Ellis et al. | |
| 2010/0062740 | A1 | 3/2010 | Ellis et al. | |
| 2010/0063778 | A1 | 3/2010 | Schrock et al. | |
| 2010/0063779 | A1 | 3/2010 | Schrock et al. | |
| 2010/0065836 | A1 | 3/2010 | Lee | |
| 2010/0072948 | A1 | 3/2010 | Sun et al. | |
| 2010/0082735 | A1 | 4/2010 | Petersen et al. | |
| 2010/0088023 | A1 | 4/2010 | Werner | |
| 2010/0094147 | A1 | 4/2010 | Inan et al. | |
| 2010/0111705 | A1 | 5/2010 | Sato et al. | |
| 2010/0113160 | A1 | 5/2010 | Belz et al. | |
| 2010/0129780 | A1 | 5/2010 | Homsi et al. | |
| 2010/0134701 | A1 | 6/2010 | Eyer | |
| 2010/0152619 | A1 | 6/2010 | Kalpaxis et al. | |
| 2010/0152630 | A1 | 6/2010 | Matsuoka et al. | |
| 2010/0170117 | A1 | 7/2010 | Kim | |
| 2010/0184563 | A1 | 7/2010 | Molyneux et al. | |
| 2010/0184564 | A1 | 7/2010 | Molyneux et al. | |
| 2010/0191490 | A1 | 7/2010 | Martens et al. | |
| 2010/0201500 | A1 | 8/2010 | Stirling et al. | |
| 2010/0201512 | A1 | 8/2010 | Stirling et al. | |
| 2010/0204616 | A1 | 8/2010 | Shears et al. | |
| 2010/0225763 | A1 | 9/2010 | Vock et al. | |
| 2010/0231580 | A1 | 9/2010 | Miyasaka | |
| 2010/0286601 | A1 | 11/2010 | Yodfat et al. | |
| 2010/0292599 | A1 | 11/2010 | Oleson et al. | |
| 2010/0298659 | A1 | 11/2010 | McCombie et al. | |
| 2010/0312083 | A1 | 12/2010 | Southerland | |
| 2010/0324455 | A1 | 12/2010 | Rangel et al. | |
| 2010/0332188 | A1 | 12/2010 | Vock et al. | |
| 2011/0003665 | A1 | 1/2011 | Burton et al. | |
| 2011/0021280 | A1 | 1/2011 | Boroda et al. | |
| 2011/0087445 | A1 | 4/2011 | Sobolewski | |
| 2011/0107369 | A1 | 5/2011 | O'Brien et al. | |
| 2011/0119027 | A1 | 5/2011 | Zhu et al. | |
| 2011/0119058 | A1 | 5/2011 | Berard et al. | |
| 2011/0136627 | A1 | 6/2011 | Williams | |
| 2011/0152695 | A1 | 6/2011 | Granqvist et al. | |
| 2011/0167678 | A1 | 7/2011 | Peikert | |
| 2011/0203390 | A1 | 8/2011 | Tao et al. | |
| 2011/0208444 | A1 | 8/2011 | Solinsky | |
| 2011/0214501 | A1 | 9/2011 | Ross et al. | |
| 2012/0035509 | A1 | 2/2012 | Wilson et al. | |
| 2012/0041767 | A1 | 2/2012 | Hoffman et al. | |
| 2012/0050351 | A1 | 3/2012 | Dobler et al. | |
| 2012/0050529 | A1 | 3/2012 | Bentley | |
| 2012/0059432 | A1 | 3/2012 | Emborg et al. | |
| 2012/0166091 | A1 | 6/2012 | Kim et al. | |
| 2012/0234111 | A1 | 9/2012 | Molyneux et al. | |
| 2012/0291563 | A1 | 11/2012 | Schrock et al. | |
| 2012/0291564 | A1 | 11/2012 | Amos et al. | |
| 2013/0002533 | A1 | 1/2013 | Burroughs et al. | |
| 2013/0019694 | A1 | 1/2013 | Molyneux et al. | |
| 2013/0061494 | A1 | 3/2013 | Linth | |
| 2013/0079907 | A1 | 3/2013 | Homsi et al. | |
| 2013/0171599 | A1 | 7/2013 | Bleich et al. | |
| 2013/0190903 | A1 | 7/2013 | Balakrishnan et al. | |
| 2013/0213145 | A1 | 8/2013 | Owings et al. | |
| 2013/0213146 | A1 | 8/2013 | Amos et al. | |
| 2014/0033572 | A1 | 2/2014 | Steier et al. | |
| 2014/0174205 | A1 | 6/2014 | Clarke et al. | |
| 2014/0222173 | A1 | 8/2014 | Giedwoyn et al. | |
| 2014/0259779 | A1 | 9/2014 | Hashish et al. | |
| 2014/0350435 | A1 | 11/2014 | Lam | |
| 2015/0257475 | A1 | 9/2015 | Langvin et al. | |
| 2016/0242500 | A1 | 8/2016 | Langvin et al. | |
| 2016/0345663 | A1 | 12/2016 | Walker et al. | |
| 2017/0284875 | A1 | 10/2017 | Walker | |
| 2017/0306539 | A1 | 10/2017 | Gladish et al. | |

FOREIGN PATENT DOCUMENTS

| | | | |
|---|---|---|---|
| CN | 1596083 | A | 3/2005 |
| CN | 1839724 | A | 10/2006 |
| CN | 200977748 | Y | 11/2007 |
| CN | 200994779 | Y | 12/2007 |
| CN | 101116561 | A | 2/2008 |
| CN | 101240461 | A | 8/2008 |
| CN | 101242880 | A | 8/2008 |

(56) References Cited

FOREIGN PATENT DOCUMENTS

| | | | |
|---|---|---|---|
| CN | 101367011 | A | 2/2009 |
| CN | 101367012 | A | 2/2009 |
| CN | 101524196 | A | 9/2009 |
| CN | 101784230 | A | 7/2010 |
| CN | 101890215 | A | 11/2010 |
| CN | 101894206 | A | 11/2010 |
| CN | 101951798 | A | 1/2011 |
| CN | 102143695 | A | 8/2011 |
| CN | 201948063 | U | 8/2011 |
| CN | 102266140 | A | 12/2011 |
| DE | 3704870 | C1 | 4/1988 |
| DE | 10201134 | A1 | 7/2003 |
| EP | 0160880 | A1 | 11/1985 |
| EP | 0662600 | A1 | 7/1995 |
| EP | 1707065 | A1 | 10/2006 |
| EP | 2189191 | A2 | 5/2010 |
| FR | 2929827 | A1 | 10/2009 |
| GB | 251054 | A | 4/1926 |
| GB | 2421416 | A | 6/2006 |
| JP | 5664301 | | 5/1981 |
| JP | S60234603 | A | 11/1985 |
| JP | S61176429 | U | 11/1986 |
| JP | H023020 | A | 1/1990 |
| JP | 05161724 | | 6/1993 |
| JP | H06014803 | A | 1/1994 |
| JP | H0641505 | U | 6/1994 |
| JP | H06336967 | A | 12/1994 |
| JP | H08089482 | A | 4/1996 |
| JP | H10241648 | A | 9/1998 |
| JP | 3036281 | B2 | 4/2000 |
| JP | 2000516509 | A | 12/2000 |
| JP | 2001351591 | A | 12/2001 |
| JP | 2002131155 | A | 5/2002 |
| JP | 2002163404 | A | 6/2002 |
| JP | 2003061779 | A | 3/2003 |
| JP | 2003236002 | A | 8/2003 |
| JP | 2004158242 | A | 6/2004 |
| JP | 2005019305 | A | 1/2005 |
| JP | 2005079019 | A | 3/2005 |
| JP | 2005507678 | A | 3/2005 |
| JP | 2005156531 | A | 6/2005 |
| JP | 2005270640 | A | 10/2005 |
| JP | 2006086072 | A | 3/2006 |
| JP | 2006280955 | A | 10/2006 |
| JP | 200715117 | A | 1/2007 |
| JP | 2007134473 | A | 5/2007 |
| JP | 20083752 | A | 10/2008 |
| JP | 2009148338 | A | 7/2009 |
| JP | 2009535157 | A | 10/2009 |
| JP | 2010088886 | A | 4/2010 |
| JP | 2010517725 | A | 5/2010 |
| JP | 2011105138 | A | 6/2011 |
| JP | 2011112938 | A | 6/2011 |
| JP | 2011524207 | A | 9/2011 |
| JP | 2011196931 | A | 10/2011 |
| JP | 2012065942 | A | 4/2012 |
| JP | 2012115709 | A | 6/2012 |
| JP | 2012524638 | A | 10/2012 |
| JP | 2013106773 | A | 6/2013 |
| JP | 2013537436 | A | 10/2013 |
| JP | 2014505577 | A | 3/2014 |
| JP | 5925490 | B2 | 5/2016 |
| JP | 20229776 | A | 1/2022 |
| KR | 20010035162 | A | 5/2001 |
| KR | 20010079094 | A | 8/2001 |
| KR | 20050032119 | | 4/2005 |
| KR | 20060021632 | | 3/2006 |
| KR | 20060034353 | A | 4/2006 |
| KR | 20070090474 | A | 9/2007 |
| KR | 20090102550 | | 9/2009 |
| KR | 20100012845 | U | 12/2010 |
| KR | 20100127148 | A | 12/2010 |
| KR | 20100130860 | A | 12/2010 |
| KR | 20110071728 | A | 6/2011 |
| KR | 20110124964 | A | 11/2011 |
| KR | 20120130306 | A | 11/2012 |
| KR | 20130130051 | | 11/2013 |
| KR | 20140004206 | A | 1/2014 |
| KR | 20167008215 | | 3/2016 |
| TW | 200838475 | | 10/2008 |
| WO | 98007341 | A2 | 2/1998 |
| WO | 200033031 | A1 | 6/2000 |
| WO | 2002035184 | A2 | 5/2002 |
| WO | 2006035469 | A2 | 4/2006 |
| WO | 2006065679 | | 6/2006 |
| WO | 2006067434 | A1 | 6/2006 |
| WO | 2006091715 | A1 | 8/2006 |
| WO | 2007064735 | A2 | 6/2007 |
| WO | 2007082389 | A1 | 7/2007 |
| WO | 2007128049 | A1 | 11/2007 |
| WO | 2007130287 | A2 | 11/2007 |
| WO | 2008061023 | A2 | 5/2008 |
| WO | 2008101085 | A2 | 8/2008 |
| WO | 2008134583 | A1 | 11/2008 |
| WO | 2009027917 | A1 | 3/2009 |
| WO | 2009126818 | A2 | 10/2009 |
| WO | 2009152456 | A2 | 12/2009 |
| WO | 2010065836 | A2 | 6/2010 |
| WO | 2010065886 | A1 | 6/2010 |
| WO | 2010111705 | A2 | 9/2010 |
| WO | 2011157607 | A1 | 12/2011 |
| WO | 2012021507 | A2 | 2/2012 |
| WO | 2012061804 | A1 | 5/2012 |
| WO | 2012109244 | A1 | 8/2012 |
| WO | 2012112930 | A1 | 8/2012 |
| WO | 2012112931 | A2 | 8/2012 |
| WO | 2012112934 | A2 | 8/2012 |
| WO | 2012112938 | A2 | 8/2012 |
| WO | 2012143274 | A2 | 10/2012 |
| WO | 2014100045 | A1 | 6/2014 |

OTHER PUBLICATIONS

Jul. 11, 2012—(WO) ISR & WO App No. PCT/US2012/025709.

Aug. 21, 2013—(WO) International Preliminary Report on Patentability App No. PCT/US2012/025713.

Morris, Stacy J., A Shoe-Integrated Sensor System for Wireless Gait Analysis and Real-Time Therapeutic Feedback, dissertation, 2004, pp. 1-314, Massachusetts Institute of Technology, MA.

May 28, 2013—(WO) ISR & WO App No. PCT/US2013/027421.

Fleming et al, Athlete and Coach Perceptions of Technology Needs for Evaluating Running Performance, article, Aug. 14, 2010, 18 pp. 13:1-18, UK.

Salpavaara, et al. Wireless Insole Sensor System for Plantar Force Measurements during Sports Events, article, Sep. 6-11, 2009, XIX IMEKO World Congress, Fundamental and Applied Metrology, 6 pages, Lisbon, Portugal.

Mar. 7, 2012—(WO) ISR and WO- App. PCT/US2011/060187.

Jul. 15, 2013—(WO) Search Report and Written Opinion—App. No. PCT/US2013/022219.

Lovell, "A system for real-time gesture recognition and classification of coordinated motion," Massachusetts Institute of Technology, Dept. of Electrical Engineering and Computer Science, 2005, <http://dspace.mit.edu/handle/1721.1/33290> (2 pages).

Chee et al, "A low cost wearable wireless sensing system for upper limb home rehabilitation," Robotics Automation and Mechatronics (RAM) 2010 IEEE Conference on Jun. 28-30, 2010; Abstract printout (1 page).

Guraliuc et al., "Channel model for on the body communication along and around the human torso at 2.4Ghz and 5.8Ghz," Antenna Technology (IWAT), 2010 International Workshop on Mar. 1-3, 2010; Abstract printout (1 page).

Jun. 21, 2012—(WO) ISR—App No. PCT/US2012/025701.

Frazier, Karen, "How Many Calories to 1 Carb?" published Nov. 12, 2010, Livestrong.com, 3 pages.

Oct. 1, 2013—(WO) ISR and WO—App No. PCT/US2013/048157.

Llosa et al., "Design of a Motion Detector to Monitor Rowing Performance Based on Wireless Sensor Networks," Intelligent Networking and Collaborativge Systems, 2009, http://ieeexplore.ieee.org/xpl/freeabs_all.jsp?arnumber=5369324 (1 page).

(56) References Cited

OTHER PUBLICATIONS

Choquette et al., "Accelerometer-based wireless body area network to estimate intensity of therapy in post-acute rehabilitation," Journal of NeuroEngineering and Rehabilitation 2008, http://www.jneuroengrehab.com/content/5/1/20/ abstract (1 page).
Morris, "A shoe-integrated sensor system for wireless gait analysis and real-time therapeutic feedback," Harvard-MIT Division of Health Sciences and Technology, 2004, http://dspace.mitedu/handle/1721.1/28601 (3 pages).
Lapinski, "A wearable, wireless sensor system for sports medicine," Massachusetts Institute of Technology, School of Architecture and Planning, Program in Media Arts and Sciences, 2008, http://dspace.mit.edulhandle/1721.1/46581(3 pages).
Aylward, "Sensemble : a wireless inertial sensor system for the interactive dance and collective motion analysis,"Massachusetts Institute of Technology, School of Architecture and Planning, Program in Media Arts and Sciences, 2006, http://dspace.mitedu/handle/1721.1/37391 (3 pages).
Danko; How to Work a Nike Sensor; Dec. 26, 2010; eHow website; 4 pages.
Coyne; Stout's Shoes on Mass Ave Oldest Shoe Store in the USA; Jun. 18, 2013; FunCityFinder website; 5 pages.
Davis, The Re-emergence of the Minimal Running Shoe, Clinical Commentary, Journal of Orthopaedic & Sports Physical Therapy, vol. 44, No. 10, pp. 775-784, Oct. 2014.
Lim, Joo-Tack, STO Ltd., Final Report on IT development cooperative project, "Development of IT running shoes that an transmit athletic information of the shoes when running and development of receiver technology," Ministry of Knowledge Economy (Institute For Information Technology Advancement (ITA)) (Jun. 30, 2009).
Aug. 9, 2016—(EP) Extended Search Report—App. No. 16170589.2.
Sep. 1, 2016—(EP) Extended Search Report—App. No. 16167470.0.
Sep. 25, 2012—(WO) ISR & WO, App. No. PCT/US12/025713.
Mar. 15, 2017—(EP) ESR—App. No. 16199665.7.
Dec. 11, 2009—(WO) ISR—App. No. PCT/US09/047246.
May 28, 2013—(WO) Partial ISR—App. No. PCT/US13/027397.
Aug. 7, 2013—(WO) ISR—App. No. PCT/US13/027397.

* cited by examiner

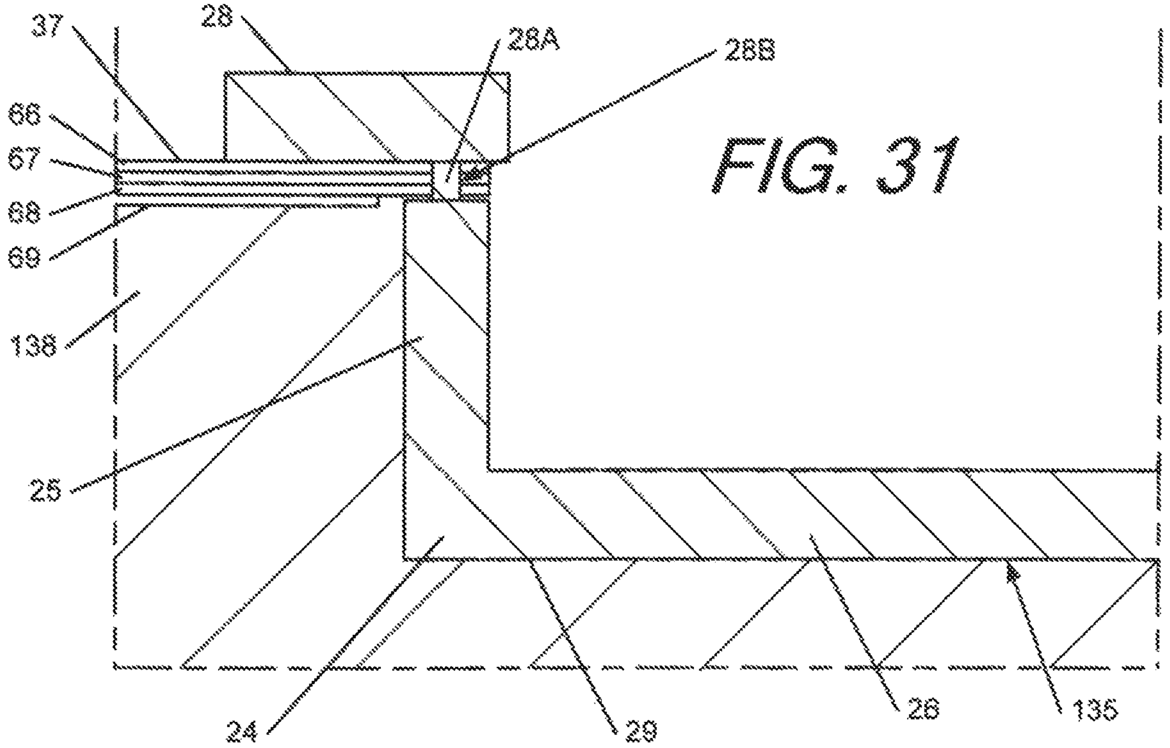
FIG. 31
FIG. 32
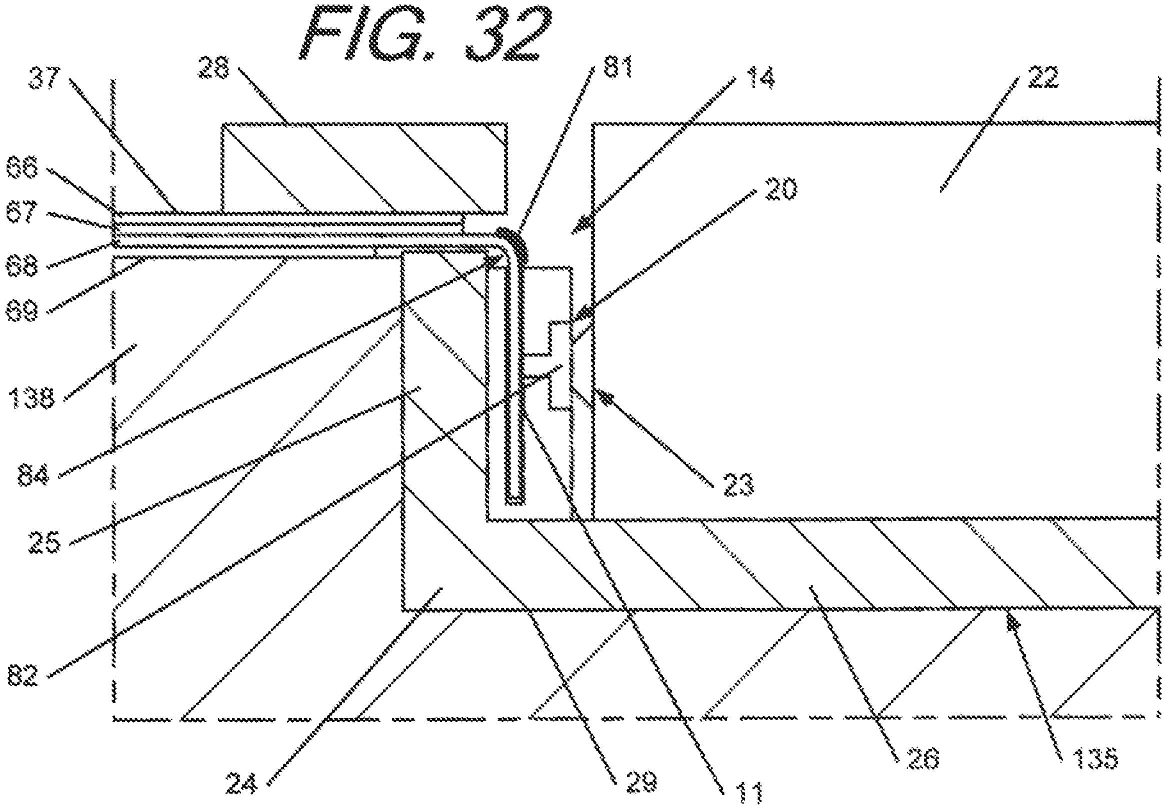

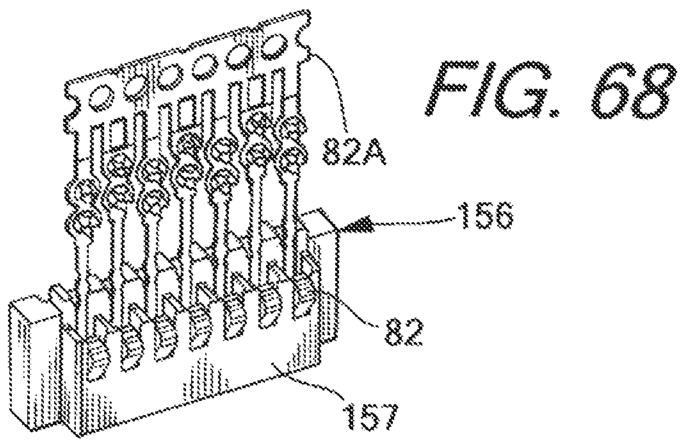
FIG. 68
FIG. 69
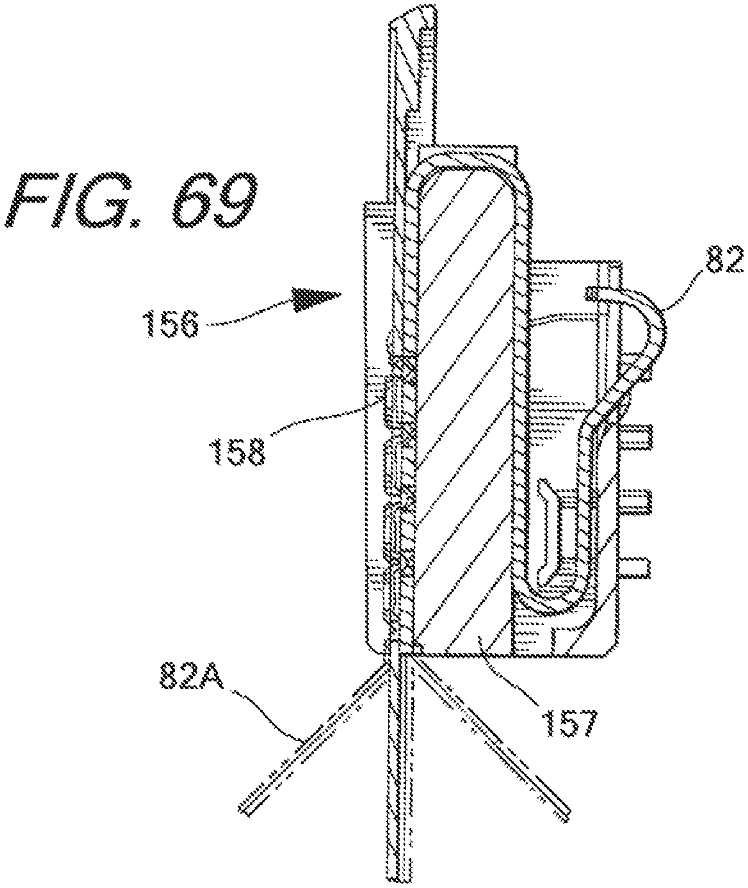

FOOTWEAR HAVING SENSOR SYSTEM

CROSS-REFERENCE TO RELATED APPLICATION

This application is a continuation of U.S. patent application Ser. No. 17/300,505, filed Jul. 26, 2021, and issued as U.S. Pat. No. 11,793,264 on Oct. 24, 2023, which is a continuation of U.S. patent application Ser. No. 16/513,057, filed Jul. 16, 2019, and issued as U.S. Pat. No. 11,071,345 on Jul. 27, 2021, which is a continuation of U.S. patent application Ser. No. 15/677,709, filed Aug. 15, 2017, and issued as U.S. Pat. No. 10,357,078 on Jul. 23, 2019, which is a continuation of U.S. patent application Ser. No. 14/559,680, filed Dec. 3, 2014, and issued as U.S. Pat. No. 9,756,895 on Sep. 12, 2017, which is a continuation of U.S. patent application Ser. No. 13/401,918, filed Feb. 22, 2012, which prior applications are incorporated herein by reference in their entireties and made part hereof.

TECHNICAL FIELD

The present invention generally relates to footwear having a sensor system and, more particularly, to a shoe having a force and/or pressure sensor assembly operably connected to a communication port located in the shoe.

BACKGROUND

Shoes having sensor systems incorporated therein are known. Sensor systems collect performance data wherein the data can be accessed for later use such as for analysis purposes. In certain systems, the sensor systems are complex or data can only be accessed or used with certain operating systems. Thus, uses for the collected data can be unnecessarily limited. Accordingly, while certain shoes having sensor systems provide a number of advantageous features, they nevertheless have certain limitations. The present invention seeks to overcome certain of these limitations and other drawbacks of the prior art, and to provide new features not heretofore available.

BRIEF SUMMARY

The present invention relates generally to footwear having a sensor system. Aspects of the invention relate to an article of footwear that includes an upper member and a sole structure, with a sensor system connected to the sole structure. The sensor system includes a plurality of sensors that are configured for detecting forces and/or pressure exerted by a user's foot on the sensor.

Aspects of the invention relate to a sensor system adapted for use with an article of footwear. The sensor system includes an insert member configured to be inserted into a foot-receiving chamber of an article of footwear, the insert member including a first layer and a second layer, a port connected to the insert and configured for communication with an electronic module, a plurality of force and/or pressure sensors on the insert member, and a plurality of leads connecting the sensors to the port.

The system may also include a pathway providing electrical communication between the first and second layers. The system may further include a housing connected to the insert and configured to support the electronic module in communication with the port. The insert may further include at least one additional layer, such as a spacer layer having holes aligned with the sensors and/or the pathway to permit engagement of such components through the spacer layer.

According to one aspect, the sensor system includes a first resistor located on the first layer and a second resistor located on the second layer, each connected to one or more of the leads. The port, the pathway, the sensors, the leads, and the first and second resistors form a circuit on the insert member, and the circuit is configured to have a voltage applied between a first terminal and a ground located at the port. The first and second resistors are arranged in parallel between the first terminal and the ground. Each of the resistors may include an inner section connected to a first lead, an outer section connected to a second lead, and a bridge extending between the inner section and the outer section and partially overlapping both the inner section and the outer section, wherein the resistor is configured such that an electronic signal can pass between the first lead and the second lead through the inner section, the bridge, and the outer section.

According to another aspect, the pathway may further include a substantially annular stiffener positioned around the pathway on at least one of the first and second layers, wherein the stiffener has decreased flexibility compared to the pathway. The pathway may additionally or alternately include a first conductive portion on the first layer and a second conductive portion on the second layer, wherein the first and second conductive portions are in continuous engagement with each other through the hole to provide electrical communication between the first and second layers, with the first and second conductive portions each having a gap extending therethrough and dividing the first and second conductive portions into separate first and second sections. In this configuration, the gap may be elongated and aligned substantially perpendicular to a virtual line extending between a front edge of the first metatarsophalangeal sensor and a rear edge of the fourth metatarsophalangeal sensor. The pathway in this configuration may constitute two separate pathways, on opposite sides of the gap.

According to another aspect, the spacer layer may include a first hole aligned with one of the sensors to permit at least partial engagement between the first and second contacts of the sensor through the spacer layer, and may further include a channel extending from the hole to a vent in the insert member, wherein the channel permits air to flow between the first and second layers from the sensor to an exterior of the insert member, through the first vent. The vent may have a selectively permeable closure member positioned to cover the vent. Additionally, the vent may be connected to more than one sensor through additional channels, and/or the insert may contain a second vent connected to one or more sensors in a similar arrangement. An article of footwear incorporating the insert may include a cavity within a sole member of the footwear that is located at least partially below the vent. The cavity extends laterally from the vent to a distal end located outside a peripheral boundary of the insert, such that the cavity is configured to permit the air exiting the first vent to pass away from the insert member. Further, a patch of dielectric material may be connected to one of the first and second layers and may extend across the channel to be positioned between the first and second layers, resisting shorting of one or more conductive members between the first and second layers through the channel.

According to a further aspect, the insert may include an extension extending into the well and consolidating the ends of the leads to form the interface, the extension having a strip of reinforcing material extending across the ends of the leads. The extension has a bend area where the extension bends downwardly at or near a peripheral edge of the housing and a depending portion that extends downwardly from the bend area into the well. In this configuration, the interface is located on the depending portion within the well, and the strip extends transversely across the bend area to provide reinforcement and wear resistance to the bend area. The system may also contain an interface assembly that includes a base member and a plurality of electrical connectors supported by the base member, where at least a portion of the depending portion is received in the base member and the ends of the leads engage the electrical connectors to form the interface.

According to yet another aspect, the insert includes a first cut-out on a medial edge of the insert member and a second cut-out on a lateral edge of the insert member, proximate a juncture between the forefoot portion and the midfoot portion. A width of the insert defined between the medial and lateral edges is larger in the midfoot portion than the width measured between the first and second cut-outs and the width measured at the heel portion. The insert may also include a hole in the midfoot portion configured to receive the housing, and the hole may make up less than half the width of the midfoot portion. The insert may also include other cut-out portions.

Other aspects of the invention relate to sensor systems that include various combinations of the above-discussed features.

Further aspects of the invention relate to a system that includes an article of footwear with a sensor system as described above, with an electronic module connected to the sensor system, and an external device configured for communication with the electronic module. The module is configured to receive data from the sensors and to transmit the data to the external device, and the external device is configured for further processing the data.

According to one aspect, the system also includes an accessory device connected to the external device, configured to enable communication between the electronic module and the external device. The accessory device may also be configured for connection to a second external device to enable communication between the electronic module and the second external device.

Still other features and advantages of the invention will be apparent from the following specification taken in conjunction with the following drawings.

BRIEF DESCRIPTION OF THE DRAWINGS

FIG. 31 is a cross-sectional view schematically depicting the view taken along lines 31-31 of FIG. 10;

FIG. 32 is a cross-sectional view schematically depicting the view taken along lines 32-32 of FIG. 10;

FIGS. 68-71 illustrate views of an interface assembly used in the port;

DETAILED DESCRIPTION

Figure 1:
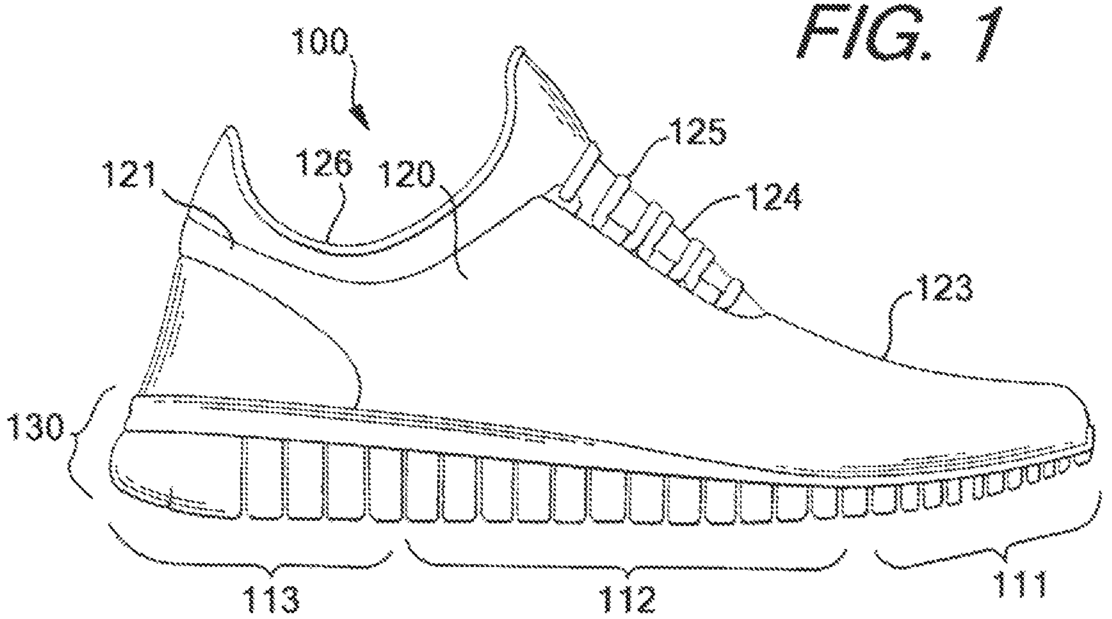
FIG. 1 is a side view of a shoe.

While this invention is susceptible of embodiment in many different forms, there are shown in the drawings, and will herein be described in detail, preferred embodiments of the invention with the understanding that the present disclosure is to be considered as an exemplification of the principles of the invention and is not intended to limit the broad aspects of the invention to the embodiments illustrated and described.

Figure 2:
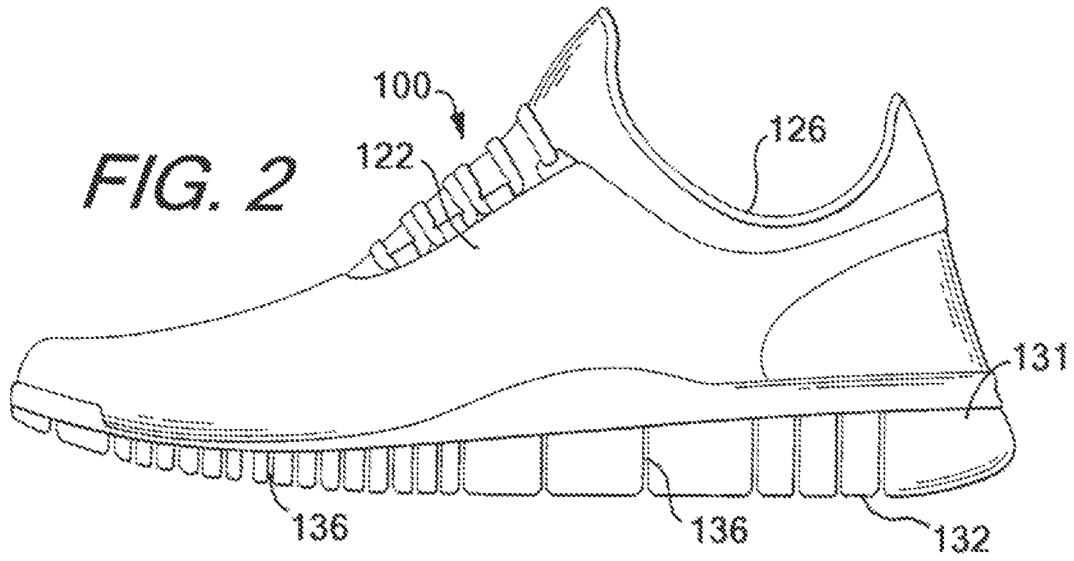
FIG. 2 is an opposed side view of the shoe of FIG. 1.

Footwear, such as a shoe, is shown as an example in FIGS. 1-2 and generally designated with the reference numeral 100. The footwear 100 can take many different forms, including, for example, various types of athletic footwear. In one exemplary embodiment, the shoe 100 generally includes a force and/or pressure sensor system 12 operably connected to a universal communication port 14.

As described in greater detail below, the sensor system 12 collects performance data relating to a wearer of the shoe 100. Through connection to the universal communication port 14, multiple different users can access the performance data for a variety of different uses as described in greater detail below.

An article of footwear 100 is depicted in FIGS. 1-2 as including an upper 120 and a sole structure 130. For purposes of reference in the following description, footwear 100 may be divided into three general regions: a forefoot region 111, a midfoot region 112, and a heel region 113, as illustrated in FIG. 1. Regions 111-113 are not intended to demarcate precise areas of footwear 100. Rather, regions 111-113 are intended to represent general areas of footwear 100 that provide a frame of reference during the following discussion. Although regions 111-113 apply generally to footwear 100, references to regions 111-113 also may apply specifically to upper 120, sole structure 130, or individual components included within and/or formed as part of either upper 120 or sole structure 130.

As further shown in FIGS. 1 and 2, the upper 120 is secured to sole structure 130 and defines a void or chamber for receiving a foot. For purposes of reference, upper 120 includes a lateral side 121, an opposite medial side 122, and a vamp or instep area 123. Lateral side 121 is positioned to extend along a lateral side of the foot (i.e., the outside) and generally passes through each of regions 111-113. Similarly, medial side 122 is positioned to extend along an opposite medial side of the foot (i.e., the inside) and generally passes through each of regions 111-113. Vamp area 123 is positioned between lateral side 121 and medial side 122 to correspond with an upper surface or instep area of the foot. Vamp area 123, in this illustrated example, includes a throat 124 having a lace 125 or other desired closure mechanism that is utilized in a conventional manner to modify the dimensions of upper 120 relative the foot, thereby adjusting the fit of footwear 100. Upper 120 also includes an ankle opening 126 that provides the foot with access to the void within upper 120. A variety of materials may be used for constructing upper 120, including materials that are conventionally utilized in footwear uppers. Accordingly, upper 120 may be formed from one or more portions of leather, synthetic leather, natural or synthetic textiles, polymer sheets, polymer foams, mesh textiles, felts, non-woven polymers, or rubber materials, for example. The upper 120 may be formed from one or more of these materials wherein the materials or portions thereof are stitched or adhesively bonded together, e.g., in manners that are conventionally known and used in the art.

Upper 120 may also include a heel element (not shown) and a toe element (not shown). The heel element, when present, may extend upward and along the interior surface of upper 120 in the heel region 113 to enhance the comfort of footwear 100. The toe element, when present, may be located in forefoot region 111 and on an exterior surface of upper 120 to provide wear-resistance, protect the wearer's toes, and assist with positioning of the foot. In some embodiments, one or both of the heel element and the toe element may be absent, or the heel element may be positioned on an exterior surface of the upper 120, for example. Although the configuration of upper 120 discussed above is suitable for footwear 100, upper 120 may exhibit the configuration of any desired conventional or non-conventional upper structure without departing from this invention.

Figure 3:
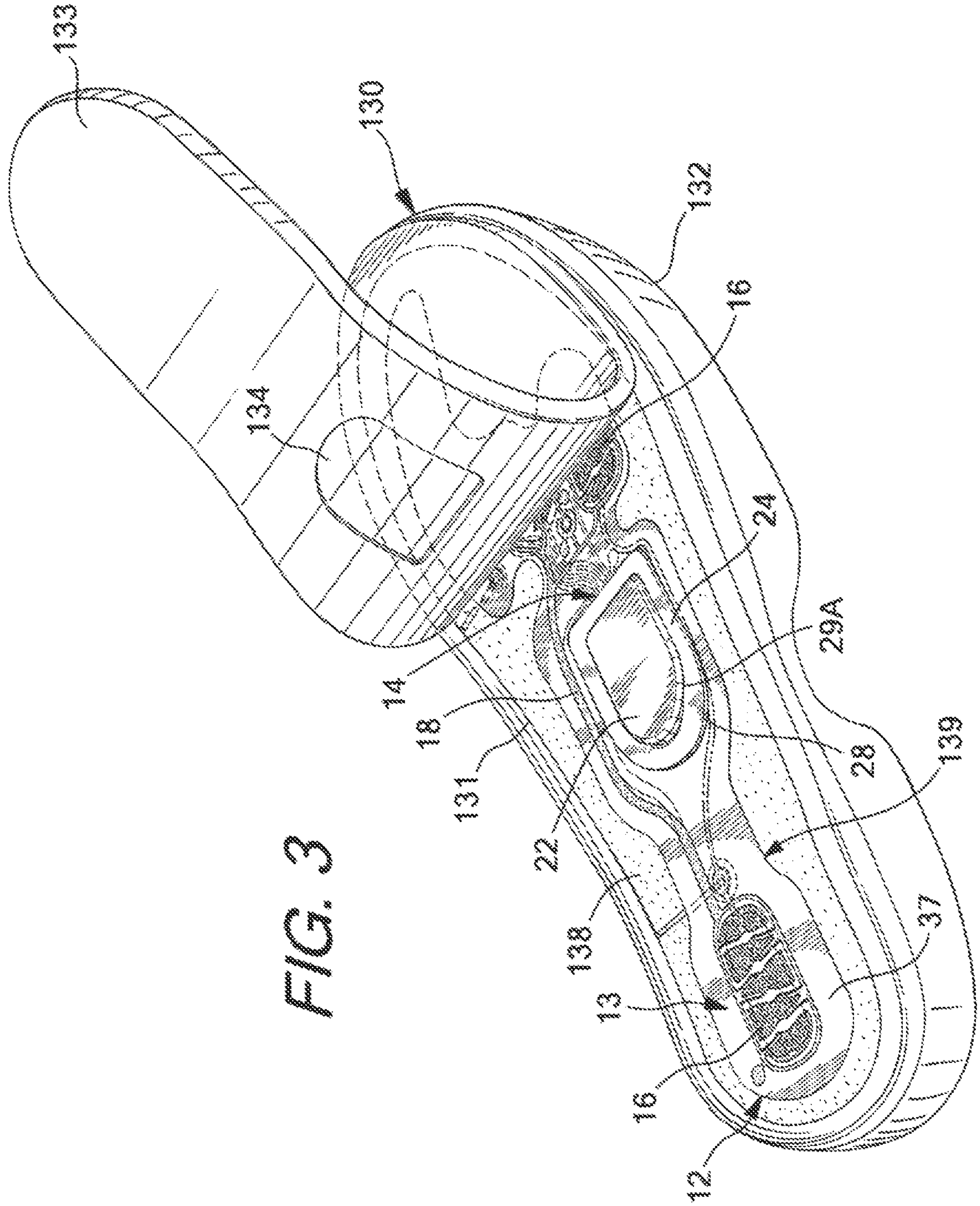
FIG. 3 is a top perspective view of a sole of a shoe (having a shoe upper removed and a foot contacting member folded aside) incorporating one embodiment of a sensor system according to aspects of the present invention.

As shown in FIG. 3, the sole structure 130 is secured to a lower surface of upper 120 and may have a generally conventional shape. The sole structure 130 may have a multipiece structure, e.g., one that includes a midsole 131, an outsole 132, and a foot contacting member 133. The foot contacting member 133 is typically a thin, compressible member that may be located within the void in upper 120 and adjacent to a lower surface of the foot (or between the upper 120 and midsole 131) to enhance the comfort of footwear 100. In various embodiments, the foot contacting member 133 may be a sockliner, a strobel, an insole member, a bootie element, a sock, etc. In the embodiment shown in FIGS. 3-5, the foot contacting member 133 is an insole member or a sockliner. The term "foot contacting member," as used herein does not necessarily imply direct contact with the user's foot, as another element may interfere with direct contact. Rather, the foot contacting member forms a portion of the inner surface of the foot-receiving chamber of an article of footwear. For example, the user may be wearing a sock that interferes with direct contact. As another example, the sensor system 12 may be incorporated into an article of footwear that is designed to slip over a shoe or other article of footwear, such as an external bootie element or shoe cover. In such an article, the upper portion of the sole structure may be considered a foot contacting member, even though it does not directly contact the foot of the user. In some arrangements, an insole or sockliner may be absent, and in other embodiments, the footwear 100 may have a foot contacting member positioned on top of an insole or sockliner.

Midsole member 131 may be or include an impact attenuating member, and may include multiple members or elements in some embodiments. For example, the midsole member 131 may be formed of polymer foam material, such as polyurethane, ethylvinylacetate, or other materials (such as phylon, phylite, etc.) that compress to attenuate ground or other contact surface reaction forces during walking, running, jumping, or other activities. In some example structures according to this invention, the polymer foam material may encapsulate or include various elements, such as a fluid-filled bladder or moderator, that enhance the comfort, motion-control, stability, and/or ground or other contact surface reaction force attenuation properties of footwear 100. In still other example structures, the midsole 131 may include additional elements that compress to attenuate ground or other contact surface reaction forces. For instance, the midsole 131 may include column type elements to aid in cushioning and absorption of forces.

Outsole 132 is secured to a lower surface of midsole 131 in this illustrated example footwear structure 100 and is formed of a wear-resistant material, such as rubber or a flexible synthetic material, such as polyurethane, that contacts the ground or other surface during ambulatory or other activities. The material forming outsole 132 may be manufactured of suitable materials and/or textured to impart enhanced traction and slip resistance. The outsole 132 shown in FIGS. 1 and 2 is shown to include a plurality of incisions or sipes 136 in either or both sides of the outsole 132, although many other types of outsoles 132 with various types of treads, contours, and other structures may be used in connection with the present invention. It is understood that embodiments of the present invention may be used in connection with other types and configurations of shoes, as well as other types of footwear and sole structures.

FIGS. 1-5 illustrate exemplary embodiments of the footwear 100 incorporating a sensor system 12 in accordance with the present invention, and FIGS. 3-22B illustrate exemplary embodiments of the sensor system 12. The sensor system 12 includes an insert member 37 having a force and/or pressure sensor assembly 13 connected thereto. The insert member 37 is configured to be positioned in contact with the sole structure 130 of the footwear 100, and in one embodiment, the insert member 37 is configured to be positioned underneath the foot contacting member 133 and over the top of the midsole member 131 and in general confronting relation. The sensor assembly 13 includes a plurality of sensors 16, and a communication or output port 14 in communication with the sensor assembly 13 (e.g., electrically connected via conductors). The port 14 is configured for communicating data received from the sensors 16, such as to an electronic module (also referred to as an electronic control unit) 22 as described below. The port 14 and/or the module 22 may be configured to communicate with an external device, as also described below. In the embodiment illustrated in FIGS. 3-5, the system 12 has four sensors 16: a first sensor 16*a* at the big toe (first phalange or hallux) area of the shoe, two sensors 16*b-c* at the forefoot area of the shoe, including a second sensor 16*b* at the first metatarsal head region and a third sensor 16*c* at the fifth metatarsal head region, and a fourth sensor 16*d* at the heel. These areas of the foot typically experience the greatest degree of pressure during movement. Each sensor 16 is configured for detecting a pressure exerted by a user's foot on the sensor 16. The sensors communicate with the port 14 through sensor leads 18, which may be wire leads and/or another electrical conductor or suitable communication medium. For example, in the embodiment of FIGS. 3-5, the sensor leads 18 may be an electrically conductive medium that is printed on the insert member 37, such as a silver-based ink or other metallic ink, such as an ink based on copper and/or tin. The leads 18 may alternately be provided as thin wires in one embodiment. In other embodiments, the leads 18 may be connected to the foot contacting member 133, the midsole member 131, or another member of the sole structure 130.

Other embodiments of the sensor system 12 may contain a different number or configuration of sensors 16, and generally include at least one sensor 16. For example, in one embodiment, the system 12 includes a much larger number of sensors, and in another embodiment, the system 12 includes two sensors, one in the heel and one in the forefoot of the shoe 100. In addition, the sensors 16 may communicate with the port 14 in a different manner, including any known type of wired or wireless communication, including Bluetooth and near-field communication. A pair of shoes may be provided with sensor systems 12 in each shoe of the pair, and it is understood that the paired sensor systems may operate synergistically or may operate independently of each other, and that the sensor systems in each shoe may or may not communicate with each other. The communication of the sensor systems 12 is described in greater detail below. It is understood that the sensor system 12 may be provided with computer programs/algorithms to control collection and storage of data (e.g., pressure data from interaction of a user's foot with the ground or other contact surface), and that these programs/algorithms may be stored in and/or executed by the sensors 16, the module 22, and/or the external device 110.

Figure 4:
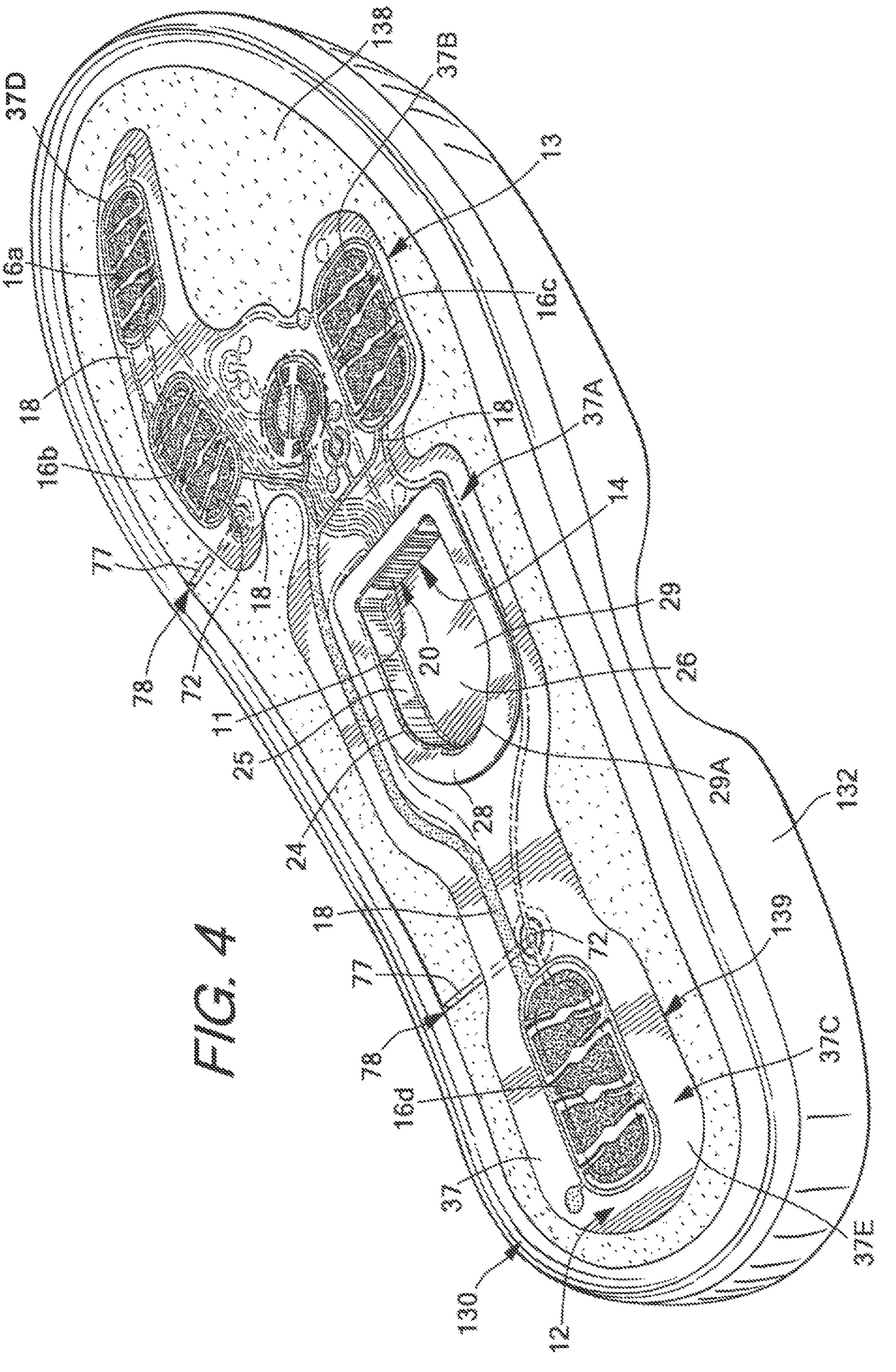
FIG. 4 is a top perspective view of the sole and the sensor system of FIG. 3, with a foot contacting member of the shoe removed and an electronic module removed.
Figure 5:
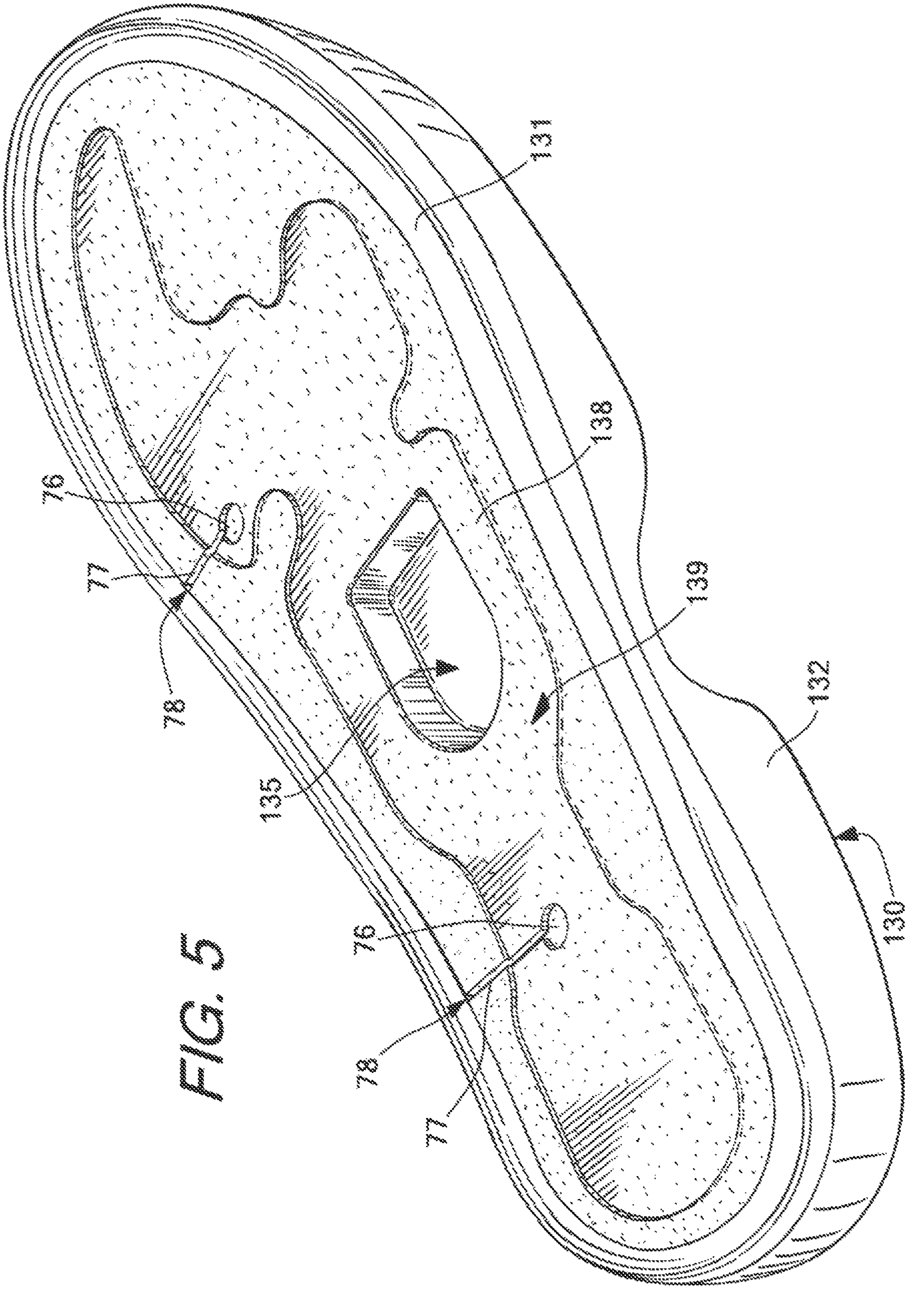
FIG. 5 is a top perspective view of the sole of FIG. 3, with the foot contacting member of the shoe removed and without the sensor system.

The sensor system 12 can be positioned in several configurations in the sole 130 of the shoe 100. In the examples shown in FIGS. 3-5, the port 14, the sensors 16, and the leads 18 can be positioned between the midsole 131 and the foot contacting member 133, such as by positioning the insert member 37 between the midsole 131 and the foot contacting member 133. The insert member 37 may be connected to one or both of the midsole and the foot contacting member 133 in one embodiment. A cavity or well 135 can be located in the midsole 131 (FIG. 5) and/or in the foot contacting member 133 for receiving the electronic module 22, as described below, and the port 14 may be accessible from within the well 135 in one embodiment. The well 135 may further contain a housing 24 for the module 22, and the housing 24 may be configured for connection to the port 14, such as by providing physical space for the port 14 and/or by providing hardware for interconnection between the port 14 and the module 22. In the embodiment shown in FIG. 5, the well 135 is formed by a cavity in the upper major surface of the midsole 131. As shown in FIG. 5, the sole structure 130 may include a compressible sole member 138 that has a hole formed therein to receive the housing 24, which provides access to the well 135 and/or may be considered a portion of the well 135. The insert 37 can be placed on top of the compressible sole member 138 to place the housing 24 in the well 135. The compressible sole member 138 may confront the midsole 131 in one embodiment, and may be in direct contact with the midsole 131. It is understood that the compressible sole member 138 may confront the midsole 131 with one or more additional structures positioned between the compressible sole member 138 and the midsole 131, such as a strobel member. In the embodiment of FIGS. 3-5, the compressible sole member 138 is in the form of a foam member 138 (e.g. an EVA member) located between the foot contacting member 133 and the midsole 131, which may be considered a lower insole/sockliner in this embodiment. The foam member 138 may be bonded to a strobel 133A (FIG. 58) of the midsole 131 in one embodiment, such as by use of an adhesive, and may cover any stitching on the strobel, which can prevent abrasion of the insert 37 by the stitching. This configuration is shown schematically in FIG. 58. In the embodiment shown in FIGS. 3-5, the housing 24 has a plurality of walls, including side walls 25 and a base wall 26, and also includes a flange or lip 28 that extends outward from the tops of the side walls 25 and is configured for connection to the insert 37. In one embodiment, the flange 28 is a separate member that connects to a tub 29 to form the housing 24, via pegs 28A that connect through holes 28B in the insert 37 located at the front end of the hole 27. The pegs 28A may be connected via ultrasonic welding or other technique, and may be received in receivers in one embodiment. In an alternate embodiment, an article of footwear 100 may be manufactured with the tub 29 formed in the sole structure 130, and the flange 28 may be later connected, such as by a snap connection, optionally after other portions of the port have also been assembled. The housing 24 may include retaining structure to retain the module 22 within the housing 24, and such retaining structure may be complementary with retaining structure on the module 22, such as a tab/flange and slot arrangement, complementary tabs, locking members, friction-fit members, etc. The housing 24 also includes a finger recess 29A located in the flange 28 and/or the tub 29, which provides room for the user's finger to engage the module 22 to remove the module 22 from the housing 24. The flange 28 provides a wide base engaging the top of the insert 37, which spreads out the forces exerted on the insert 37 and/or on the foot contacting member 133 by the flange 28, which creates less likelihood of severe deflection and/or damage of such components. The rounded corners on the flange 28 also assists in avoiding damage to the insert 37 and/or the foot contacting member 133. It is understood that the flange 28 may have a different shape and/or contour in other embodiments, and may provide similar functionality with different shapes and/or contours.

Figure 60:
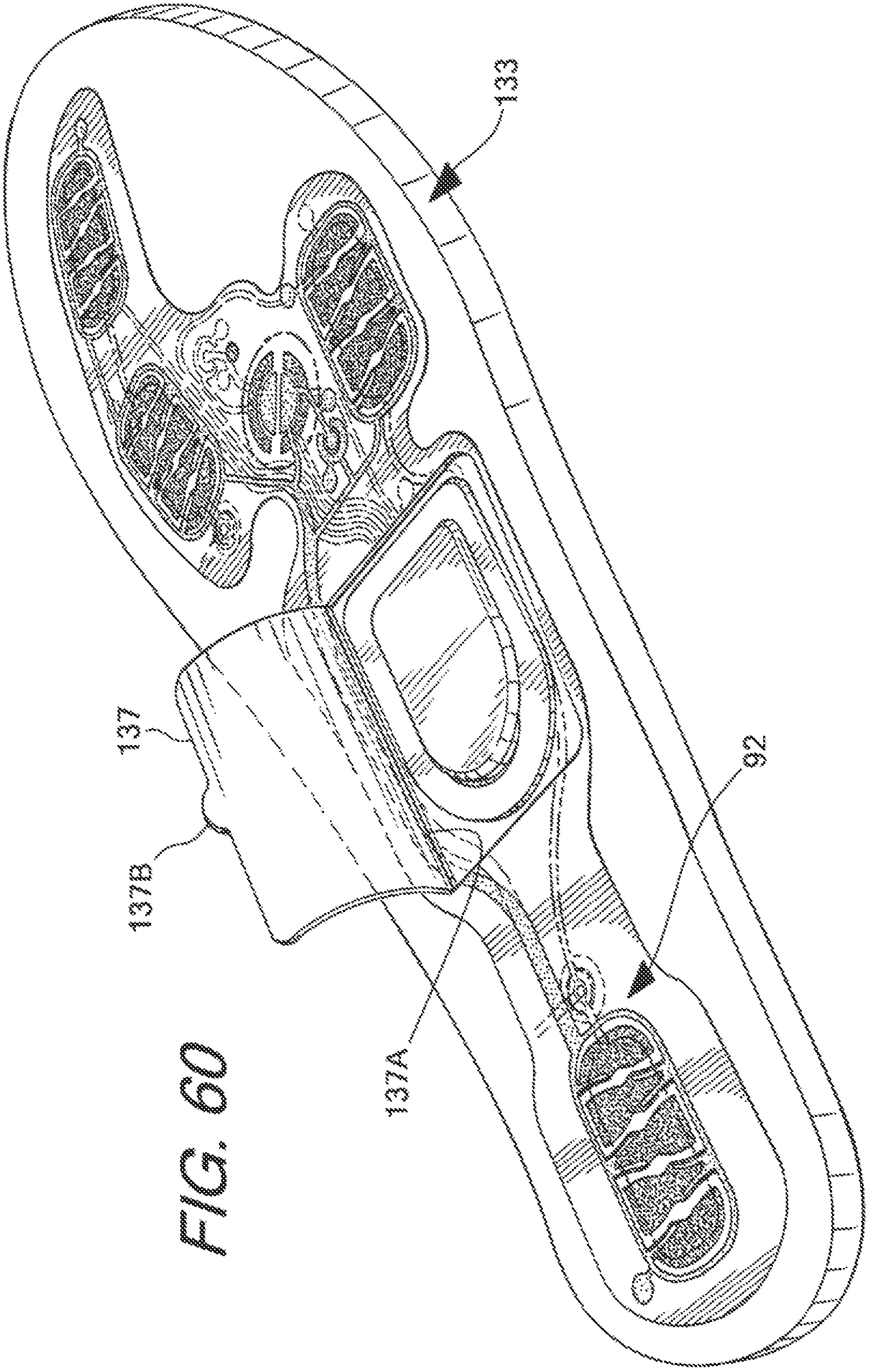
FIG. 60 is a perspective view of one embodiment of a foot contacting member configured for use with a sensor system according to aspects of the present invention.

The foot contacting member 133 is configured to be placed on top of the foam member 138 to cover the insert 37, and may contain an indent 134 in its lower major surface to provide space for the housing 24, as shown in FIG. 3. The foot contacting member 133 may be adhered to the foam member 138, and in one embodiment, may be adhered only in the forefoot region to permit the foot contacting member 133 to be pulled up to access the module 22, as shown in FIG. 3. Additionally, the foot contacting member 133 may include a tacky or high-friction material (not shown) located on at least a portion of the underside to resist slippage against the insert 37 and/or the foam member 138, such as a silicone material. For example, in an embodiment where the foot contacting member 133 is adhered in the forefoot region and free in the heel region (e.g. FIG. 3), the foot contacting member 133 may have the tacky material located on the heel region. The tacky material may also provide enhanced sealing to resist penetration of dirt into the sensor system. In another embodiment, as shown in FIG. 60, the foot contacting member 133 may include a door or hatch 137 configured to be located over the port 14 and sized to permit insertion and/or removal of the module 22 through the foot contacting member 133. The embodiment of the foot contacting member 133 shown in FIG. 60 may be usable in place of the foot contacting member 133 in FIG. 3, 36, or 45, to provide access to the port 14 and the module 22. In the embodiment shown in FIG. 60, the door 137 has a hinge 137A formed by material attachment along one edge of the door 137, allowing the door 137 to be opened and closed by swinging. Additionally, the door 137 is formed of the same material as the foot contacting member 133 in this embodiment, so that no significant loss of cushioning is lost by inclusion of the door 137. Further, the door 137 may have a tab 137B or other structure to aid in gripping and manipulation of the door 137 by the user. In one embodiment, the sensor system 12 may be positioned on the underside of the foot contacting member 133, and the door 137 may provide access to the port 14 in such an embodiment (not shown). In another embodiment, the door 137 may have a hinge on another edge, or may open in a different manner, such as by removal, sliding, etc. In one embodiment, the foot contacting member 133 may also have graphic indicia 92 thereon, as described below.

In one embodiment, as shown in FIGS. 3-5 and 7, the foam member 138 may also include a recess 139 having the same peripheral shape as the insert 37 to receive the insert 37 therein, and the bottom layer 69 (FIG. 13) of the insert member 37 may include adhesive backing to retain the insert 37 within the recess 139. In one embodiment, a relatively strong adhesive, such as a quick bonding acrylic adhesive, may be utilized for this purpose. The insert 37 has a hole or space 27 for receiving and providing room for the housing 24, and the foam member 138 in this embodiment may also allow the housing 24 to pass completely through into and/or through at least a portion of the strobel and/or the midsole 131. In the embodiment shown in FIGS. 3-5, the foot contacting member 133 may have a thickness that is reduced relative to a typical foot contacting member 133 (e.g. sockliner), with the thickness of the foam member 138 being substantially equal to the reduction in thickness of the foot contacting member 133, to provide equivalent cushioning. In one embodiment, the foot contacting member 133 may be a sockliner with a thickness of about 2-3 mm, and the foam member 138 may have a thickness of about 2 mm, with the recess 139 having a depth of about 1 mm. The foam member 138 may be adhesively connected to the insert member 37 prior to connecting the foam member 138 to the article of footwear 100 in one embodiment. This configuration permits the adhesive between the foam member 138 and the insert 37 to set in a flat condition before attaching the foam member to the strobel or other portion of the footwear 100, which is typically bends or curves the foam member 138 and may otherwise cause delamination. The foam member 138 with the insert 37 adhesively attached may be provided in this configuration as a single product for insertion into an article of footwear 100 in one embodiment. The positioning of the port 14 in FIGS. 3-5 not only presents minimal contact, irritation, or other interference with the user's foot, but also provides easy accessibility by simply lifting the foot contacting member 133.

Figure 57:
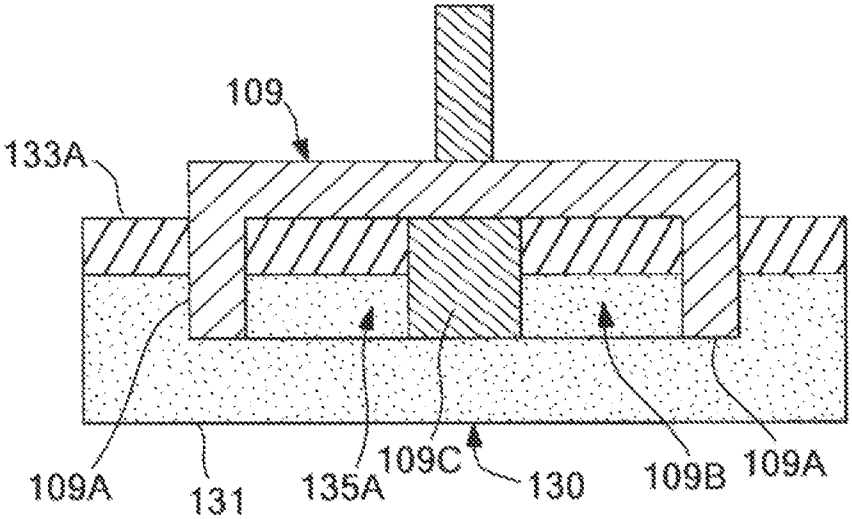
FIG. 57 is a schematic cross-sectional view illustrating one embodiment of a method and equipment for forming a well in a sole structure of an article of footwear, according to aspects of the present invention.
Figure 58:
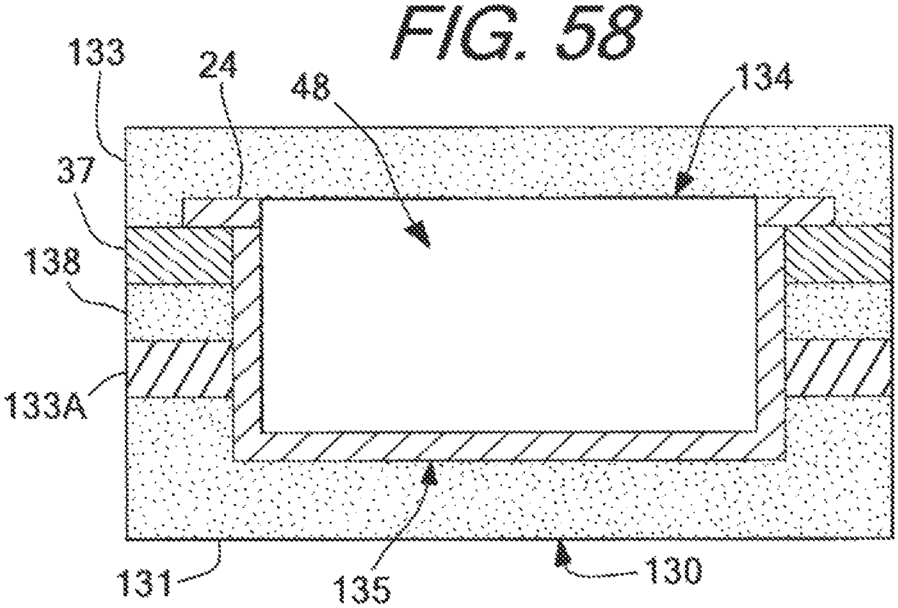
FIG. 58 is a schematic cross-sectional view illustrating the sole structure of the article of footwear of FIG. 57 with an insert member of a sensor system and a foot contacting member connected thereto.

In the embodiment of FIGS. 3-5, the housing 24 extends completely through the insert 37 and the foam member 138, and the well 135 also extends completely through the strobel 133A and partially into the midsole 131 of the footwear 100 to receive the housing 24, as illustrated schematically in FIG. 58. In another embodiment, the well 135 may be differently configured, and may be positioned completely underneath the strobel 133A in one embodiment, with a window through the strobel 133A to permit access to the module 22 in the well 135. The well 135 may be formed using a variety of techniques, including cutting or removing material from the strobel 133A and/or the midsole 131, forming the strobel 133A and/or the midsole 131 with the well contained therein, or other techniques or combinations of such techniques. In one embodiment, a hot knife 109 is used to cut through the strobel 133A and into the midsole 131 to remove a piece 135A of material to form the well 135, as illustrated schematically in FIG. 57. In this embodiment, the hot knife 109 includes a wall 109A extending around the periphery of the hot knife 109 to define a cavity 109B that receives the piece 135A to be removed, as well as prongs 109C that extend down through the middle of the piece 135A. The wall 109A cuts down into the strobel 133A and the midsole 131 to cut the outer boundaries of the piece 135A to be removed. The prongs 109C both weaken the bottom side of the piece 135A to facilitate removal and also assist in retaining the piece 135A within the cavity 109B during removal, so the piece 135A can be removed by simply lifting the hot knife 109 away from the sole structure 130. In one embodiment, the hot knife 109 may be heated to a temperature of between 250-260° C. In other embodiments, a hot knife 109 (which may be differently configured) may be utilized to form a differently shaped and/or configured well 135 in the sole structure 130. FIG. 58 schematically illustrates the insert 37 connected to the sole structure 130 and the housing 24 received in the well 135 after formation. As shown in FIG. 58, the housing 24 fits closely with the walls of the well 135, which can be advantageous, as gaps between the housing 24 and the well 135 may be sources of material failure. The process of removing the piece 135 may be automated using appropriate computer control equipment.

Figure 59:
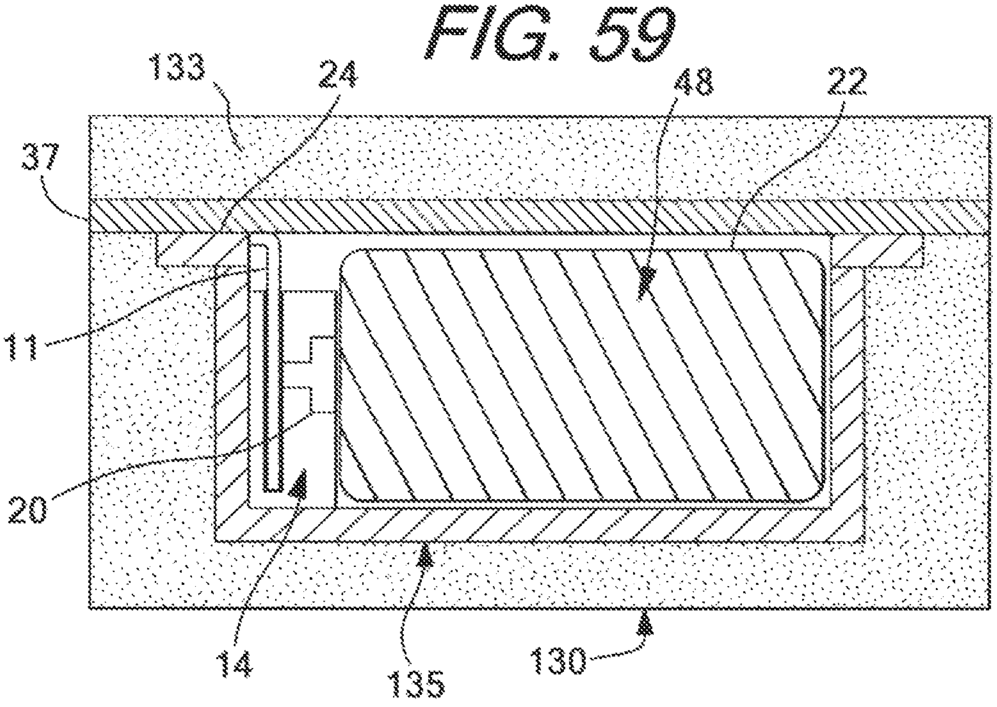
FIG. 59 is a schematic cross-sectional view illustrating another embodiment of a sensor system positioned within a sole structure of an article of footwear, according to aspects of the present invention.
Figure 59A:
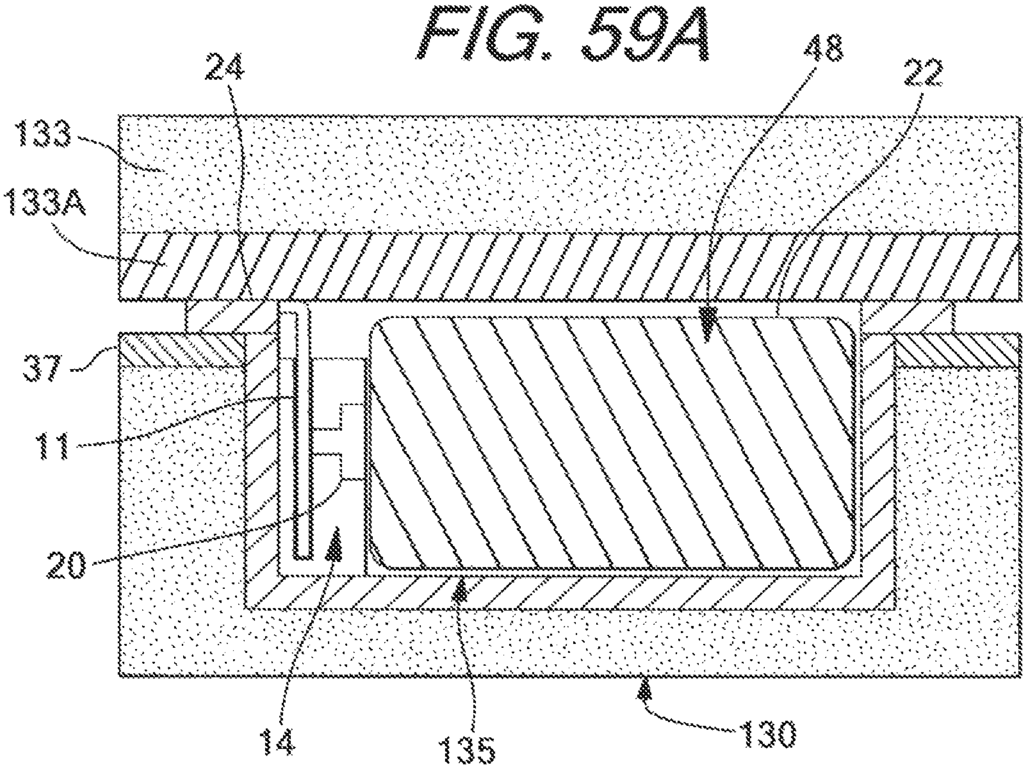
FIG. 59A is a schematic cross-sectional view illustrating another embodiment of a sensor system positioned within a sole structure of an article of footwear, according to aspects of the present invention.

The well 135 may be located elsewhere in the sole structure 130 in further embodiments. For example, the well 135 may be located in the upper major surface of the foot contacting member 133 and the insert 37 can be placed on top of the foot contacting member 133. As another example, the well 135 may be located in the lower major surface of the foot contacting member 133, with the insert 37 located between the foot contacting member 133 and the midsole 131. As a further example, the well 135 may be located in the outsole 132 and may be accessible from outside the shoe 100, such as through an opening in the side, bottom, or heel of the sole 130. In the configurations illustrated in FIGS. 3-5, the port 14 is easily accessible for connection or disconnection of an electronic module 22, as described below. In the embodiment illustrated in FIG. 59, the foot contacting member 133 has the insert 37 connected to the bottom surface, and the port 14 and the well 135 are formed in the sole structure 130, such as in the same configuration described above and shown in FIG. 58. The interface 20 is positioned on the side of the housing 24 as similarly shown with respect to other embodiments, although it is understood that the interface 20 could be positioned elsewhere, such as for engagement through the top of the module 22. The module 22 may be altered to accommodate such a change. In this embodiment, the foot contacting member 133 may be provided with an opening for accessing the module 22 (such as in FIG. 60) or may be able to be pulled upward to access the module 22, as shown in FIG. 3. In the embodiment illustrated in FIG. 59A, the insert 37 is positioned below both the foot contacting member 133 and the strobel 133A, and in contact with the midsole member 131. In this embodiment, the strobel 133A and/or the foot contacting member 133 may be provided with openings for accessing the module 22 and/or may be able to be pulled upward to access the module 22, as shown in FIG. 3.

In other embodiments, the sensor system 12 can be positioned differently. For example, in one embodiment, the insert 37 can be positioned within the outsole 132, midsole 131, or foot contacting member 133. In one exemplary embodiment, insert 37 may be positioned within a foot contacting member 133 positioned above an insole member, such as a sock, sockliner, interior footwear bootie, or other similar article, or may be positioned between the foot contacting member 133 and the insole member. Still other configurations are possible, and some examples of other configurations are described below. As discussed, it is understood that the sensor system 12 may be included in each shoe in a pair.

Figure 12:
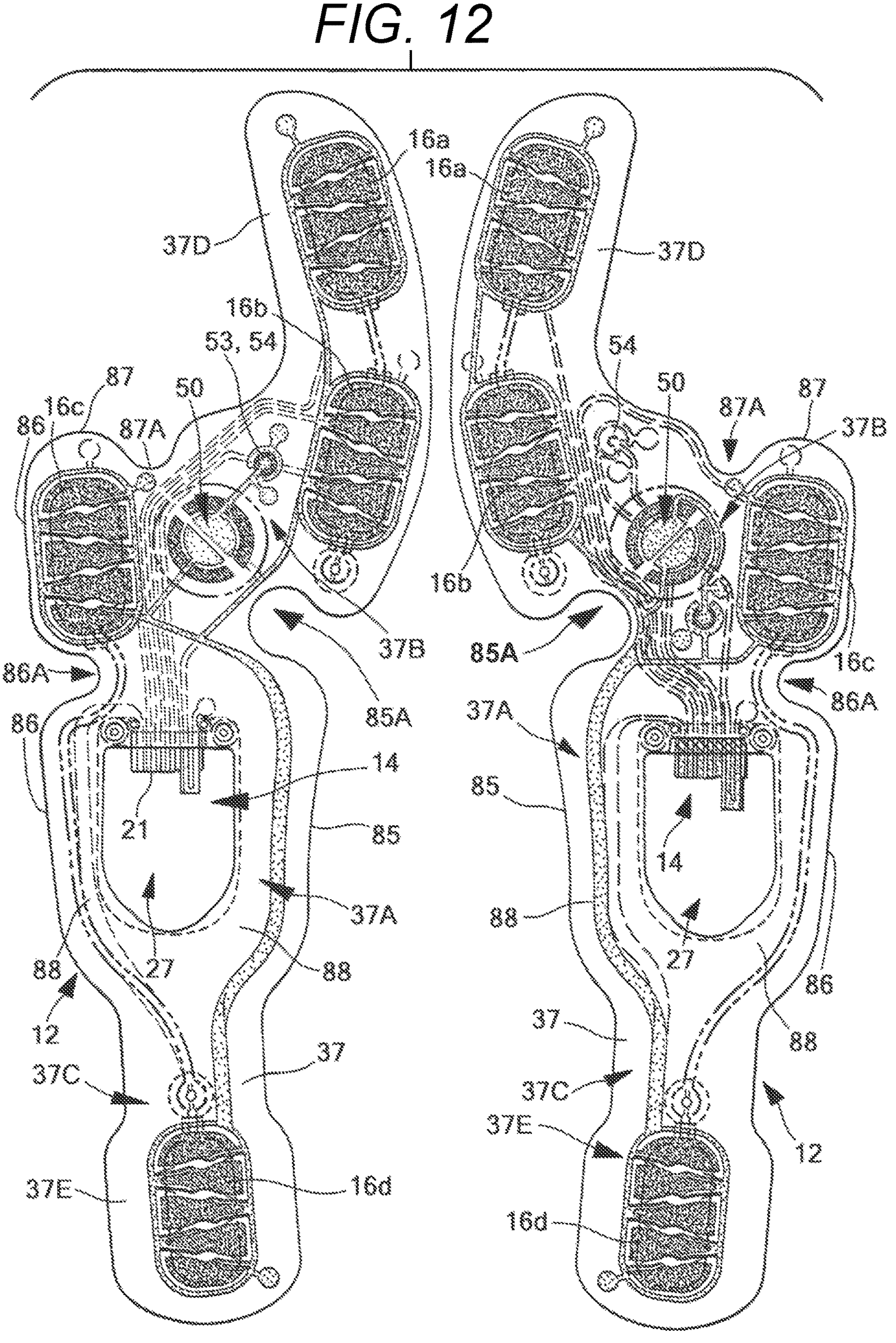
FIG. 12 is a top view of a pair of sensor systems including the sensor system of FIG. 9 and a similar sensor system adapted for use in the sole structure of an article of footwear for a user's left foot.
Figure 13:
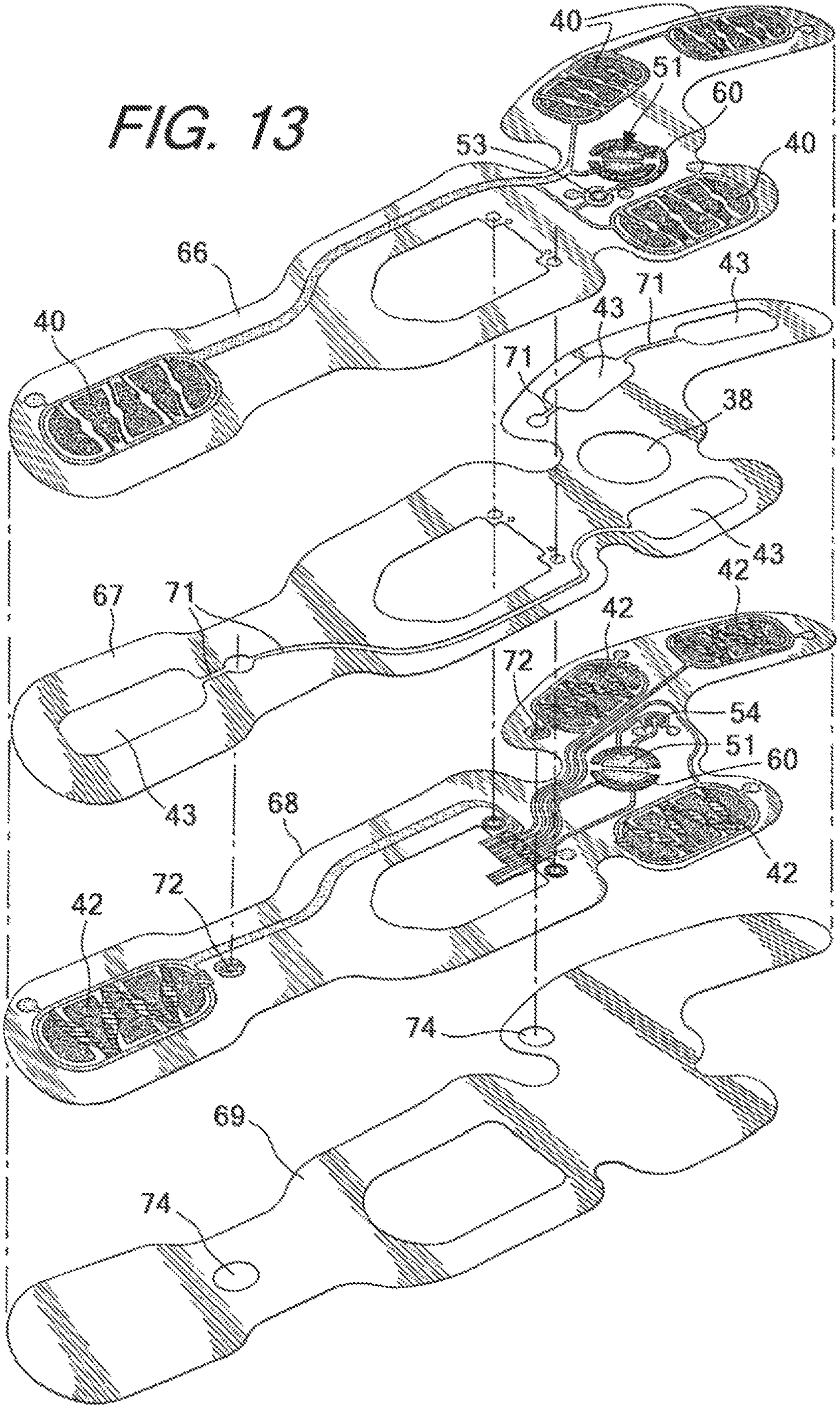
FIG. 13 is an exploded perspective view of the insert of FIG. 7, showing four different layers.
Figure 14:
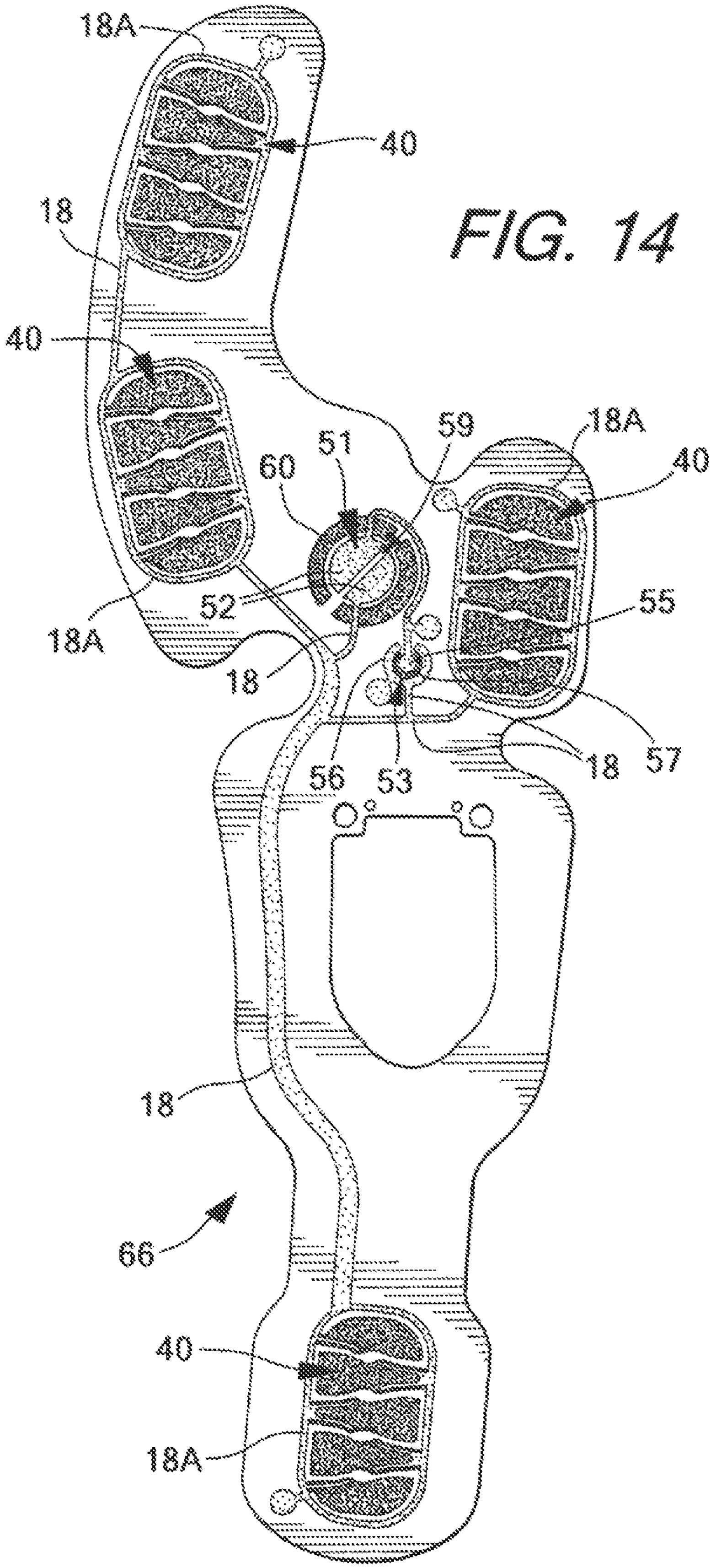
FIG. 14 is a top view of a first layer of the insert of FIG. 13.

The insert member 37 in the embodiment illustrated in FIGS. 3-22B is formed of multiple layers, including at least a first layer 66 and a second layer 68. The first and second layers 66, 68 may be formed of a flexible film material, such as a Mylar® or other PET (polyethylene terephthalate) film, or another polymer film, such as polyamide. In one embodiment, the first and second layers 66, 68 may each be PET films having thicknesses of 0.05-0.2 mm, such as a thickness of 125 μm. Additionally, in one embodiment, each of the first and second layers 66, 68 has a minimum bend radius of equal to or less than 2 mm. The insert 37 may further include a spacer layer 67 positioned between the first and second layers 66, 68 and/or a bottom layer 69 positioned on the bottom of the insert 37 below the second layer 68, which are included in the embodiment illustrated in FIGS. 3-22B. The layers 66, 67, 68, 69 of the insert 37 are stacked on top of each other and in confronting relation to each other, and in one embodiment, the layers 66, 67, 68, 69 all have similar or identical peripheral shapes and are superimposed on one another (FIG. 13). In one embodiment, the spacer layer 67 and the bottom layer 69 may each have a thickness of 89-111 μm, such as a thickness of 100 μm. The entire thickness of the insert member 37 may be about 450 μm in one embodiment, or about 428-472 μm in another embodiment, and about 278-622 μm in a further embodiment. The insert 37 may also include additional adhesive that is 100-225 μm thick, and may further include one or more selective reinforcement layers, such as additional PET layers, in other embodiments. Additionally, in one embodiment, the entire four-layer insert as described above has a minimum bend radius of equal to or less than 5 mm. It is understood that the orientations of the first and second layers 66, 68 may be reversed in another embodiment, such as by placing the second layer 68 as the top layer and the first layer 66 below the second layer 68. In the embodiment of FIGS. 3-22B, the first and second layers 66, 68 have various circuitry and other components printed thereon, including the sensors 16, the leads 18, resistors 53, 54, a pathway 50, dielectric patches 80, and other components, which are described in greater detail below. The components are printed on the underside of the first layer 66 and on the upper side of the second layer 68 in the embodiment of FIGS. 3-22B, however in other embodiments, at least some components may be printed on the opposite sides of the first and second layers 66, 68. It is understood that components located on the first layer 66 and/or the second layer 68 may be moved/transposed to the other layer 66, 68. In one embodiment, the components may be printed on the layers 66, 68 in a manner so as to limit the total number of printer passes required, and in one embodiment, all the components on an individual layer 66, 68 may be printed in a single pass.

The layers 66, 67, 68, 69 can be connected together by an adhesive or other bonding material in one embodiment. The spacer layer 67 may contain adhesive on one or both surfaces in one embodiment to connect to the first and second layers 66, 68. The bottom layer 69 may likewise have adhesive on one or both surfaces, to connect to the second layer 68 as well as to the article of footwear 100. The first or second layers 66, 68 may additionally or alternately have adhesive surfaces for this purpose. A variety of other techniques can be used for connecting the layers 66, 67, 68, 69 in other embodiments, such as heat sealing, spot welding, or other known techniques.

The insert 37, the foot contacting member 133, and/or other components of the sensor system 12 and the footwear 100 may also include a graphic design or other indicia (not shown) thereon. The graphic design may be provided on one or more graphic layers (not shown) that may be connected to the insert 37, such as by overlaying the graphic layer on top of the first layer 66. The graphic design may correspond to the sensor assembly 13, leads 18 and the various other components supported by the layer. For example, in the embodiment of FIG. 60, the foot contacting member 133 has graphical indicia 92 that forms a graphical depiction of the insert 37 of the sensor system 12 that is positioned below the foot contacting member 133. Other graphical designs may be used in other embodiments, including informative, stylistic, and other such designs.

The insert 37 illustrated in FIGS. 3-22B has a configuration that may utilize less material than other insert configurations and may provide greater resistance to tearing at common stress points. In this embodiment, the insert 37 has several portions of material cut out of areas of the insert 37 that may be superfluous, such as in the lateral forefoot area or the lateral and medial heel areas. The insert 37 in this configuration has a midfoot portion 37A configured to be engaged by the midfoot region of the user's foot and a forefoot portion 37B configured to be engaged by the forefoot (i.e. metatarsal) region of the user's foot, with a heel portion 37C extending rearwardly from the midfoot portion 37A and a first phalange portion 37D extending forwardly from the forefoot portion, configured to be engaged by the heel region and the first phalange region of the user's foot, respectively. FIGS. 4, 8, 10, and 22A illustrate these features in greater detail. It is understood that, depending on the shape of the user's foot, the first phalange portion 37D may engage only the first phalange region of the user's foot. In this embodiment, the width of the forefoot portion 37B is greater than the width of the midfoot portion 37A, and both the midfoot and forefoot portions 37A-B have greater width than the first phalange portion 37D and the heel portion 37C, such that the first phalange portion 37D and the heel portion 37C are configured as peninsulas that extend forward or rearward, respectively, from a base at the wider midfoot and forefoot portions 37A-B to a free end in elongated manners. As referred to herein, the width of a portion of the insert 37 is measured in the medial-to-lateral direction, and the length is measured in the front-to-rear (toe-to-heel) direction. In the embodiment of FIGS. 3-22B, the first phalange portion 37D has one of the sensors 16*a* located thereon, to be engaged by the first phalange of the user, and the heel portion 37C has another one of the sensors 16*d* thereon, to be engaged by the heel of the user. The remaining two sensors 16*b*, 16*c* are located on the forefoot portion 37B of the insert 37, specifically at the first metatarsal head region and at the fifth metatarsal head region, to be engaged by the first and fifth metatarsal head regions of the user's foot, respectively. The midfoot portion 37A contains the hole 27 for receiving the housing 24 and module 22, and the hole 27 defines two strips 88 that extend between and connect the forefoot portion 37B and the heel portion 37C. In one embodiment, the strips 88 have minimum widths of 8 mm or widths within a range of 3-5% of the overall length of the insert 37. In this usage, the length of the insert 37 is measured from the forefoot-most end of the first phalange portion 37D to the heel-most end of the heel portion 37C. These strips 88 undergo high stresses during use, and this width assists in avoiding failure during use. In other embodiments, the strips 88 may be reinforced by additional structure. For example, in one embodiment, the strips 88 and/or other portions of the insert 37 may be reinforced by fibers or similar structures. As another example, the insert 37 may include an additional structural layer over at least a portion of the insert 37 in one embodiment, such as an additional structural layer that completely surrounds the housing 24 and occupies the entireties of both strips 88 and the junctures between the strips 88 and the remainder of the insert 37.

In the embodiment shown in FIGS. 3-22B, the insert 37 has a peripheral edge defining a periphery of the insert 37, and including a medial edge 85 extending along the medial side of the insert 37 from the back of the heel portion 37C to the front end of the first phalange portion 37D, a lateral edge 86 extending from the back of the heel portion 37C to the front of the forefoot portion 37B, and a front edge 87 extending from the lateral edge 86 to the first phalange portion 37D along second, third, fourth, and fifth metatarsal areas of the insert 37. The medial edge 85, the lateral edge 86, and the front edge 87 each have a cut-out portion in this embodiment, as shown, for example, in FIGS. 8, 10, and 22A. The cut-out portion 87A along the front edge 87 is located between the lateral edge 86 and the first phalange portion (i.e. peninsula) 37D. The cut-out portions 85A, 86A along the medial and lateral edges 85, 86 are located proximate the juncture between the forefoot portion 37B and the midfoot portion 37A, and the width W1 of the insert 37 (defined between the medial and lateral edges 85, 86) in the midfoot portion 37A and the width W2 in the forefoot portion 37B are greater than the width W3 of the insert measured between the first and second cut-outs 85A, 86A. This configuration creates a narrowed neck 89 between the midfoot portion 37A and the forefoot portion 37B that is narrower than either the midfoot portion 37A or the forefoot portion 37B. The widths W1, W2 of the midfoot portion 37A and forefoot portion 37B are also greater than the width W4 measured at the heel portion 37C, and the forefoot portion 37B has the greatest relative width W2. The heel portion 37C in this embodiment includes a widened tail portion 37E that is wider than the more forward portions of the heel portion 37C, such that the heel portion 37C increases in width from the midfoot portion 37A toward the heel end of the insert member 37.

The cut out portions 85A, 86A, 87A each extend inwardly into the body of the insert 37 and generally have a concave and/or indented shape. In the embodiment illustrated in FIGS. 3-22B, each of the cut out portions 85A, 86A, 87A has a smooth and concave inwardly curved (curvilinear) shape, which resists ripping, tearing, or propagation of cracks in the insert 37. In this embodiment, each of the cut out portions 85A, 86A, 87A is at least partially defined by a concave curvilinear edge defining an arc of at least 120°. Additionally, in one embodiment, at least one of the cut out portions 85A, 86A, 87A is at least partially defined by a concave curvilinear edge defining an arc of at least 180°. As seen, for example, in FIGS. 8, 10, and 22A, at least the medial and lateral cut out portions 85A, 86A are each at least partially defined by a concave curvilinear edge defining an arc of at least 180°. Additionally, each of the cut out portions 85A, 86A, 87A in this embodiment is bounded on both sides by smoothly curved edges located on the outer periphery of the insert, at the medial, lateral, and front edges 85, 86, 87. One or both of the smoothly curved edges bounding each of the cut out portions 85A, 86A, 87A in this embodiment defines an arc of at least 90°. The use of the cut out portions 85A, 86A, 87A in these locations and with these configurations can increase the durability and longevity of the insert 37, for example, by resisting ripping, tearing, or propagation of cracks in the insert 37 as described above. In this embodiment, the cut out portions 85A, 86A, 87A are positioned in high stress areas, where this damage resistance is most beneficial. The insert 37 configured as shown in FIGS. 3-22B may have sufficient fatigue resistance to withstand stresses of up to 20 MPa over at least 500,000 cycles.

In further embodiments, the insert 37 may have different cut out portions and/or may have cut out portions in the same locations but with different shapes. For example, the insert 37' shown in FIGS. 22C-D has cut out portions 85A, 86A, 87A in similar locations as compared to the insert 37 of FIGS. 3-22B, with the cut out portions 85A, 86A, 87A having slightly different peripheral shapes. In this embodiment, the medial cut out portion 85A defines a smaller arc as compared to the medial cut out portion 85A of the insert 37 of FIGS. 3-22B. The front cut out portion 87A of this embodiment defines a shape that is less symmetrical and evenly curved as compared to the front cut out portion 87A of the insert 37 of FIGS. 3-22B.

FIGS. 36-47 illustrate additional embodiments of sensor systems 412, 512 with inserts 437, 537 that have different shapes and configurations than the sensor system 12 and the insert 37 described above and shown in FIGS. 3-22B. The sensor systems 412, 512 of FIGS. 36-47 include many structural and functional features in common with the sensor system 12 of FIGS. 3-22B. For example, the sensor systems 412, 512 include sensors 16 that are configured and positioned substantially the same and function in a similar manner as the sensor system 12 of FIGS. 3-22B. As another example, the sensor systems 412, 512 include two fixed resistors 53, 54 in parallel and a pathway 50 between the layers 66, 68, similar to the sensor system 12 of FIGS. 3-22B. These and other such common features may not be described again herein for the sake of brevity.

In the embodiment of FIGS. 36-44, the insert 437 has cut out portions 85A, 86A, 87A in similar locations as compared to the insert 37 of FIGS. 3-22B, with the cut out portions 85A, 86A, 87A having slightly different peripheral shapes. In this embodiment, the medial cut out portion 85A defines a smaller arc as compared to the medial cut out portion 85A of the insert 37 of FIGS. 3-22B. The front cut out portion 87A of this embodiment is deeper and defines a larger arc as compared to the front cut out portion 87A of the insert 37 of FIGS. 3-22B. The lateral cut out portion 86A of this embodiment is shallower and defines a smaller arc as compared to the lateral cut out portion 86A of the insert 37 of FIGS. 3-22B. Additionally, the insert 437 of FIGS. 36-44 has a heel portion 37C with a substantially constant width, and has no widened tail portion 37E.

Figure 45:
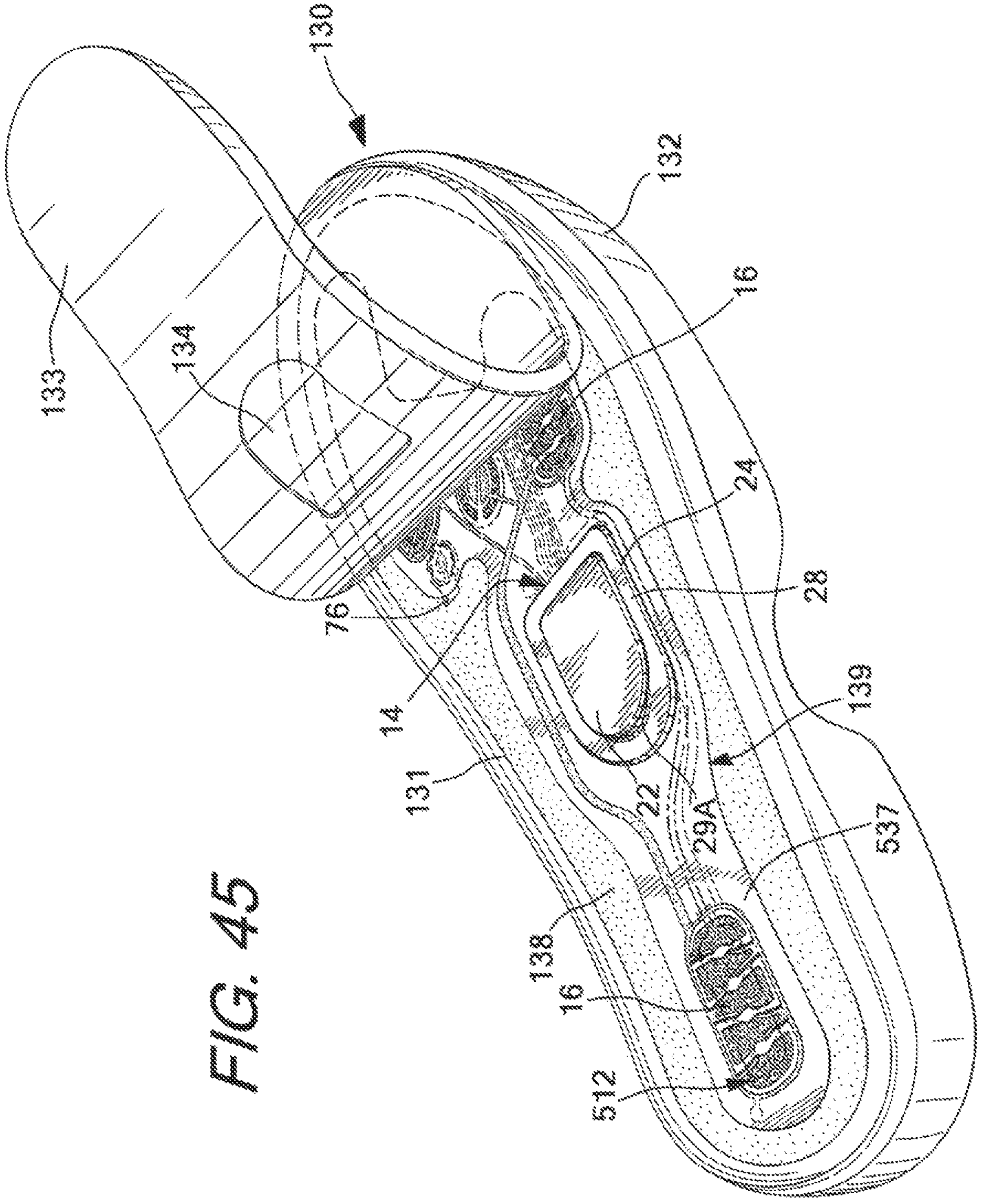
FIG. 45 is a top perspective view of a sole of a shoe (having a shoe upper removed and a foot contacting member folded aside) incorporating another embodiment of a sensor system according to aspects of the present invention.
Figure 46:
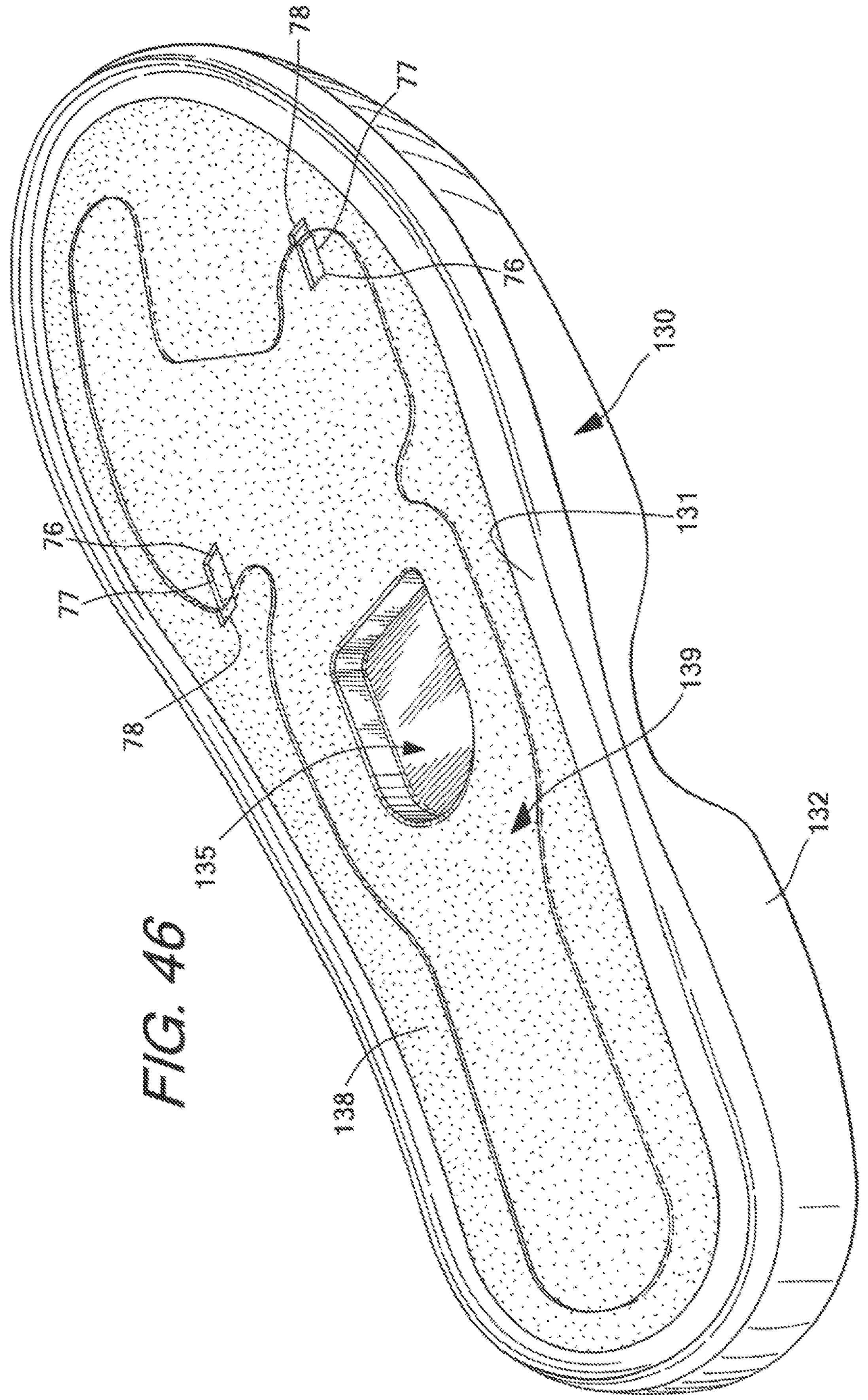
FIG. 46 is a top perspective view of the sole of FIG. 45, with the foot contacting member of the shoe removed and without the sensor system.
Figure 47:
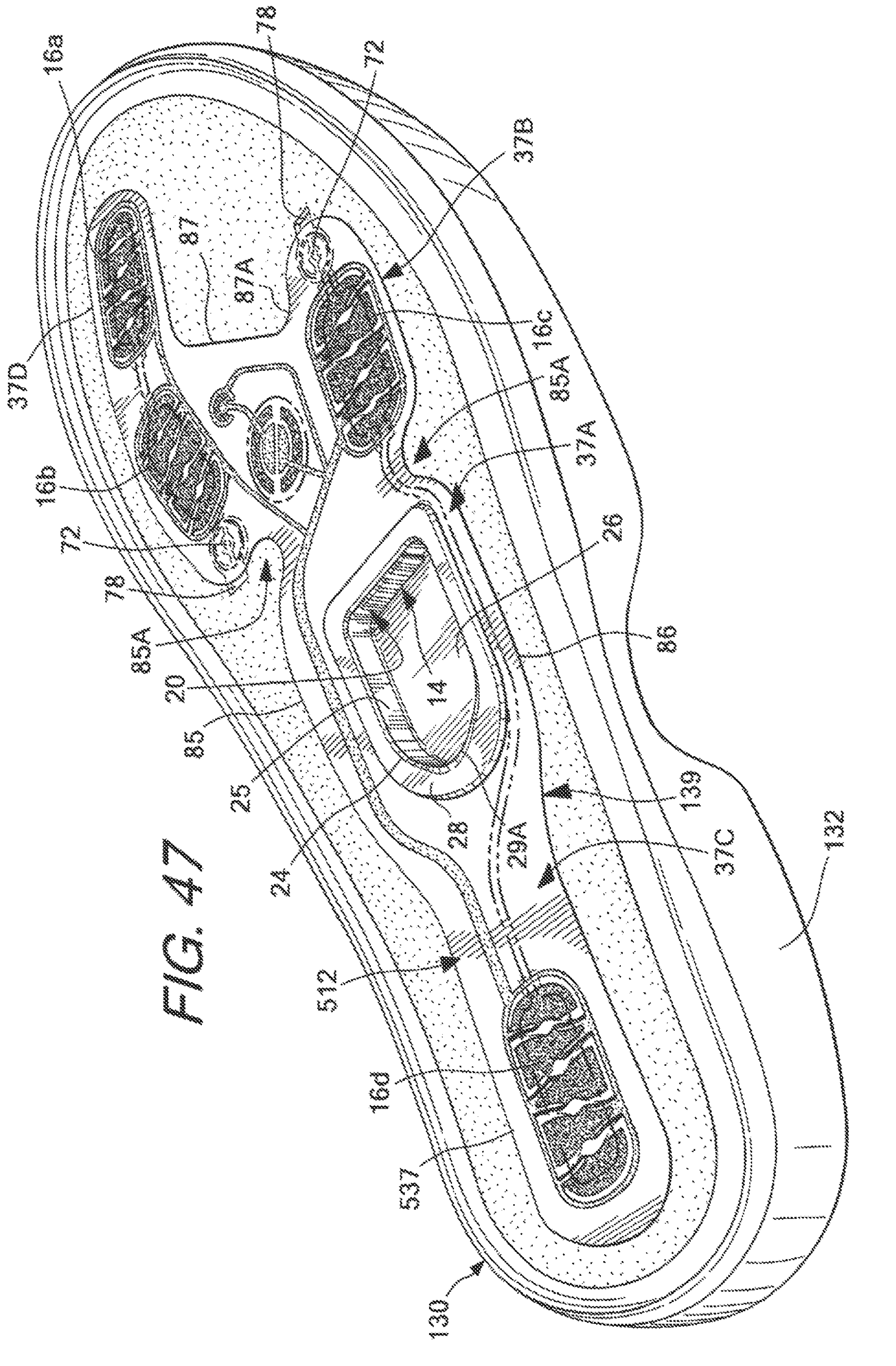
FIG. 47 is a top perspective view of the sole and the sensor system of FIG. 45, with a foot contacting member of the shoe removed and an electronic module removed.
Figure 48:
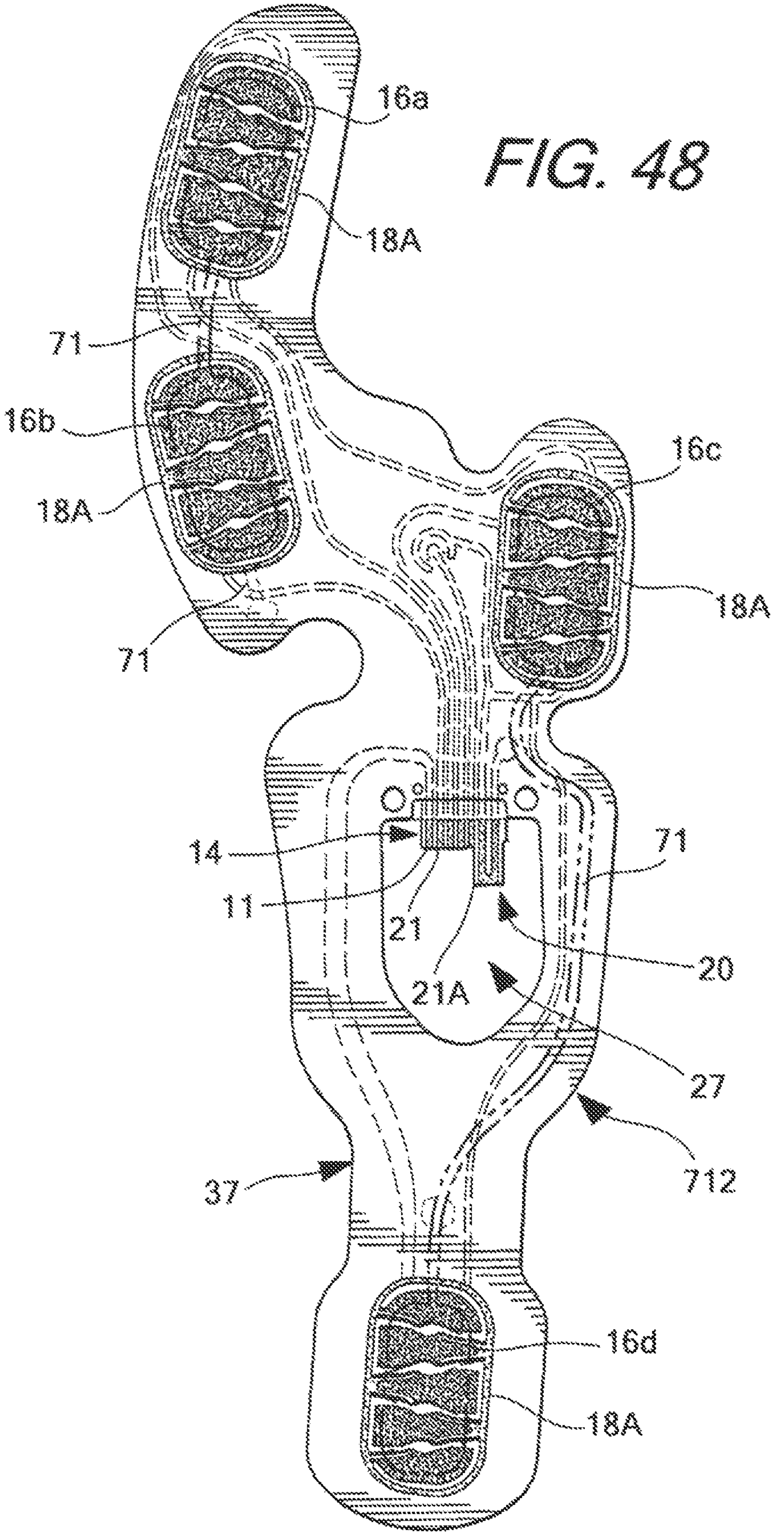
FIG. 48 is a top view of another embodiment of an insert of the sensor system adapted to be positioned within the sole structure of an article of footwear for a user's right foot, according to aspects of the present invention.

In the embodiment of FIGS. 45-47, the insert 537 has cut out portions 85A, 86A, 87A in similar locations as compared to the insert 37 of FIGS. 3-22B, with the cut out portions 85A, 86A, 87A having slightly different peripheral shapes. In this embodiment, the medial cut out portion 85A defines a smaller arc as compared to the medial cut out portion 85A of the insert 37 of FIGS. 3-22B. The lateral cut out portion 86A of this embodiment is shallower and defines a smaller arc as compared to the lateral cut out portion 86A of the insert 37 of FIGS. 3-22B. The front edge 87 of the insert 537 of FIGS. 45-48 is angled steadily from the first phalange portion 37D toward the fifth metatarsal sensor 16*c*, and defines a substantially straight edge that extends directly into the front cut out portion 87A. The resultant front cut out portion 87A defines a smaller arc as compared to the front cut out portion 87A of the insert 37 of FIGS. 3-22B. Additionally, the insert 537 of FIGS. 45-48 has a heel portion 37C with a substantially constant width, and has no widened tail portion 37E. The leads 18 and many other components of the sensor system 512 of FIGS. 45-48 are not illustrated and/or referenced herein, and it is understood that such components may be configured similarly or identically to the corresponding components in the sensor system 12 of FIGS. 3-22B and/or the sensor system 412 in FIGS. 36-44 (structurally and/or functionally).

It is understood that inserts 37, 37', 437, 537 may have any number of different configurations, shapes, and structures, and including a different number and/or configuration of sensors 16, and a different insert structure or peripheral shape. For example, any of the inserts 37, 37', 437, 537 described herein may include some or all of the structural features and the functions associated with such structural features as described above, such as the cut-out portions 85A, 86A, 87A and other features of the peripheral shape, while being contoured, dimensioned, and configured differently. Additionally, any of the inserts 37, 37', 437, 537 described herein may include additional or different structural features that may provide different shapes and/or functionalities.

Figures 35A, 35B:
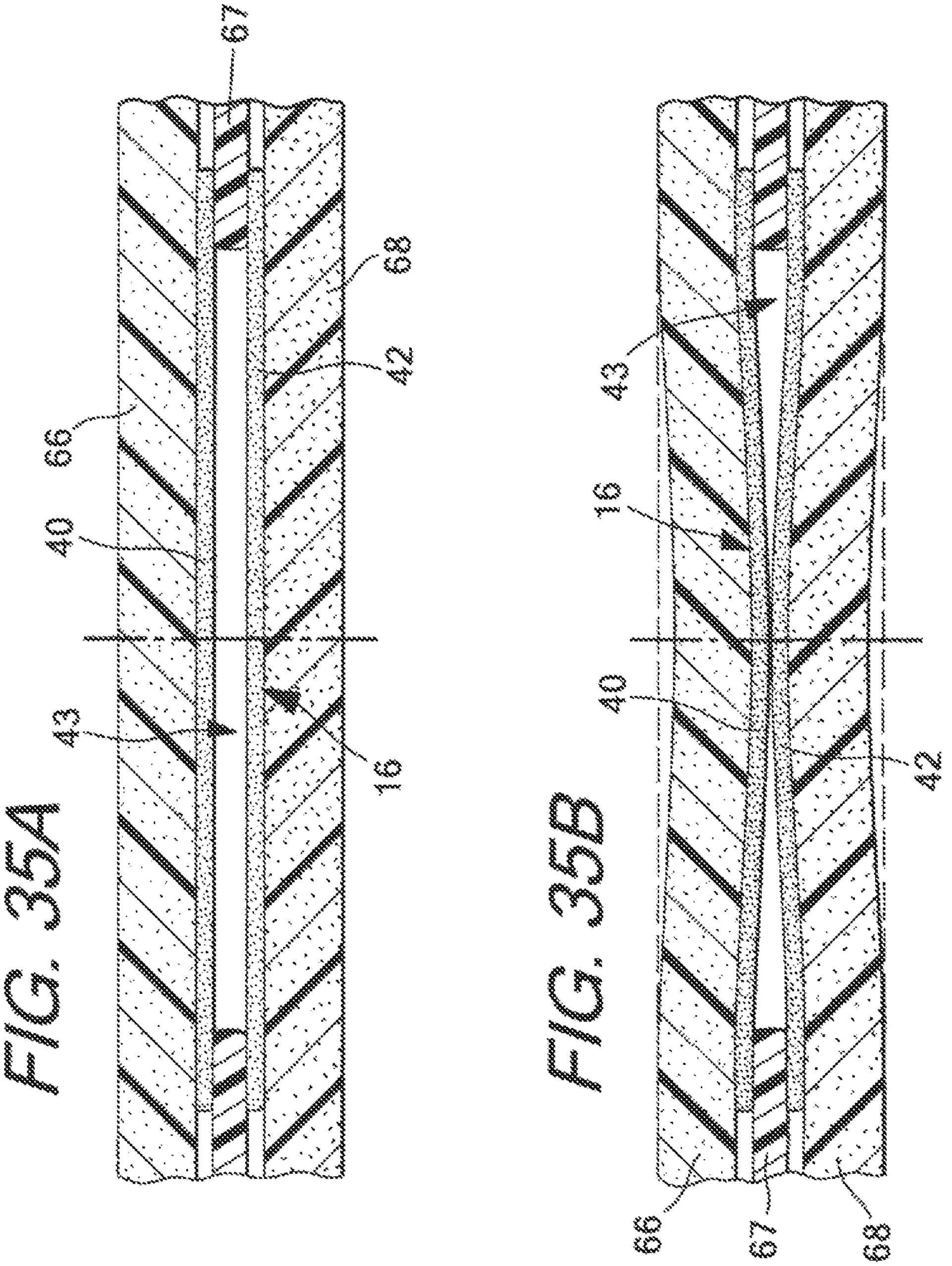
FIGS. 35A and 35B are schematic cross-sectional views of a sensor of the sensor system of FIG. 7.

In the embodiment illustrated in FIGS. 3-22B, the sensors 16 are force and/or pressure sensors for measuring pressure and/or force on the sole 130. The sensors 16 have a resistance that decreases as pressure on the sensor 16 increases, such that measurement of the resistance through the port 14 can be performed to detect the pressure on the sensor 16. The sensors 16 in the embodiment illustrated in FIGS. 3-22B are elliptical or obround in shape, which enables a single sensor size to be utilized in several different shoe sizes. The sensors 16 in this embodiment each include two contacts 40, 42, including a first contact 40 positioned on the first layer 66 and a second contact 42 positioned on the second layer 68. It is understood that the figures illustrating the first layer 66 herein are top views, and that the electronic structures (including the contacts 40, the leads 18, etc.) are positioned on the bottom side of the first layer 66 and viewed through a transparent or translucent first layer 66 unless specifically noted otherwise. The contacts 40, 42 are positioned opposite each other and are in superimposed relation to each other, so that pressure on the insert member 37, such as by the user's foot, causes increased engagement between the contacts 40, 42. The resistance of the sensor 16 decreases as the engagement between the contacts 40, 42 increases, and the module 22 is configured to detect pressure based on changes in resistance of the sensors 16. In one embodiment, the contacts 40, 42 may be formed by conductive patches that are printed on the first and second layers 66, 68, such as in the embodiment of FIGS. 3-22B, and the two contacts 40, 42 may be formed of the same or different materials. Additionally, in one embodiment, the leads 18 are formed of a material that has a higher conductivity and lower resistivity than the material(s) of the sensor contacts 40, 42. For example, the patches may be formed of carbon black or another conductive carbon material. Further, in one embodiment, the two contacts 40, 42 may be formed of the same material or two materials with similar hardnesses, which can reduce abrasion and wear due to differences in hardness of the materials in contact with each other. In this embodiment, the first contacts 40 are printed on the underside of the first layer 66, and the second contacts 42 are printed on the top side of the second layer 68, to permit engagement between the contacts 40, 42. The embodiment illustrated in FIGS. 3-22B includes the spacer layer 67, which has holes 43 positioned at each sensor 16 to permit engagement of the contacts 40, 42 through the spacer layer 67, while insulating other portions of the first and second layers 66, 68 from each other. In one embodiment, each hole 43 is aligned with one of the sensors 16 and permits at least partial engagement between the contacts 40, 42 of the respective sensor 16. In the embodiment illustrated in FIGS. 7-18, the holes 43 are smaller in area than the sensor contacts 40, 42, allowing the central portions of the contacts 40, 42 to engage each other, while insulating outer portions of the contacts 40, 42 and the distribution leads 18A from each other (See, e.g., FIGS. 13 and 35A-B). In another embodiment, the holes 43 may be sized to permit engagement between the contacts 40, 42 over their entire surfaces. It is understood that the size, dimensions, contours, and structure of the sensors 16 and the contacts 40, 42 may be altered in other embodiments while retaining similar functionality. It is also understood that sensors 16 having the same sizes may be utilized in different sizes of inserts 37 for different shoe sizes, in which case the dimensions of the sensors 16 relative to the overall dimensions of the insert 37 may be different for different insert 37 sizes.

Figure 33:
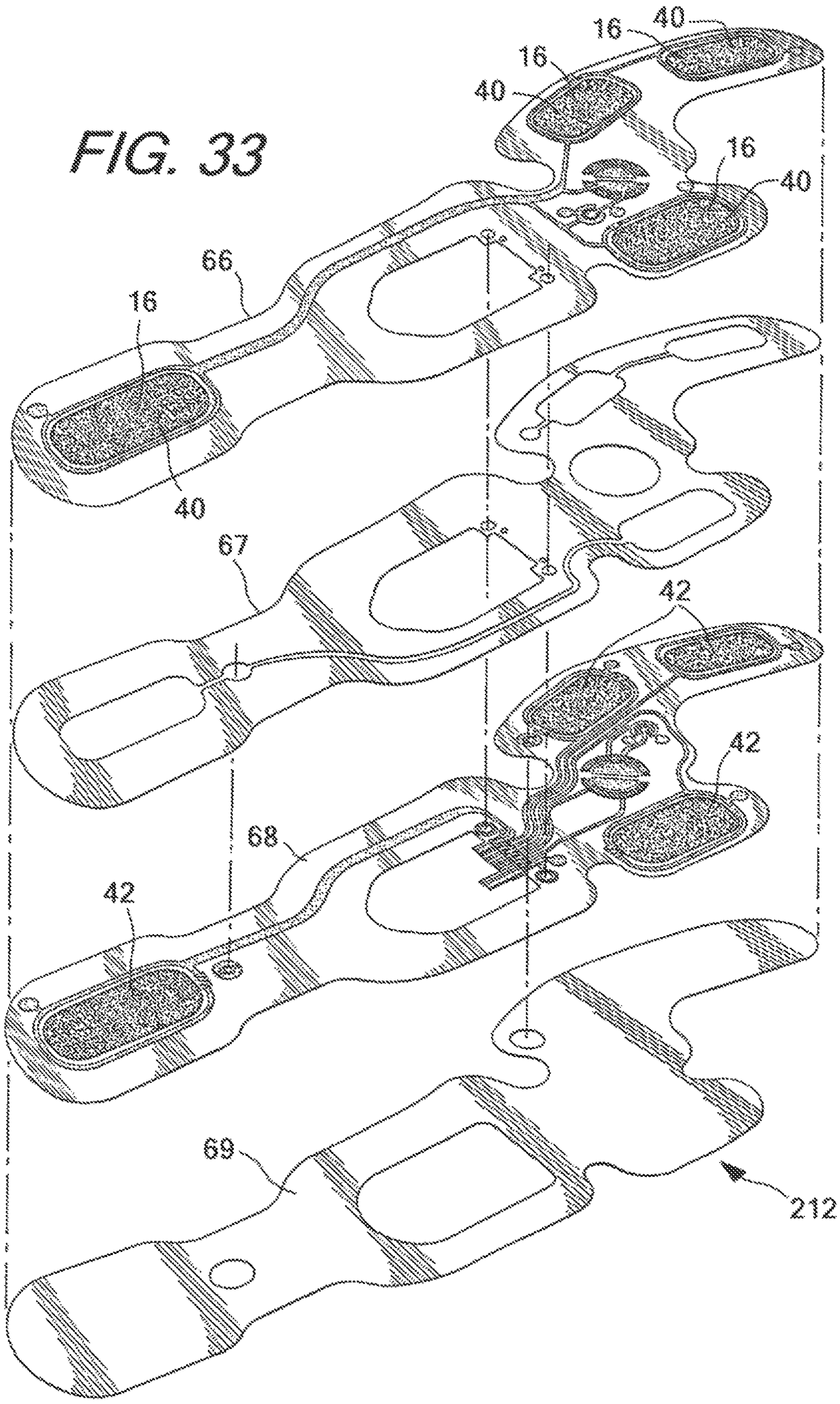
FIG. 33 is an exploded perspective view of another embodiment of a sensor system according to aspects of the present invention.
Figure 34:
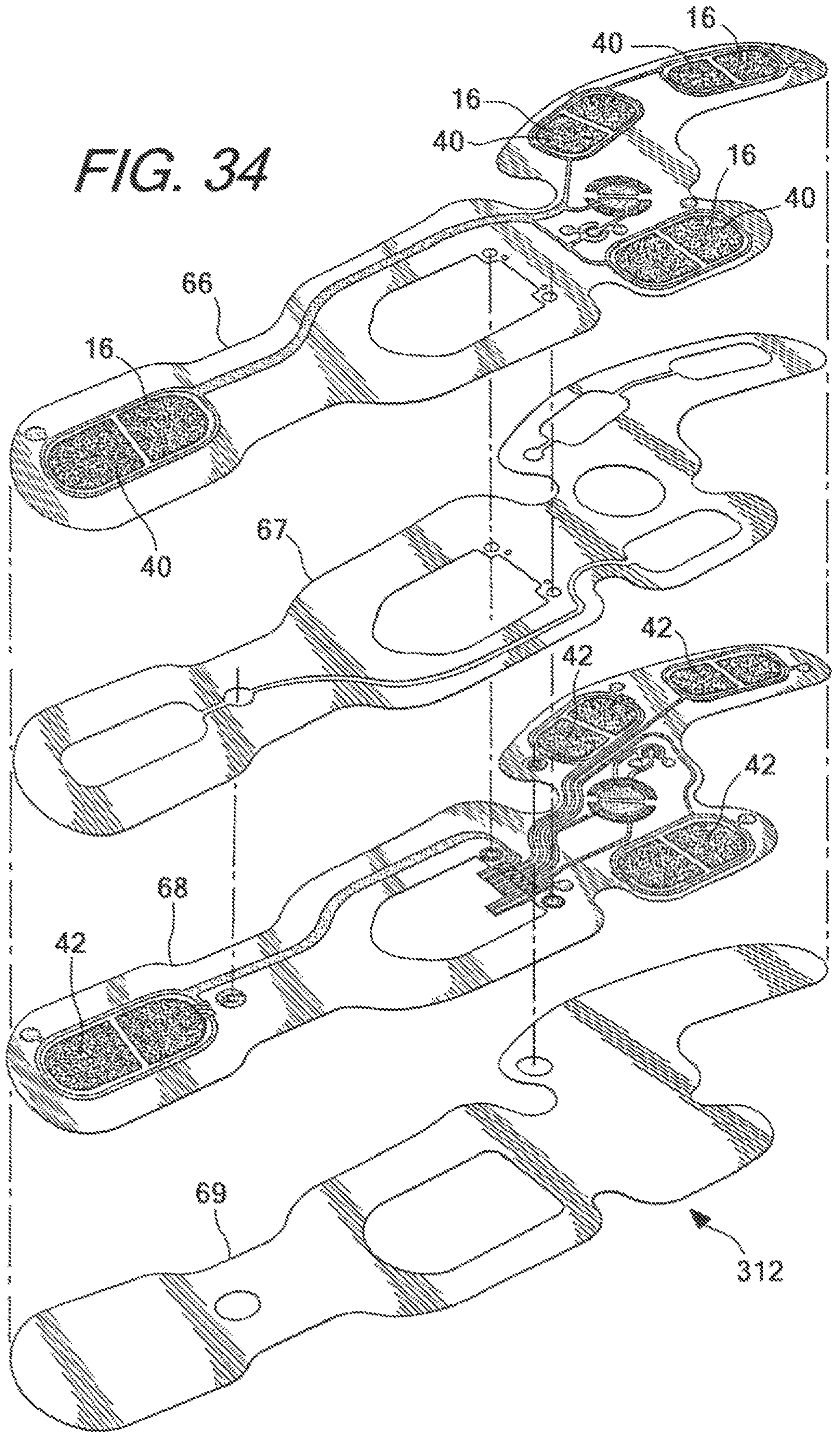
FIG. 34 is an exploded perspective view of another embodiment of a sensor system according to aspects of the present invention.

In other embodiment, the sensor system 12 may have sensors 16 that are differently configured than the sensors 16 of the embodiment of FIGS. 3-22B. For example, FIGS. 33-34 illustrate additional embodiments of sensor systems 212, 312 that have sensors 16 that are configured differently from the sensors 16 in the sensor system 12 of FIGS. 3-22B. In the embodiments illustrated in FIGS. 33-34, the contacts 40, 42 of the sensors 16 in FIGS. 33-34 are configured differently from the contacts 40, 42 of the sensors 16 in the embodiment of FIGS. 3-22B. Other components and features of the sensor systems 212, 312 are similar or identical to those of the sensor system 12 of FIGS. 3-22B, including any variations or alternate embodiments described herein. As another example, FIGS. 48-51 illustrate an embodiment of a sensor system 712 that includes sensors 16 that have contacts 740, 742, 744 that are configured differently from the sensors 16 and contacts 40, 42 of the embodiment of FIGS. 3-22B. In a further example, the sensors 16 may utilize a different configuration that does not include carbon-based or similar contacts 40, 42 and/or may not function as a resistive sensor 16. Examples of such sensors include a capacitive pressure sensor or a strain gauge pressure sensor, among other examples.

Figure 17:
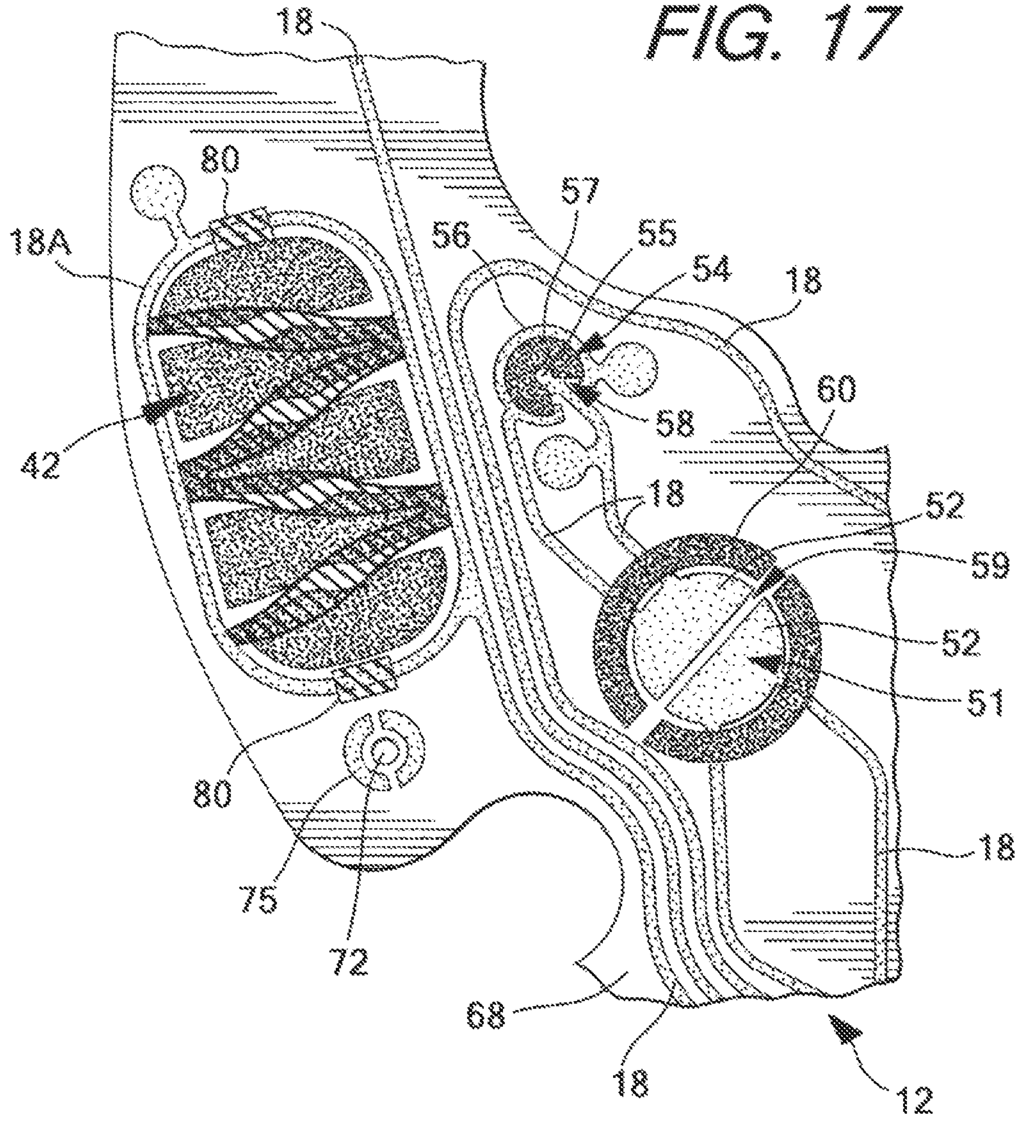
FIG. 17 is a magnified top view of a portion of the second layer of FIG. 16.
Figure 18:
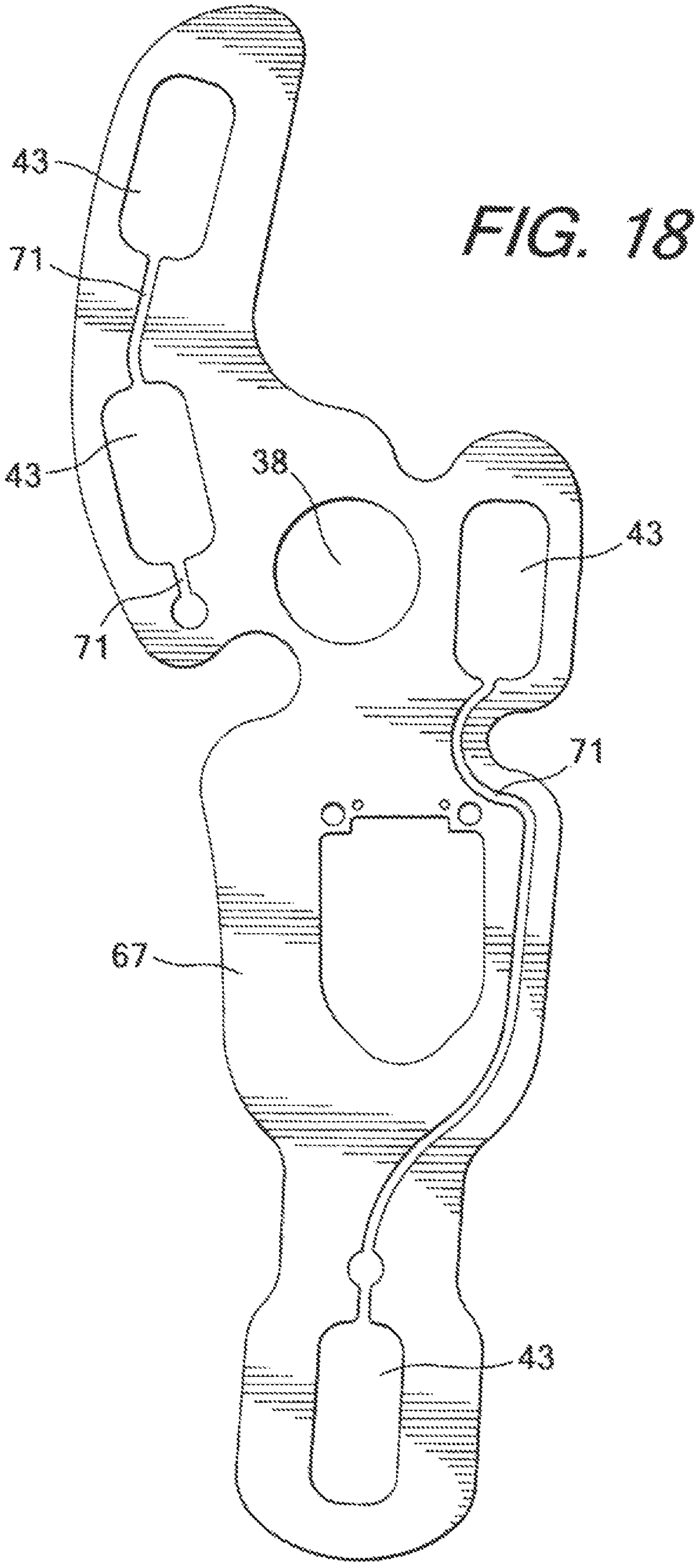
FIG. 18 is a top view of a spacer layer of the insert of FIG. 13.
Figure 19:
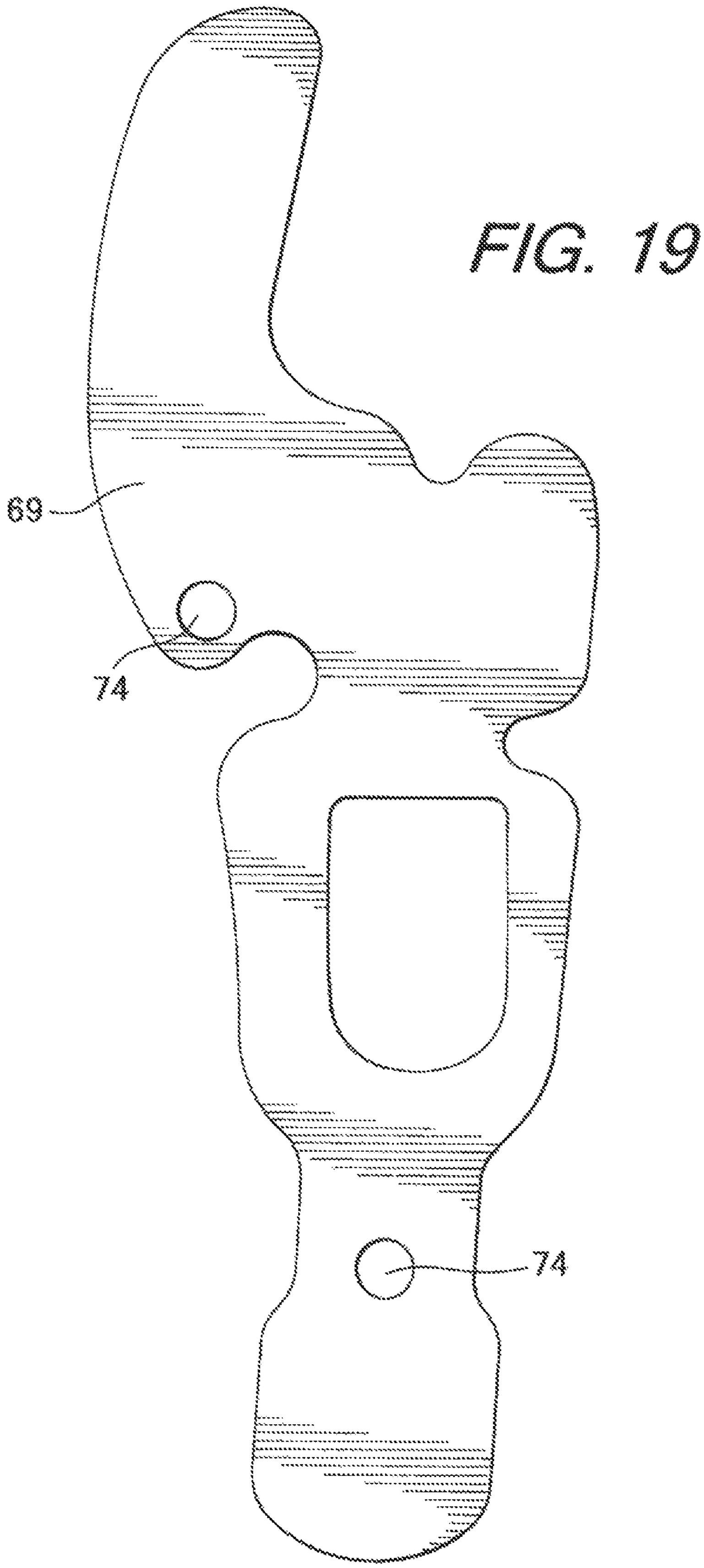
FIG. 19 is a top view of a bottom layer of the insert of FIG. 13.
Figure 21:
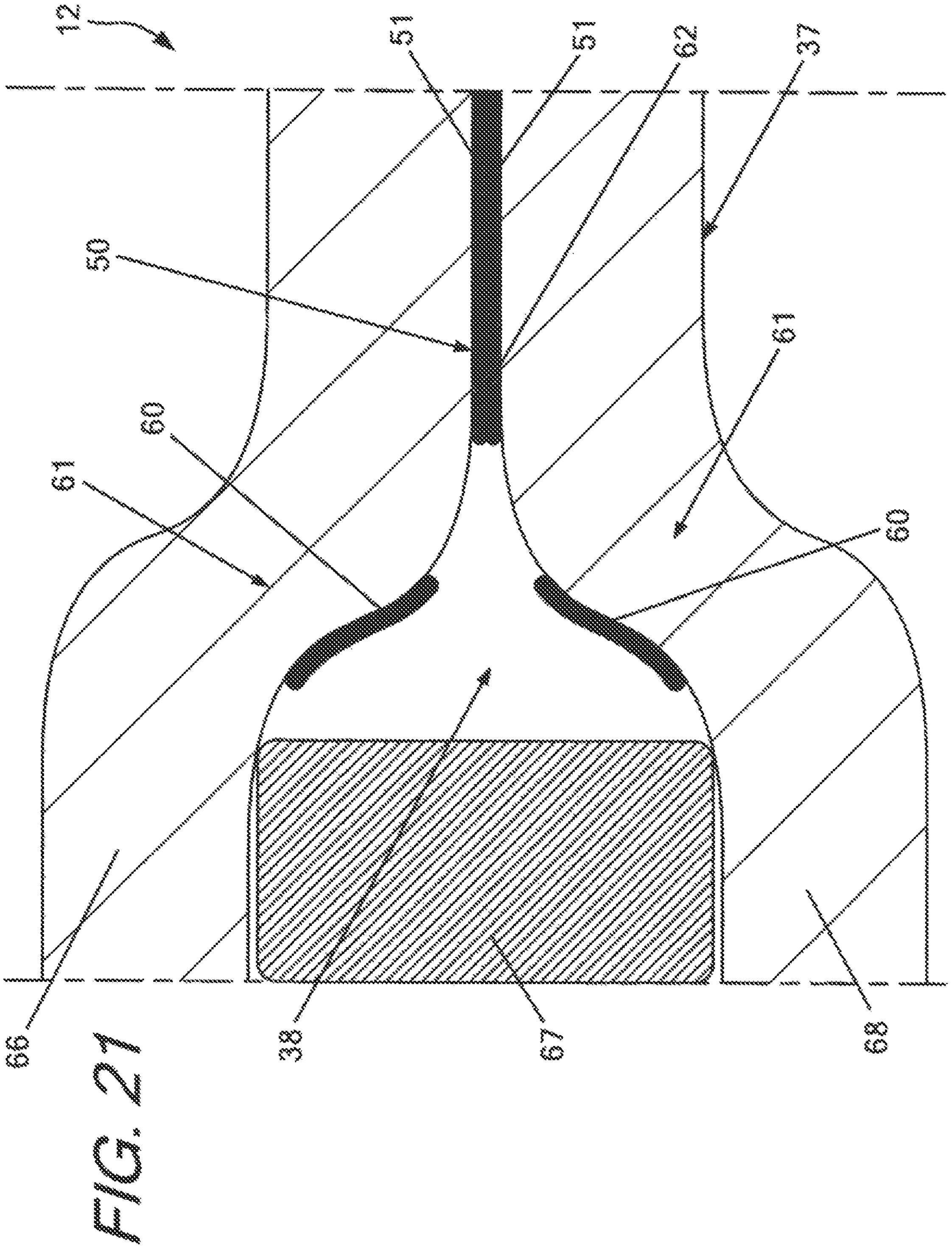
FIG. 21 is magnified cross-sectional view schematically illustrating the area indicated by lines 21-21 in FIG. 11.
Figure 22A:
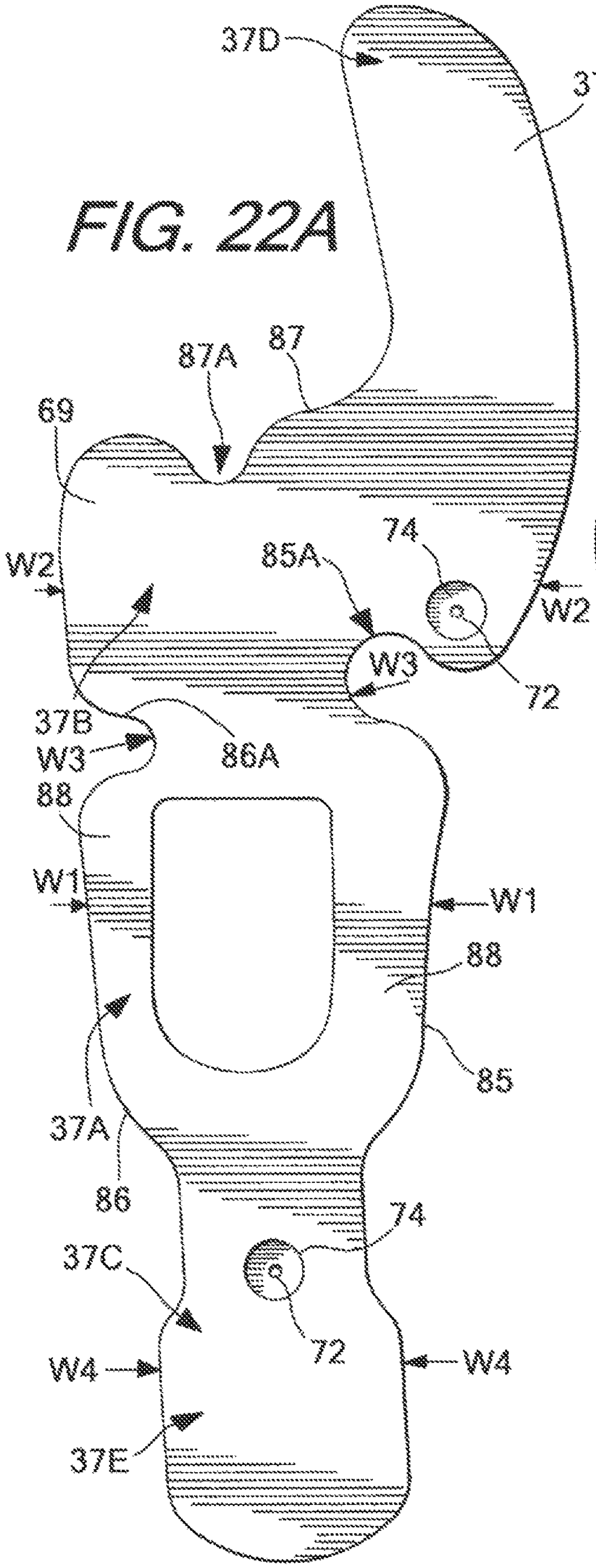
FIG. 22A is a bottom view of the sensor system of FIG. 9.
Figure 22B:
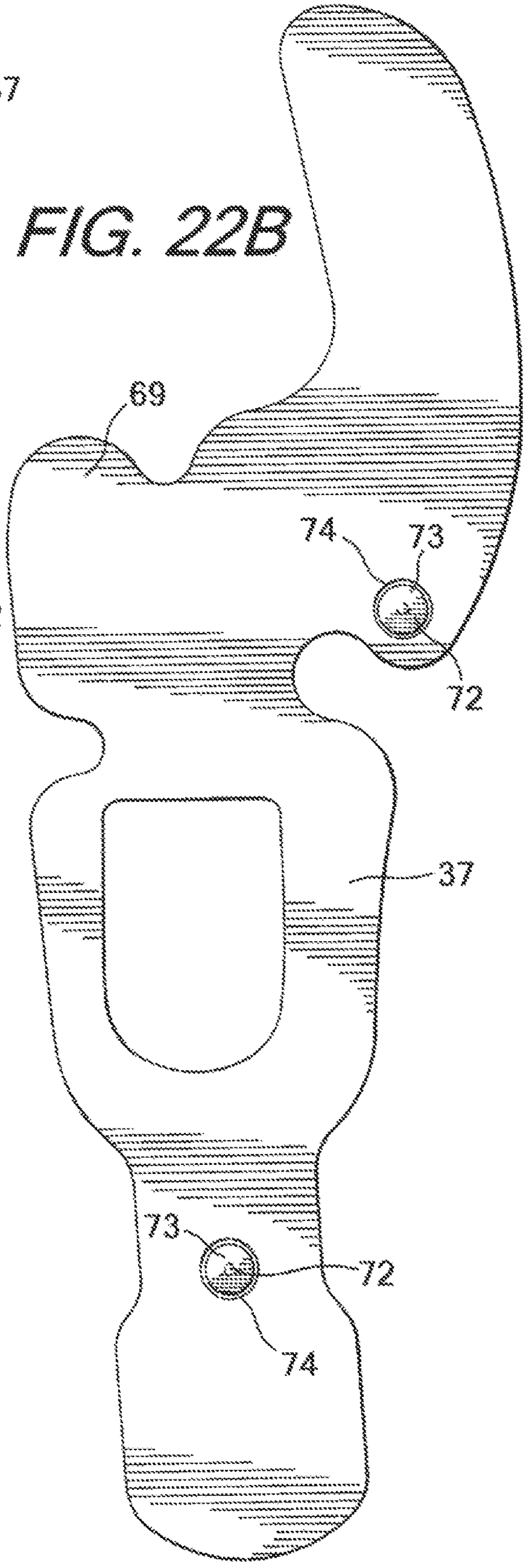
FIG. 22B is a bottom view of the sensor system as illustrated in FIG. 22A, having filters connected over vents in the sensor system.

As further shown in FIGS. 3-22B, in one embodiment, the insert 37 may include an internal airflow system 70 configured to allow airflow through the insert 37 during compression and/or flexing of the insert 37. FIGS. 9, 11, 13, 18, 22A-B, and 28-30 illustrate the components of the airflow system 70 in greater detail. The airflow system 70 may include one or more air passages or channels 71 that lead from the sensors 16 to one or more vents 72, to allow air to flow from the sensor 16 during compression, between the first and second layers 66, 68 and outward through the vent(s) 72 to the exterior of the insert 37. The airflow system 70 resists excessive pressure buildup during compression of the sensors 16, and also permits consistent separation of the contacts 40, 42 of the sensors 16 at various air pressures and altitudes, leading to more consistent performance. The channels 71 may be formed between the first and second layers 66, 68. As shown in FIG. 18, the spacer layer 67 has the channels 71 formed therein, and the air can flow through these channels 71 between the first and second layers 66, 68, to the appropriate vent(s) 72. The vents 72 may have filters 73 covering them in one embodiment, as shown in FIG. 22B. These filters 73 may be configured to permit air, moisture, and debris to pass out of the vents 72 and resist moisture and debris passage into the vents 72. In another embodiment, the insert 37 may not contain a spacer layer, and the channels 71 may be formed by not sealing the layers 66, 68 together in a specific pattern, such as by application of a non-sealable material. Thus, the airflow system 70 may be considered to be integral with or directly defined by the layers 66, 68 in such an embodiment. In other embodiments, the airflow system 70 may contain a different number or configuration of air channels 71, vents 72, and/or other passages.

In the embodiment illustrated in FIGS. 3-22B, 28, and 30, the airflow system 70 includes two vents 72 and a plurality of air channels 71 connecting each of the four sensors 16 to one of the vents 72. The spacer layer 67 includes holes 43 at each sensor in this embodiment, and the channels 71 are connected to the holes 43 to permit air to flow away from the sensor 16 through the channel 71. Additionally, in this embodiment, two of the sensors 16 are connected to each of the vents 72 through channels 71. For example, as illustrated in FIGS. 4 and 7-18, the first metatarsal sensor 16*b* has a channel 71 that extends to a vent 72 slightly behind the first metatarsal area of the insert 37, and the first phalangeal sensor 16*a* has a channel 71 that also extends to the same vent 72, via a passageway that includes traveling through the first metatarsal sensor 16*b*. In other words, the first phalangeal sensor 16*a* has a channel 71 that extends from the hole 43 at the first phalangeal sensor 16*a* to the hole 43 at the first metatarsal sensor 16*b*, and another channel 71 extends from the first metatarsal sensor 16*b* to the vent 72. The fifth metatarsal sensor 16*c* and the heel sensor 16*d* also share a common vent 72, located in the heel portion of the insert 37. One channel 71 extends rearward from the hole 43 at the fifth metatarsal sensor 16*c* to the vent 72, and another channel 71 extends forward from the hole 43 at the heel sensor 16*d* to the vent 72. Sharing the vents 72 among multiple sensors can decrease expense, particularly by avoiding the need for additional filters 73. In other embodiments, the airflow system 70 may have a different configuration, such as the configuration shown in FIGS. 22C-D and discussed below. In further embodiments, each sensor 16 may have its own individual vent 72, or more than two sensors 16 may share the same vent 72.

Each vent 72 is formed as an opening in a bottom side of the second layer 68 (i.e. opposite the first layer 66), such that the opening permits outward flow of air, moisture, and/or debris from the airflow system 70, as seen in FIGS. 16-18 and 22A-B. In another embodiment, the vent 72 may include multiple openings. In a further embodiment, the vent 72 may additionally or alternately be formed by an opening in the first layer 66, causing the air to vent upwards out of the insert 37. In an additional embodiment, the vent 72 may be on the side (thin edge) of the insert 37, such as by extending the channel 71 to the edge, such that the channel 71 opens through the edge to the exterior of the insert 37. The venting of the air downward, as in the embodiment illustrated in FIGS. 3-22B, 28, and 30, makes it more difficult for debris to enter the vent 72. The bottom layer 69, if present, also includes apertures 74 located below the vents 72, to permit the air flowing out of the vents 72 to pass through the bottom layer 69. The apertures 74 are significantly larger than the vents 72, in order to allow the filters 73 to be adhesively attached to the second layer 68 through the bottom layer 69 around the periphery of each vent 72, as described below. Additionally, in this embodiment, each vent 72 has a reinforcement material 75 positioned around the vent 72, to add stability and strength to the material and prevent breaking/tearing. In the embodiment illustrated, the reinforcement material 75 is formed of the same material as the leads 18 (e.g. silver or other metallic ink) to facilitate printing, but may also be formed of the same material as the sensor contacts 40, 42 (e.g. carbon) or the dielectric material discussed herein.

Figure 28:
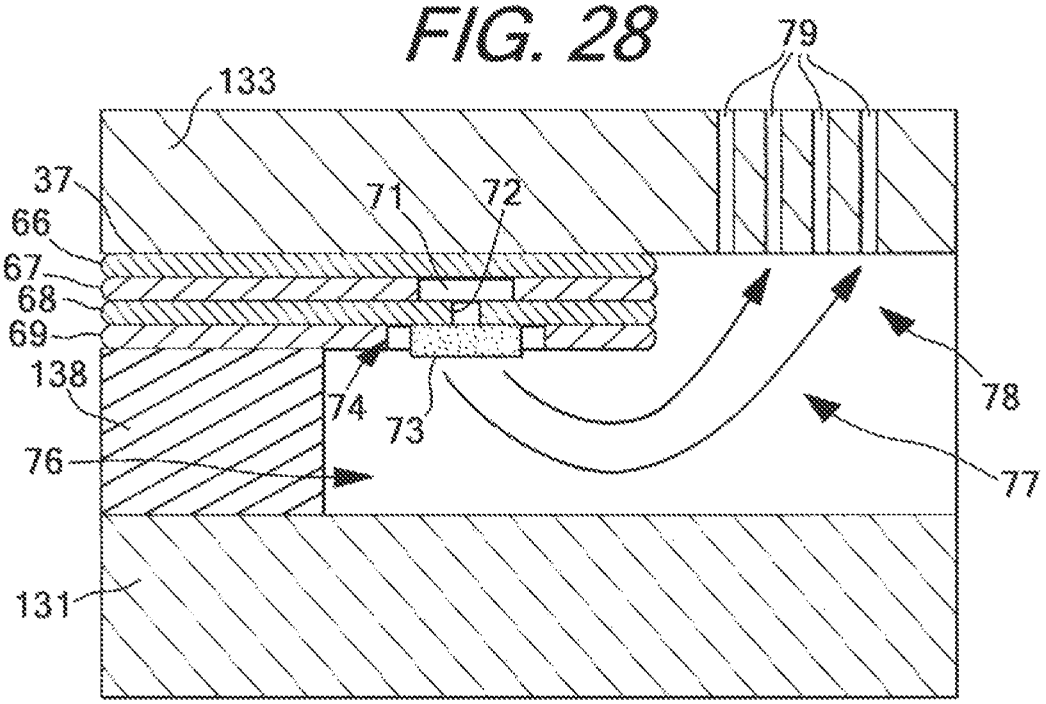
FIG. 28 is a schematic cross-sectional view of a portion of the sole and sensor system of FIG. 4.

The vents 72 in the embodiment illustrated in FIGS. 3-22B, 28, and 30 open downward and the air passing through the vents 72 passes downward toward the midsole 131 and toward the foam member 138 if present. In the embodiment illustrated in FIGS. 3-5, 28, and 30, the foam member 138 has cavities 76 located directly below the vents 72 and configured such that the air exiting the vents passes into the respective cavity 76. In the embodiment illustrated in FIGS. 3-5, 28, and 30, each cavity 76 is formed as a slot that extends completely through the foam member 138, which may be formed by punching, cutting, or another technique. In another embodiment, the cavity 76 may be a recess that extends through only a portion of the foam member 138, or may extend deeper than the foam member 138, such as through at least a portion of a structure below the foam member 138 (e.g. a strobel, midsole, etc.). In a further embodiment, the sole structure may not contain the foam member 138, and the cavity 76 may be formed at least in part by a slot, recess, or other cavity-like structure in another sole member, such as a strobel, midsole, etc. As shown in FIG. 5, at least a portion of the cavity 76 may be circular in one embodiment, and may extend wider than the vent 72 to provide space for air venting. This configuration allows air to pass out of the vents 72 without obstruction from the foam member 138. In another embodiment, the insert 37 may be positioned above another sole member (such as a portion of the midsole 131), which may contain one or more cavities 76 as described above. In a further embodiment, no cavity may be present, and the air may vent 72 directly downward into the foam member 138 or other sole member. One or both of the cavities 76 may have extending portions that form passages 77 that further allow air to pass out of the cavity 76. In the embodiment of FIGS. 3-5, 28, and 30, each of the cavities 76 has a channel portion 77 extending laterally away from the cavity 76 and beyond the peripheral boundary of the insert 37. In other words, the channel portion 77 of the cavity 76 extends laterally from the vent 72 to a distal end 78 located outside the peripheral boundary of the insert 37. It is understood that if the foam member 138 has a recess 139 to receive the insert member 37, the distal end 78 of the channel portion 77 of the cavity 76 may also be located outside the peripheral boundary of the recess 139. In the embodiment shown in FIGS. 3-5, the distal end 78 extends to the edge of the foam member 138. This configuration permits air passing into the cavity 76 to exit the sole structure 130 by passing laterally through the channel portion 77 and then upward and/or outward away from the foam member 138. FIG. 28 shows a schematic cross-section of this configuration, with arrows illustrating the flow of air. The configuration illustrated in FIGS. 3-5, 28, and 30 permits air flow out of the vent 72, and possibly back into the vent 72, while resisting migration of debris (e.g. dirt, fibers, etc.) and moisture from migrating to and through the vent 72. The combined downward, lateral, and upward paths that the air must pass through to travel to and from the vent 72 acts to resist this migration, and debris will often become trapped near the distal end 78 of the cavity 76, much like a drain trap in a plumbing application.

Figure 29:
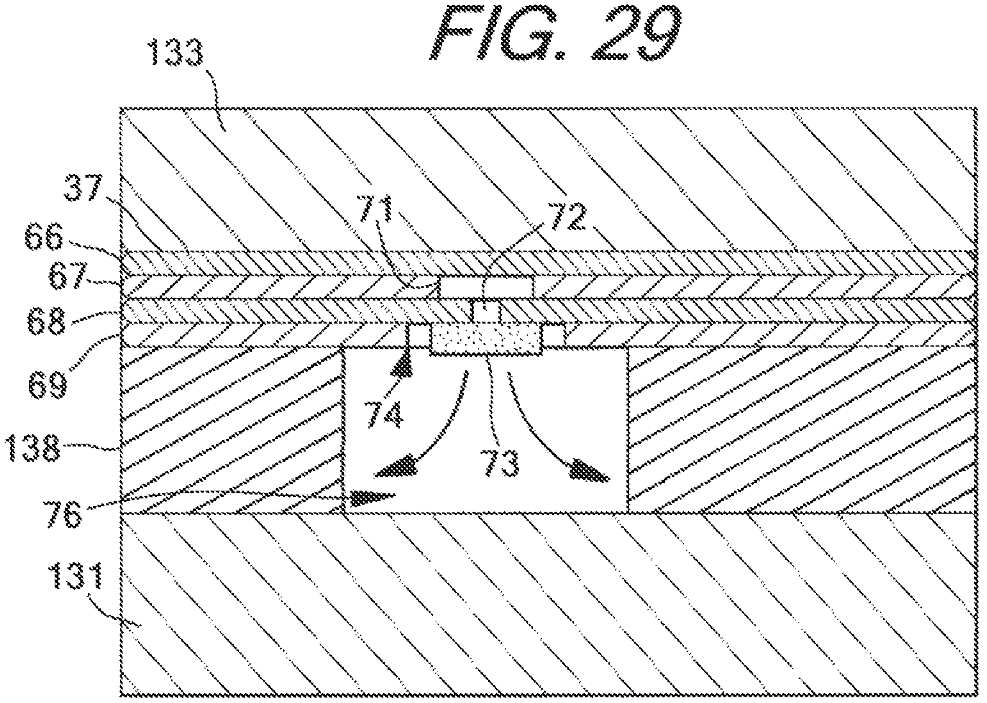
FIG. 29 is a schematic cross-sectional view of a portion of another embodiment of a sole and sensor system according to aspects of the present invention.

In another embodiment, the distal end 78 may stop at a point within the foam member 138 and still outside the peripheral boundary of the insert 37, which allows the air to vent upward out of the cavity 76 at the distal end 78 and provides the same or similar functionality. FIGS. 36-38 and 47 illustrate an example embodiment of this configuration. It is understood that the foot contacting member 133 in the embodiments of FIGS. 36-38 and 47 may include passages positioned around the distal ends 78 of the cavities 76 to allow air passage through the foot contacting member 133, such as the passages 79 shown in FIGS. 28 and 30. In a further embodiment, at least a portion of the channel portion 77 may be a tunnel within the foam member 138, rather than a slit. In such a configuration, the channel portion 77 may have a tunnel portion and an open portion that permits air passing through the tunnel to vent upward, or the tunnel portion may extend all the way to the edge of the foam member 138 to permit sideways venting. FIG. 29 shows a cross-section of an alternate embodiment, where the foam member 138 contains a cavity 76 but no channel portion 77.

Figure 30:
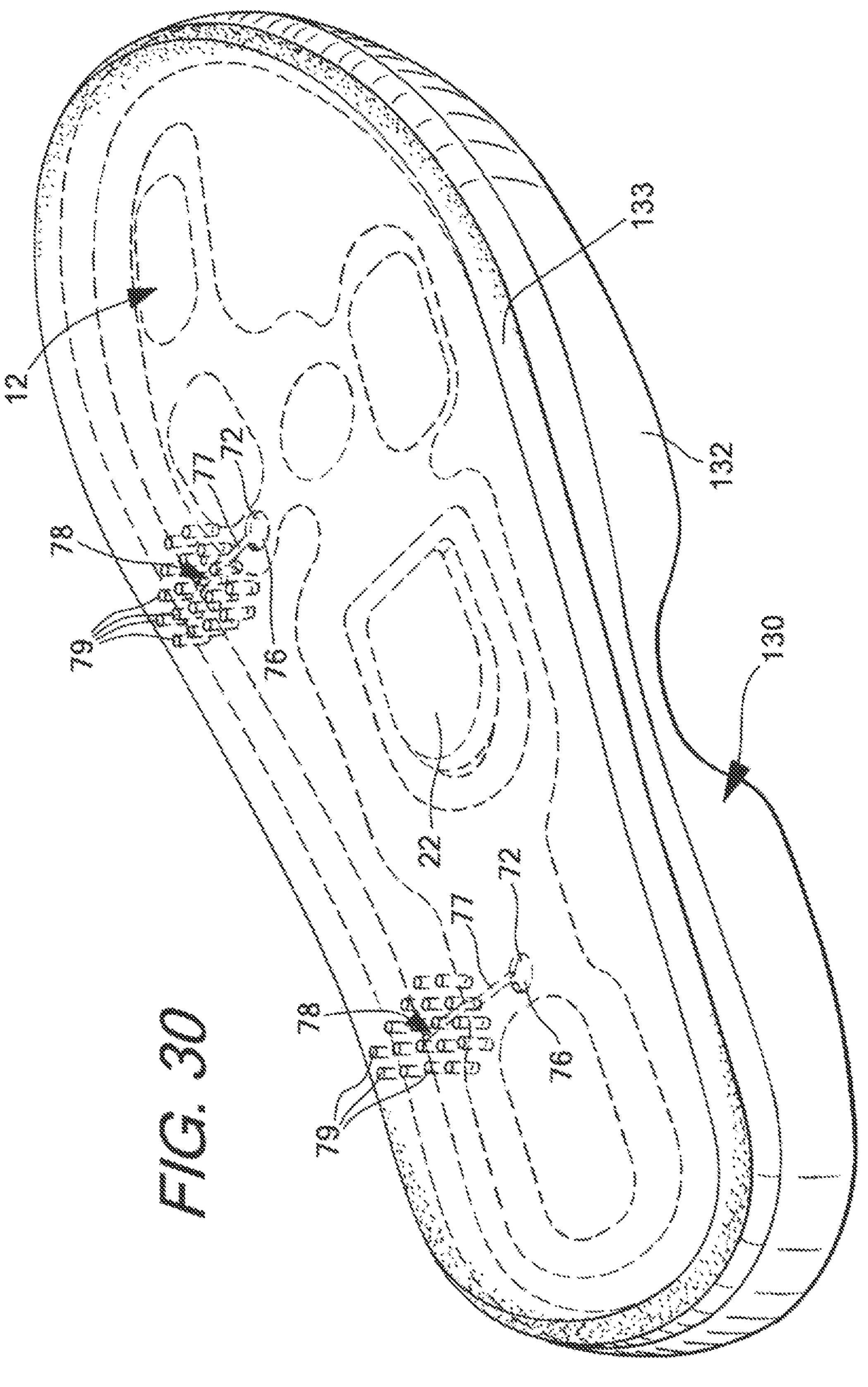
FIG. 30 is a top view of the sole of FIG. 3 with the foot contacting member in operational position.

Additionally, the foot contacting member 133 includes one or more passages 79 extending through the foot contacting member 133 located at the distal end 78 of the cavity 76, in the embodiment of FIGS. 3-5, 28, and 30. As shown in FIGS. 28 and 30, the passages 79 may be pinhole-type passages 79 that extend vertically through the foot contacting member 133. In another embodiment, a different type of passage 79 may be used, including slits or grooves, and at least one passage 79 may extend laterally to a side of the foot contacting member 133, rather than upward through the thickness of the foot contacting member 133. The passages 79 allow the air exiting through the vent 72 and outward through the cavity 76 to pass through the foot contacting member 133 and out of the sole structure 130. In another embodiment, the foot contacting member 133 may not include any passage(s) 79. The foot contacting member 133 may still provide ventilation in a configuration without any passage(s) 79, such as by using a breathable foam or other breathable material for constructing the foot contacting member 133.

As described above, in one embodiment, the insert 37 may have one or more filters 73 that at least partially cover the vent(s) 72, as seen in FIGS. 22B and 28-29. The filter 73 may be considered to be a selectively permeable closure that covers the vent 72, which at least allows passage of air out of the vent 72 and resists passage of certain undesirable substances into the vent. For example, in the embodiment of FIGS. 3-22B, 28, and 30, the filter 73 is a selectively permeable closure that permits inward and outward flow of air, and also permits outward flow of moisture, while resisting the inward flow of moisture and/or particles. One type of filter 73 that may achieve this function is a fluoroplastic porous membrane, for example, a porous membrane comprising PTFE (i.e. Teflon) fibers. Such a porous membrane may be a 10 μm to 100 μm thick porous membrane in one embodiment. In a filter 73 including PTFE fibers, the high surface energy of the PTFE causes water to ball up on the surface of the filter 73, rather than penetrating. The filter 73 may also have an adhesive on one side to permit the filter 73 to be connected to the insert 37, and may further have another material connected to either the inward or outward facing side, such as a polyester material to provide shear strength for the porous membrane. In the embodiment shown in FIGS. 3-22B, 28, and 30, the filter 73 is adhesively attached to the bottom side of the second layer 68 around the periphery of the vent 72 to cover the vent 72. The bottom layer 69 includes apertures 74 that are significantly larger than the vents 72, in order to allow the filters 73 to be adhesively attached to the second layer 68, in the embodiment of FIGS. 3-22B, 28, and 30. In other embodiments, a different type of filter 73 may be used, and/or the filter 73 may be connected to the insert 37 in another manner. In a further embodiment, no filter 73 may be used.

Figures 22C, 22D:
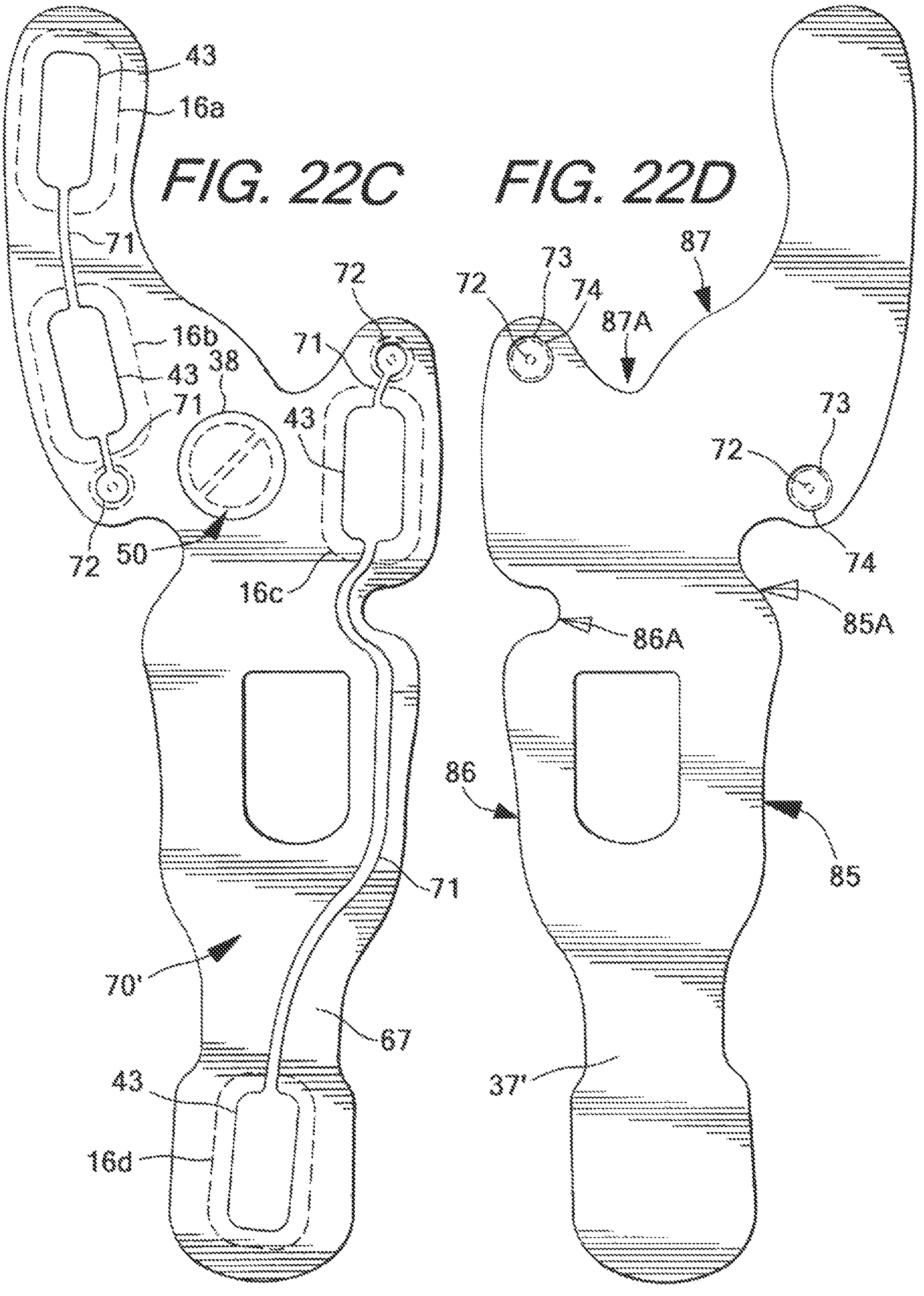
FIG. 22C is a top view of a spacer layer of another embodiment of an insert for a sensor system according to aspects of the present invention, with broken lines showing positions of sensors.
FIG. 22D is a bottom view of an insert for a sensor system incorporating the spacer layer of FIG. 22C, with broken lines showing positions of filters connected to insert.
Figure 36:
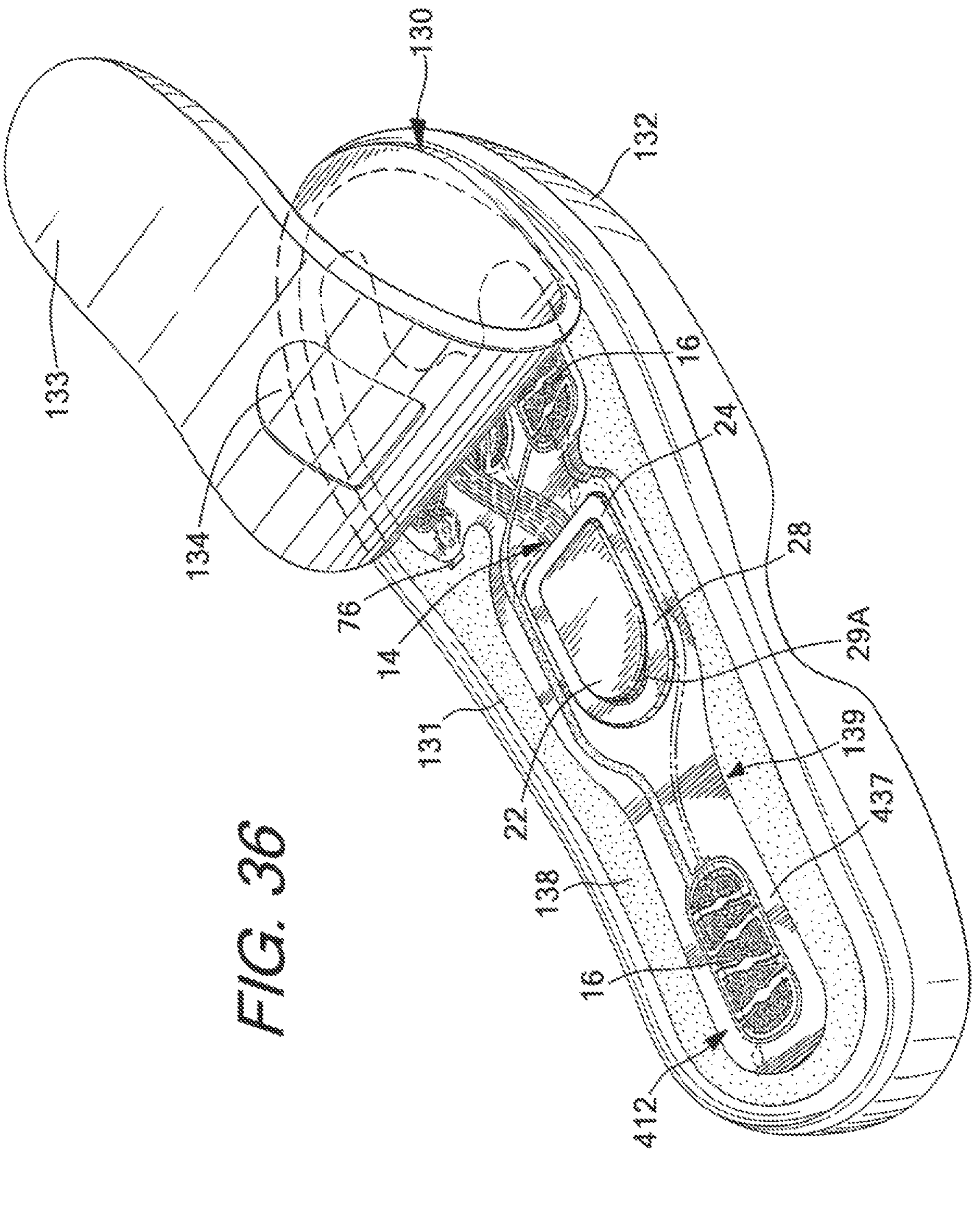
FIG. 36 is a top perspective view of a sole of a shoe (having a shoe upper removed and a foot contacting member folded aside) incorporating another embodiment of a sensor system according to aspects of the present invention.
Figure 37:
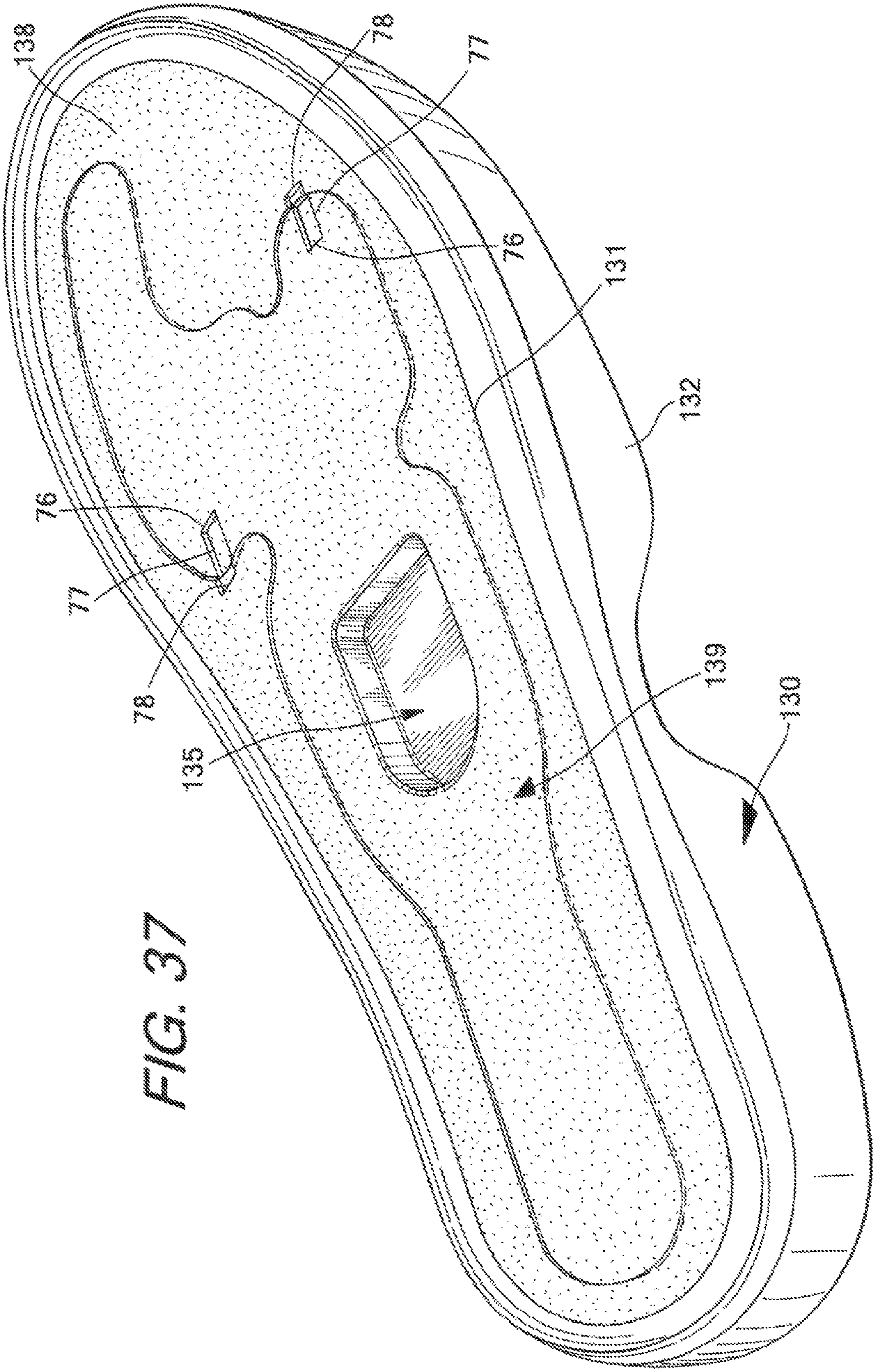
FIG. 37 is a top perspective view of the sole of FIG. 36, with the foot contacting member of the shoe removed and without the sensor system.
Figure 38:
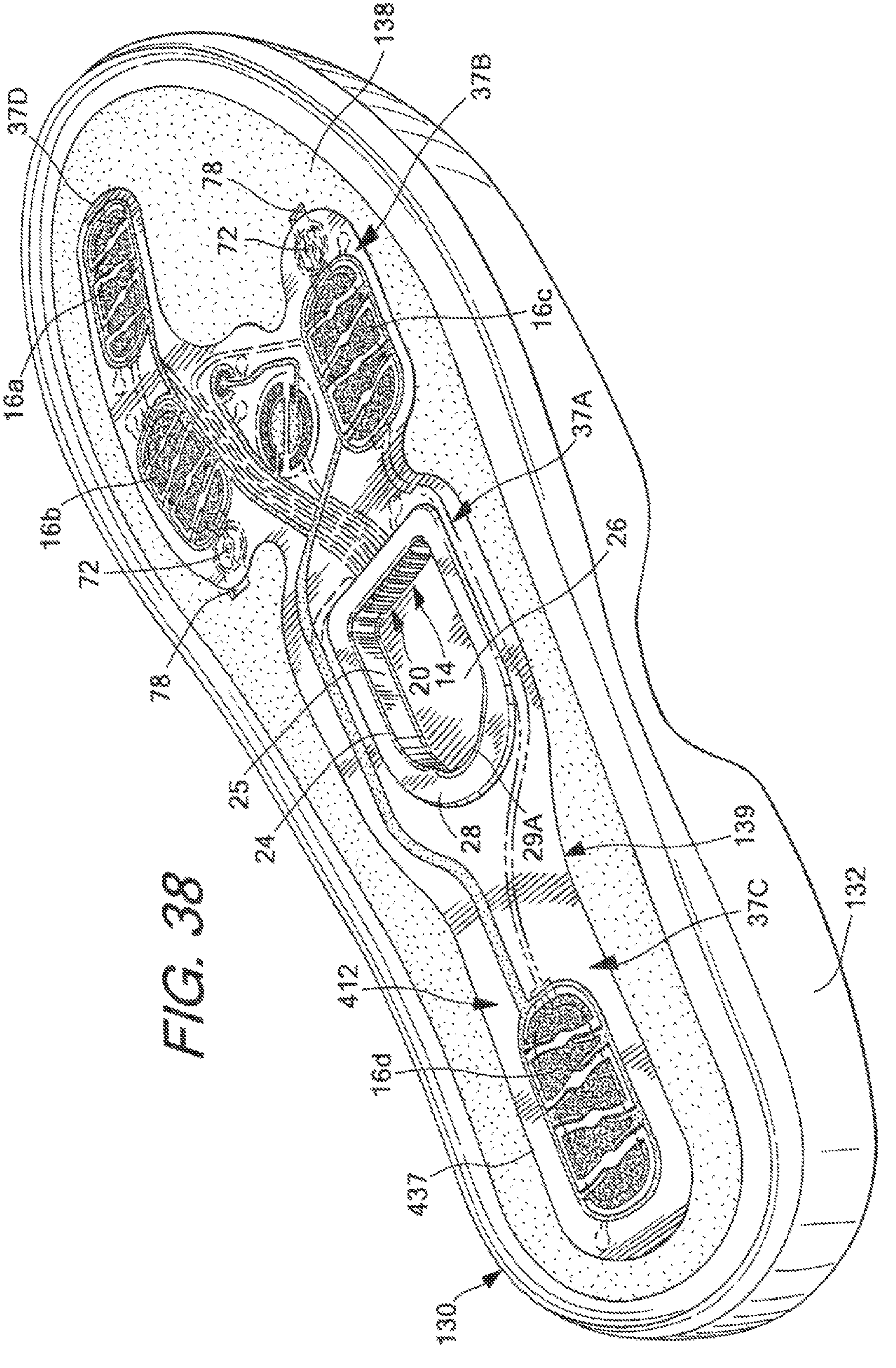
FIG. 38 is a top perspective view of the sole and the sensor system of FIG. 36, with a foot contacting member of the shoe removed and an electronic module removed.
Figure 39:
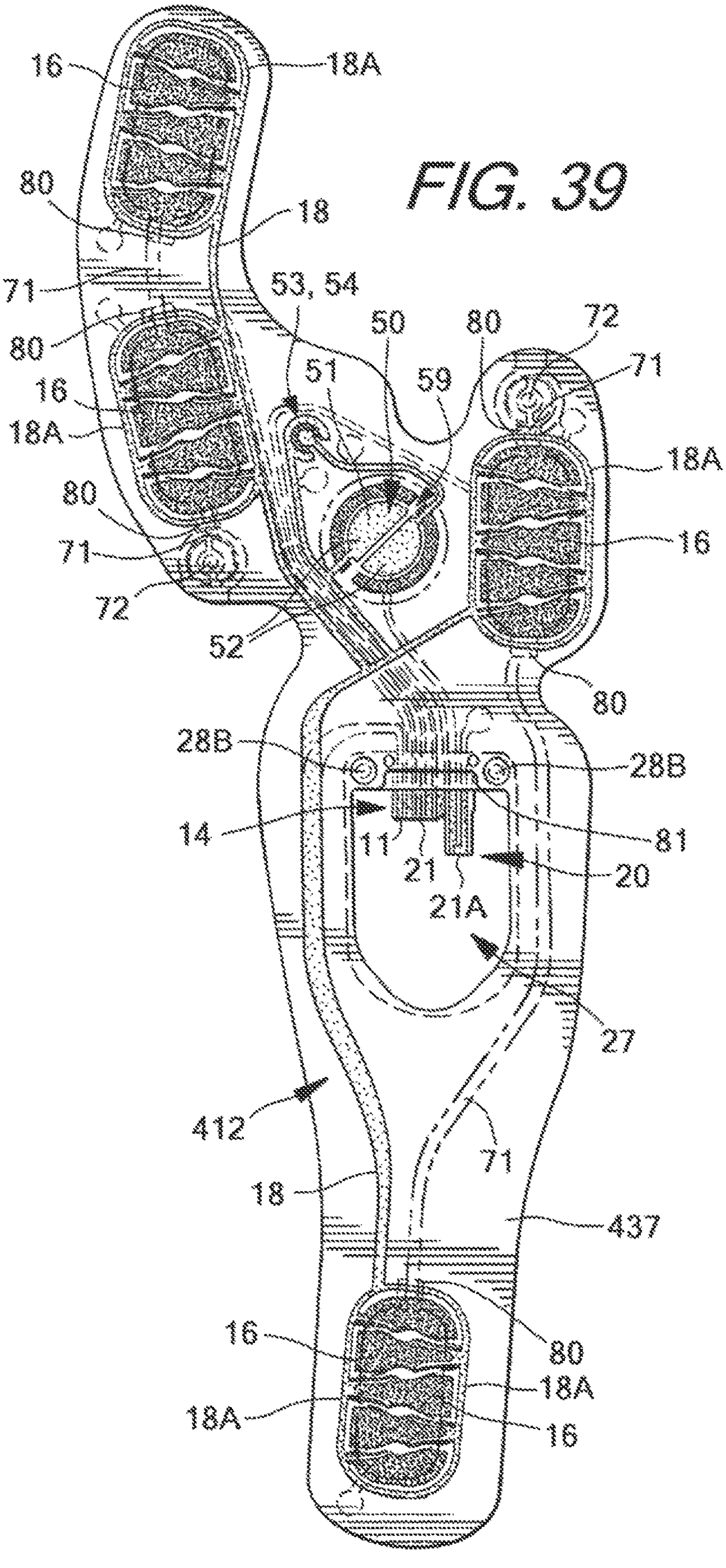
FIG. 39 is a top view of an insert of the sensor system of FIG. 36, adapted to be positioned within the sole structure of an article of footwear for a user's right foot.
Figure 40:
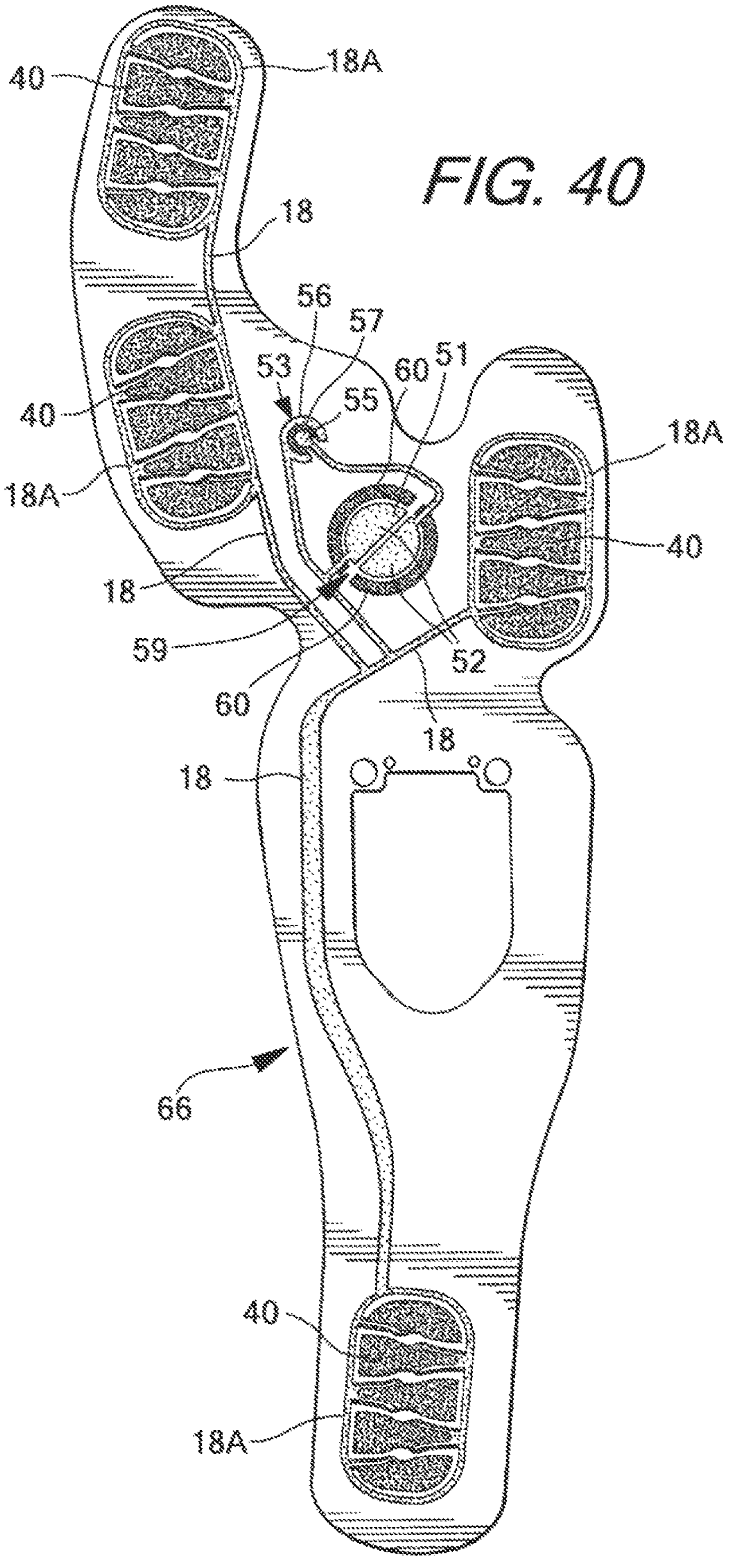
FIG. 40 is a top view of a first layer of the insert of FIG. 39.
Figure 41:
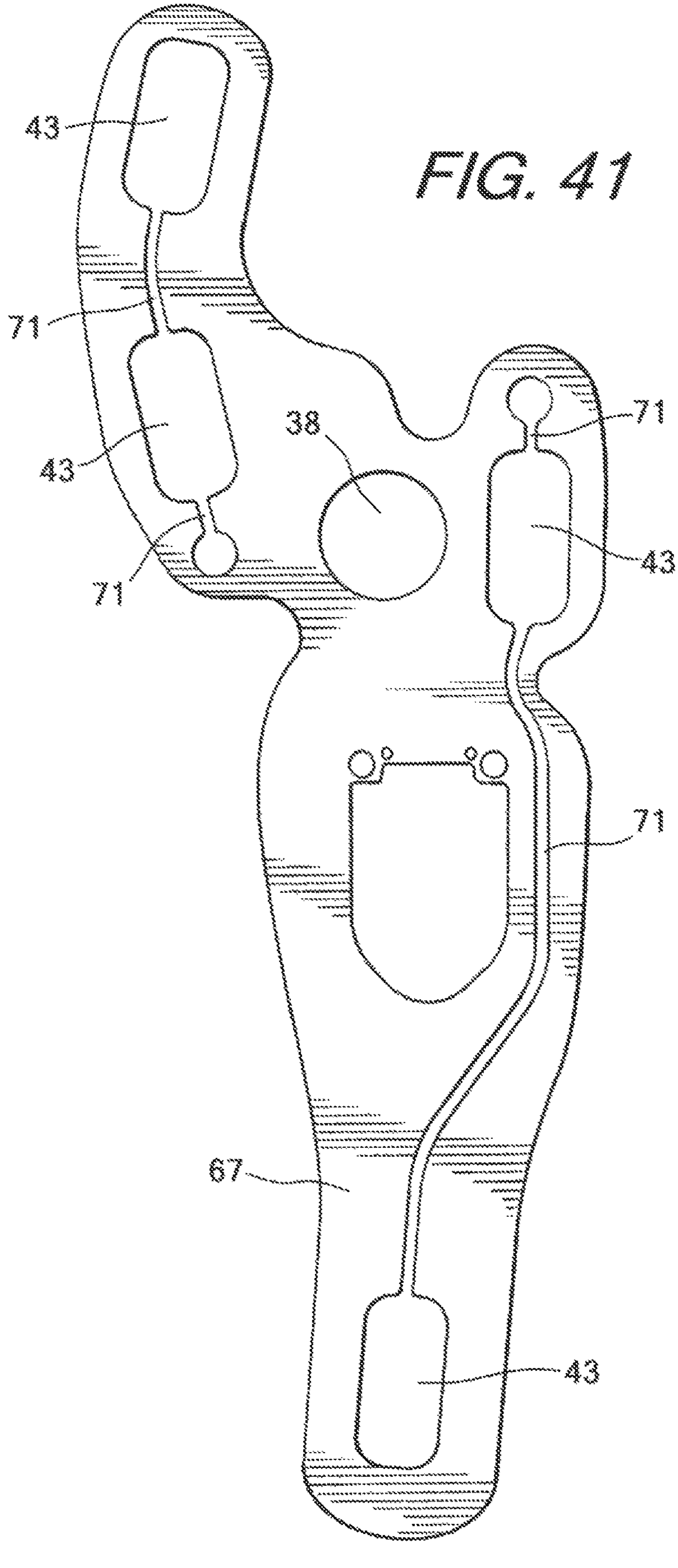
FIG. 41 is a top view of a second layer of the insert of FIG. 39.
Figure 42:
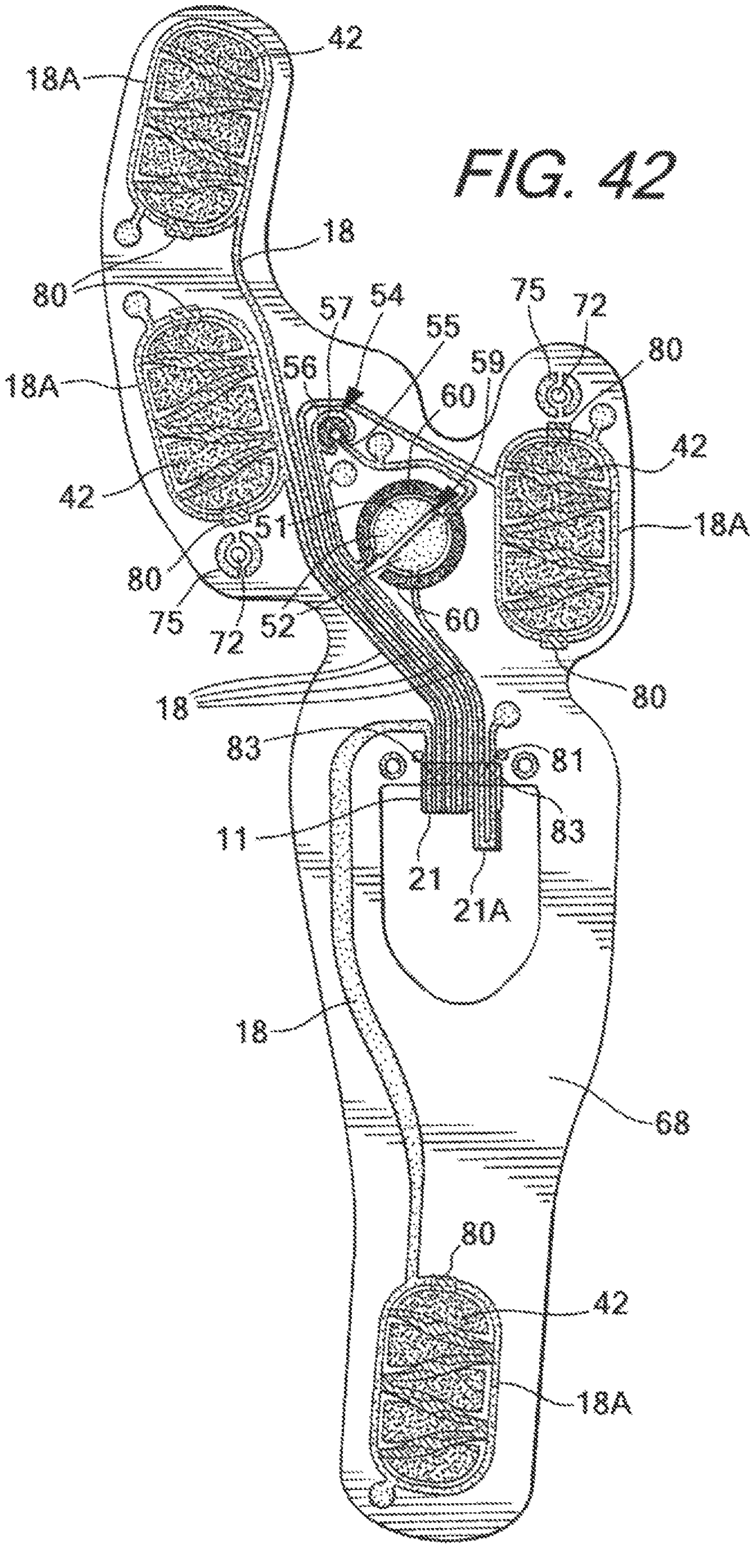
FIG. 42 is a top view of a spacer layer of the insert of FIG. 39.
Figure 43:
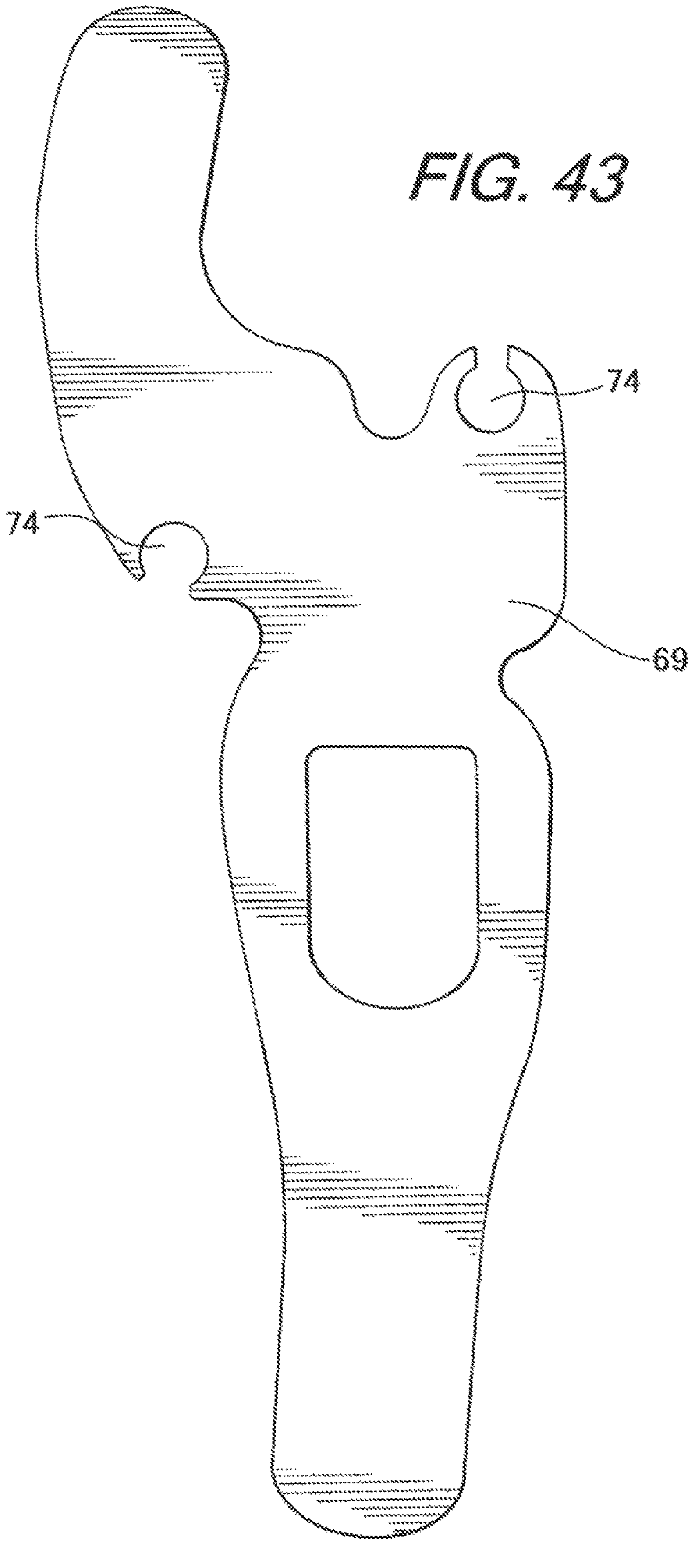
FIG. 43 is a top view of a bottom layer of the insert of FIG. 39.
Figure 44:
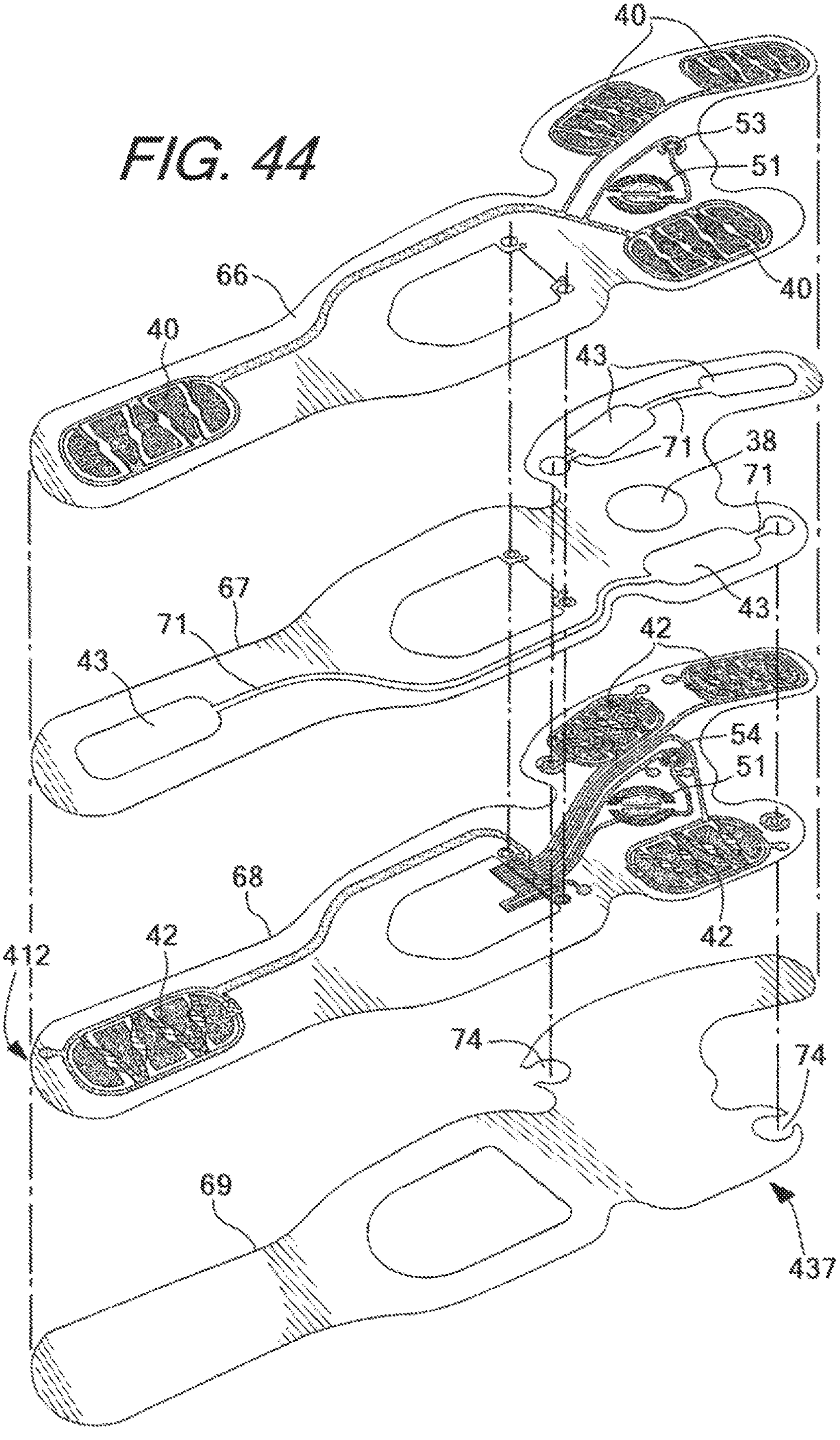
FIG. 44 is an exploded perspective view of the insert of FIG. 39, showing four different layers.

FIGS. 36-44 illustrate a sensor system 412 with an insert 437 that includes an airflow system 70 with a different arrangement of channels 71 and vents 72 than the insert 37 described above and shown in FIGS. 3-22B. FIGS. 22C-D and FIGS. 45-47 illustrate additional embodiments of insert members 37', 537 that include an airflow system 70 with a channels 71 and vents 72 arranged similarly to the insert 437 of FIGS. 36-44. The positions of the sensors 16*a-d* in the embodiment of FIGS. 22C-D are generally the same as in the embodiment of FIGS. 3-22B, 28, and 30, and are illustrated in broken lines on the spacer layer 67 in FIG. 22C. Such structural features are not described again herein for the sake of brevity. In the embodiment of the insert 437 in FIGS. 36-44, the first phalangeal sensor 16*a* and the first metatarsal sensor 16*b* are connected to the same vent 72 by channels 71 in substantially the same configuration described above. The fifth metatarsal sensor 16*c* and the heel sensor 16*d* also share a common vent 72, which is located in the fifth metatarsal area of the insert 437, rather than in the heel portion as in the embodiment of FIGS. 3-22B, 28, and 30. In this configuration, the heel sensor 16*d* has a channel 71 that extends from the hole 43 at the heel sensor 16*d* to the hole 43 at the fifth metatarsal sensor 16*c*, and another channel 71 extends from the fifth metatarsal sensor 16*c* to the vent 72. As shown in FIGS. 36-44, the locations of the vents 72 are different from the embodiment described above, and accordingly, the insert 437 may be used with a sole structure 130 that contains features specifically adapted for vents 72 in these locations. FIGS. 36-38 illustrate a sole structure 130 and a foam member 138 that includes cavities 76 positioned for cooperation with the vents 72 of the insert 437. These cavities 76 function similarly to the cavities 76 of the embodiment shown in FIGS. 3-5 and described herein. For example, the foam member 138 has a cavity 76 in the fifth metatarsal area of the sole structure 130 extending forward beyond the peripheral edge of the insert 437 in order to provide venting of air from the vent 72 in the fifth metatarsal area of the insert 437. The foam member 138 also has a cavity 76 in the first metatarsal area of the sole structure 130 extending rearward beyond the peripheral edge of the insert 437 in order to provide venting of air from the vent 72 in the first metatarsal area of the insert 437. The inserts 37', 537 of FIGS. 22C-D and 45-47 may utilize foam members 138 with cavities 76 positioned in similar locations in various embodiments. It is understood that different positions and configurations of cavities 76 may be utilized in other embodiments. In a further embodiment, a single sole structure 130 may contain multiple cavities 76 arranged for use with several different types of inserts 37, 37', 437, 537 having different vent 72 locations. In this embodiment, at least some of the cavities 76 may be unused, depending on the configuration of the insert 37, et seq. In further embodiments, any of the features, characteristics, etc., of the embodiments of airflow systems 70 described herein may be combined with other embodiments of airflow systems 70, as well as other embodiments of sensor systems 12, inserts 37, and/or footwear 100.

Figure 15:
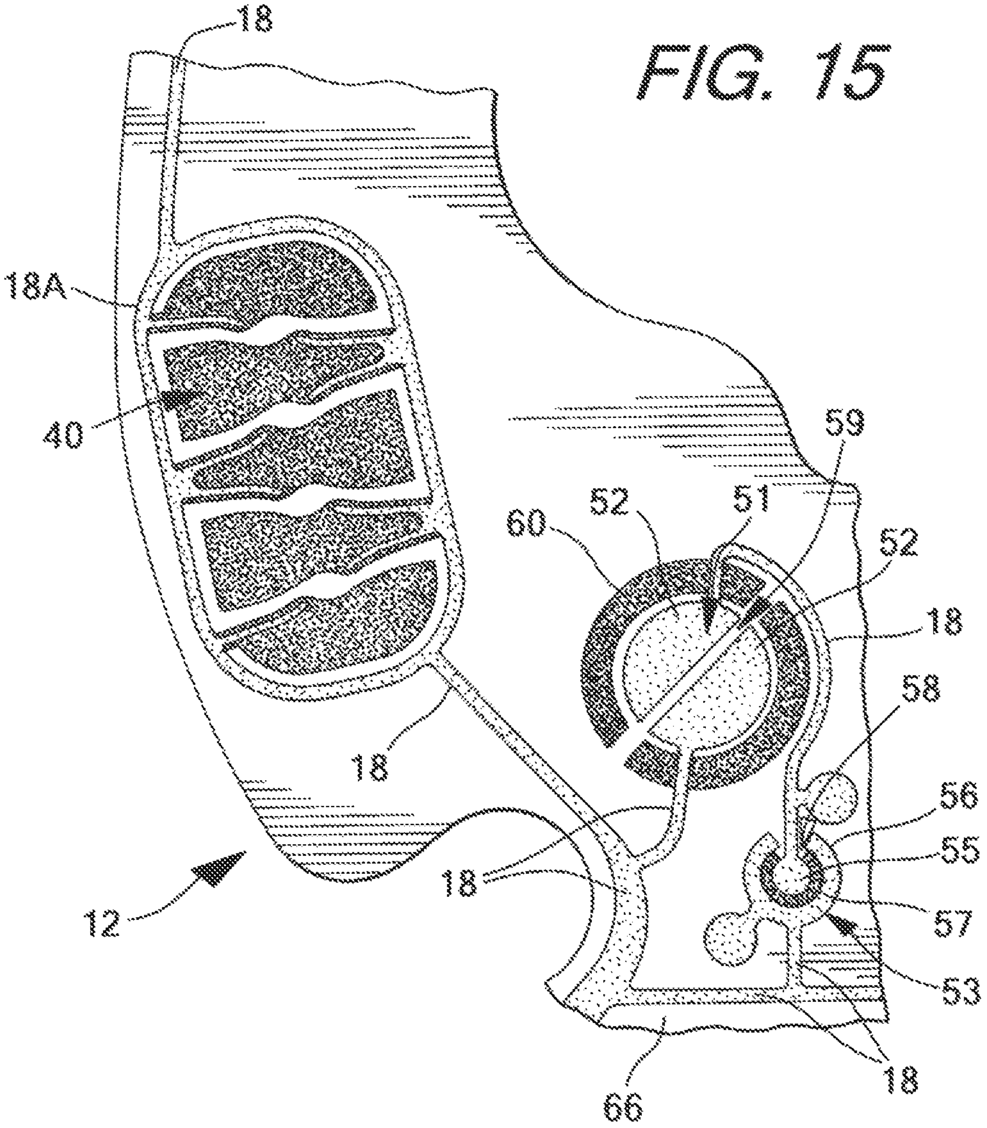
FIG. 15 is a magnified top view of a portion of the first layer of FIG. 14.
Figure 16:
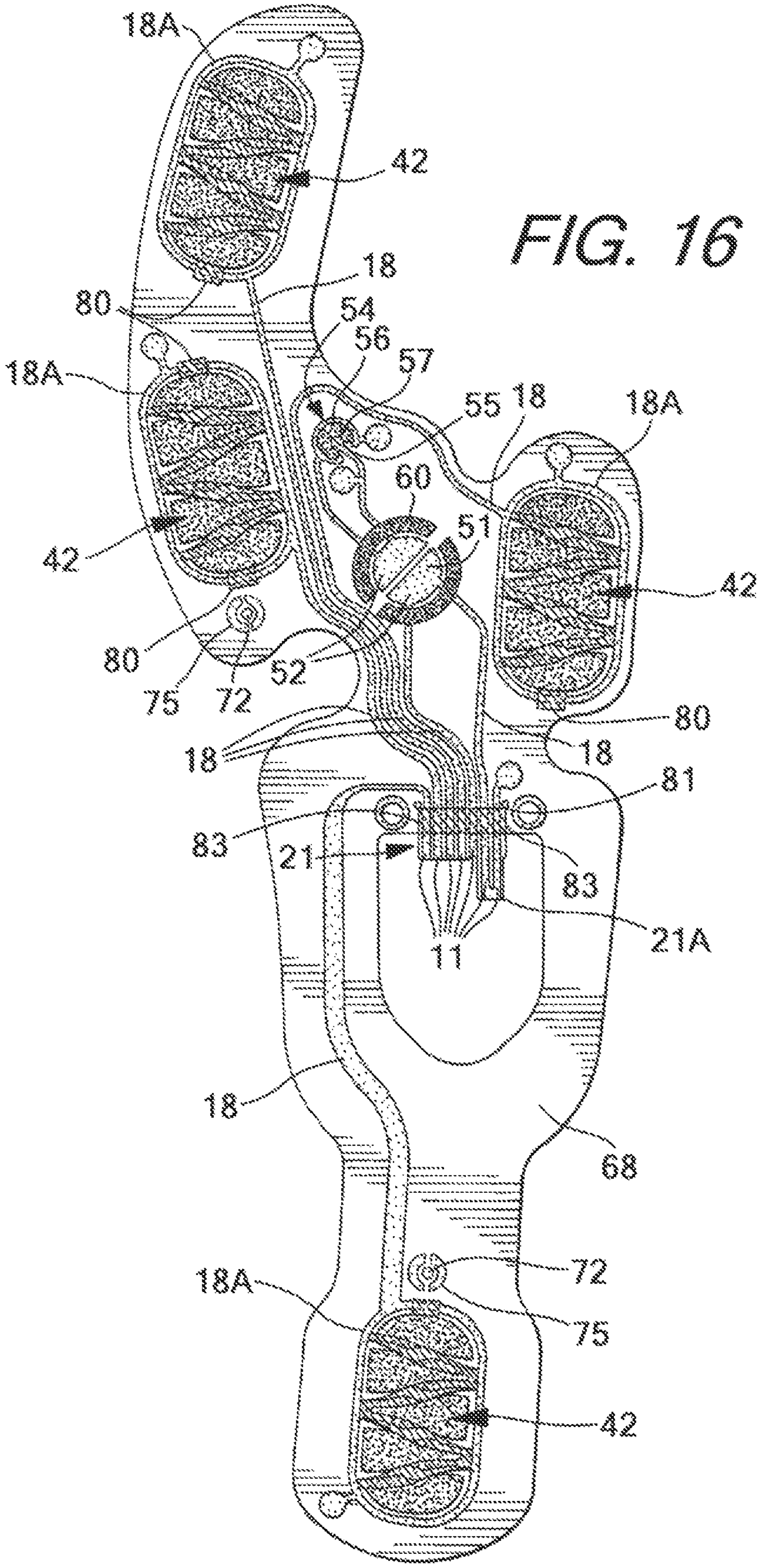
FIG. 16 is a top view of a second layer of the insert of FIG. 13.

In the embodiment of FIGS. 3-22B, as described above, the spacer layer 67 generally insulates conductive members/components on the first and second layers 66, 68 from each other, except in areas where electrical contact is desired, such as at the pathway 50 and between the contacts 40, 42 of the sensors 16. The spacer layer 67 has holes 38, 43 to define areas of desired electrical contact between the layers 66, 68. The components of the airflow system 70, in particular the channels 71 may provide a route for shorting or other undesired electrical contact by one or more conductive members between the first and second layers 66, 68. In one embodiment, the sensor system 12 may include one or more patches of dielectric material 80 to resist or prevent undesired shorting by one or more conductive members across open areas of the spacer layer 67, such as the channels 71. This dielectric material 80 may be in the form of an acrylic ink or other UV-curable ink, or another insulating material suitable for the application. In the embodiment shown in FIGS. 16-17, the insert 37 has several patches of dielectric material 80 extending across the channel 71, to insulate the distribution leads 18A located around the sensor contacts 40, 42 from each other. As shown in FIGS. 16-17, the dielectric material 80 is connected to the top side of the second layer 68 and covers the distribution lead 18A, although in another embodiment, the dielectric material 80 may be connected to the first layer 66, 68, or both layers may have the dielectric material 80. The spacer layer 67 may have a dielectric "bridge" over the channel 71 in a further embodiment. Additionally, the dielectric material completely covers a portion of the distribution lead 18A and is wider than the width of the channel 71, which compensates for movement or displacement of the spacer layer 67 or differences in manufacturing tolerances. In this embodiment, the insert 37 has patches of the dielectric material 80 located at each intersection of one of the channels 71 with the distribution leads 18A, including one patch 80 on the rear side of the first phalangeal sensor 16*a*, two patches 80 on the front and rear ends of the first metatarsal sensor 16*b*, one patch 80 on the rear side of the fifth metatarsal sensor 16*c*, and one patch 80 on the front side of the heel sensor 16*d*. In other embodiments, the insert 37 may have patches of the dielectric material located elsewhere on the insert 37, to insulate other portions of the distribution leads 18A or other conductive members from shorting between the layers 66, 68. It is understood that a spacer layer 67 having a different configuration with holes, apertures, openings, etc. that are differently shaped and/or located may give rise to the use of the dielectric material 80 in other locations for insulation purposes. As discussed herein, the dielectric material 80 may be used in other places as a reinforcement or stiffening material.

In the embodiment of FIGS. 3-22B, the port 14, the sensors 16, and the leads 18 form a circuit 10 on the insert member 37. The port 14 has a plurality of terminals 11, with four terminals 11 each dedicated to one of the four sensors 16 individually, one terminal 11 for applying a voltage to the circuit 10, and one terminal 1 for voltage measurement. In this embodiment, the sensor system 12 also includes a pair of resistors 53, 54, each located on one of the layers 66, 68, and a pathway 50 connecting the circuitry on the first layer 66 with the circuitry on the second layer 68. The resistors 53, 54 provide a reference point for the module 22 to measure the resistance of each sensor 16, and permit the module 22 to convert the variable current from the active sensor 16 into a measurable voltage. Additionally, the resistors 53, 54 are arranged in parallel within the circuit 10, which compensates for variations in the circuit 10 and/or variations in the manufacturing processes used to create the resistors 53, 54, such as variations in conductivity of the inks used to print the leads 18 and/or the sensor contacts 40, 42. In one embodiment, the equivalent resistance of the two resistors 53, 54 is 1500+/−500 kΩ. In another embodiment, a single resistor 53, 54 or two resistors 53, 54 in series could be used. In a further embodiment, the resistors 53, 54 may be positioned elsewhere on the insert 37, or may be located within the circuitry of the module 22. A more technical depiction of the circuit 10 of this embodiment is described below and shown in FIG. 20.

Figure 20:
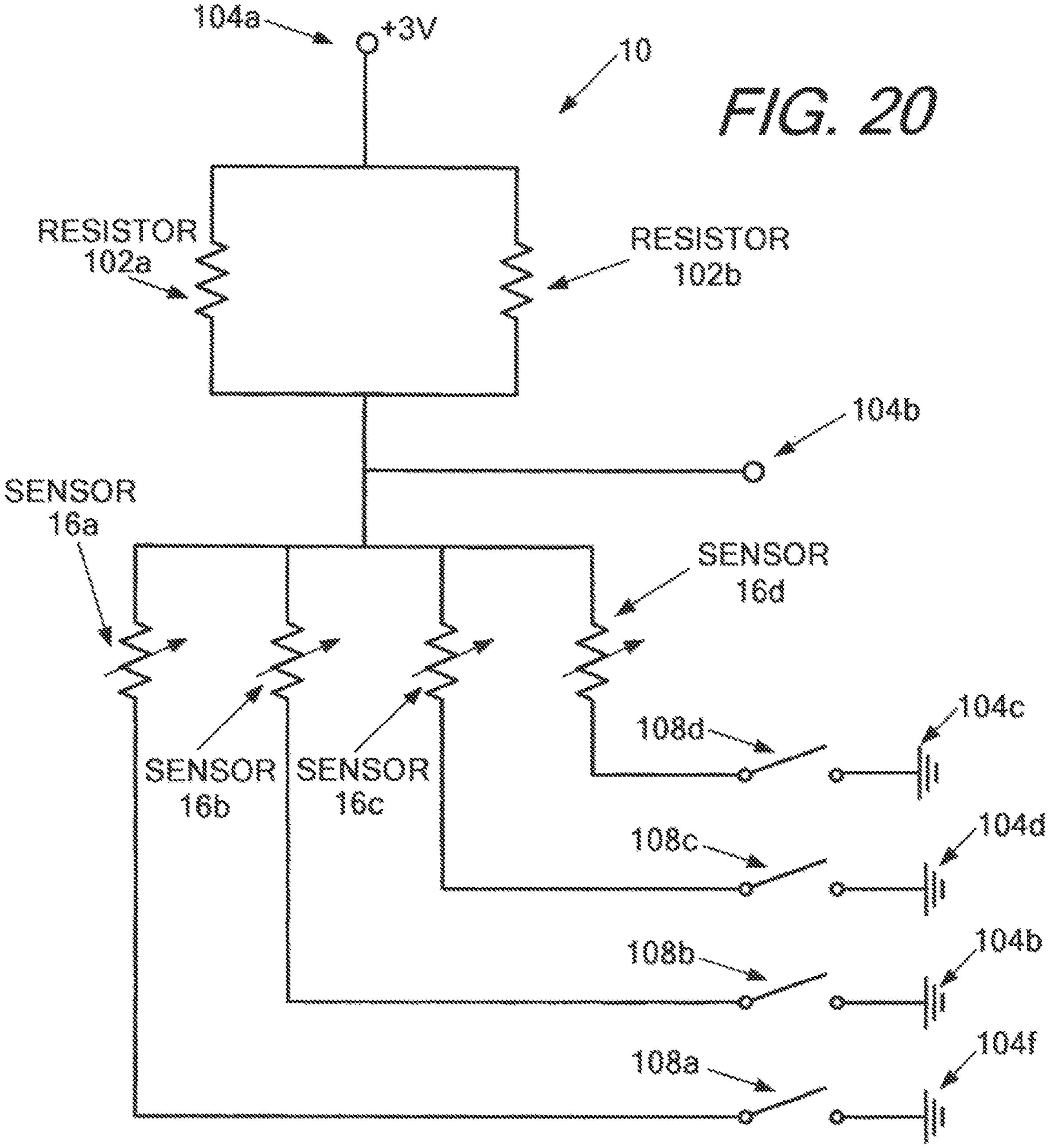
FIG. 20 is a schematic circuit diagram illustrating one embodiment of a circuit formed by the components of the sensor system of FIG. 9.

FIG. 20 illustrates a circuit 10 that may be used to detect and measure pressure in accordance with an embodiment of the invention. The circuit 10 includes six terminals 104*a*-104*f*, including a power terminal 104*a* for applying a voltage to the circuit 10, a measurement terminal 104*b* for measuring a voltage as described below, and four sensor terminals 104*c*-104*f*, each of which is dedicated to one of the sensors 16*a*-16*d* individually, and each of which represents ground in this embodiment. The terminals 104*a*-104*f* represent the terminals 11 of the port 14. In the embodiment shown, fixed resistors 102*a* and 102*b*, which represent resistors 53 and 54, are connected in parallel. Fixed resistors 102*a* and 102*b* may be physically located on separate layers. The equivalent resistance across terminals 104*a* and 104*b* is determined by the well-known equation of:

$$R_{eq}=R_{102a}\cdot R_{102b}/(R_{102a}+R_{102b}) \quad \text{(Equation 1)}$$

Where:

$R_{102a}$=Resistance of fixed resistors 102*a*

$R_{102b}$=Resistance of fixed resistors 102*b*

$R_{eq}$=Equivalent resistance

Electrically connecting fixed resistors 102*a* and 102*b* in parallel compensates for variations in the manufacturing processes used to create fixed resistors 102*a* and 102*b*. For example, if fixed resistor 102*a* has a resistance that deviates from a desired resistance, the deviation of the equivalent resistance determined by equation 1 is minimized by the averaging effect of fixed resistor 102*b*. One skilled in the art will appreciate that two fixed resistors are shown for illustration purposes only. Additional fixed resistors may be connected in parallel and each fixed resistor may be formed on a different layer.

In the embodiment shown in FIG. 20, fixed resistors 102*a* and 102*b* are connected to sensors 16*a*-16*d*. Sensors 16*a*-16*d* may be implemented with variable resistors that change resistance in response to changes in pressure, as described above. Each of sensors 16*a*-16*d* may be implemented with multiple variable resistors. In one embodiment, each of sensors 16*a*-16*d* is implemented with two variable resistors which are physically located on different layers and electrically connected in parallel. For example, as described above with respect to one embodiment, each sensor 16*a*-16*d* may contain two contacts 40, 42 that engage each other to a greater degree as applied pressure increases, and the resistance of the sensor 16*a*-16*d* may decrease as the engagement increases. As mentioned above, connecting resistors in parallel creates an equivalent resistance that minimizes deviations created during manufacturing processes. In another embodiment, the contacts 40, 42 may be arranged in series. Sensors 16*a*-16*d* may be connected to ground via switches 108*a*-108*d*. Switches 108*a*-108*d* may be closed one at a time to connect a sensor. In some embodiments, switches 108*a*-108*d* are implemented with transistors or integrated circuits.

In operation a voltage level, such as 3 volts, is applied at terminal 104*a*. Switches 108*a*-108*d* are closed one at a time to connect one of sensors 16*a*-16*d* to ground. When connected to ground, each of sensors 16*a*-16*d* forms a voltage divider with the combination of fixed resistors 102*a* and 102*b*. For example, when switch 108*a* is closed, the voltage between terminal 104*a* and ground is divided between the combination of fixed resistors 102*a* and 102*b* and sensor 16*a*. The voltage measured at terminal 104*b* changes as the resistance of sensor 16*a* changes. As a result, pressure applied to sensor 16*a* may be measured as a voltage level at terminal 104*b*. The resistance of the sensor 16*a* is measured utilizing the voltage applied to the sensor 16*a* in series with the combined fixed resistors 104*a* and 104*b* of known value. Similarly, selectively closing switches 108*b*-108*d* will generate voltage levels at terminal 104*b* that are related to the pressure applied at sensors 16*b*-16*d*. It is understood that the connections between the sensors 16*a-d* and the terminals 104*c-f* may be different in other embodiments. For example, the sensors 16*a-d* are connected to different pins of the interface 20 in the left shoe insert 37 as compared to the right shoe insert 37, as shown in FIG. 12. In another embodiment, the voltage level may be applied in the opposite manner, with the ground located at terminal 104*a* and the voltage applied at terminals 104*c-f*. In further embodiments, another circuit configuration may be used to achieve a similar result and functionality.

The two resistors 53, 54 have similar or identical structures in the embodiment illustrated, however it is understood that the resistors may have different structures in other embodiments. Each resistor 53, 54 has two sections 55, 56 spaced from each other and a bridge 57 positioned between and connecting the sections 55, 56. FIGS. 15 and 17 illustrate more detailed views of the resistors 53, 54, with one resistor 53 shown from the top and the other resistor 54 shown from the underside. The sections 55, 56 may be connected to different leads 18, such that an electronic signal or current that enters the resistor 53, 54 through one lead 18 would travel between the sections 55, 56 across the bridge 57, and then exit through the other lead 18. The sections 55, 56 may be formed as an inner section 55 and an outer section 56 that substantially surrounds the inner section 55, to provide a large length for transmission between the sections 55, 56 within a small area. In this embodiment, the bridge 57 also substantially surrounds the inner section 55 and is substantially surrounded by the outer section 56. As seen and appreciated in FIGS. 15-17, the bridge 57 overlaps partially with both the inner section 55 and the outer section 56, in order to permit transmission through the bridge 57. In the embodiment of FIGS. 15 and 17, the inner section 55 is formed in a circular or substantially circular shape. The outer section 56 is at least partially formed by a semi-annular ring shape that at least partially surrounds the inner section 55 and is spaced from the inner section around the inner edge of the ring, in this embodiment. The bridge 57 in this embodiment is also at least partially formed by a semi-annular ring shape with inner and outer semi-circular edges, and the bridge 57 at least partially surrounds the inner section 55 and at least partially fills the spaces between the sections 55, 56. The inner edge of the bridge 57 overlaps the inner section 55 and the outer edge of the bridge 57 overlaps the outer section 56, as illustrated in FIG. 17. Additionally, in this embodiment, a gap 58 is defined through the outer section 56 and the bridge 57 to permit the lead 18 to connect to the inner section 55 and pass away from the inner section 55 without contacting the outer section 56 or the bridge 57. In other words, the semi-annular ring-shaped outer section 56 and bridge 57 have ends that define the gap 58 therebetween. It is understood that the relative shapes, sizes, and arrangements of the sections 55, 56 and the bridge 57 may be different in other embodiments.

In one embodiment, the bridge 57 may be formed of a more resistive material than the sections 55, 56, and may thus provide the majority of the resistance of each resistor 53, 54. The sections 55, 56 may be at least partially formed of a high-conductivity material, such as a silver material. In the embodiment illustrated in FIGS. 3-22B, the inner and outer sections 55, 56 are formed of the same material as the leads 18, such as a printed silver-based or other metallic-based ink. In this embodiment, the bridge 57 is formed of the same material as the sensor contacts 40, 42, such as carbon black or another conductive carbon material. It is understood that the inner and outer sections 55, 56 and/or the bridge 57 may be formed of different materials in other embodiments.

The pathway 50 generally permits continuous and/or uninterrupted electrical communication and passes electronic signals between the first and second layers 66, 68. In the embodiment of FIGS. 3-22B, the port 14 is directly connected to the second layer 68, and the pathway 50 may serve as a vertical path between the port 14 and the sensor contacts 40 on the first layer 66, 68. In this embodiment, the pathway 50 includes conductive portions 51 on the first layer 66 and the second layer 68, such that conductive portions 51 are in continuous engagement with each other to provide continuous electrical communication between the first and second layers 66, 68 (See, e.g., FIG. 21). The spacer layer 67 in this embodiment includes a hole 38 that is aligned with the pathway 50 and allows for continuous engagement between the conductive portions 51 through the spacer layer 67. Additionally, in the embodiment of FIGS. 3-22B, each of the conductive portions 51 is divided into two sections 52 that are separated by an elongated gap 59 (FIG. 15). These conductive sections 52 have substantially half-circular shapes in the embodiment shown in FIGS. 3-22B, and the conductive portions 51 have a generally circular shape. The sections 52 on the first layer 66 are shaped, sized, and located substantially the same as the sections 52 on the second layer 68, such that the sections on each layer 66, 68 engage the corresponding sections 52 on the other layer 66, 68. The gaps 59 on the two layers 66, 68 are also substantially aligned in this embodiment. In other words, the conductive portions 51 may be arranged so that the left sections 52 of the conductive portions 51 engage each other and the right sections 52 of the conductive portions 51 engage each other, with no direct engagement between either of the left sections 52 and either of the right sections 52. This configuration may alternately be described as creating two separate, side-by-side pathways between the first and second layers 66, 68, and each section 52 may be considered to be separate conductive portions forming each pathway. The conductive portions 51 of the pathway 50 are formed of a conductive material, and in one embodiment, the conductive portions 51 may be formed of the same material as the leads 18, such as a silver-based ink or other metallic ink. In other embodiments, the pathway 50, and the components thereof described herein, may have a different size, shape, form, or location, and may be formed of a different material.

The pathway 50 may be at least partially surrounded by or bounded by a stiffening structure 60 in one embodiment to provide structural support and/or effects. As illustrated in FIGS. 7-17 and 21, the conductive portions 51 are surrounded by a substantially annular stiffener 60. The stiffener 60 in this embodiment is not completely annular, as the gap 59 extends through the stiffener 60, and the stiffener 60 may also include additional gaps for leads 18 to pass through and connect to the conductive portions 51, in another embodiment. The stiffener 60 in this embodiment serves to assist with engagement between the conductive portions 51, to achieve maximum engagement between the conductive portions 51. FIG. 21 illustrates this configuration in greater detail. It is understood that FIG. 21 is at least partially schematic in nature, and the relative sizes of the components shown in FIG. 21 may be exaggerated for effect and understanding. Additionally, FIG. 21 does not show the bottom layer 69, for clarity in illustrating the other layers 66, 67, 68. In general, the spacer layer 67 provides separation between the conductive portions 51, such that the layers 66, 68 must be deflected toward each other at the pathway 50 in order for the conductive portions 51 to engage each other.

In the embodiment shown in FIG. 21, the hole 38 in the spacer layer 67 permits the conductive portions 51 to deflect toward each other and engage each other. The first and second layers 66, 68 may be vacuumed or otherwise pressed together to achieve this contact, such as by passing a roller over the assembled insert 37 at the location of the pathway 50 to remove excess air. The deflection of the layers 66, 68 toward each other creates an annular transition region 61 on one or both of the layers 66, 68 around the rim of the hole 38, where the layer or layers 66, 68 deflect toward each other. The transition region 61 in this embodiment is defined by an outer annular break line 61*a* and an inner annular break line 61*b*, with the transition region 61 between the break lines 61*a*, 61*b*, and with the conductive portions 51 within the inner break line 61*b*. In this configuration, the first and second layers 66, 68 are generally horizontal outside the outer break line 61*a* and within the inner break line 61*a*, and the first and second layers 66, 68 slope toward each other at the transition region 61 to create engagement between the conductive portions 51. The hole 38 is larger in dimension than the stiffener 60, such that the stiffener 60 is positioned adjacent the edge of the hole 38. In this configuration, the increased stiffness of the stiffener 60 tends to cause the layers 66, 68 to make a sharp transition from horizontal to at least partially vertical at the location of the stiffener 60, and thus the stiffener 60 tends to define the transition region 61.

As seen in FIG. 21, the location of the transition region 61 at the stiffener 60 permits maximum contact between the conductive portions 51 inside the area 62 bounded by the transition region 61. In one embodiment, majorities of the conductive portions 51 are in continuous engagement with each other through the hole 38 inside an area 62 bounded by the transition region 61. In another embodiment, the conductive portions 51 are in continuous engagement with each other through the hole 38 over the entirety or substantially the entirety of the area 62 bounded by the transition region 61. This continuous contact assists in ensuring that the pathway 50 and the circuit 10 will be uninterrupted and will function properly. Adhesives may be utilized at or around the pathway 50 to enhance the engagement between the layers 66, 68 at the pathway 50. The stiffener 60 may be formed of any material that has suitable stiffness, and in one embodiment, may be formed of a material with greater stiffness than the material of the conductive portions 51. One example of such a material is carbon black or other carbon-based material, although other materials may be used in other embodiments, including other types of printable substances.

The stiffener 60 may also assist in achieving continuous engagement between the conductive portions 51 in a different way. In the embodiment of FIGS. 3-22B, the stiffener 60 is formed by a carbon-based ink that is more absorptive of many wavelengths of light as compared to the metallic-based ink of the conductive portions 51, which may tend to be reflective. The ink on the layers 66, 68 may be cured using IR radiation, and in this embodiment, the stiffener 60 may absorb a greater amount of the IR radiation than the conductive portions 51. This absorption may tend to heat the area of the layer 66, 68 immediately below the stiffener 60 to cause a temperature gradient across the thickness of the layer 66, 68, such that the layer 66, 68 is warmer on the surface on which the stiffener 60 is printed and cooler on the opposite surface. This temperature gradient, in turn, may cause differential expansion/contraction at the opposed surfaces of the layer 66, 68 around the stiffener 60, such that the warmer surface at the stiffener 60 may contract relative to the surface opposite the stiffener 60, causing the region of each layer 66, 68 inside the stiffener 60 (i.e. at the conductive portions 51) to protrude or dimple slightly upward. This protrusion of the layers 66, 68 extends the conductive portions 51 on the layers 66, 68 closer to each other, which may result in increased engagement between the conductive portions 51, assisting in achieving continuous or substantially continuous engagement of the conductive portions 51 within the stiffener 60. The protrusion of the layers 66, 68 may additionally or alternately be enhanced by mechanical stamping or other pre-straining action to create a protruding or dimpling effect. Bonding techniques, such as ultrasonic spot welding or other spot welding, may additionally or alternately be used increase engagement between the conductive portions 51. In one embodiment, ultrasonic spot welding may be used in a waffle pattern between the conductive portions 51 to retain the conductive portions 51 in engagement with each other.

Figure 10:
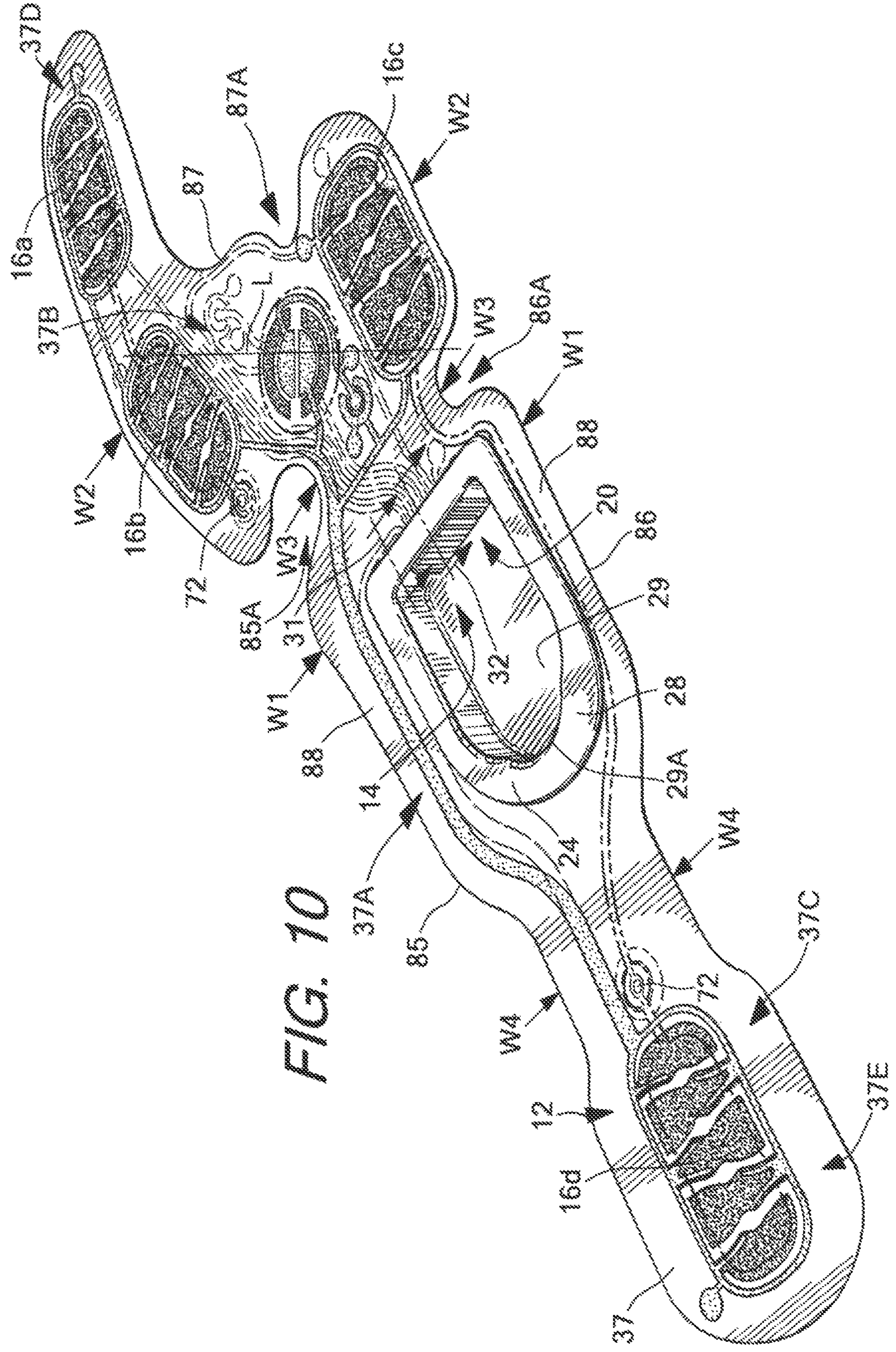
FIG. 10 is a top perspective view of the sensor system of FIG. 9.
Figure 11:
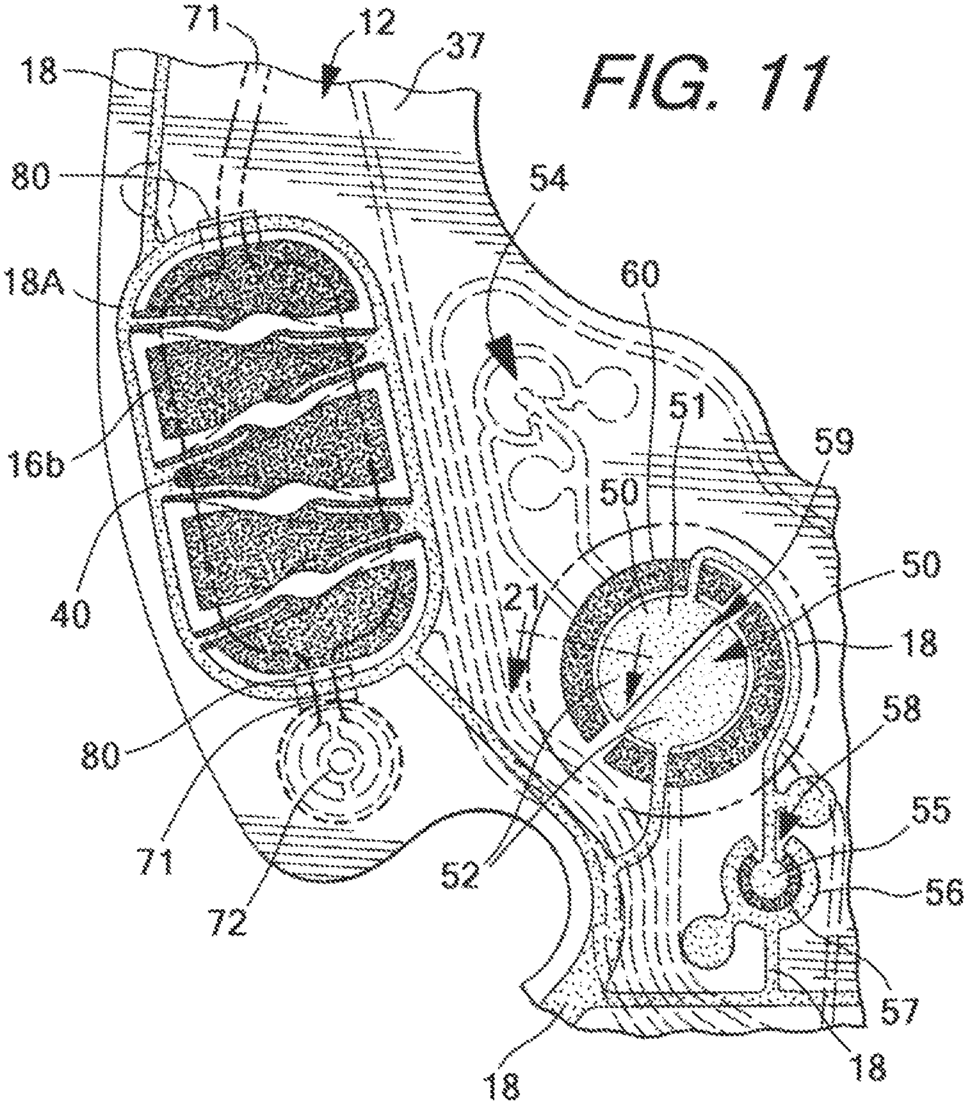
FIG. 11 is a magnified top view of a portion of the sensor system of FIG. 9.

The gap 59 in the pathway 50 may serve multiple functions. One function that may be served by the gap 59 is to create electrical separation between the sections 52 of the pathway 50, in order to create separate connections between the layers 66, 68. Another function that may be served by the gap 59 is to increase the durability of the pathway 50 during flexing of the insert 37. In general, the foot of the user will tend to "roll" from the fifth metatarsal area (also referred to as the fifth metatarsal head area or the fifth metatarsophalangeal area) to the first metatarsal area (also referred to as the first metatarsal head area or the first metatarsophalangeal area). In the embodiment of FIGS. 3-22B, the pathway 50 is located around the second and/or third metatarsal areas of the insert 37, so that the roll of the user's foot passes directly over the pathway 50. Repeated rolling of this nature can cause bending of the conductive portions 51, which can in turn, cause abrasion, fracture, separation, etc. The gap 59 can serve as a flexing point to minimize bending of the conductive portions 51 if aligned properly. In the embodiment of FIGS. 3-22B, the gap 59 is generally aligned perpendicular to the direction of the typical roll of the user's foot, or in other words, perpendicular to a line extending between the fifth metatarsal area and the first metatarsal area of the insert 37. In one embodiment, a virtual line L (see FIG. 10) may be drawn between the sensor 16*b* in the first metatarsal area and the sensor 16*c* in the fifth metatarsal area, and the gap 59 may be aligned perpendicular to this line L or within +/−45° of being perpendicular to the line L. The line L as shown in FIG. 10 is drawn between the front edge (e.g. front center) of the first metatarsal sensor 16*b* and the rear edge (e.g. rear center) of the fifth metatarsal sensor 16*c*. In other embodiments, the gap 59 (if present) may be positioned differently, particularly if the pathway 50 is located in a different area of the insert 37.

FIGS. 52-56 illustrate another embodiment of a sensor system 612 that includes an insert member 37, which are similar to the sensor system 12 and the insert 37 of FIGS. 3-22B. In the embodiment of FIGS. 52-56, the pathway 50 does not include a stiffener 60 as in the embodiment of FIGS. 3-22B. Additionally, the conductive portions 51 of the pathway 50 in this embodiment are enlarged to cover the area that is covered by the stiffener 60 in the embodiment of FIGS. 3-22B. In other words, in this embodiment, the conductive portions 51 extend almost to the edge of the hole 38 that is aligned with the pathway 50, and portions of the conductive portions 51 are positioned within the transition region 61, as illustrated schematically in FIG. 56. The increased sizes of the conductive portions 51 in the embodiment of FIGS. 52-56 may provide a greater surface area for potential engagement between the conductive portions 51, and thereby provide more consistent and uninterrupted function of the pathway 50. In other respects, the pathway 50 shares structural and functional features with the embodiments of the pathway 50 shown in FIGS. 3-22B and described elsewhere herein. Such similar structures and functions are not described again for the sake of brevity. In one embodiment, mechanical stamping or other pre-straining action can be used to create a protruding or dimpling effect of the layers 66, 68, enhancing engagement between the conductive portions 51, as described above. Bonding techniques, such as ultrasonic spot welding or other spot welding, may additionally or alternately be used increase engagement between the conductive portions 51, as also described above.

In another embodiment, the pathway 50 may be positioned in another location or have another configuration. For example, in one embodiment, the pathway 50 may be formed at or near the terminals 11, such as by utilizing a two-pin connection (not shown) on the first layer 66 and connecting the two-pin connection to the fifth and sixth terminals 11 of the interface 20, such as by a crimping connection. Other structures for forming a pathway 50 may be utilized in further embodiments.

FIGS. 48-51 illustrate another embodiment of a sensor system 712 that is configured differently than the sensor systems 12, 412, 512, 612 described herein and has a different mode of operation compared to the sensor systems 12, 412, 512, 612 described herein. The sensor system 712 of FIGS. 48-51 includes many structural and functional features in common with the sensor system 12 described above and shown in FIGS. 3-22B. For example, the external shape of the insert 37, the general positions of the sensors 16, and the configuration of the airflow system 70 in the embodiment of FIGS. 48-51 are similar or identical to the shape of the insert 37, the general positions of the sensors 16, and the configuration of the airflow system 70 in FIGS. 3-22B. These and other such common features may not be described again herein for the sake of brevity.

In the embodiment of FIGS. 48-51, the sensor system 712 has sensors 16 that include two contacts or electrodes 740, 742 positioned on the second layer 68 and a third contact 744 positioned on the first layer 66. In this embodiment, all the contacts 40, 742, 744 are formed of a carbon-based ink as described above, having one or more distribution leads 18A at the edges of each of the contacts 740, 742, 744. The contacts 740, 742 on the second layer 68 may have a different conductivity than the contacts 744 on the first layer 66, and may be formed of a carbon-based ink that is doped to achieve higher conductivity. The contacts 740, 742 on the second layer 68 are electrically separate from each other and are each connected to the port 14 by leads 18. A single power or ground lead 18B connects to a first contact 740 of all of the sensors 16, and the second contact 742 of each individual sensor 16 is connected by an individual lead 18 to the port 14.

The structures of the sensors 16 in the sensor system 712 of FIGS. 48-51 are otherwise similar to the sensors 16 in the embodiment of FIGS. 3-22B. In this embodiment, the combined first and second contacts 740, 742 are structured similarly to the contact 42 on the second layer 68 of the embodiment of FIGS. 3-22B, except that the first and second contacts 740, 742 are electrically separate from each other and the third contact 744 is structured similarly to the contact 40 on the first layer 66 in the embodiment of FIGS. 3-22B. In other embodiments, the sensors 16 and/or the contacts 740, 742, 744 may have different configurations. For example, in one embodiment, the contact 744 on the first layer 66 may be a single patch of the carbon-based ink.

In the embodiment of the sensor system 712 in FIGS. 48-51, the first and second contacts 740, 742 are electrically separate from each other, and the third contact 744 is in confronting relation to the first and second contacts 740, 742, such that the third contact 744 engages the first and second contacts 740, 742 upon application of vertical pressure to the sensor 16. In this configuration, the signals from the port 14 travel between the two electrodes 740, 742 of each sensor 16 on the second layer 68 by passing through the electrode 744 of that sensor 16 on the first layer 66. Accordingly, the resistivity of the sensor 16 is determined by the engagement between the contacts 740, 742 on the second layer 68 and the electrode 744 on the first layer 66, and the relationship between the pressure applied to the sensor 16 and the resistance of the sensor 16 is similar to that of the sensors 16 of the embodiment in FIGS. 3-22B described herein and shown in FIG. 27. The sensitivity range, activation pressure, and other functional properties of the sensors 16 of FIGS. 48-51 may also be similar to those of the sensors 16 of the sensor system 12 in FIGS. 3-22B.

Figure 49:
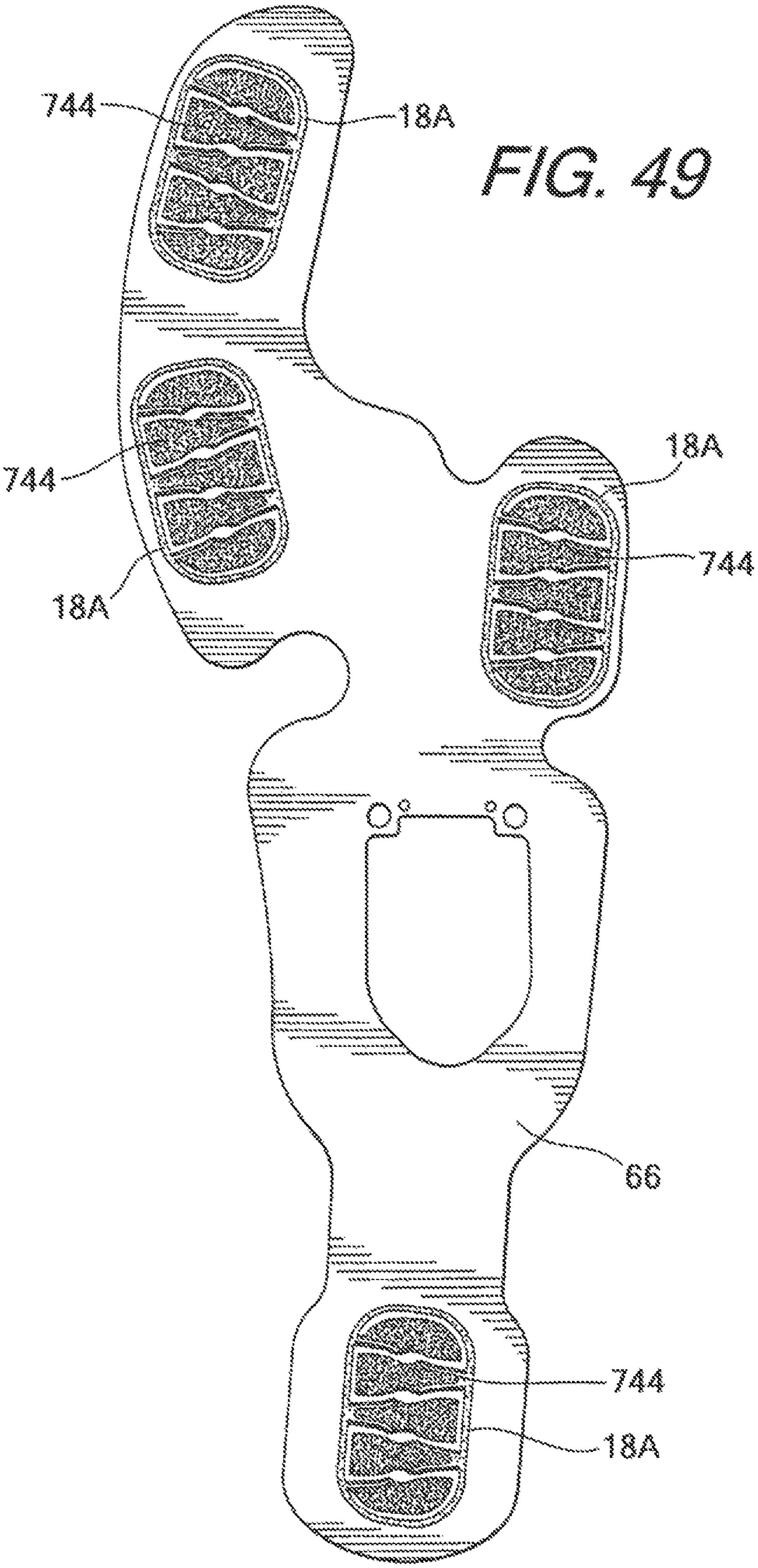
FIG. 49 is a top view of a first layer of the insert of FIG. 48.
Figure 50:
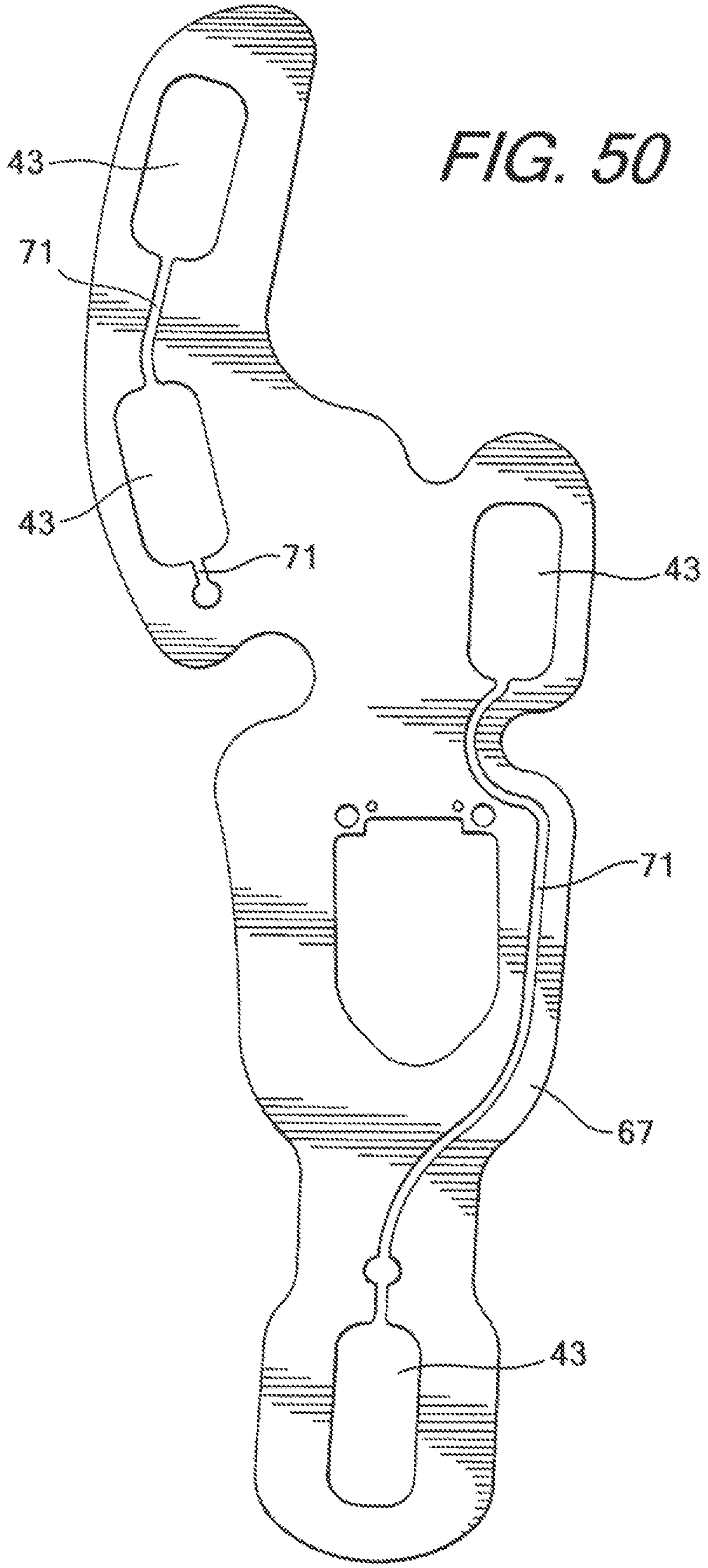
FIG. 50 is a top view of a spacer layer of the insert of FIG. 48.
Figure 51:
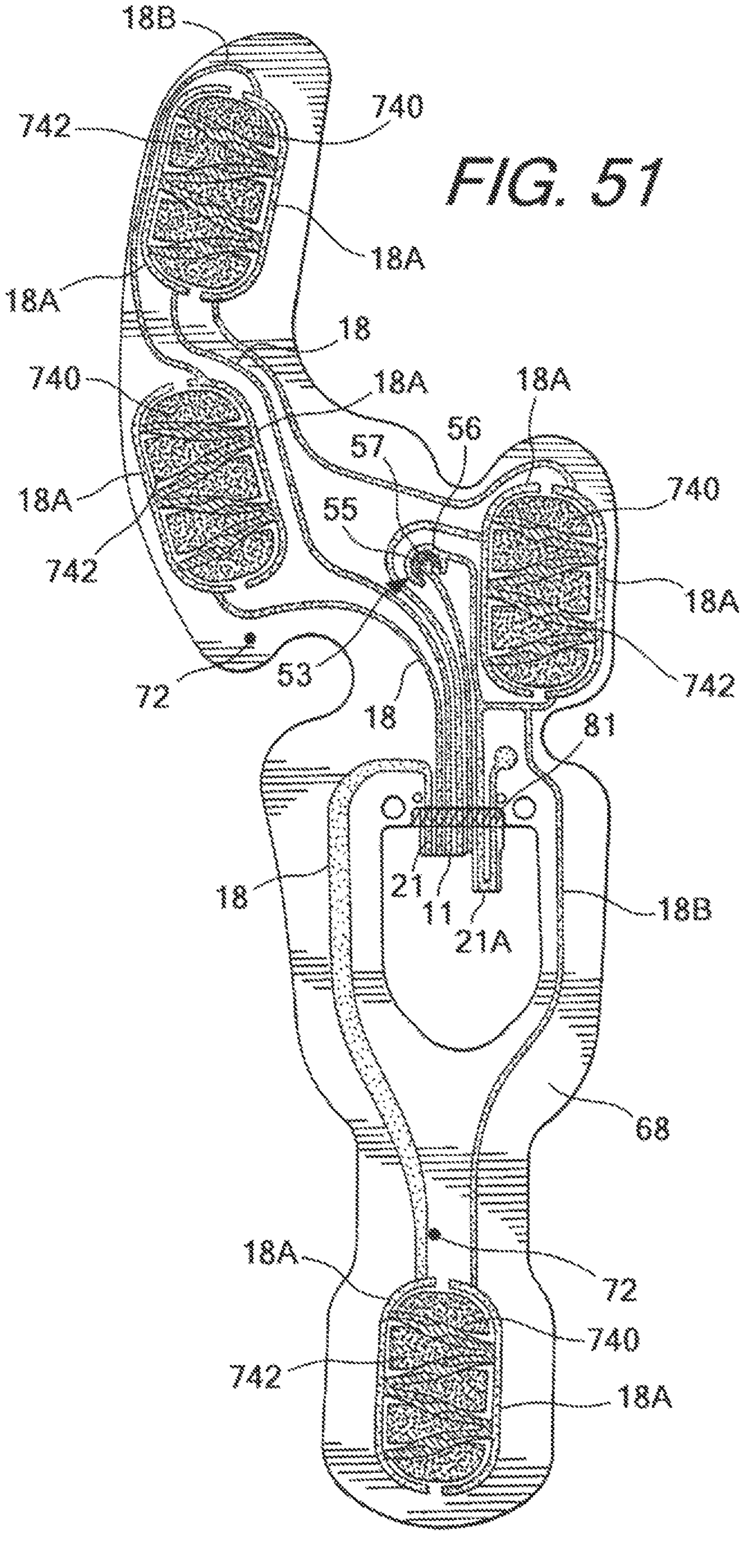
FIG. 51 is a top view of a second layer of the insert of FIG. 48.
Figure 52:
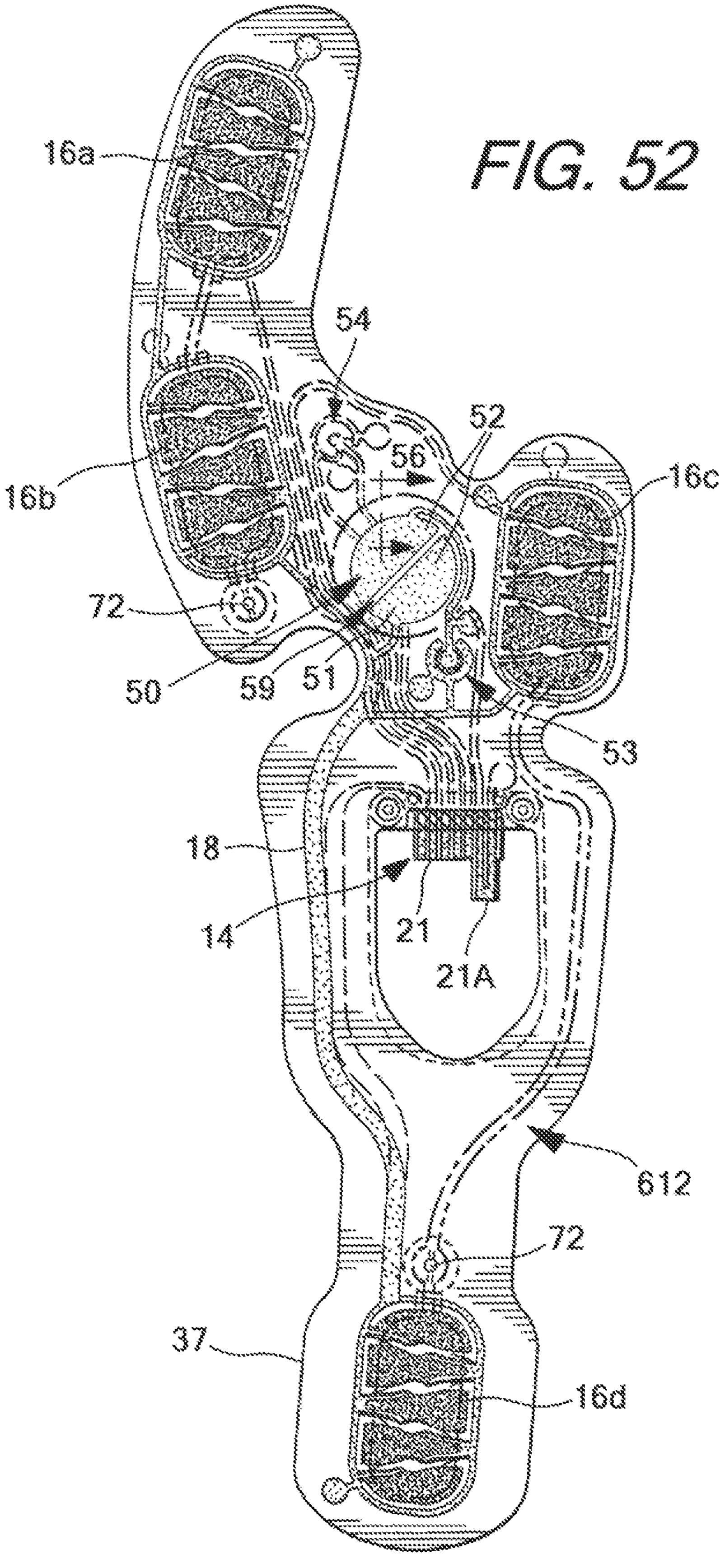
FIG. 52 is a top view of another embodiment of an insert of a sensor system according to aspects of the present invention.
Figure 53:
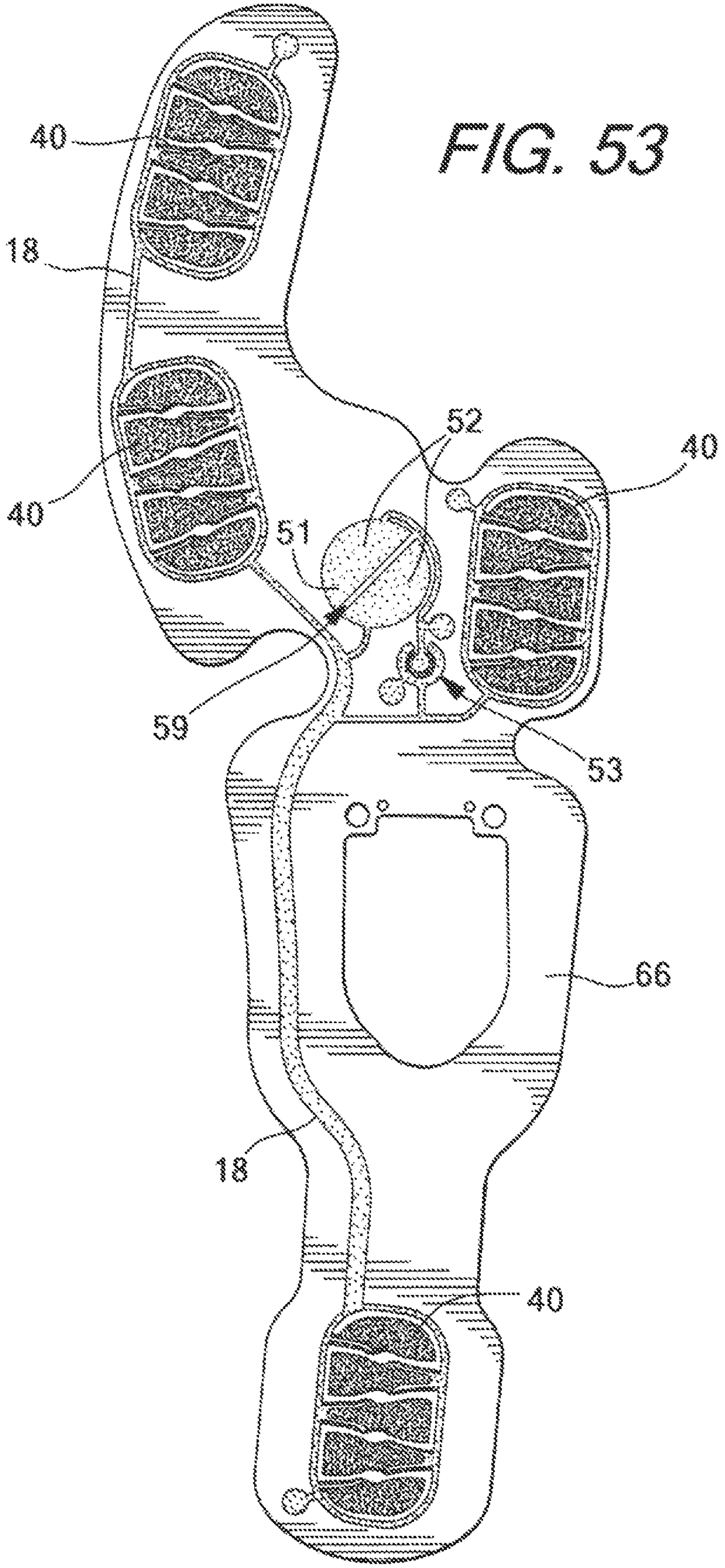
FIG. 53 is a top view of a first layer of the insert of FIG. 52.
Figure 54:
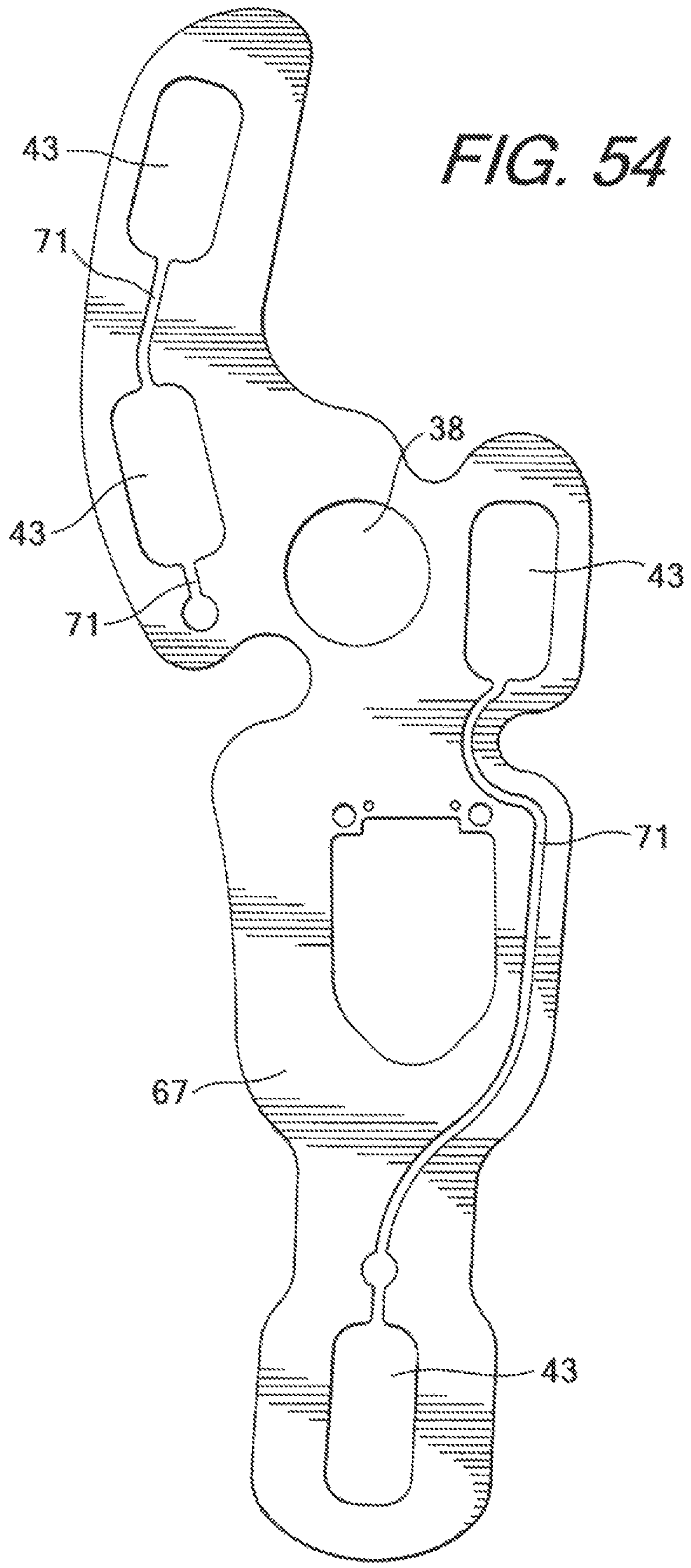
FIG. 54 is a top view of a spacer layer of the insert of FIG. 52.
Figure 55:
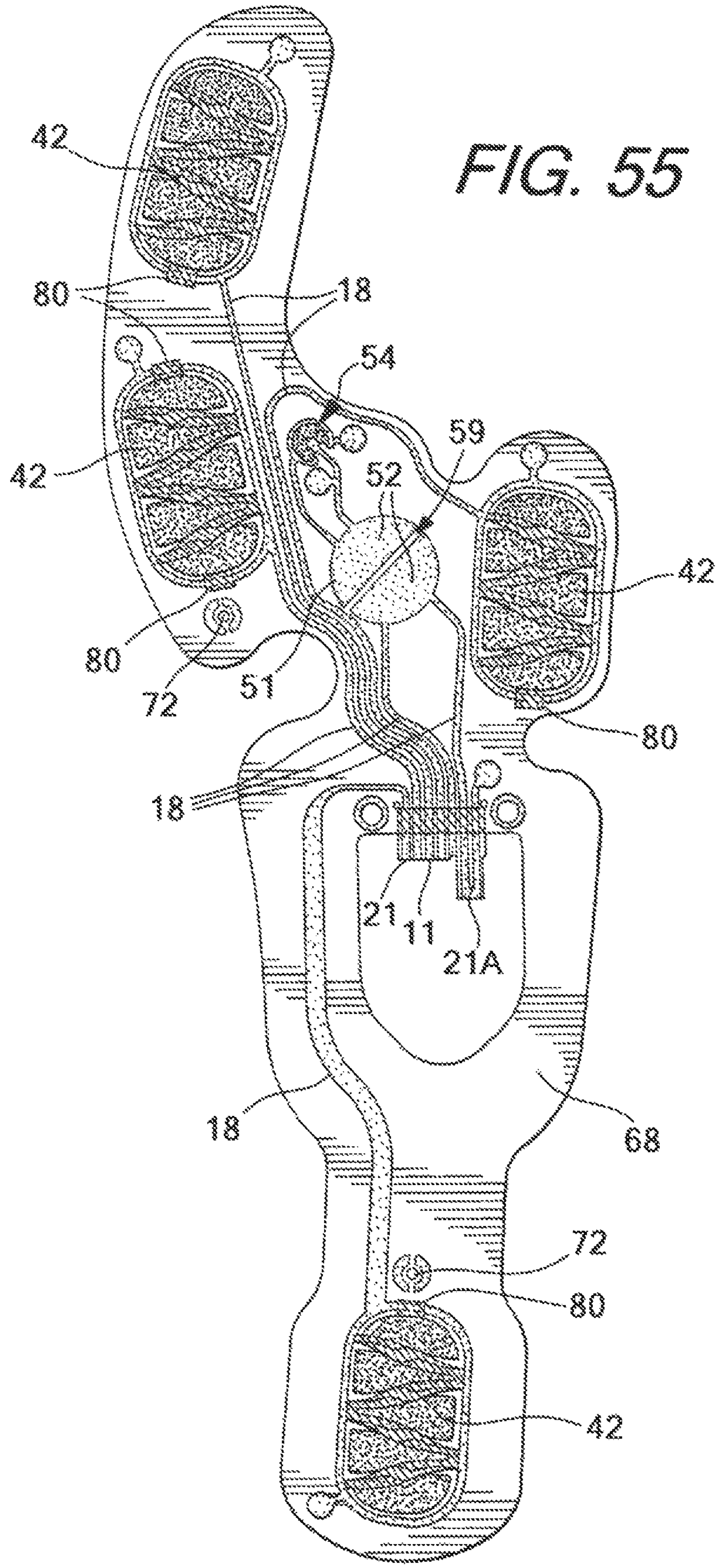
FIG. 55 is a top view of a second layer of the insert of FIG. 52.
Figure 56:
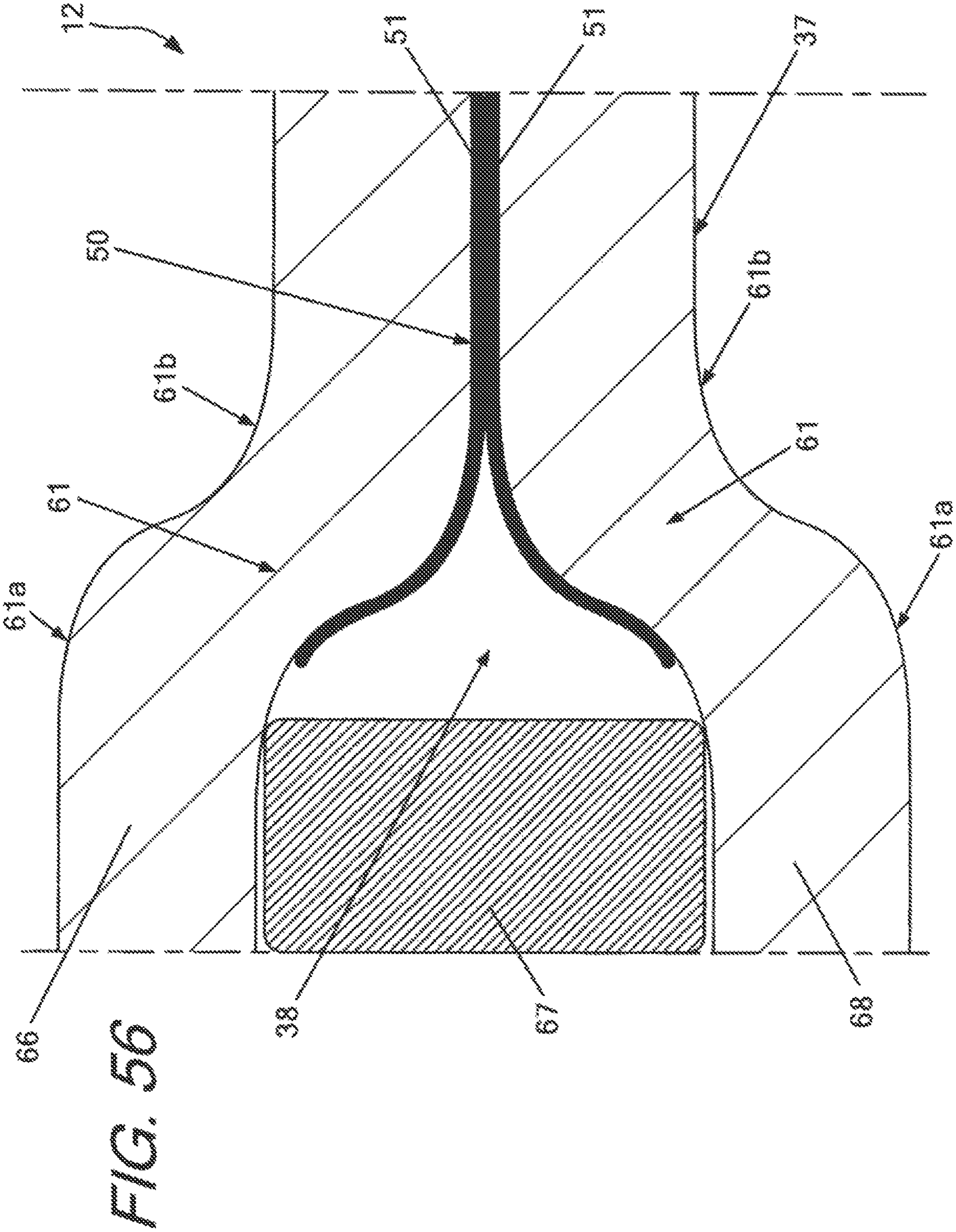
FIG. 56 is a cross-sectional view taken along lines 56-56 in FIG. 52.

The connections at the port 14 in the sensor system 712 of FIGS. 49-51 are similar to those in the embodiment of FIGS. 3-22B and illustrated schematically in FIG. 20, including a power terminal 104*a*, a measurement terminal 104*b*, and four sensor terminals 104*c-f*. Resistivity/resistance measurements may be completed in the same or a similar manner as described above. The circuit in the embodiment of FIGS. 48-51 is similar to that shown in FIG. 20, however this embodiment includes only a single fixed resistor 53, rather than two fixed resistors 53, 54 in parallel as in the embodiment of FIGS. 3-22B. Additionally, each sensor 16 in the embodiment of FIGS. 3-22B may be considered to be five resistors in parallel, while each sensor 16 in the sensor system 712 of FIGS. 49-51 may be considered to be two resistors in parallel (contact 742) arranged in series with three additional resistors in parallel (contact 740). In another embodiment, the sensor system 712 of FIGS. 48-51 may be wired to have two fixed resistors in parallel or any other resistor configuration described herein. It is understood that because the leads 18 connected to the port 14 exist on only the second layer 68, no pathway 50 between the layers 66, 68 is necessary in this embodiment. Accordingly, the spacer layer 67 in the sensor system 712 of FIGS. 48-51 may not contain the hole 38 as in the spacer layer 67 of FIGS. 3-22B.

The insert 37 may be constructed by depositing the various components on a polymer (e.g. PET) film. In one embodiment, the insert 37 is constructed by first depositing the conductive metallic material on each layer 66, 68, such as by printing in the traced pattern of the leads 18 (including the distribution lead 18A, the conductive portions 51 of the pathway 50, the inner and outer sections 55, 56 of the resistors 53, 54, etc. The additional carbon material can then be deposited on each layer 66, 68, such as by printing, to form the contacts 40, 42, the stiffener 60 of the pathway 50, the bridge 57 of the resistors 53, 54, etc. Any additional components can then be deposited, such as any dielectric portions. The layers 66, 68 may be printed on PET sheets and then cut out to form the outer peripheral shape after printing in one embodiment.

The port 14 is configured for communication of data collected by the sensors 16 to an outside source, in one or more known manners. In one embodiment, the port 14 is a universal communication port, configured for communication of data in a universally readable format. In the embodiments shown in FIGS. 3-22B, the port 14 includes an interface 20 for connection to an electronic module 22, shown in connection with the port 14 in FIG. 3. Additionally, in this embodiment, the port 14 is associated with the housing 24 for insertion of the electronic module 22, located in the well 135 in the middle arch or midfoot region of the midsole 131. As illustrated in FIGS. 7-16, the sensor leads 18 converge together to form a consolidated interface 20 at their terminals 11, in order to connect to the port 14. In one embodiment, the consolidated interface may include individual connection of the sensor leads 18 to the port interface 20, such as through a plurality of electrical contacts. In another embodiment, the sensor leads 18 could be consolidated to form an external interface, such as a plug-type interface or another configuration, and in a further embodiment, the sensor leads 18 may form a non-consolidated interface, with each lead 18 having its own separate terminal 11. As also described below, the module 22 may have an interface 23 for connection to the port interface 20 and/or the sensor leads 18.

In the embodiment shown in FIGS. 3-22B, the interface 20 takes the form of electrical contacts or terminals 11. In one embodiment, the terminals 11 are formed on a tongue or extension 21 that extends from one of the layers 66, 68 into the hole 27 provided for the housing 24. The extension consolidates the ends of the leads 18 to a single area to form the interface 20. In the embodiment of FIGS. 3-22B, the extension 21 extends from the second layer 68 into the hole 27, and is bent downward within the housing 24 to place the terminals 11 within the housing 24 and make the interface 20 accessible within the housing 24. The second layer 68 further has slits 83 on both sides of the extension 21 in this embodiment, to increase the length of the extension 21 and permit the extension 21 to be bent downwardly and extend down into the housing 24. The rounded ends of the slits 83 can resist formation and/or propagation of cracks and tears in the material of the second layer 68 around the extension 21. The extension 21 may pass underneath the flange 28 of the housing 24 and through a slot or other space underneath the lip 28 in order to extend into the housing 24. When the flange 28 is a separate piece, such as in the embodiment shown in FIGS. 31-32, the extension 21 may be inserted between the flange 28 and the tub 29 before the flange 28 is connected to the tub 29. In the embodiment shown in FIGS. 3-22B, the extension 21 is formed of the same polymeric film material as the second layer 68 and is integral (e.g. formed as a single piece) with the second layer 68. In other embodiments, the extension 21 may extend from the first layer 66, may include portions connected to both layers 66, 68, and/or may be formed of a separate piece that is connected to one or both layers.

The extension 21 as illustrated in FIGS. 3-22B and 32 has a reinforcing material 81 that is connected to the extension to reinforce a portion of the extension 21. This reinforcing material 81 may be selected from a number of different materials that provide strength, stiffness, wear resistance, and other reinforcement. For example, the reinforcing material 81 may be formed of the same material as the dielectric material 80 used to insulate between the layers 66, 68 at the channels 71, such as an acrylic ink or other UV-curable ink. In the embodiment illustrated in FIGS. 3-22B and 32, the reinforcing material 81 is in the form of an elongated strip that extends across the entire width of the extension 21 midway along the length of the extension 21. The extension 21 in this embodiment extends from the second layer 68 into the hole 27, and the reinforcing material 81 is deposited on the top side of the extension 21, extending over and across the ends of the leads 18. The reinforcing material 81 may have a stiffness that is greater than the stiffness of the material of the leads 18 in one embodiment, and may also have a greater stiffness than the film material forming the layers 66, 68 in another embodiment.

In the configuration illustrated in FIGS. 3-22B and 32, the extension 21 bends downwardly into the well 135 and into the housing 24, as discussed above, to place the terminals 11 within the housing 24 and forming the interface 20 within the housing 24. As shown in FIG. 32, the extension 21 has a bend area 84 where the extension 21 bends downwardly at the peripheral edge of the housing 24, to extend downwardly along the side wall 25 of the housing 24. The bend area 84 is generally linear and extends transversely across the extension 21. In the embodiment illustrated, the reinforcing material 81 is located on the extension 21 such that the strip of reinforcing material 81 extends transversely across the extension 21 at the bend area 84 and generally parallel to the bend area 84. In one embodiment, the reinforcing material 81 is formed as an elongated rectangular strip and has a width that is sufficient so that the reinforcing material 81 covers the entire bend area 84. In this position, the reinforcing material 81 serves several functions. One such function is protecting the leads 18 and/or the film of the extension 21 from damage due to the bending of the extension 21. Another such function is protecting the leads 18 and/or the film of the extension 21 from wear and abrasion at the bend area 84, such as from rubbing against the housing 24 at that location. A further such function is to add stiffness and/or strength to the extension 21. Other benefits of the reinforcing material 81 may be apparent to those skilled in the art. It is understood that, in other embodiments, the reinforcing material 81 may be positioned, shaped, or configured differently, or the reinforcing material 81 may additionally or alternately be used in a different location to impart strength, stiffness, wear resistance, etc. to another component of the sensor assembly 12. In a further embodiment, no reinforcing material 81 may be used, or the majority of the extension 21 may be covered by the reinforcing material 81.

The housing 24 may contain connection structure, such as connector pins or springs (not shown) for establishing connection between the interface 20 and the module 22. In one embodiment, the port 14 includes an electrical connector 82 forming the interface 20, which may include contacts that individually attach to the terminals 11, as mentioned above and shown in FIG. 32. The connector 82 may connect to the extension 21 and the terminals 11 via a crimping connection. The interface 20 in this embodiment includes seven terminals: four terminals 11 each individually connected to one of the sensors 16, one terminal 11 serving as the measurement terminal (104*b* in FIG. 20), and one terminal serving as a power terminal (104*a* in FIG. 20) to apply a voltage to the circuit 10. As discussed above, the power terminal may instead be configured as a ground terminal in another embodiment, with the sensor terminals (104*c-f* in FIG. 20) being configured as power terminals. As illustrated in FIG. 12, the arrangement of the sensors 16, the leads 18, and other components of the sensor system 12 may be different between the left and right foot inserts 37, and the sensors 16 may be connected to different terminals 11 in the left insert 37 as compared to the right insert 37. In this embodiment, the first four terminals 11 are still reserved for connection to the sensors 16 (albeit in potentially a different order), with the fifth, sixth, and seventh terminals 11 retaining the same function in both the left and right inserts 37. This configuration may be different in other embodiments. In another embodiment, the module 22 may be specifically configured for use with a left or right shoe 100 and insert 37. The seventh terminal may be utilized for powering of accessories, such as a unique identification chip. In one embodiment, the sixth and seventh terminals 11 are extended on a tail 21A that extends from the end of the extension 21. An accessory may be connected across the two terminals 11 on the tail 21A to power the accessory. The accessory may include a small printed circuit board (PCB) with a memory chip that are attached via anisotropic contact formation to the tail 21A. In one embodiment, an accessory chip may include information uniquely identifying the article of footwear 100, such as a serial number, as well as substantive information such as whether the footwear 100 is a left or right shoe, a men's or women's shoe, a specific type of shoe (e.g. running, tennis, basketball, etc.), and other types of information. This information may be read by the module 22 and subsequently used in analysis, presentation, and/or organization of data from the sensors. The accessory may be sealed into the housing 24, such as via epoxy or other material.

Figure 61:
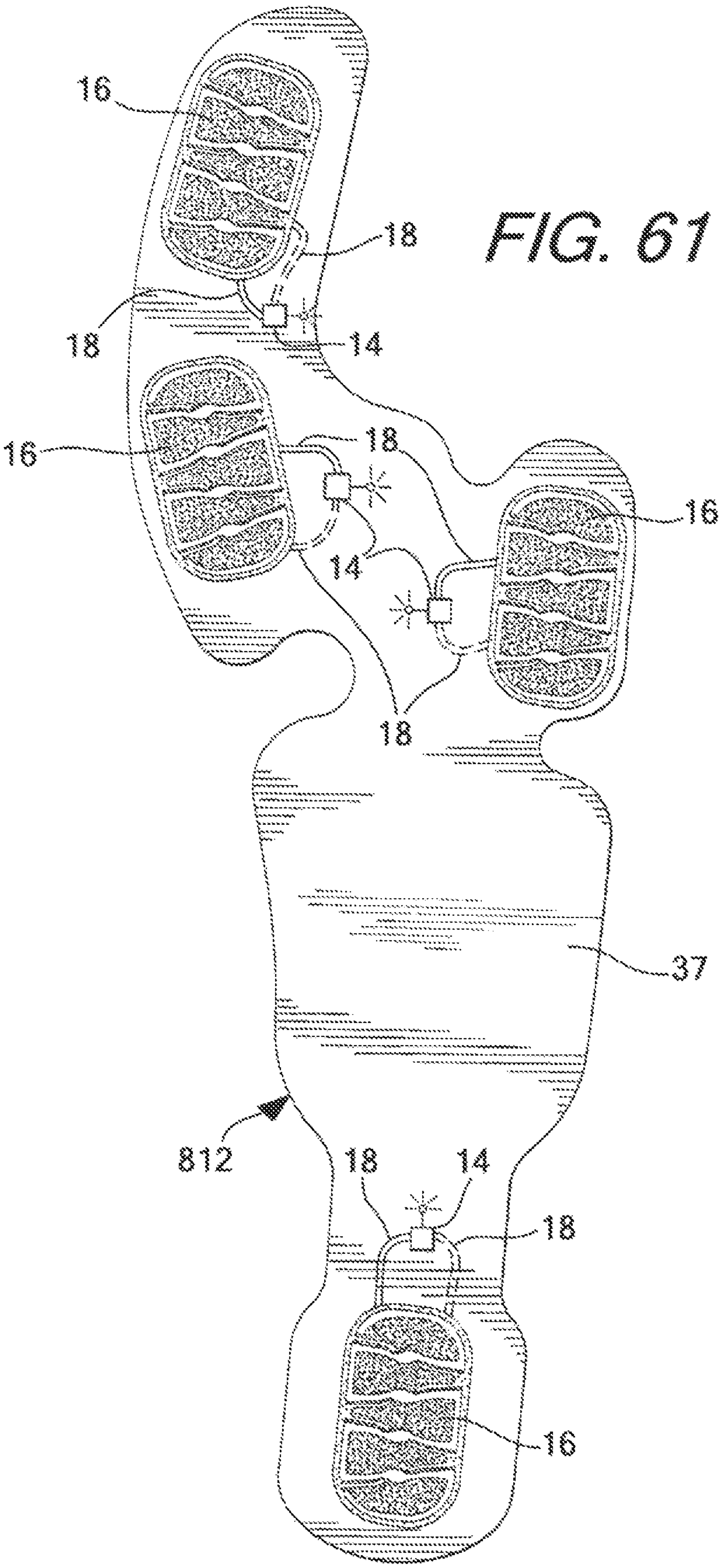
FIG. 61 is a perspective view of another embodiment of a sensor system according to aspects of the present invention.

The port 14 is adapted for connection to a variety of different electronic modules 22, which may be as simple as a memory component (e.g., a flash drive) or which may contain more complex features. It is understood that the module 22 could be as complex a component as a personal computer, mobile device, server, etc. The port 14 is configured for transmitting data gathered by the sensors 16 to the module 22 for storage, transmission, and/or processing. In some embodiments, the port 14, the sensors 16, and/or other components of the sensor system 12 may be configured for processing the data. The port 14, sensors 16, and/or other components of the sensor system 12 may additionally or alternately be configured for transmission of data directly to an external device 110 or a plurality of modules 22 and/or external devices 110. It is understood that the port 14, the sensors 16, and/or other components of the sensor system 12 may include appropriate hardware, software, etc., for these purposes. Examples of a housing and electronic modules in a footwear article are illustrated in U.S. patent application Ser. No. 11/416,458, published as U.S. Patent Application Publication No. 2007/0260421, which is incorporated by reference herein and made part hereof. Although the port 14 is illustrated with electronic terminals 11 forming an interface 20 for connection to a module 22, in other embodiments, the port 14 may contain one or more additional or alternate communication interfaces. For example, the port 14 may contain or comprise a USB port, a Firewire port, 16-pin port, or other type of physical contact-based connection, or may include a wireless or contactless communication interface, such as an interface for Wi-Fi, Bluetooth, near-field communication, RFID, Bluetooth Low Energy, Zigbee, or other wireless communication technique, or an interface for infrared or other optical communication technique. In another embodiment, the sensor system 12 may include more than one port 14 configured for communication with one or more modules 22 or external devices 110. This configuration may alternately be considered to be a single distributed port 14. For example, each of the sensors 16 may have a separate port 14 for communication with one or more electronic modules 22, as in the embodiment of the sensor system 812 illustrated in FIG. 61. The separate ports 14 may be configured for wireless communication using wireless or contactless communications as described above. In one embodiment, each port 14 may include an RFID chip with an antenna, and in another embodiment, the port(s) 14 may utilize the user's body as a transmission system, transmitting information from the user's feet to a module 22 located elsewhere on the user's body. The ports 14 in this embodiment are connected to the sensors 16 by leads 18, and it is understood that the leads 18 in broken lines in FIG. 61 represent leads 18 on a lower layer of the insert 37. The ports 14 may be located between the layers of the insert 37, within a hole in the insert 37, or above or below the insert 37 in various embodiments. It is understood that multiple or distributed port(s) 14 may be used, with combinations of two or more sensors connected to a single port 14. In further embodiments, the sensor system 12 may include one or more ports 14 having different configurations, which may include a combination of two or more configurations described herein.

The module 22 may additionally have one or multiple communication interfaces for connecting to an external device 110 to transmit the data for processing, as described below and shown in FIGS. 6 and 23. Such interfaces can include any of the contacted or contactless interfaces described above. In one example, the module 22 includes at least a retractable USB connection for connection to a computer and/or for charging a battery of the module 22. In another example, the module 22 may be configured for contacted or contactless connection to a mobile device, such as a watch, cell phone, portable music player, etc. The module 22 may be configured for wireless communication with the external device 110, which allows the device 22 to remain in the footwear 100. However, in another embodiment, the module 22 may be configured to be removed from the footwear 100 to be directly connected to the external device 110 for data transfer, such as by the retractable USB connection described above. In a wireless embodiment, the module 22 may be connected to an antenna for wireless communication. The antenna may be shaped, sized, and positioned for use with the appropriate transmission frequency for the selected wireless communication method. Additionally, the antenna may be located internally within the module 22 or external to the module. In one example, the sensor system 12 itself (such as the leads 18 and conductive portions of the sensors 16) could be used to form an antenna. The module 22 may further be placed, positioned, and/or configured in order to improve antenna reception, and in one embodiment, may use a portion of the user's body as an antenna. In one embodiment, the module 22 may be permanently mounted within the footwear 100, or alternately may be removable at the option of the user and capable of remaining in the footwear 100 if desired. Additionally, as further explained below, the module 22 may be removed and replaced with another module 22 programmed and/or configured for gathering and/or utilizing data from the sensors 16 in another manner. If the module 22 is permanently mounted within the footwear 100, the sensor system 12 may further contain an external port (not shown) to allow for data transfer and/or battery charging, such as a USB or Firewire port. It is understood that the module 22 may be configured for both contacted and contactless communication.

While the port 14 may be located in a variety of positions without departing from the invention, in one embodiment, the port 14 is provided at a position and orientation and/or is otherwise structured so as to avoid or minimize contact with and/or irritation of the wearer's foot, e.g., as the wearer steps down in and/or otherwise uses the article of footwear 100, such as during an athletic activity. The positioning of the port 14 in FIGS. 3-4 illustrates one such example. In another embodiment, the port 14 is located proximate the heel or instep regions of the shoe 100. Other features of the footwear structure 100 may help reduce or avoid contact between the wearer's foot and the port 14 (or an element connected to the port 14) and improve the overall comfort of the footwear structure 100. For example, as described above and illustrated in FIGS. 3-5, the foot contacting member 133 may fit over and at least partially cover the port 14, thereby providing a layer of padding between the wearer's foot and the port 14. Additional features for reducing contact between and modulating any undesired feel of the port 14 at the wearer's foot may be used. If desired, the opening to the port 14 may be provided through the top surface of the foot contacting member 133 without departing from the invention. Such a construction may be used, for example, when the housing 24, electronic module 22, and other features of the port 14 include structures and/or are made from materials so as to modulate the feel at the user's foot, when additional comfort and feel modulating elements are provided, etc. Any of the various features described above that help reduce or avoid contact between the wearer's foot and a housing (or an element received in the housing) and improve the overall comfort of the footwear structure may be provided without departing from this invention, including the various features described above in conjunction with the attached figures, as well as other known methods and techniques.

FIGS. 62-76 disclose further views of one embodiment of the port 14 configured to be utilized with the insert member 37. Similar structures described above will be designated with identical or similar reference numerals. This embodiment and variations of the embodiment are described in detail below. As discussed and disclosed herein, the port 14 defines or supports an interface 20 for an operable connection with the module 22. The module 22 will also be described in greater detail below. Through the operable connection between the port 14 and the module 22, data sensed by the sensor assembly 12 can be acquired, stored and/or processed for further use and analysis.

Figure 62:
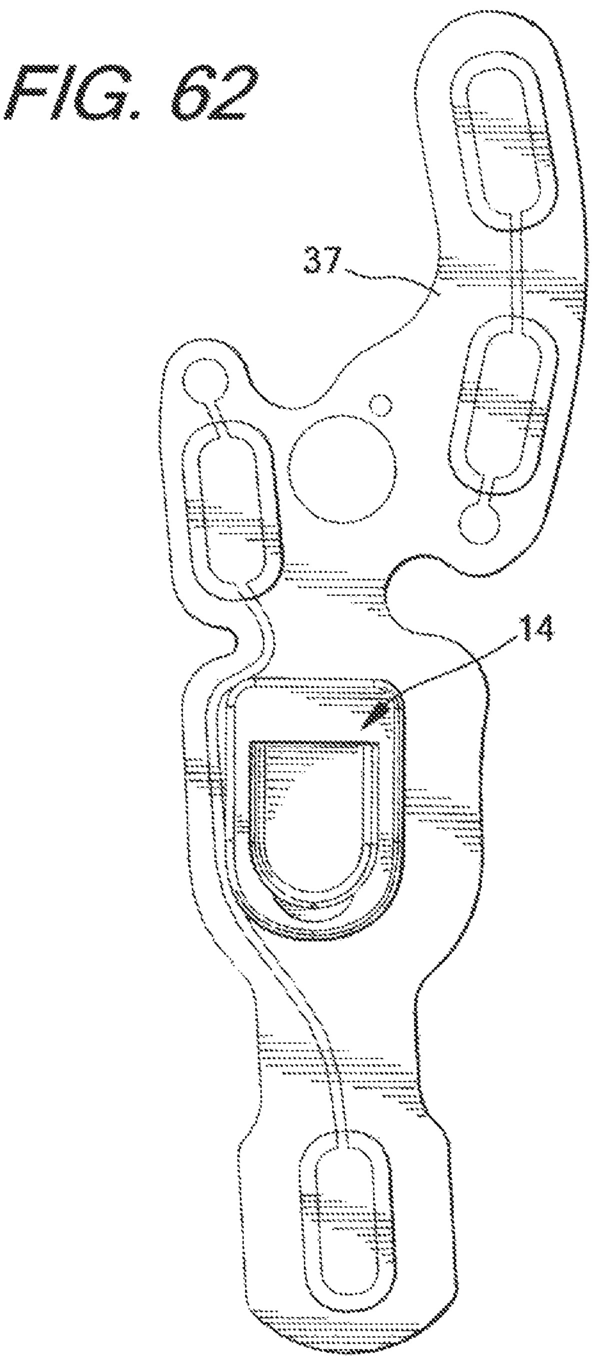
FIGS. 62-64 illustrate a plan view and perspective views of the port in the insert member according to aspects of the invention.
Figure 64:
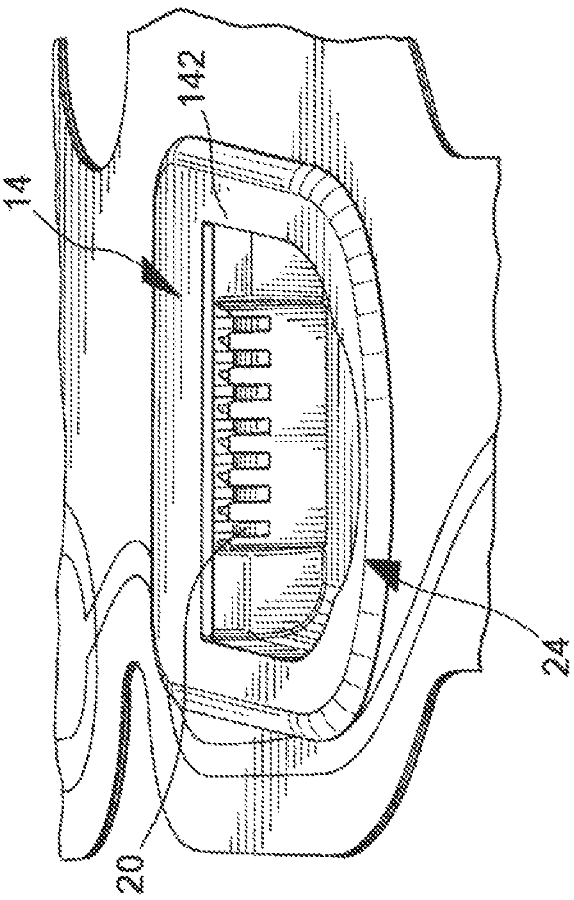
Figure 63:
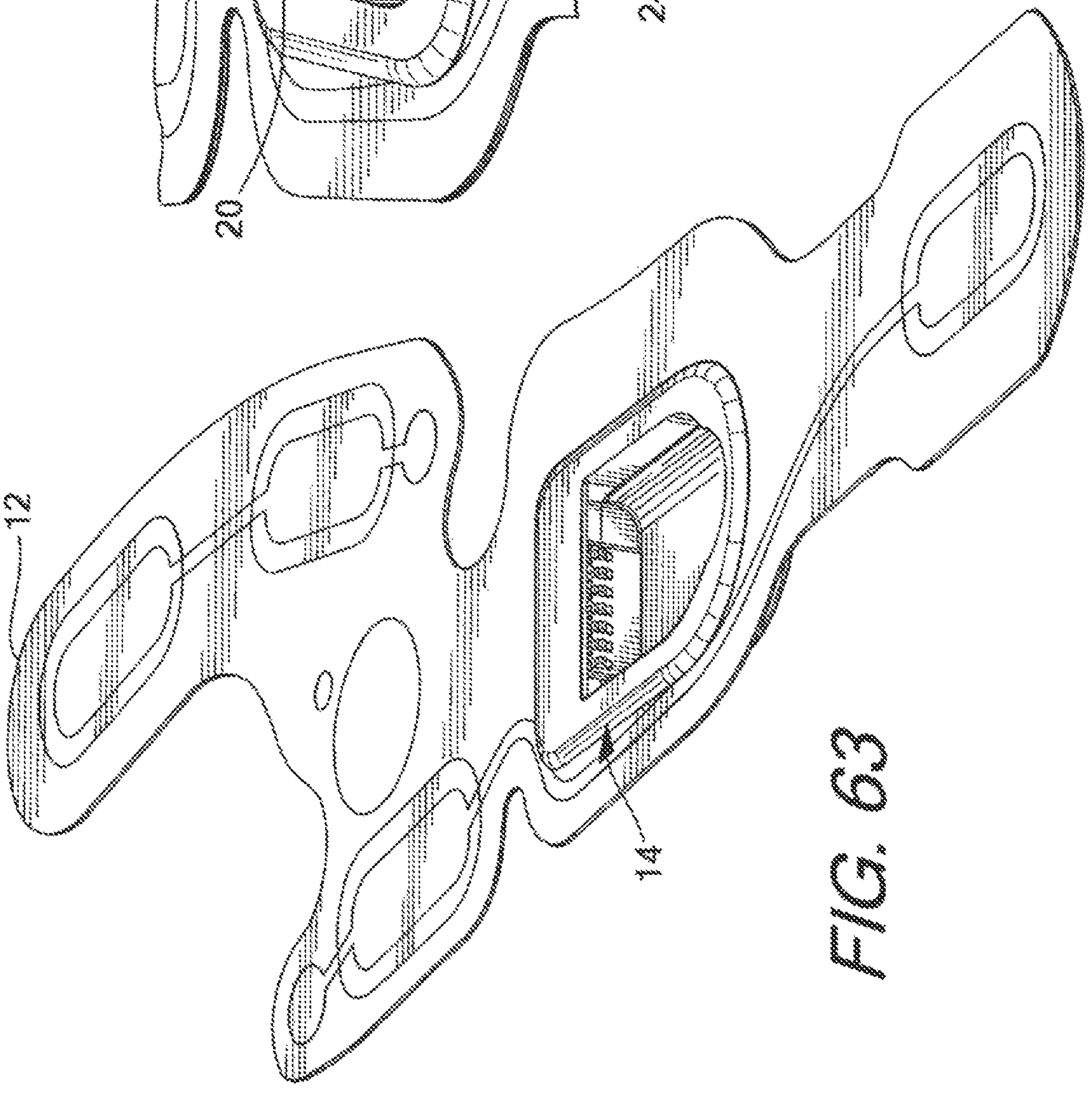

As appreciated from FIGS. 62-64, the port 14 is generally supported at a mid-portion of the insert assembly 37. The port 14 generally includes the housing 24 that supports an interface assembly 156. As will be described in greater detail below, the interface assembly 156 is operably connected to the extension 21 having the leads 11 thereon of the insert member 37. With such connection, the interface 20 is established for further operable connection with the interface 23 of the module 22.

Figure 65:
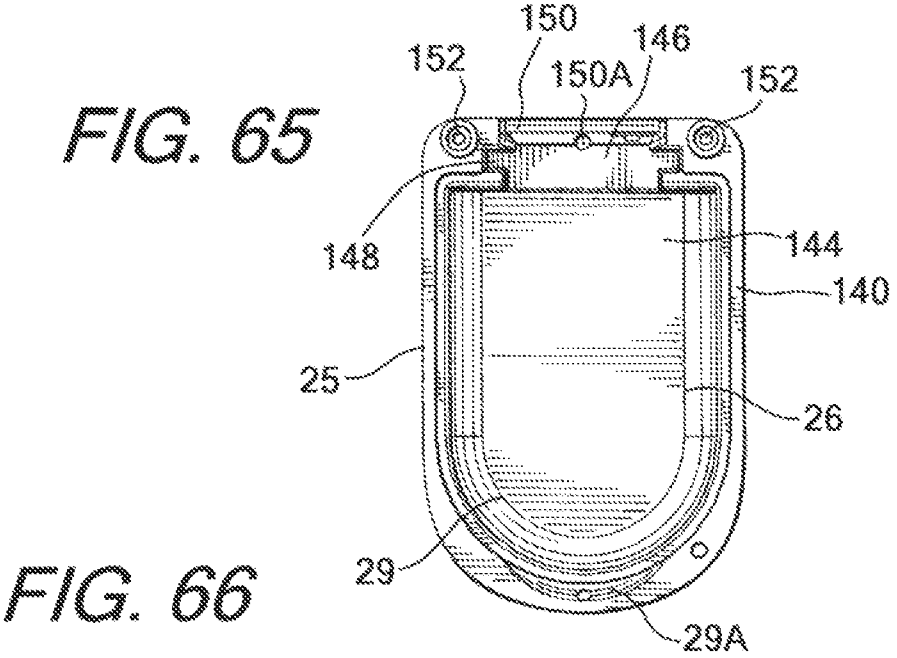
FIGS. 65-67 illustrate components of a housing of the port.
Figure 66:
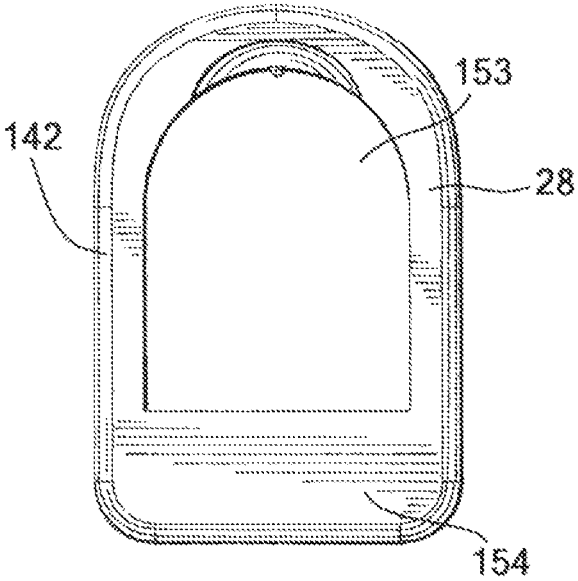
Figure 67:
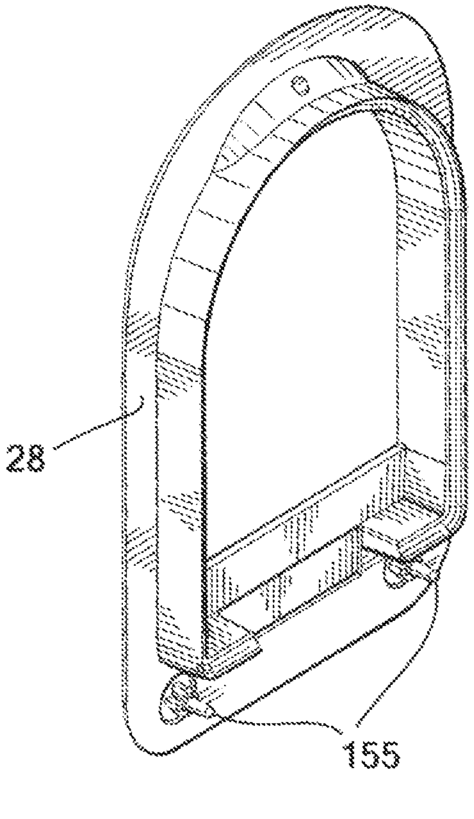
Figure 70:
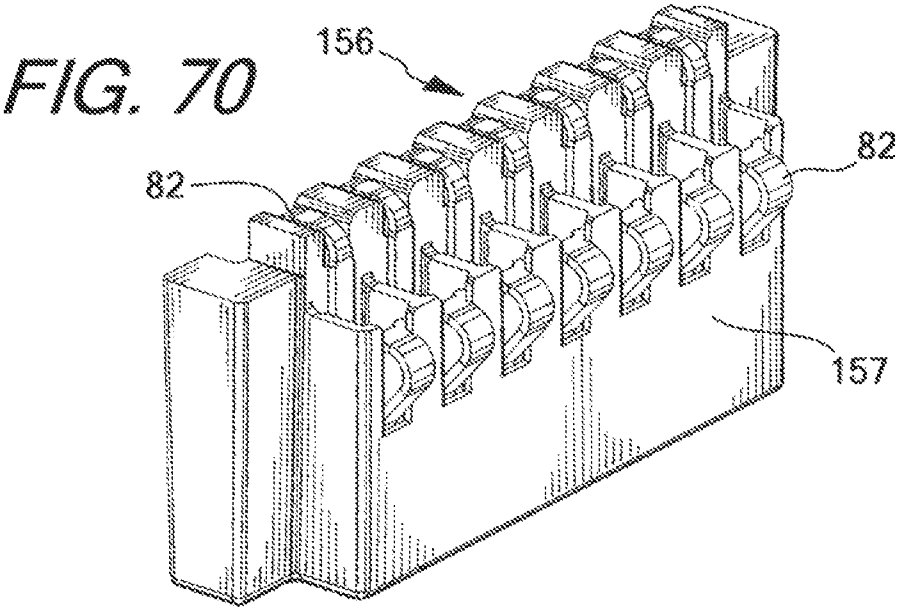
Figure 71:
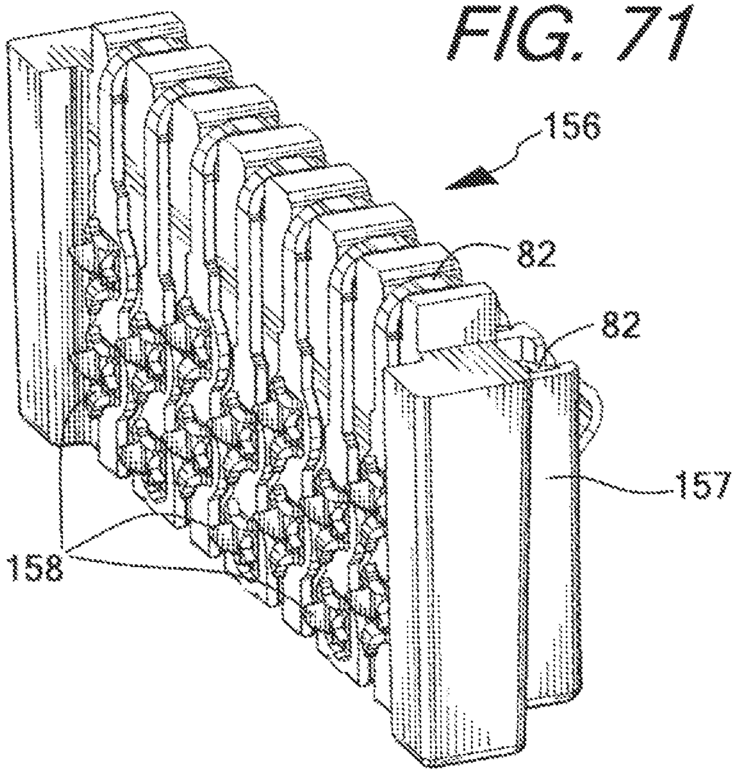

As further shown in FIGS. 65-67, the housing 24 in this embodiment includes a base member 140 and a cover member 142. The base member 140 may correspond to the tub 29 as described above that defines the side walls 25 and the base wall 26. A first end of the base member 140 has a generally squared configuration that receives the extension 21 of the insert member 37. A second end of the base member 140 has a rounded configuration. The base member 140 defines a first section 144 and a second section 146. The first section 144 is generally dimensioned to correspond in shape and receive the module 22, and the second section 146 is dimensioned to receive and support the interface assembly 156. The second section 146 further has a first lateral slot 148 and a second lateral slot 150 that are in communication with one another. The first lateral slot 148 may extend wider and be larger than the second lateral slot 150. The housing 24 further defines a projection 151 at the second end for retaining the module 22 in the housing 24. The finger recess 29A is generally positioned proximate the projection 151. The base member 140 further has a pair of receivers 152 for cooperation with the cover member 142.

As further shown in FIGS. 66-67, the cover member 142 has a central aperture 153 dimensioned to receive the module 22 therethrough. The cover member 142 further has a beam member 154 at a first end and a second end of the cover member 142 has a rounded configuration. The beam member 154 overhangs above a portion of the first section 144 when connected to the base member 140 as will be described. An underside of the cover member 142 has a pair of depending posts 155 that cooperate with the receivers 152 on the base member 140 as will be described. An outer periphery of the cover member 142 defines the lip or flange 28. In an exemplary embodiment, the cover member 142 may have depending walls that cooperatively define the side walls 25 of the housing 24. In such configuration, the base member 140 may define a ledge on the side wall to receive the depending walls on the cover member 142.

FIGS. 68-71 further show components of the interface assembly 156. The interface assembly 156 has a carrier 157 that supports the electrical connectors 82 such as described schematically in reference to FIG. 32. The electrical connectors 82 each have a distal end defining a contact that is resiliently supported by the carrier 157 that will cooperate with a corresponding contact on the module 22. The electrical connectors 82 have bends around the carrier 157 and have proximate ends having a plurality of fingers 158 thereon. In one embodiment, four fingers 158 are associated with each connector 82, and the fingers 158 may be arranged in a flower-petal arrangement. As explained in greater detail below, the interface assembly 156 may further include a filler material 159 or potting compound 159. It is also understood that ends 82A of the connectors are snapped off at a predetermined location prior to connection with the extension 21 of the insert member 37, as shown in FIG. 69.

Figure 72:
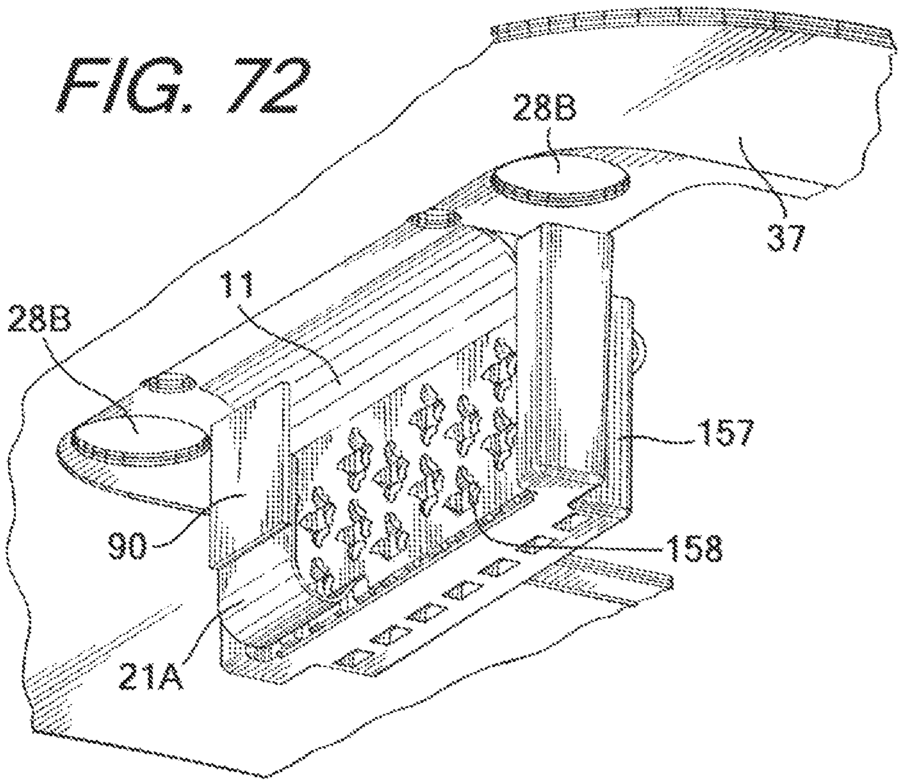
FIGS. 72-73 illustrate views of the interface assembly operably connected to the insert member.
Figure 73:
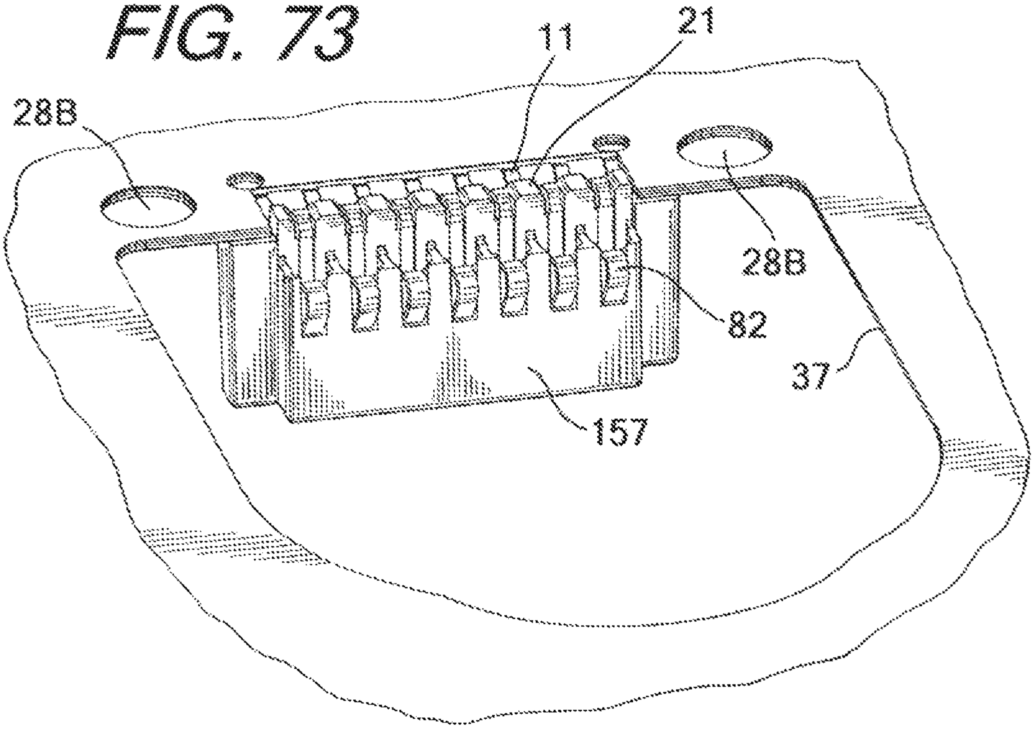
Figure 74:
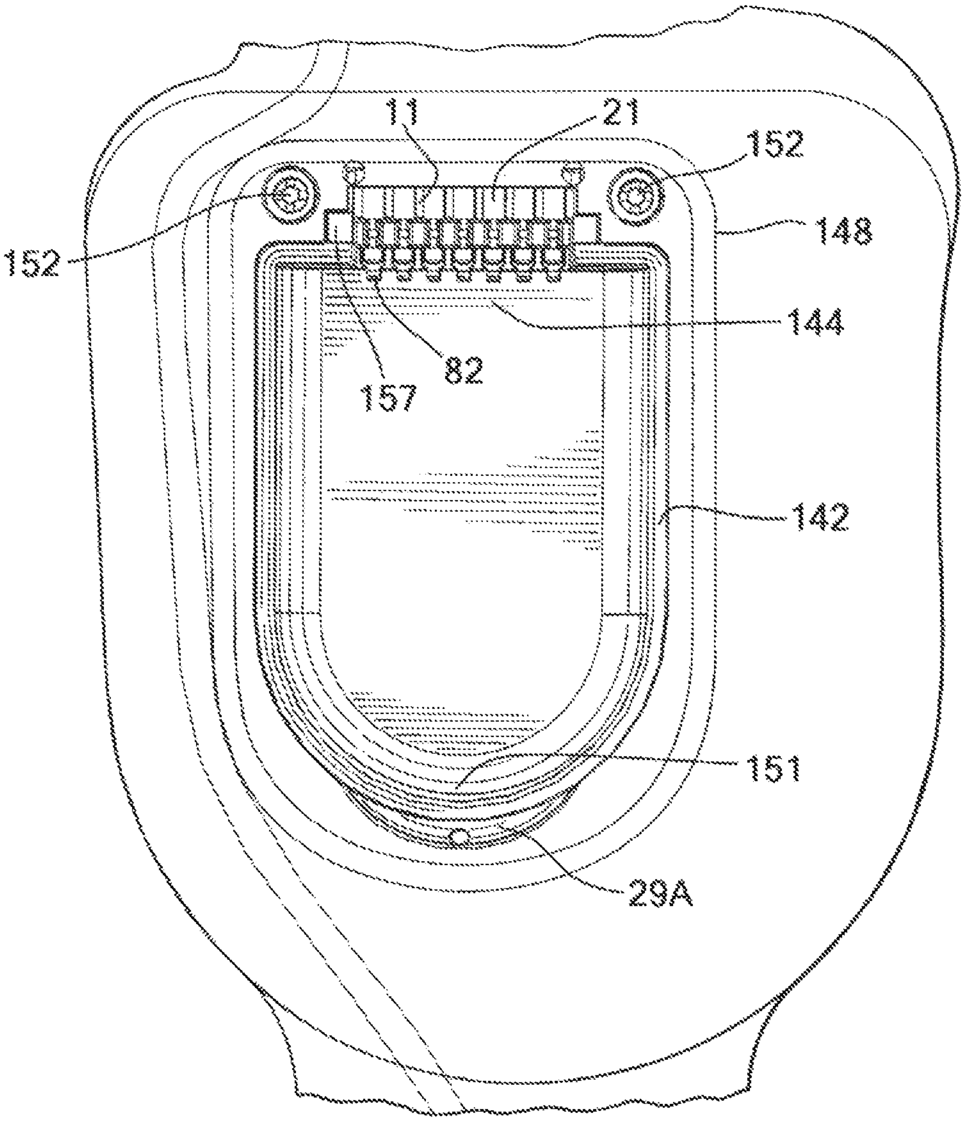
FIG. 74 is a partial enlarged plan view of the port connected to the insert member and having a cover member removed.
Figure 75:
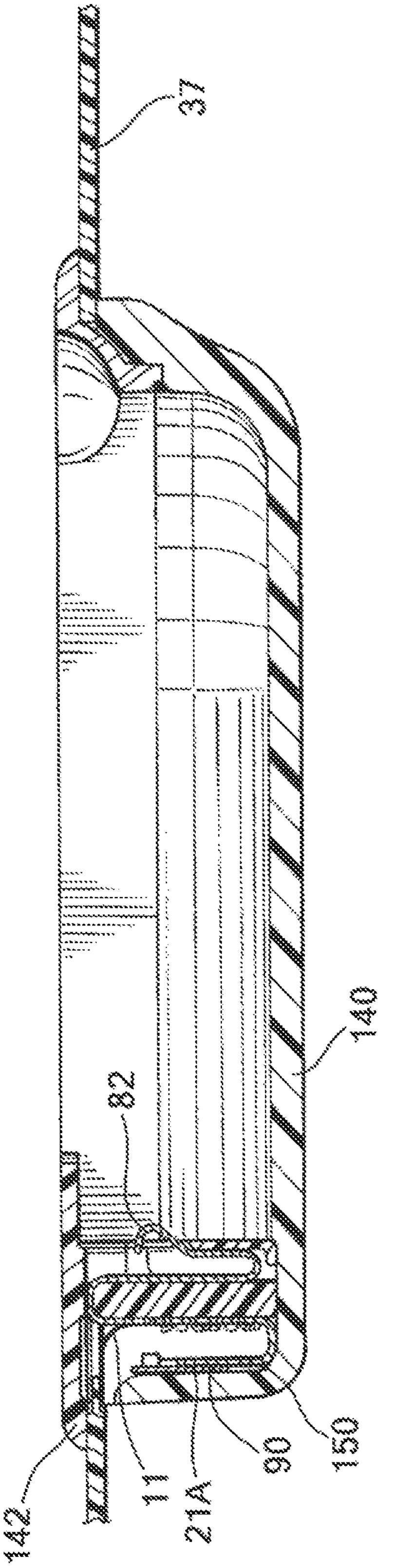
FIGS. 75-76 are side elevation views of the port attached to the insert member.
Figure 76:
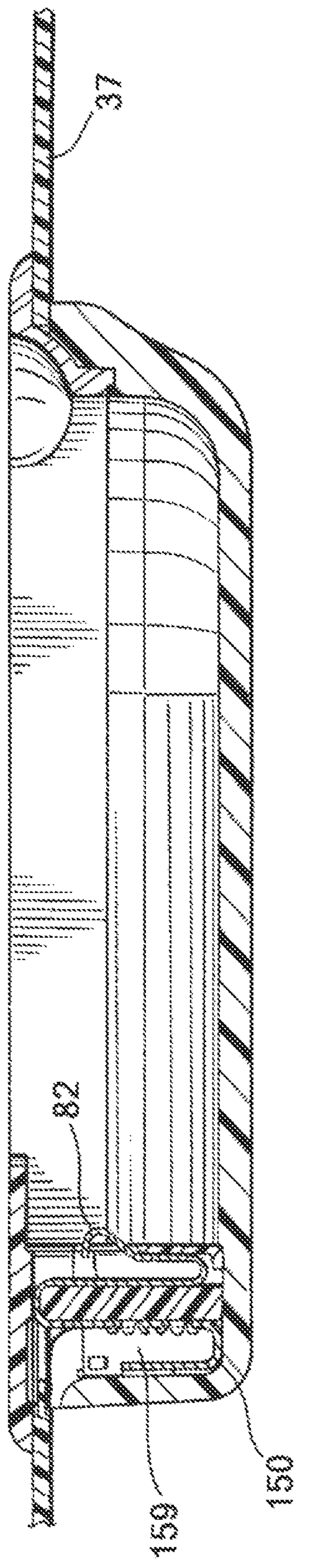
Figure 79:
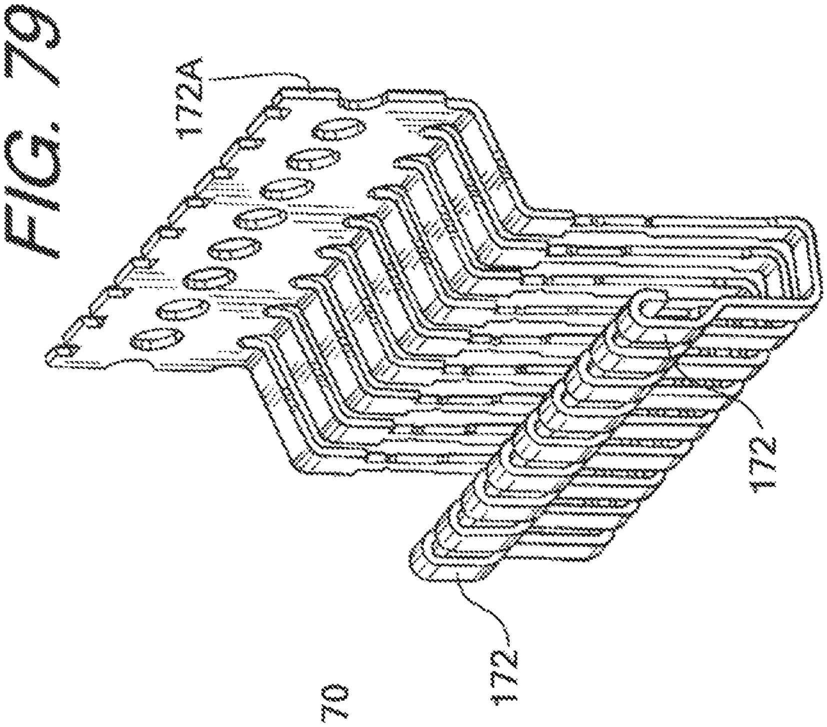
FIGS. 79-80 are perspective views of contacts and a module carrier according to aspects of the invention.
Figure 77:
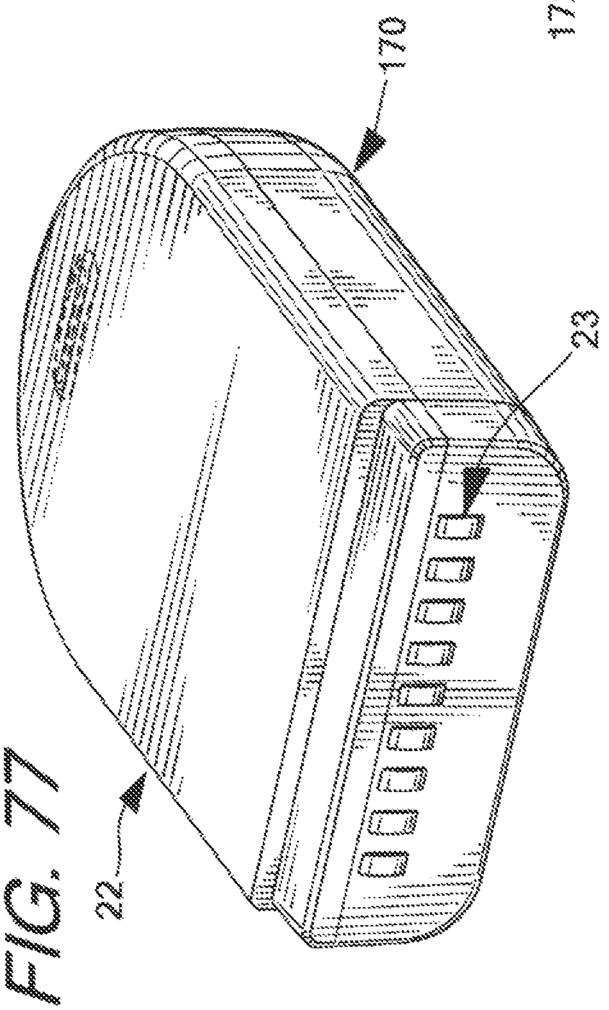
FIGS. 77-78 are additional views of the module according to aspects of the invention.
Figure 78:
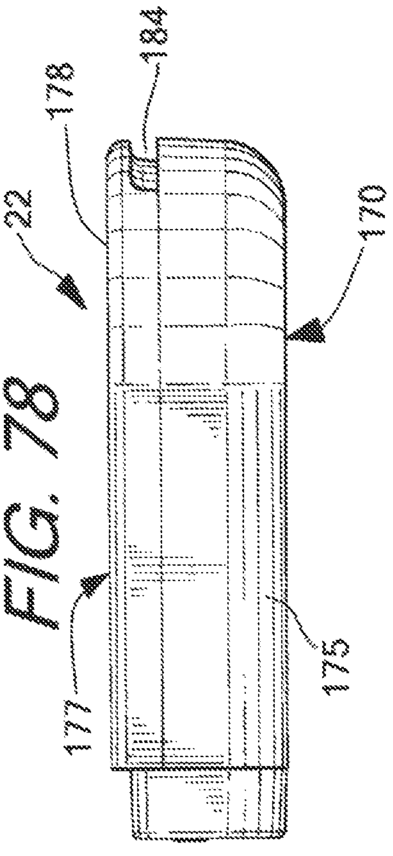
Figure 81:
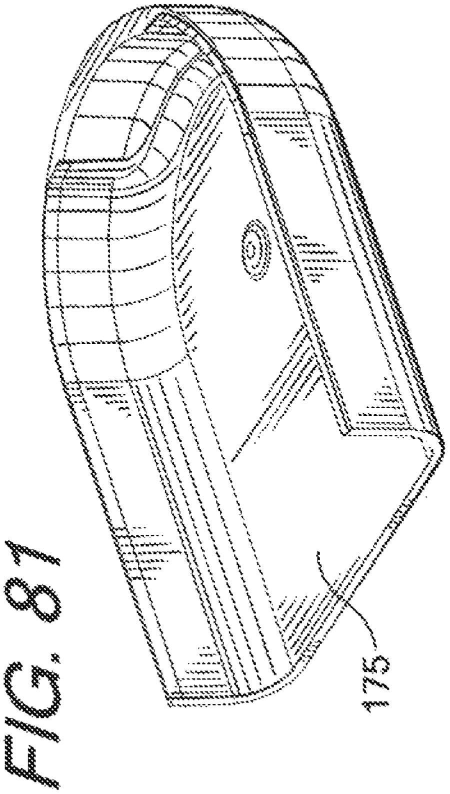
FIGS. 81-83 are perspective view of components of the module.
Figure 83:
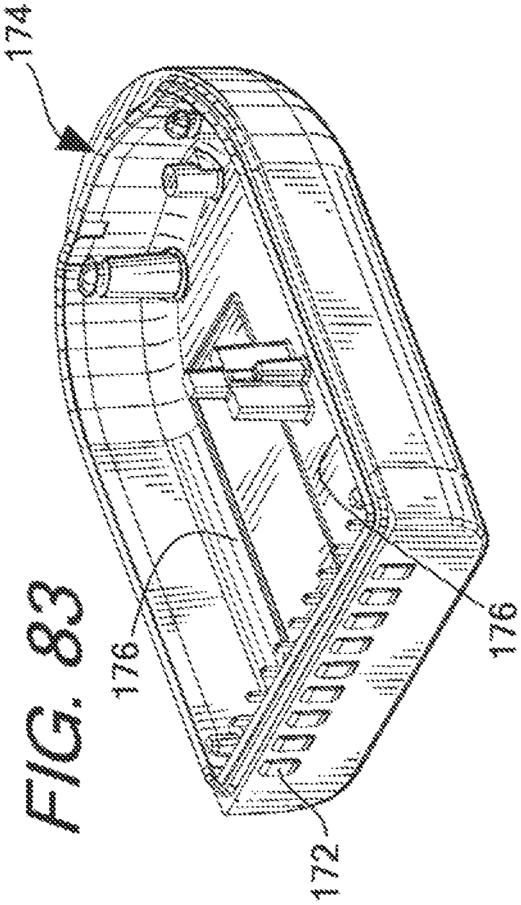
Figure 80:
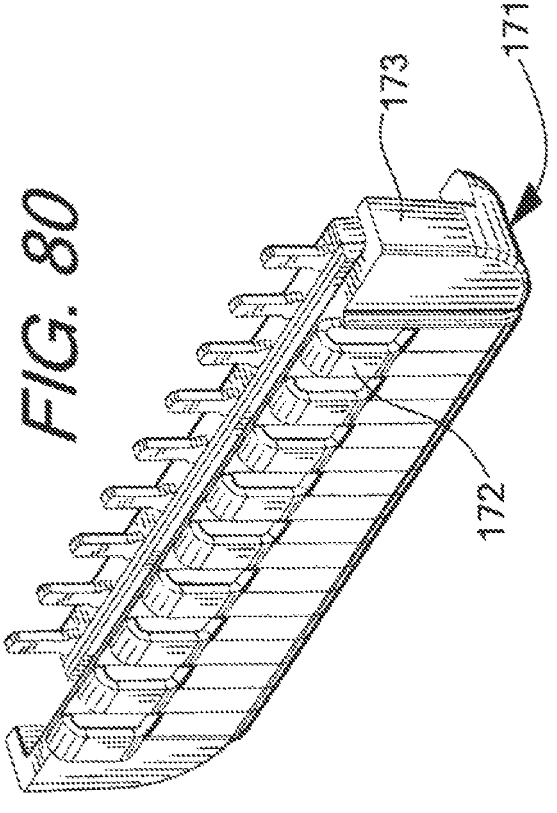
Figure 82:
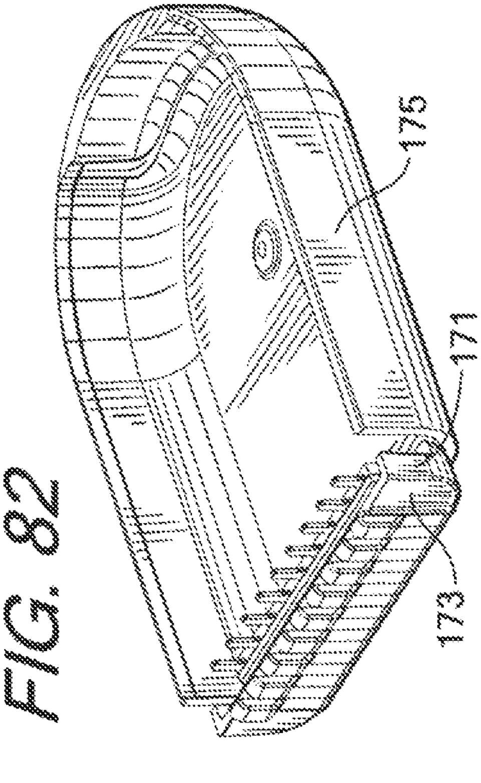

As shown in FIGS. 72-73, the interface assembly 156 is operably connected to the extension 21 having the leads 11 thereon of the insert member 37. To that end, the fingers 158 are connected to the extension 21 where there is engagement between the leads 11 and the connectors 82. This engagement can be seen and appreciated from FIG. 72 and also understood from FIG. 32. In an exemplary embodiment, the fingers 158 protrude through the extension 21, wherein each plurality of fingers 158 extend through and engage the extension 21 in a circumferential manner. As further shown in FIGS. 72, it is understood that the tail 21A can be further folded over to be positioned adjacent a back side of the extension 21. As discussed, the tail 21A having the sixth and seventh connectors may have a PCB member 90, which may be an unique identification chip, connected thereto to function as previously described. It is understood that the extension 21 and carrier 157 are positioned to depend from an upper planar surface of the insert member 37. As further shown in FIG. 74, the carrier 157 is positioned in the first lateral slot 148 of the base member 140 of the housing 24. The carrier 157 is dimensioned to fit snugly and be retained in the first lateral slot 148. The connectors 82 face into the first section 144 defined by the housing 24. As can be appreciated from FIGS. 75-76, it is understood that the filler material 159 or potting compound 159 may be injected into the second lateral slot 150 through an opening 150A (FIG. 65) in the base member 140 proximate the second lateral slot 150. The potting compound 159 may be a thermosetting plastic in an exemplary embodiment and could also be one or more other materials. The potting compound 159 fills the second lateral slot 150 and extends around the area wherein the extension 21 is connected to the connectors 82 held by the carrier 157, thus providing a protective connection. In one embodiment, the potting compound 159 maintains a desired amount of flexibility to enhance the connection between the extension 21 and the port 14. The potting compound 159 can resist shock and vibration while also resisting moisture ingress and corrosive agents. It is further understood that the base member 140 is positioned at the insert member 37 wherein the receivers 152 align with corresponding openings 28B through the insert member 37. The cover member 142 is positioned on the top surface of the insert member 37 wherein the depending posts 155 fit into the receivers 152 (FIGS. 62-67). An ultrasonic welding operation is performed to connect the cover member 142 to the base member 140. This connection is similar to the connection of the pegs 28A as shown in FIG. 31. Other connection techniques for connecting the cover member 142 to the base member 140 may be utilized in other embodiments, including snapping connections or other mechanical connections. It is understood that the beam member 154 extends over the interface 20 wherein the connectors 82 are protected in the housing 24. This configuration provides a robust connection of the port 14 to the insert member 37 and for further operable connection with the module 22 as described herein.

FIGS. 77-90 disclose additional views and features of one embodiment of the module 22, which is described in greater detail below. As previously discussed, the module 22 is received by and is operably connected to the port 14 to collect, store and/or process data received from the sensor assembly 12. It is understood that the module 22 houses various components for such purposes including but not limited to, printed circuit boards, power supplies, light members, interfaces, and different types of sensors, including multi-axis accelerometer, gyroscopes and/or magnetometers.

The module 22 generally includes a housing 170 that supports an interface 23 having electrical connectors that form contacts for cooperation with the interface 20 of the port 14. As explained in greater detail below, the contacts associated with the interface 23 of the module 22 are formed such that they are in a sealed configuration to protect against moisture ingress. The module 22 further has a dead-fronted LED light indicator that is only visually perceptible upon illumination. Finally, the module 22 utilizes a unique ground plane extender that enhances operation of the module 22.

As shown in FIGS. 79-83, the housing 170 of the module 22 supports an interface assembly 171. The interface assembly 171 has a plurality of connectors 172 and a module carrier 173. The connectors 172 each have distal ends that form contacts that collectively define the interface 23 of the module 22. It is understood that the connectors 172 are insert molded such that material is formed around the connectors 172 to define the module carrier 173. It is also understood that portions 172A (FIG. 79) of the connectors 172 are snapped off at a predetermined location to place the connectors 172 at a proper length for further operable connection. The housing 170 generally has a module base member 174 having an outer base member 175 and an inner base member 176. The housing 170 further has a module top member 177 having an outer top member 178 and an inner top member 179. The module base members 175, 176, the module top members 178, 179 and interface assembly 171 cooperate to provide a sealed configuration around the connectors 172. The connectors 172 may be considered to have an over-molded configuration. These components also form an inner cavity wherein the housing 170 supports internal components including a printed circuit board 180 that is operably connected to the connectors 172.

As discussed, the connectors 172 are insert molded wherein the module carrier 173 is formed around the connectors 172. It is understood that the outer base member 175 is formed such as in an injection-molding process and defines an end opening. In such process, the connectors 172 can be sufficiently supported in the mold to withstand the pressures associated with the injection-molding process. The interface assembly 171 and outer base member 175 are placed in a mold wherein the interface assembly 171 is positioned at the end opening and supported by the outer base member 175. In a further injection-molding process, additional material is injected into the mold to form inner base member 176. The inner base member 176 is formed around the module carrier 173 and distal ends of the connectors 172 and further against surfaces of the outer base member 175. An internal cavity is defined by the inner base member 176 wherein the printed circuit board 180 is supported therein as is known. It is understood that the connectors 172 are operably connected to the printed circuit board 180. It is further understood that other components of the module 22 are supported in the internal cavity. As explained in greater detail below, the connectors 172 are configured in a sealed fashion from the over-molding process.

Figure 88:
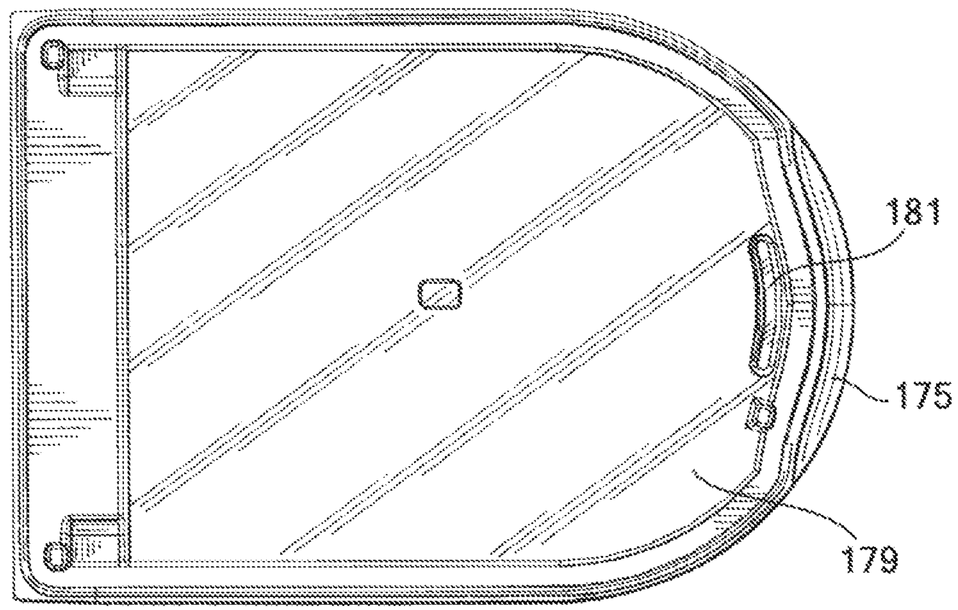
Figure 89:
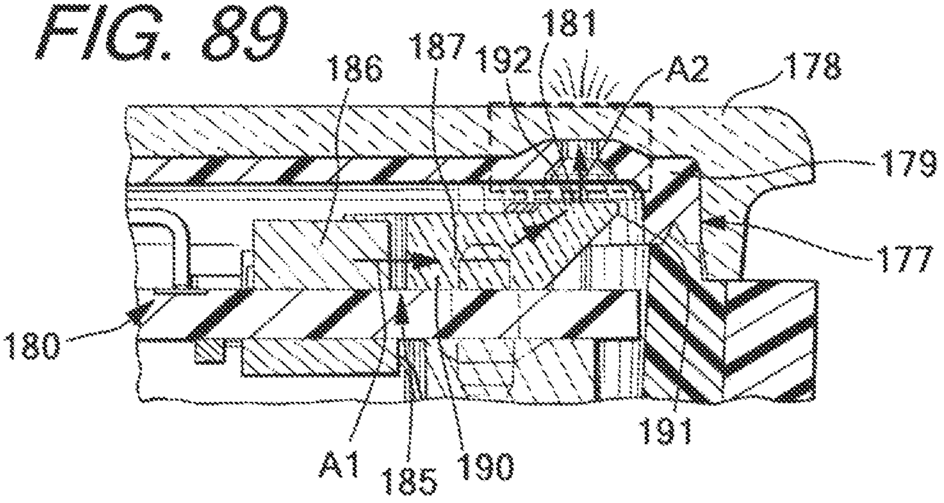
Figure 90:
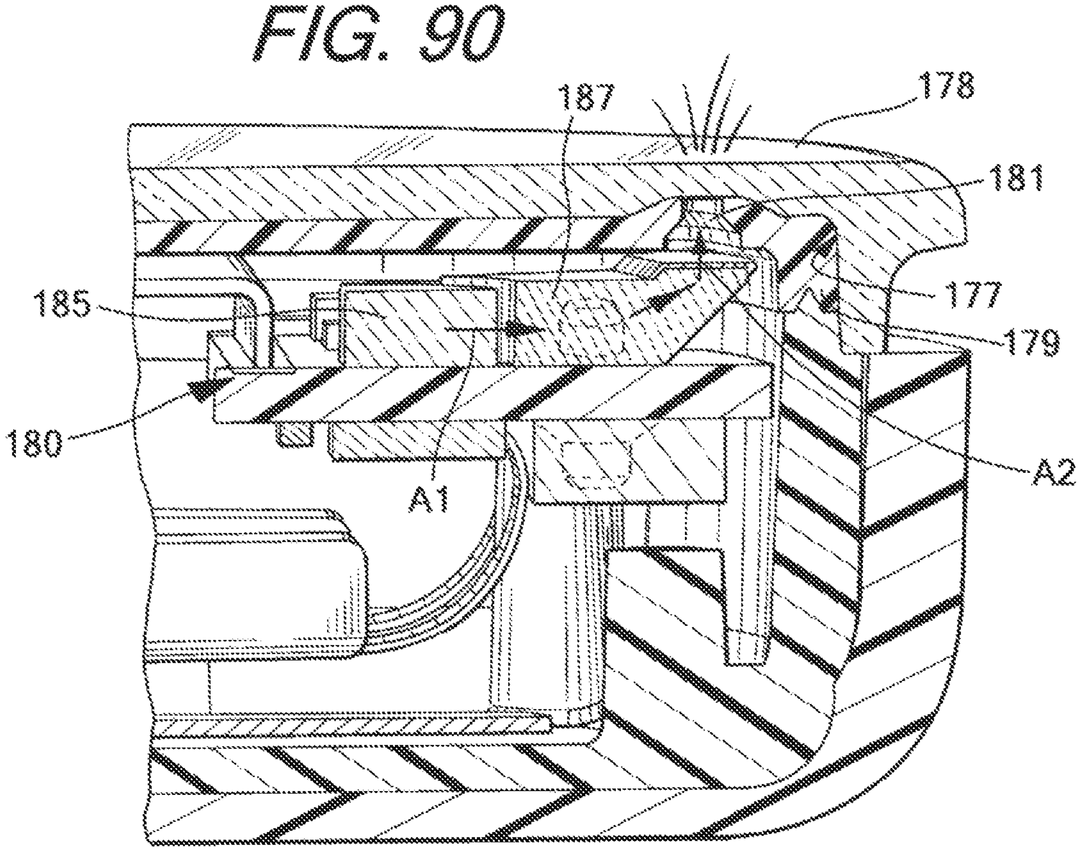

The module top member 177 as shown in FIGS. 85-86 and 89-90, including an inner top member 179 and an outer top member 178, may also be formed using an injection technique in one embodiment. As shown in FIG. 88, the inner top member 179 has an aperture 181 therethrough. The outer top member 178 is generally a planar member. The inner top member 179 is positioned over the base member 174 and the outer top member 178 is positioned over the inner top member 179. The top member 177 is connected to the base member 175 to encase the internal components of the module 22.

Figure 84:
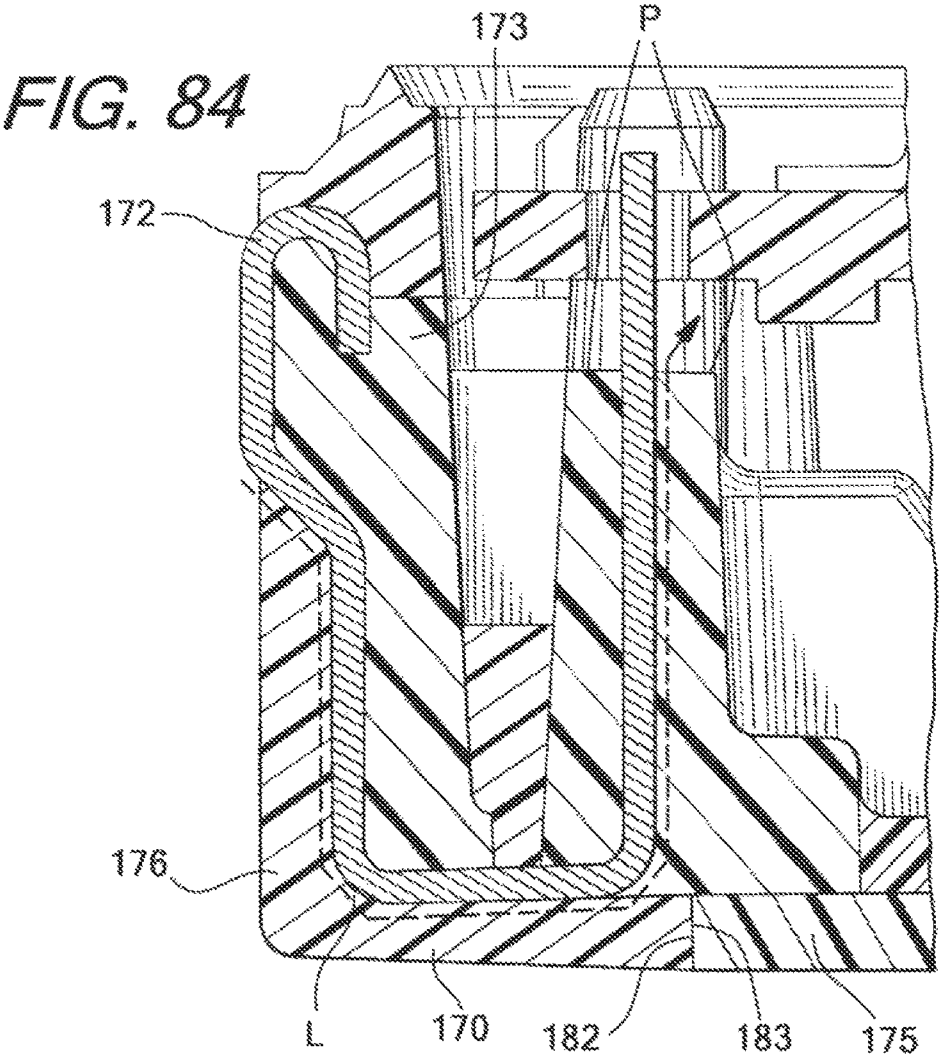
FIG. 84 is a partial cross-sectional view showing overmolding of contacts of an interface of the module.
Figure 85:
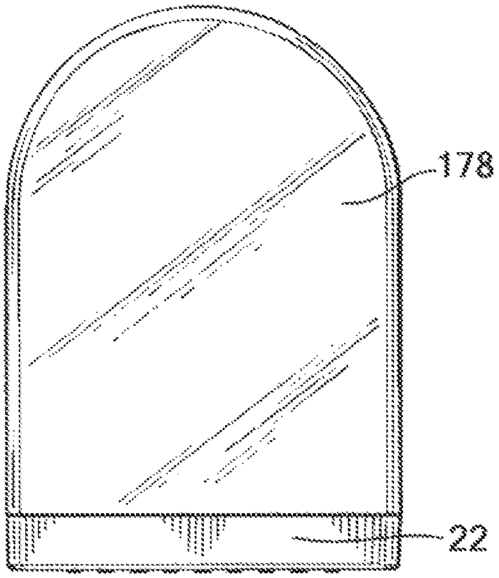
FIGS. 85-86 are plan views of the module showing a light assembly according to aspects of the invention.
Figure 86:
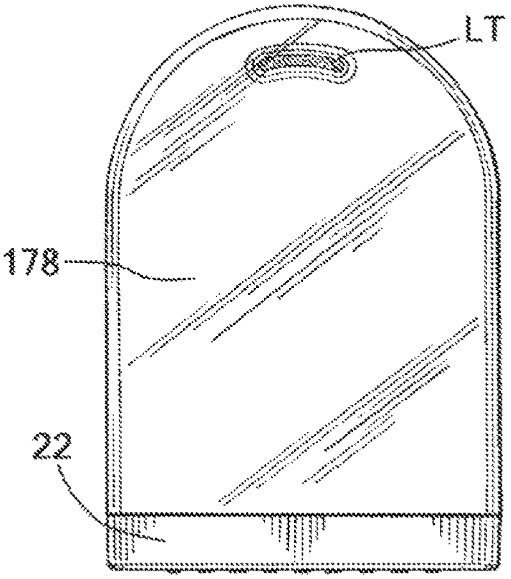
Figure 87:
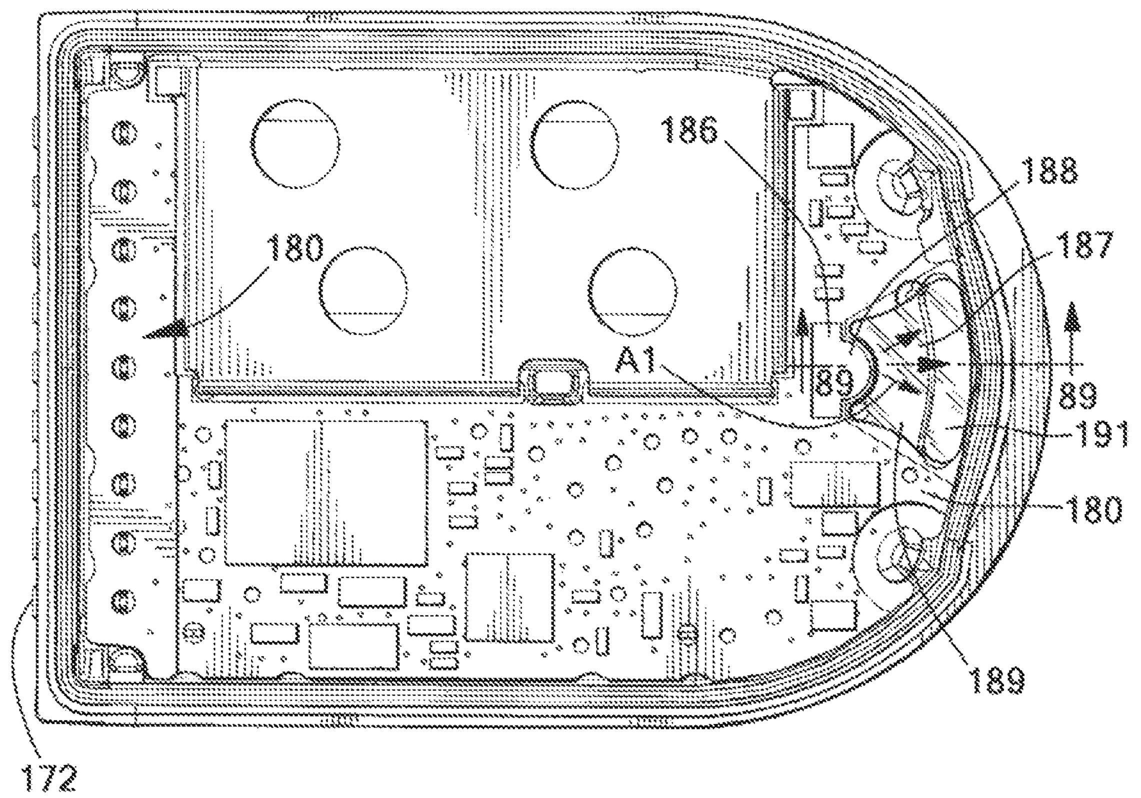
FIGS. 87-90 are internal views of the module showing components of the light assembly.

With this structural configuration, the connectors 172 are sealed to prevent potential moisture ingress. As shown in FIG. 84, the carrier 173 is in surface-to-surface engagement with the connectors 172 generally at inner surfaces of the connectors 172. In addition, the inner base member 176 is positioned around the connectors 172 generally at outer surfaces of the connectors 172. The inner base member 176 further has an engagement surface 182 that abuts and engages an engagement surface 183 defined by the outer base member 175. As further shown in FIG. 84, with such configuration, a tortuous path represented by the phantom line L, is defined. Such tortuous path L minimizes the chances for moisture ingress. For example, a user may run through water puddles during use potentially exposing the port 14 and module 22 to moisture. In an exemplary embodiment, the connectors 172 are considered to be sealed to 5 ATM. A bonding material (e.g. adhesive) may be utilized between the module carrier 173 and the inner base member 176 proximate the tortuous path L, such as at one or both points P in FIG. 84.

It is understood that the module 22 is received in the port 14. A front end of the module 22 is inserted through the central aperture 153 and into the first section 144. The module 22 is dimensioned to generally correspond in size to the first section 144 and in an interference fit. In such configuration, the interface 23 on the module 22 is operably engaged with the interface 20 on the port 14 wherein the respective contacts of the interfaces 20, 23 are in surface-to-surface contact. Thus, the construction is such that the interface 23 of the module 22 is forced against the interface 20 of the port 14. The module 22 may have a recess 184 on a rear surface that receives the projection 151 of the housing 24 to assist in retaining the module 22 in the port 14 through a snap connection. A user can easily remove the module 22 from the port by accessing the module 22 with the assistance of the finger recess 29A. Thus, the modules 22 can easily be inserted into the port 14 and removed from the port 14 when necessary such as for charging or transferring data, or when replacing one type of module 22 for one application with a different type of module for a different application, or replacing a power drained module 22 with a freshly charged module 22.

As shown in FIGS. 85-90, the module 22 is provided with a light assembly 185 to provide lighted indicia to a user. The light assembly 185 is operably connected to the printed circuit board 180. The light assembly 185 generally includes a light member 186 and a light guide 187. The light member 186 is an LED light member in an exemplary embodiment although other light members can be used. The light member 186 has an arcuate section 188 and is configured to project light in a first direction such as shown by the arrow A1, which may be a horizontal direction in an exemplary embodiment. The light member 186 may be considered to be a side-firing LED. The light guide 187 has a first section 189 defining a first passageway 190 configured in a first direction. The first section 189 has a recessed area that generally corresponds to and receives the arcuate section 188 of the light member 186 to capture as much light from the light member 186 as possible. Thus, the first section 189 is in confronting relation to the arcuate section 188 of the light member 186 and partially encircles the light member 186. As shown in the figures, the light guide 187 has a geometry that assists in spreading the light to a larger area, thus spreading the light out along an arc. The light guide 187 further has a second section 191 defining a second passageway 192 configured in a second direction. The second passageway 192 extends upwards and at an angle and is thus different from the first direction. In one exemplary embodiment, the second section 191 is inclined at approximately a 45 degree angle which was determined to enhance reflection of the light. The second passageway 192 has a distal end that is positioned proximate the aperture 181 in the inner top member 179. The light guide 187 may be treated with a dispersant agent such as by adding the agent to the resin prior to injection molding the light guide. Because the light member 186 and light guide 187 are configured in confronting relation, the components achieve a minimized footprint, which is helpful due to the limited area defined in the module 22. In operation, the light member 186 is activated as desired via the printed circuit board 180. Light is projected in the direction shown by the arrow A1. Light is also projected in an arcuate configuration based on the shape of the light guide 187. The light is projected in these directions into the first passageway 190. The light guide 187 directs the light into the second passageway 192 in the direction of arrow A2 upwards. As the light is initially projected from the side firing LED, the light transitions from the direction A1 to an inclined direction towards the second passageway 192. Light then passes through the aperture 181 in the direction A2 and shines through outer top member 178. The geometry of the light guide 187 is tailored to evenly disperse light in a very short path-length as shown. The dispersant agent used with the light guide 187 assists in diffusing light more evenly, thus minimizing concentrations of light from the light member 186. Because of the short path-length involved, the LED light member 186 could project light that had more focused brightness in certain areas. With the present design, light is more evenly spread and reflected where there is a limited gradient of light across the aperture 181. The outer top member 178 positioned over the aperture 181 is structured in thickness and colorant loading of the material to provide a desired translucency. Thus, as can be appreciated from FIGS. 90 and 91, when the light member 186 is not illuminated, a user cannot detect that an LED exists in the module 22, thus providing a blank or "dead-front" appearance. Once the light member 186 is activated, light is directed along the arrow A1 and upwards along the arrow A2, and through the aperture 181 and outer top member 178 as shown by the designation LT in FIG. 91. With the geometry and treatment of the light guide 187 and top members, light is reflected in a more enhanced manner providing an evenly dispersed light across the entire area of the light shining through the top member. Additional structures could also be added to reflect the light in a more enhanced manner. For example, the light guide 187 could be provided with a surface texture to enhance light reflection. The inclined wall of the light guide 187 or other surfaces could be painted or have a sticker applied thereon to achieve desired changes in light reflection. It is understood that the light member 186 may project light in multiple colors. The light member 186 provides indicia for indicating various parameters including battery life of the module 22.

The constructions of the port 14 and module 22 described herein provide a snug fit. The constructions provide a water tight configuration and resist moisture ingress. These properties are achieved while maintaining an operable connection between the port 14 and module 22. The fingers 158 on the interface assembly also provide a robust connection with the extension 21 of the insert member 37 as engagement locations between the fingers and extension are maximized. The filler material 159 is selected to have a desired hardness to provide sufficient flexibility and anti-corrosion properties. In one exemplary embodiment, the filler material 159 may have a shore durometer on the type A scale of 30 or lower.

The filler material 159 provides protection around the connection between the extension 21 and the interface assembly 156. The receiver/post connections of the housing and insert member 37 further provides stress relief to the insert member 37 to minimize chances that the insert member 37 could tear during use.

Figure 91:
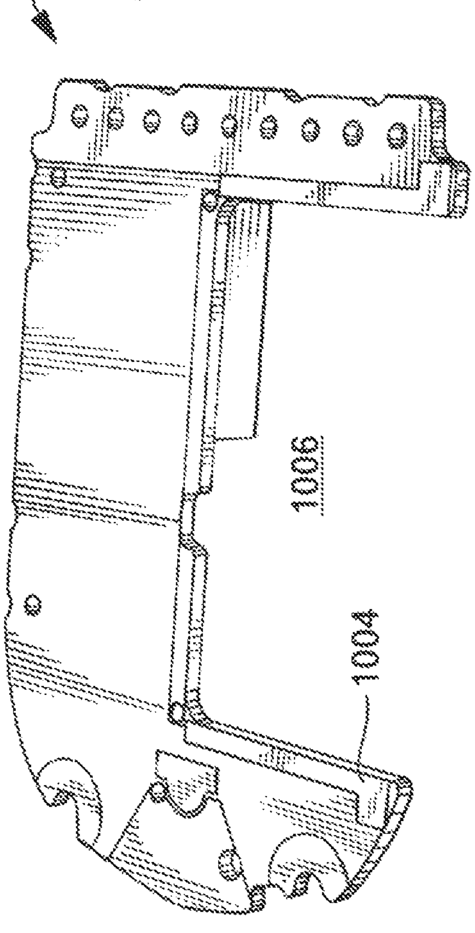
FIGS. 91-94 are views of a PCB and a ground plane extender associated with the module according to aspects of the invention.

FIGS. 91-94 disclose additional features relating to a ground plan extender associated with the module 22. In particular, further aspects relate to maximizing the surface area of a layer of a PCB of one or more electronic devices, such as the module 22. Certain aspects relate to increasing the surface area of a ground plane layer of a PCB. FIG. 91 shows a perspective top view of example PCB 1002, which may comprise on or more components in electric communication, including but not limited to processors, capacitors, diodes, resistors, and/or combinations thereof. PCB 1002 is shown to be planar across a horizontal axis ("x" axis), however, those skilled in the art will appreciate that PCB 1002 (or a plurality of individual PCBs in operative communication) may be configured to form a non-planar structure. PCB 1002 further comprises a ground plane layer (see 1004) formed of conductive material, such as for example, copper. As shown in FIG. 91, the visible portion of ground plane layer 1004 is positioned around a periphery of PCB 1002, however, portions of layer 1004 may be disposed and/or connected to other portions of PCB 1002.

Figure 92:
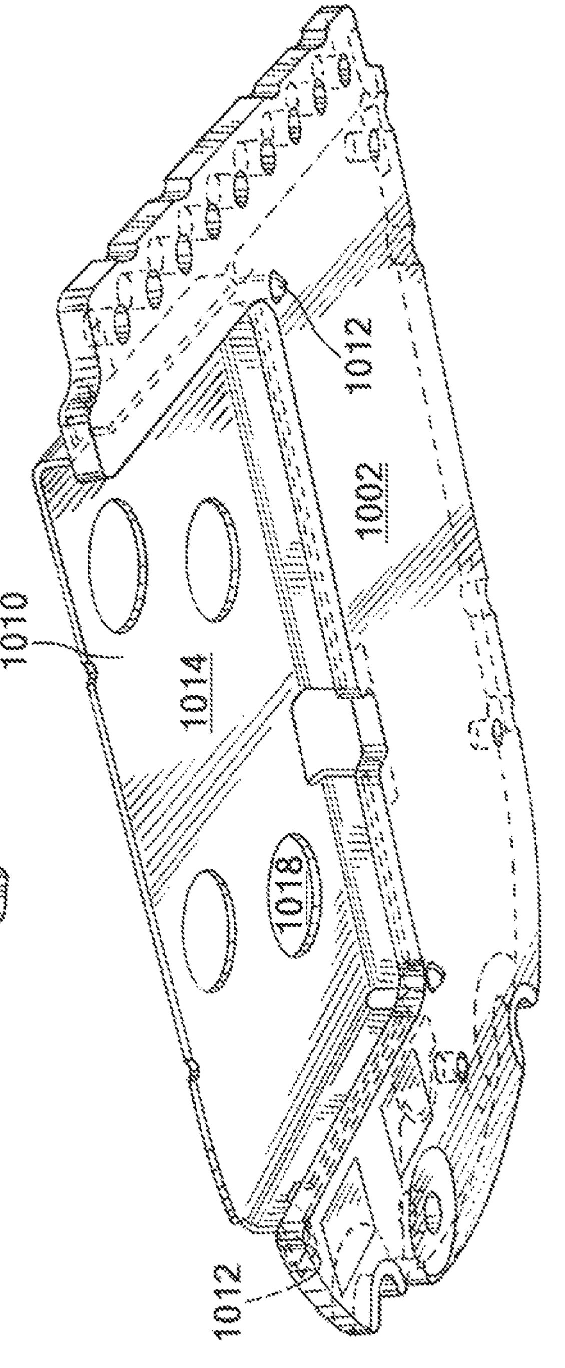
Figure 93:
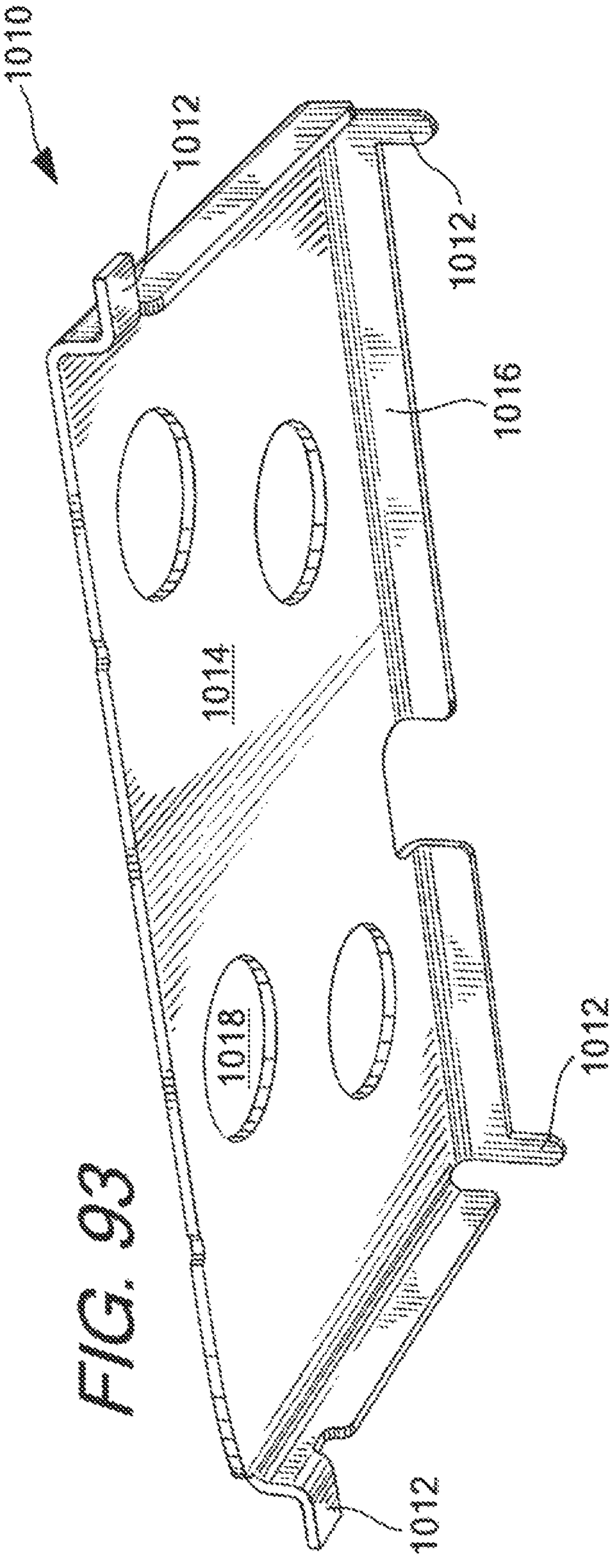
Figure 94:
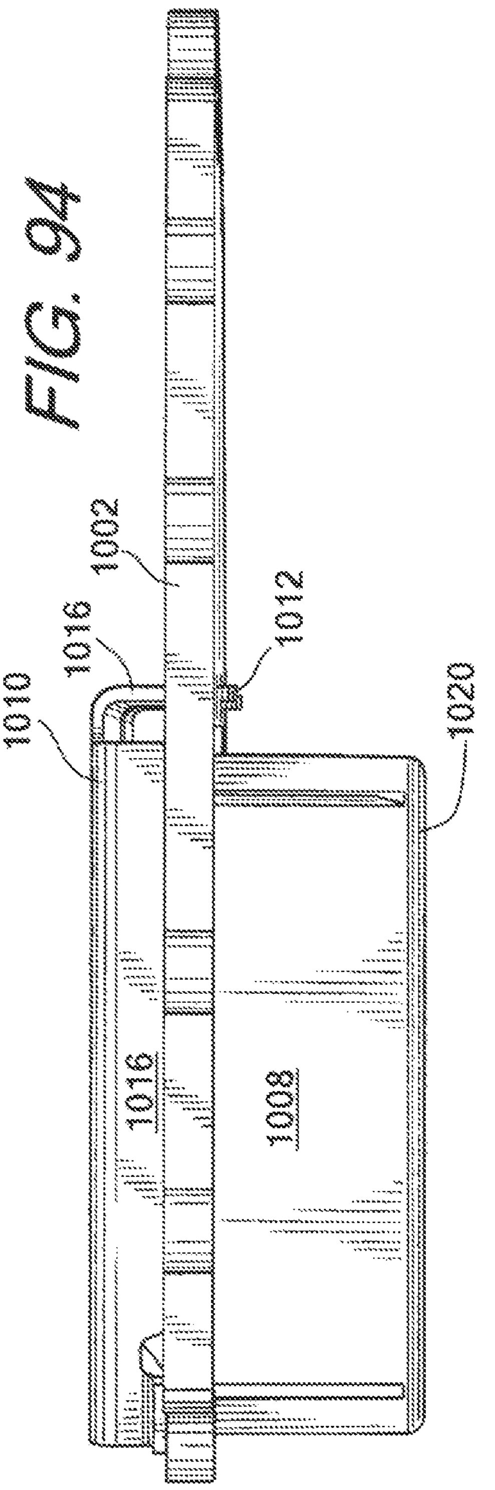

In certain embodiments, at least one component of PCB 1002 may be configurable to be in operatively communication with a portable power supply, such as for example, a battery (not shown in FIGS. 91-93 but shown in FIG. 94). PCB 1002 may be configured for placement within a portable device having limited dimensions for batteries or other forms of portable power supplies. Due to the aforementioned dimensional restrictions of portable devices, batteries are often small, and such may have limited service time between charges and/or limited rates of discharge. In accordance with one embodiment, PCB 1002 may comprise a space, such as battery space 1006. As shown in FIG. 91, battery space 1006 comprises area along the x and z plane of PCB 1002 to permit placement of a power source adjacent to PCB 1002. PCB 1002 may be manufactured to dimensions creating battery space 1002 or may be configured to be altered (such as through snap regions and/or areas of alternating thickness) to form one or more battery spaces. In this regard, although the illustrative space is a battery space, those skilled in the art will appreciate that this disclosure is not limited to only those areas and/or spaces configured for housing or positioning a battery.

Although battery space 1006 of PCB 1002 is shown as a slot configuration flanked on three sides by portions of PCB 1002, those skilled in the art will readily appreciate that the shape, size and/or configuration of PCB 1002 is merely illustrative and other shapes are within the scope of this disclosure. The exact shape and size of battery space 1006 may be dictated by its intended use and is not limited by this disclosure. The only requirement, therefore, of battery space 1006 is the inclusion of area along the horizontal plane (e.g., along the x-axis) of PCB 1002 to permit placement of a power source along the same plane and adjacent to PCB 1002. As shown in FIG. 94, which shows a side view of PCB 1002, a battery, such as battery 1008, may be positioned along the horizontal plane (x-axis) of the PCB 1002. Because battery 1008 occupies area within battery space 1006, the surface area of the PCB 1002 is minimized as compared with a PCB not having a space, such as battery space 1008, but instead includes a greater area of the ground plane layer 1004 located in the same spot.

In accordance with certain embodiments, a ground plane extender (see, e.g., 1010) may be electronically connected to the ground plane layer 1004 of the PCB 1002. FIG. 92 shows an example ground plane extender 1010 in accordance with one embodiment. Ground plane extender 1010 may be formed of any material that effectively increases the surface area of the ground plane layer 1004. In one embodiment, the ground plane extender may comprise copper and/or aluminum, however, in further embodiments any conductive material may be utilized for at least a portion of ground plane extender 1010. One or more connectors 1012 may be utilized to allow contact (and/or alignment) between extender 1010 and ground plane layer 1004, either by conductive adhesives, soldering, pass through soldering, welding, snapping in, and combinations thereof. As best shown in FIG. 92, extender 1010 may be placed adjacent to one side of the battery 1008 (e.g., the top), and comprise a portion such as a top region (e.g., 1014) that is substantially parallel to, and thus planar with, PCB 1002 along the horizontal (x) axis. For example, extender 1010 may comprise a vertical ridge 1016 that operatively connects to and extends from PCB 1002 to top region 1016. Top region 1016 may comprise one or more apertures 1018 that may permit heat exchange from the surrounding components, including battery 1008.

As seen in FIG. 94, extender 1010 is shown adjacent to a first side (e.g., top side) of battery 1008 and electronically connected with PCB 1002 and an antenna 1020 is positioned adjacent to an opposing side (e.g. the bottom) of battery 1008. In the example embodiment of FIG. 94, the ground plane extender 1010 and antenna 1020 are also in parallel configuration with PCB 1002 and each other. Thus, in at least one embodiment, a portable device may comprise three layers—a first layer comprising a ground plane extender, such as extender 1010, a second layer comprising a battery positioned such that at least a portion of the battery is along the same plane as a PCB operatively connected to the ground plane extender, and a third layer comprising an antenna, such as antenna, such as antenna 1020. In the illustrative embodiment, the layers are vertically arranged; however, other arrangements are within the scope of this disclosure. In this regard, there is no requirement that each layer be in direct physical contact with the adjacent surface of an adjacent layer, unless otherwise stated. For example, there is no requirement that antenna 1020 be in direct physical contact with the adjacent surface of battery 1008.

Figure 6:
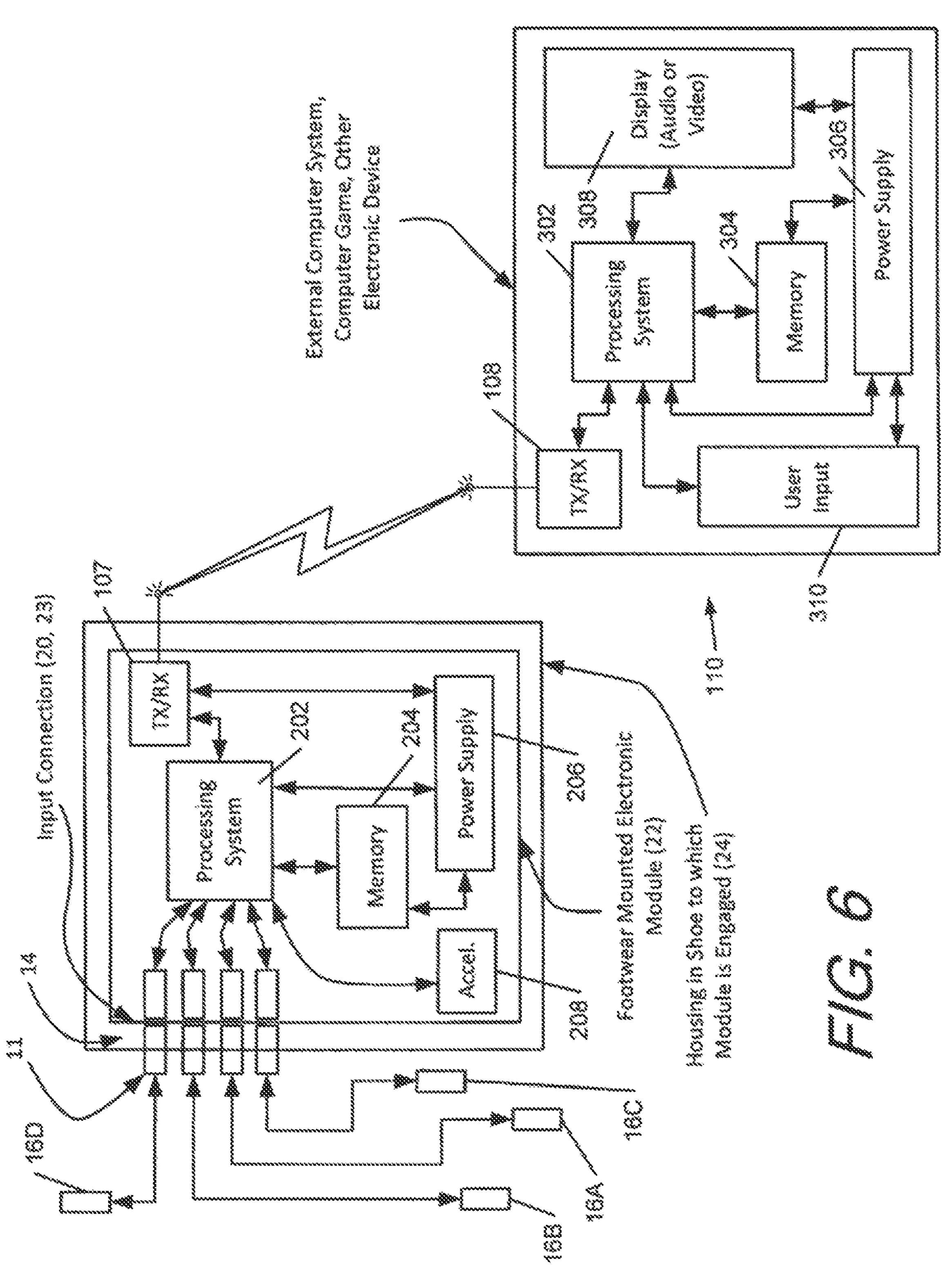
FIG. 6 is a schematic diagram of one embodiment of an electronic module capable of use with a sensor system, in communication with an external electronic device.
Figure 7:
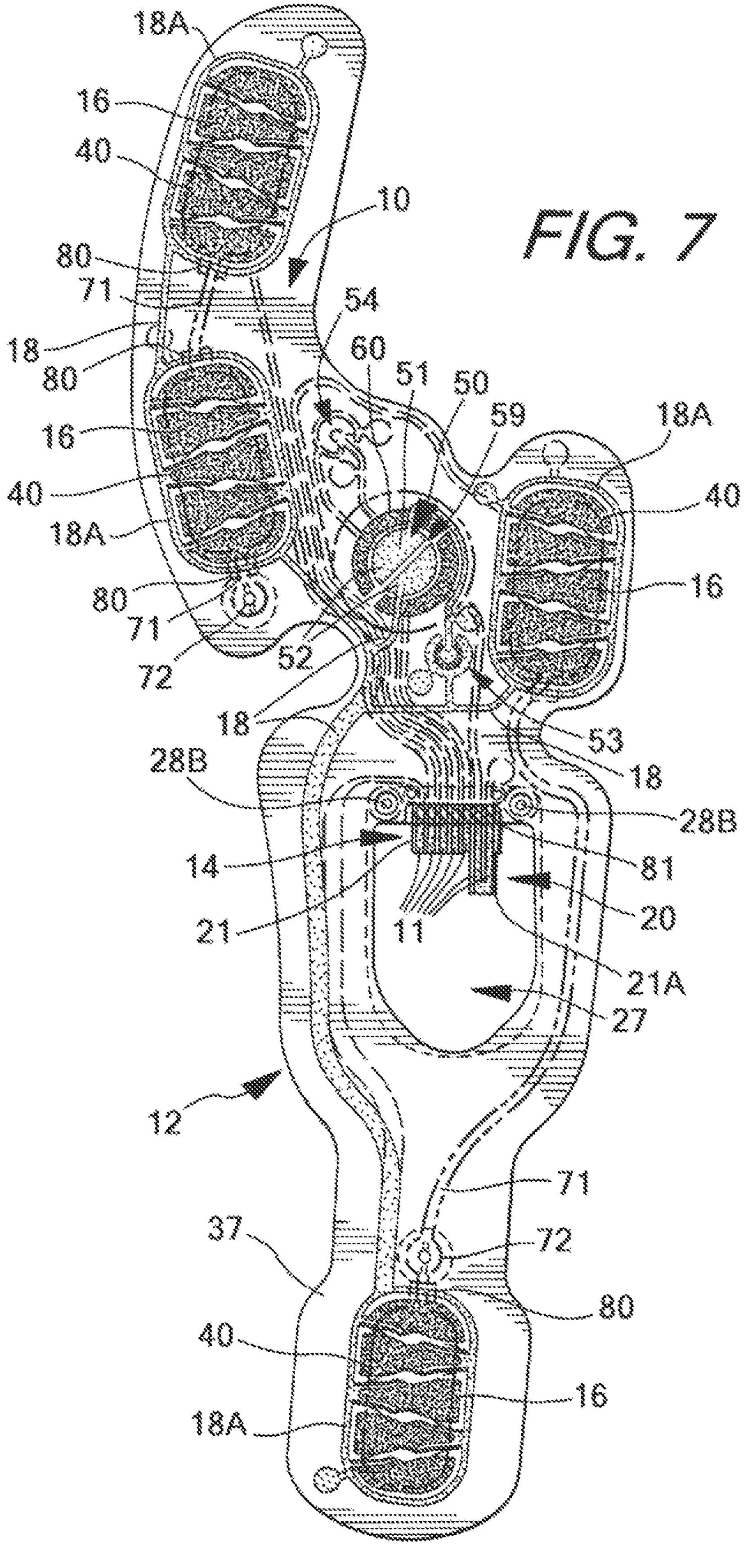
FIG. 7 is a top view of an insert of the sensor system of FIG. 3, adapted to be positioned within the sole structure of an article of footwear for a user's right foot.
Figure 8:
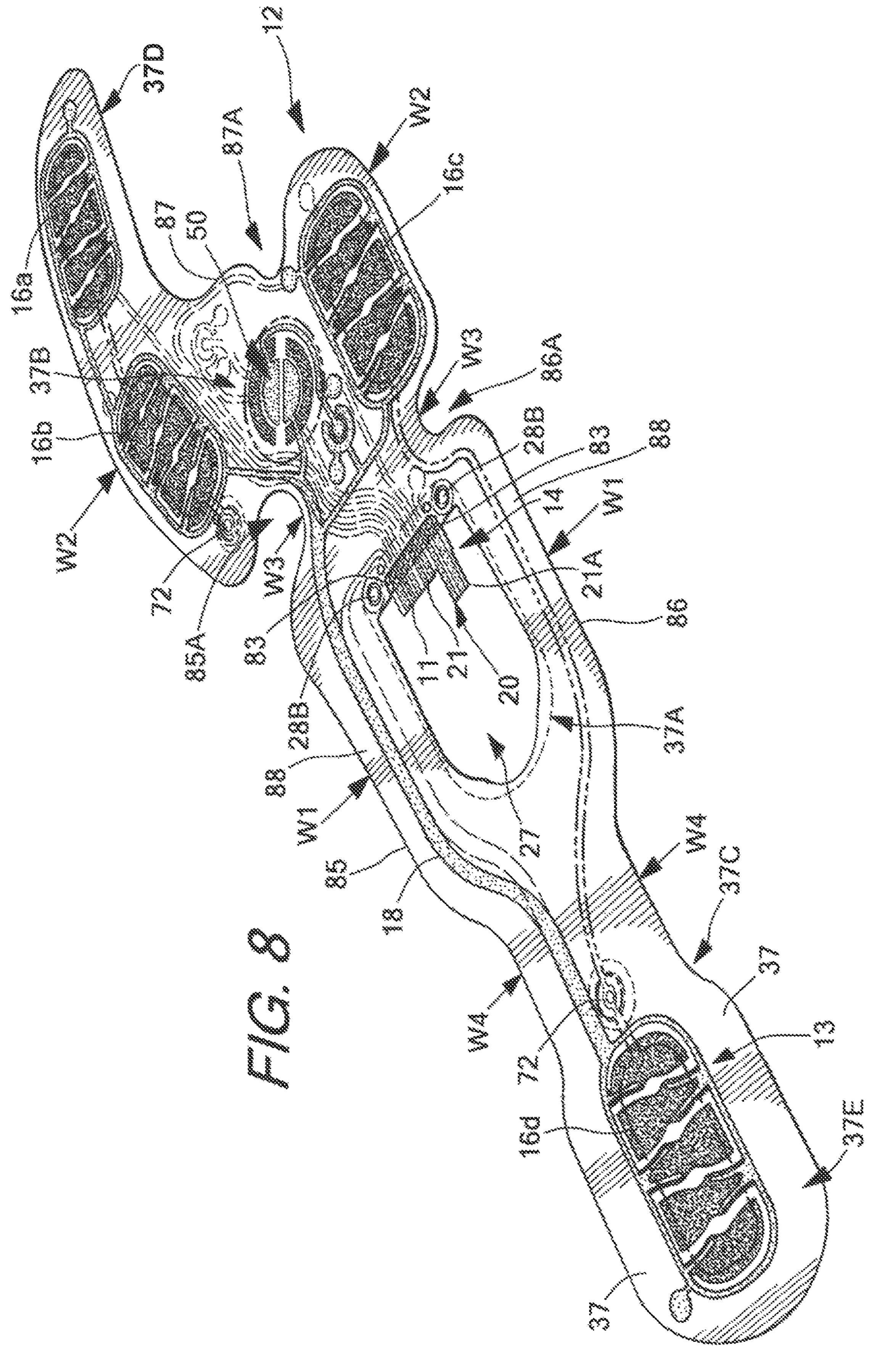
FIG. 8 is a top perspective view of the insert of FIG. 7.
Figure 9:
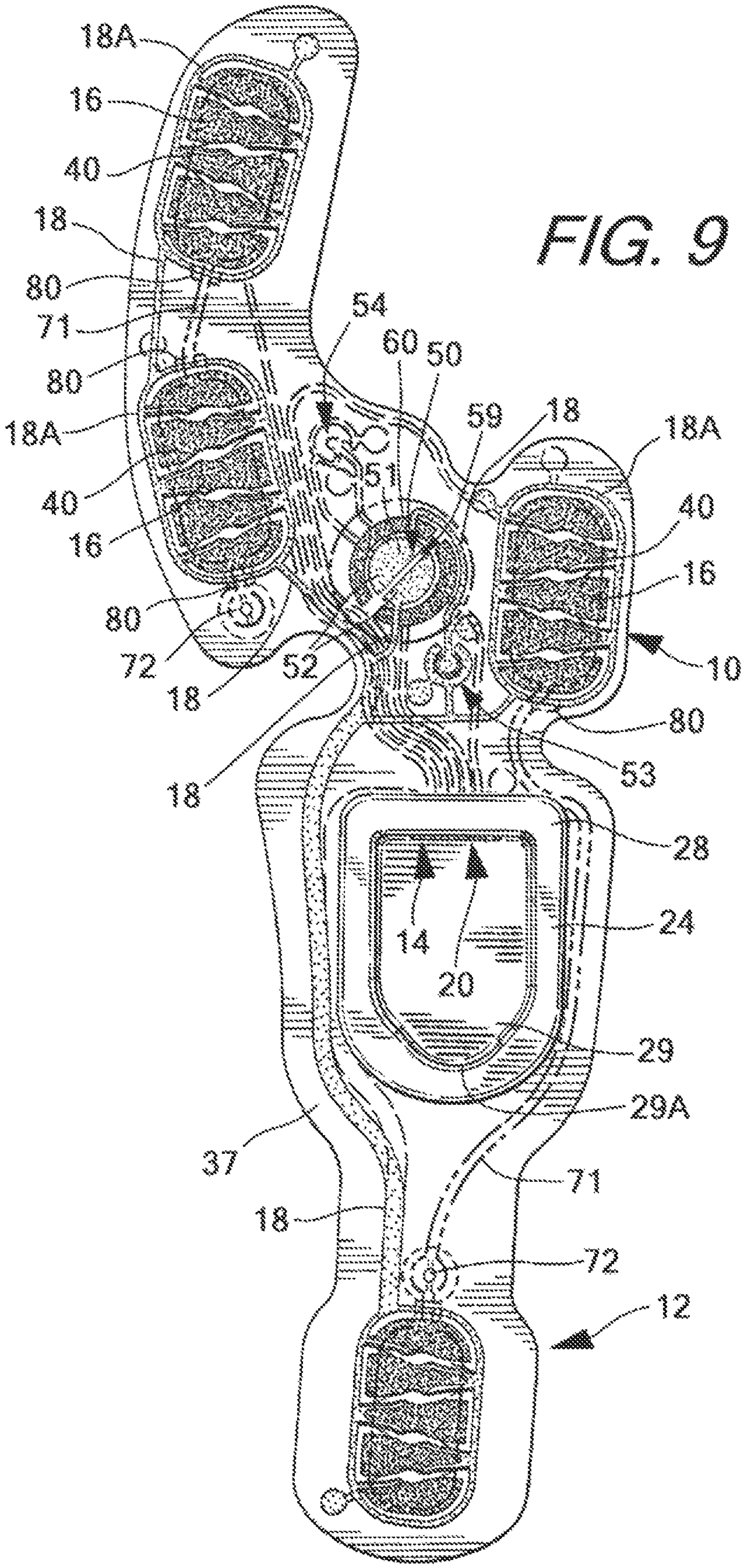
FIG. 9 is a top view of the sensor system of FIG. 3, including the insert of FIG. 7.

FIG. 6 shows a schematic diagram of an example electronic module 22 including data transmission/reception capabilities through a data transmission/reception system 107, which may be used in accordance with at least some examples of this invention. While the example structures of FIG. 6 illustrate the data transmission/reception system (TX-RX) 107 as integrated into the electronic module structure 22, those skilled in the art will appreciate that a separate component may be included as part of a footwear structure 100 or other structure for data transmission/reception purposes and/or that the data transmission/reception system 107 need not be entirely contained in a single housing or a single package in all examples of the invention. Rather, if desired, various components or elements of the data transmission/reception system 107 may be separate from one another, in different housings, on different boards, and/or separately engaged with the article of footwear 100 or other device in a variety of different manners without departing from this invention. Various examples of different potential mounting structures are described in more detail below.

In the example of FIG. 6, the electronic component 22 may include a data transmission/reception element 107 for transmitting data to and/or receiving data from one or more remote systems. In one embodiment, the transmission/reception element 107 is configured for communication through the port 14, such as by the contacted or contactless interfaces described above. In the embodiment shown in FIG. 6, the module 22 includes an interface 23 configured for connection to the port 14 and/or sensors 16. In the module 22 illustrated in FIG. 6, the interface 23 has contacts that are complementary with the terminals 11 of the interface 20 of the port 14, to connect with the port 14. In other embodiments, as described above, the port 14 and the module 22 may contain different types of interfaces 20, 23, which may be contacted or wireless. It is understood that in some embodiments, the module 22 may interface with the port 14 and/or sensors 16 through the TX-RX element 107. Accordingly, in one embodiment, the module 22 may be external to the footwear 100, and the port 14 may comprise a wireless transmitter interface for communication with the module 22. The electronic component 22 of this example further includes a processing system 202 (e.g., one or more microprocessors), a memory system 204, and a power supply 206 (e.g., a battery or other power source). In one embodiment, the power supply 206 may be configured for inductive charging, such as by including a coil or other inductive member. In this configuration, the module 22 may be charged by placing the article of footwear 100 on an inductive pad or other inductive charger, allowing charging without removal of the module 22 from the port 14. In another embodiment, the power supply 206 may additionally or alternately be configured for charging using energy-harvesting technology, and may include a device for energy harvesting, such as a charger that charges the power supply 206 through absorption of kinetic energy due to movement of the user.

Connection to the one or more sensors can be accomplished as shown in FIG. 6, but additional sensors (not shown) may be provided to sense or provide data or information relating to a wide variety of different types of parameters, such as physical or physiological data associated with use of the article of footwear 100 or the user, including pedometer type speed and/or distance information, other speed and/or distance data sensor information, temperature, altitude, barometric pressure, humidity, GPS data, accelerometer output or data, heart rate, pulse rate, blood pressure, body temperature, EKG data, EEG data, data regarding angular orientation and changes in angular orientation (such as a gyroscope-based sensor), etc., and this data may be stored in memory 204 and/or made available, for example, for transmission by the transmission/reception system 107 to some remote location or system. The additional sensor(s), if present, may also include an accelerometer (e.g., for sensing direction changes during steps, such as for pedometer type speed and/or distance information, for sensing jump height, etc.). In one embodiment, the module 22 may include an additional sensor 208, such as an accelerometer, and the data from the sensors 16 may be integrated with the data from the accelerometer 208, such as by the module 22 or the external device 110.

As additional examples, electronic modules, systems, and methods of the various types described above may be used for providing automatic impact attenuation control for articles of footwear. Such systems and methods may operate, for example, like those described in U.S. Pat. No. 6,430,843, U.S. Patent Application Publication No. 2003/0009913, and U.S. Patent Application Publication No. 2004/0177531, which describe systems and methods for actively and/or dynamically controlling the impact attenuation characteristics of articles of footwear (U.S. Pat. No. 6,430,843, U.S. Patent Application Publication No. 2003/0009913, and U.S. patent application Publication No. 2004/0177531 are each entirely incorporated herein by reference and made part hereof). When used for providing speed and/or distance type information, sensing units, algorithms, and/or systems of the types described in U.S. Pat. Nos. 5,724,265, 5,955,667, 6,018,705, 6,052,654, 6,876,947 and 6,882,955 may be used. These patents each are entirely incorporated herein by reference. Additional embodiments of sensors and sensor systems, as well as articles of footwear and sole structures and members utilizing the same, are described in U.S. Patent Application Publications Nos. 2010/0063778 and 2010/0063779, which applications are incorporated by reference herein in their entireties and made part hereof.

The electronic module 22 can also include an activation system (not shown). The activation system or portions thereof may be engaged with the module 22 or with the article of footwear 100 (or other device) together with or separate from other portions of the electronic module 22. The activation system may be used for selectively activating the electronic module 22 and/or at least some functions of the electronic module 22 (e.g., data transmission/reception functions, etc.). A wide variety of different activation systems may be used without departing from this invention, and a variety of such systems will be described in more detail below with respect to various included figures. In one example, the sensor system 12 may be activated and/or deactivated by activating the sensors 16 in a specific pattern, such as consecutive or alternating toe/heel taps. In another example, the sensor system 12 may be activated by a button or switch, which may be located on the module 22, on the shoe 100, or on an external device in communication with the sensor system 12, as well as other locations. In any of these embodiments, the sensor system 12 may contain a "sleep" mode, which can deactivate the system 12 after a set period of inactivity. In an alternate embodiment, the sensor system 12 may operate as a low-power device that does not activate or deactivate.

Figure 23:
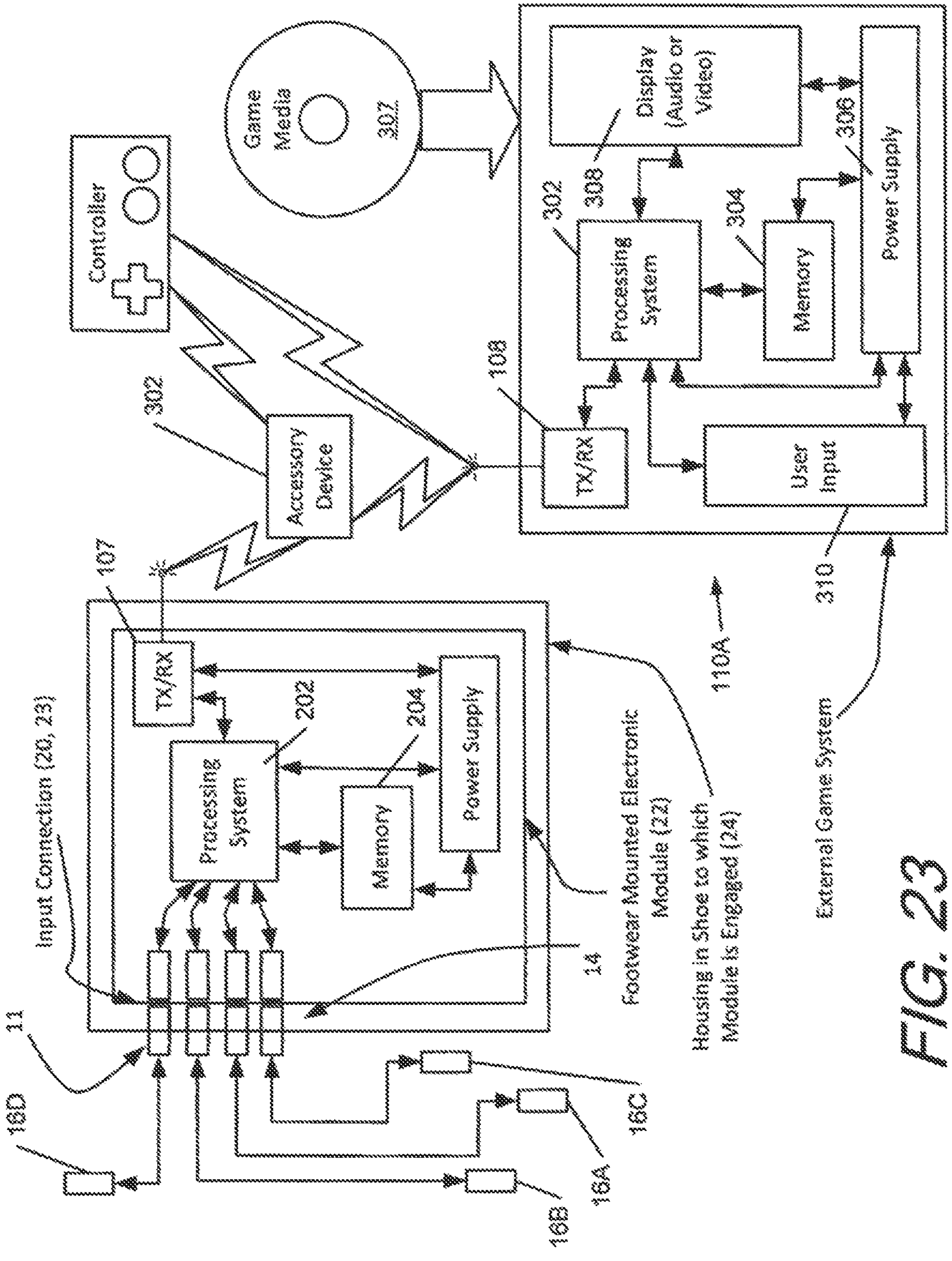
FIG. 23 is a schematic diagram of the electronic module of FIG. 6, in communication with an external gaming device.

The module 22 may further be configured for communication with an external device 110, which may be an external computer or computer system, mobile device, gaming system, or other type of electronic device, as shown in FIG. 23. The exemplary external device 110 shown in FIG. 23 includes a processor 302, a memory 304, a power supply 306, a display 308, a user input 310, and a data transmission/reception system 108. The transmission/reception system 108 is configured for communication with the module 22 via the transmission/reception system 107 of the module 22, through any type of known electronic communication, including the contacted and contactless communication methods described above and elsewhere herein. It is understood that the module 22 and/or the port 14 can be configured for communication with a plurality of external devices, including a wide variety of different types and configurations of electronic devices, and also including intermediate devices that function to pass information on to another external device and may or may not further process such data. Additionally, the transmission/reception system 107 of the module 22 may be configured for a plurality of different types of electronic communication. It is further understood that the shoe 100 may include a separate power source to operate the sensors 16 if necessary, such as a battery, piezoelectric, solar power supplies, or others. In the embodiment of FIGS. 3-22B, the sensors 16 receive power through connection to the module 22.

As described below, such sensor assemblies can be customized for use with specific software for the electronic module 22 and/or the external device 110. A third party may provide such software along with a sole insert having a customized sensor assembly, as a package. The module 22 and/or the overall sensor system 12 may cooperate with one or more algorithms for analysis of the data obtained from the sensors 16, including algorithms stored on and/or executed by the module, the external device 110, or another component.

Figure 27:
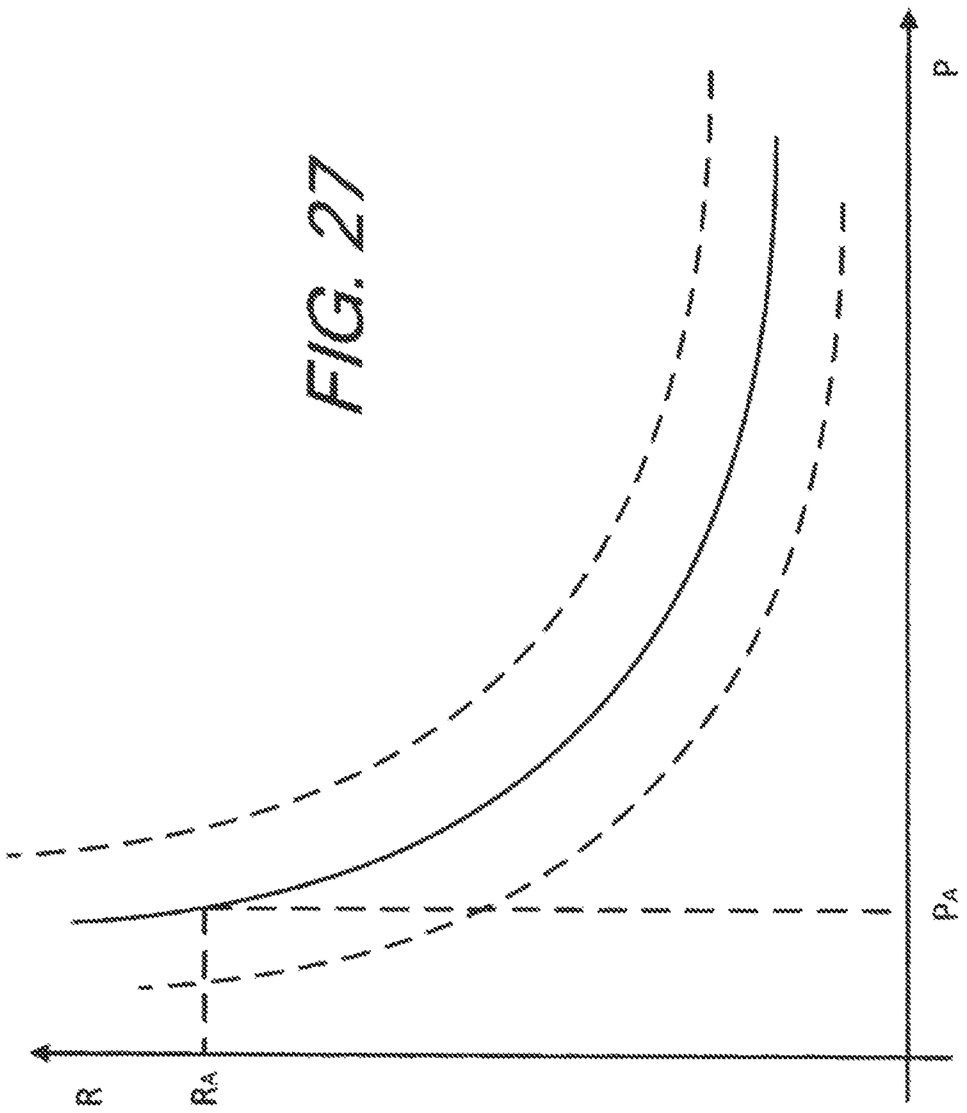
FIG. 27 is a plot showing pressure vs. resistance for one embodiment of a sensor according to aspects of the present invention.

In operation, the sensors 16 gather data according to their function and design, and transmit the data to the port 14. The port 14 then allows the electronic module 22 to interface with the sensors 16 and collect the data for later use and/or processing. In one embodiment, the data is collected, stored, and transmitted in a universally readable format, so the data is able to be accessed and/or downloaded by a plurality of users, with a variety of different applications, for use in a variety of different purposes. In one example, the data is collected, stored, and transmitted in XML format. In one embodiment, the module 22 detects pressure changes in the sensors 16 utilizing the circuit 10 as shown in FIG. 20, by measuring the voltage drop at the measurement terminal 104*b*, which is reflective of the changes in resistance of the particular sensor 16 that is currently switched. FIG. 27 illustrates one example of a pressure-resistance curve for a sensor 16, with broken lines illustrating potential shifts of the curve due to factors such as bending of the insert 37. The module 22 may have an activation resistance $R_A$, which is the detected resistance necessary for the module 22 to register the pressure on the sensor. The corresponding pressure to produce such resistance is known as the activation pressure $P_A$. The activation resistance $R_A$ may be selected to correspond to a specific activation pressure $P_A$ at which it is desired for the module 22 to register data. In one embodiment, the activation pressure $P_A$ may be about 0.15 bar, about 0.2 bar, or about 0.25 bar, and the corresponding activation resistance $R_A$ may be about 100 kΩ. Additionally, in one embodiment, the highest sensitivity range may be from 150-1500 mbar. In one embodiment, the sensor system 12 constructed as shown in FIGS. 3-22B can detect pressures in the range of 0.1-7.0 bar (or about 0.1-7.0 atm), and in another embodiment, the sensor system 12 may detect pressures over this range with high sensitivity.

In different embodiments, the sensor system 12 may be configured to collect different types of data. In one embodiment (described above), the sensor(s) 16 can collect data regarding the number, sequence, and/or frequency of compressions. For example, the system 12 can record the number or frequency of steps, jumps, cuts, kicks, or other compressive forces incurred while wearing the footwear 100, as well as other parameters, such as contact time and flight time. Both quantitative sensors and binary on/off type sensors can gather this data. In another example, the system can record the sequence of compressive forces incurred by the footwear, which can be used for purposes such as determining foot pronation or supination, weight transfer, foot strike patterns, or other such applications. In another embodiment (also described above), the sensor(s) 16 are able to quantitatively measure the compressive forces on the adjacent portions of the shoe 100, and the data consequently can include quantitative compressive force and/or impact measurement. Relative differences in the forces on different portions of the shoe 100 can be utilized in determining weight distribution and "center of pressure" of the shoe 100. The weight distribution and/or center of pressure can be calculated independently for one or both shoes 100, or can be calculated over both shoes together, such as to find a center of pressure or center of weight distribution for a person's entire body. In further embodiments, the sensor(s) 16 may be able to measure rates of changes in compressive force, contact time, flight time or time between impacts (such as for jumping or running), and/or other temporally-dependent parameters. It is understood that, in any embodiment, the sensors 16 may require a certain threshold force or impact before registering the force/impact, as described above.

As described above, the data is provided through the universal port 14 to the module 22 in a universally readable format, so that the number of applications, users, and programs that can use the data is nearly unlimited. Thus, the port 14 and module 22 are configured and/or programmed as desired by a user, and the port 14 and module 22 receive input data from the sensor system 12, which data can be used in any manner desired for different applications. The module 22 may be able to recognize whether the data received is related to a left or right shoe, such as through the use of the unique identification chip 92 as described herein. The module 22 may process the data differently according to the recognition of L/R shoe, and may also transmit the data to the external device 110 with an identification of whether the data is from a L/R shoe. The external device 110 may likewise process or otherwise handle the data differently based on the identification of L/R shoe as well. In one example, the connections of the sensors 16 to the terminals 11 and the interface 20 may be different between the left and right inserts 37, as shown in FIG. 12 and discussed above. The data from the left insert 37 may be interpreted differently from the data from the right insert 37 in accordance with this arrangement. The module 22 and/or the electronic device 110 may perform similar actions with respect to other identifying information contained on the unique identification chip 92. In many applications, the data is further processed by the module 22 and/or the external device 110 prior to use. In configurations where the external device 110 further processes the data, the module 22 may transmit the data to the external device 110. This transmitted data may be transmitted in the same universally-readable format, or may be transmitted in another format, and the module 22 may be configured to change the format of the data. Additionally, the module 22 can be configured and/or programmed to gather, utilize, and/or process data from the sensors 16 for one or more specific applications. In one embodiment, the module 22 is configured for gathering, utilizing, and/or processing data for use in a plurality of applications. Examples of such uses and applications are given below. As used herein, the term "application" refers generally to a particular use, and does not necessarily refer to use in a computer program application, as that term is used in the computer arts. Nevertheless, a particular application may be embodied wholly or partially in a computer program application.

Further, in one embodiment, the module 22 can be removed from the footwear 100 and replaced with a second module 22 configured for operating differently than the first module 22. For example, the replacement is accomplished by lifting the foot contacting member 133, disconnecting the first module 22 from the port 14 and removing the first module 22 from the housing 24, then inserting the second module 22 into the housing 24 and connecting the second module 22 to the port 14, and finally placing the foot contacting member 133 back into position. The second module 22 may be programmed and/or configured differently than the first module 22. In one embodiment, the first module 22 may be configured for use in one or more specific applications, and the second module 22 may be configured for use in one or more different applications. For example, the first module 22 may be configured for use in one or more gaming applications and the second module 22 may be configured for use in one or more athletic performance monitoring applications. Additionally, the modules 22 may be configured for use in different applications of the same type. For example, the first module 22 may be configured for use in one game or athletic performance monitoring application, and the second module 22 may be configured for use in a different game or athletic performance monitoring application. As another example, the modules 22 may be configured for different uses within the same game or performance monitoring application. In another embodiment, the first module 22 may be configured to gather one type of data, and the second module 22 may be configured to gather a different type of data. Examples of such types of data are described herein, including quantitative force and/or pressure measurement, relative force and/or pressure measurement (i.e. sensors 16 relative to each other), weight shifting/transfer, impact sequences (such as for foot strike patterns) rate of force and/or pressure change, etc. In a further embodiment, the first module 22 may be configured to utilize or process data from the sensors 16 in a different manner than the second module 22. For example, the modules 22 may be configured to only gather, store, and/or communicate data, or the modules 22 may be configured to further process the data in some manner, such as organizing the data, changing the form of the data, performing calculations using the data, etc. In yet another embodiment, the modules 22 may be configured to communicate differently, such as having different communication interfaces or being configured to communicate with different external devices 110. The modules 22 may function differently in other aspects as well, including both structural and functional aspects, such as using different power sources or including additional or different hardware components, such as additional sensors as described above (e.g. GPS, accelerometer, etc.).

One use contemplated for the data collected by the system 12 is in measuring weight transfer, which is important for many athletic activities, such as a golf swing, a baseball/softball swing, a hockey swing (ice hockey or field hockey), a tennis swing, throwing/pitching a ball, etc. The pressure data collected by the system 12 can give valuable feedback regarding balance and stability for use in improving technique in any applicable athletic field. It is understood that more or less expensive and complex sensor systems 12 may be designed, based on the intended use of the data collected thereby.

The data collected by the system 12 can be used in measurement of a variety of other athletic performance characteristics. The data can be used to measure the degree and/or speed of foot pronation/supination, foot strike patterns, balance, and other such parameters, which can be used to improve technique in running/jogging or other athletic activities. With regard to pronation/supination, analysis of the data can also be used as a predictor of pronation/supination. Speed and distance monitoring can be performed, which may include pedometer-based measurements, such as contact measurement or loft time measurement. Jump height can also be measured, such as by using contact or loft time measurement. Lateral cutting force can be measured, including differential forces applied to different parts of the shoe 100 during cutting. The sensors 16 can also be positioned to measure shearing forces, such as a foot slipping laterally within the shoe 100. As one example, additional sensors may be incorporated into the sides of the upper 120 of the shoe 100 to sense forces against the sides.

The data, or the measurements derived therefrom, may be useful for athletic training purposes, including improving speed, power, quickness, consistency, technique, etc. The port 14, module 22, and/or external device 110 can be configured to give the user active, real-time feedback. In one example, the port 14 and/or module 22 can be placed in communication with a computer, mobile device, etc., in order to convey results in real time. In another example, one or more vibration elements may be included in the shoe 100, which can give a user feedback by vibrating a portion of the shoe to help control motion, such as the features disclosed in U.S. Pat. No. 6,978,684, which is incorporated herein by reference and made part hereof. Additionally, the data can be used to compare athletic movements, such as comparing a movement with a user's past movements to show consistency, improvement, or the lack thereof, or comparing a user's movement with the same movement of another, such as a professional golfer's swing. Further, the system 12 may be used to record biomechanical data for a "signature" athletic movement of an athlete. This data could be provided to others for use in duplicating or simulating the movement, such as for use in gaming applications or in a shadow application that overlays a movement over a user's similar movement.

The system 12 can also be configured for "all day activity" tracking, to record the various activities a user engages in over the course of a day. The system 12 may include a special algorithm for this purpose, such as in the module 22, the external device 110, and/or the sensors 16.

The system 12 may also be used for control applications, rather than data collection and processing applications. In other words, the system 12 could be incorporated into footwear, or another article that encounters bodily contact, for use in controlling an external device 110, such as a computer, television, video game, etc., based on movements by the user detected by the sensors 16. In effect, the footwear with the incorporated sensors 16 and leads 18 extending to a universal port 14 allows the footwear to act as an input system, and the electronic module 22 can be configured, programmed, and adapted to accept the input from the sensors 16 and use this input data in any desired manner, e.g., as a control input for a remote system. For example, a shoe with sensor controls could be used as a control or input device for a computer, or for a program being executed by the computer, similarly to a mouse, where certain foot movements, gestures, etc. (e.g., a foot tap, double foot tap, heel tap, double heel tap, side-to-side foot movement, foot-point, foot-flex, etc.) can control a pre-designated operation on a computer (e.g., page down, page up, undo, copy, cut, paste, save, close, etc.). Software can be provided to assign foot gestures to different computer function controls for this purpose. It is contemplated that an operating system could be configured to receive and recognize control input from the sensor system 12. Televisions or other external electronic devices can be controlled in this manner. Footwear 100 incorporating the system 12 can also be used in gaming applications and game programs, similarly to the Nintendo Wii controller, where specific movements can be assigned certain functions and/or can be used to produce a virtual representation of the user's motion on a display screen. As one example, center of pressure data and other weight distribution data can be used in gaming applications, which may involve virtual representations of balancing, weight shifting, and other performance activities. The system 12 can be used as an exclusive controller for a game or other computer system, or as a complementary controller. Examples of configurations and methods of using sensor systems for articles of footwear as controls for external devices and foot gestures for such controls are shown and described in U.S. Provisional Application No. 61/138,048, which is incorporated by reference herein in its entirety.

Additionally, the system 12 may be configured to communicate directly with the external device 110 and/or with a controller for the external device. As described above, FIG. 6 illustrates one embodiment for communication between the electronic module 22 and the external device. In another embodiment, shown in FIG. 23, the system 12 can be configured for communication with an external gaming device 110A. The external gaming device 110A contains similar components to the exemplary external device 110 shown in FIG. 6. The external gaming device 110A also includes at least one game media 307 containing a game program (e.g. a cartridge, CD, DVD, Blu-Ray, or other storage device), and at least one remote controller 305 configured to communicate by wired and/or wireless connection through the transmitting/receiving element 108. In the embodiment shown, the controller 305 complements the user input 310, however in one embodiment, the controller 305 may function as the sole user input. In this embodiment, the system 12 is provided with an accessory device 303, such as a wireless transmitter/receiver with a USB plug-in, that is configured to be connected to the external device 110 and/or the controller 305 to enable communication with the module 22. In one embodiment, the accessory device 303 may be configured to be connected to one or more additional controllers and/or external devices, of the same and/or different type than the controller 305 and the external device 110. It is understood that if the system 12 includes other types of sensors described above (e.g., an accelerometer), such additional sensors can also be incorporated into controlling a game or other program on an external device 110.

An external device 110, such as a computer/gaming system, can be provided with other types of software to interact with the system 12. For example, a gaming program may be configured to alter the attributes of an in-game character based on a user's real-life activities, which can encourage exercise or greater activity by the user. In another example, a program may be configured to display an avatar of the user that acts in relation or proportion to the user activity collected by the sensing system of the shoe. In such a configuration, the avatar may appear excited, energetic, etc., if the user has been active, and the avatar may appear sleepy, lazy, etc., if the user has been inactive. The sensor system 12 could also be configured for more elaborate sensing to record data describing a "signature move" of an athlete, which could then be utilized for various purposes, such as in a gaming system or modeling system.

Figure 24:
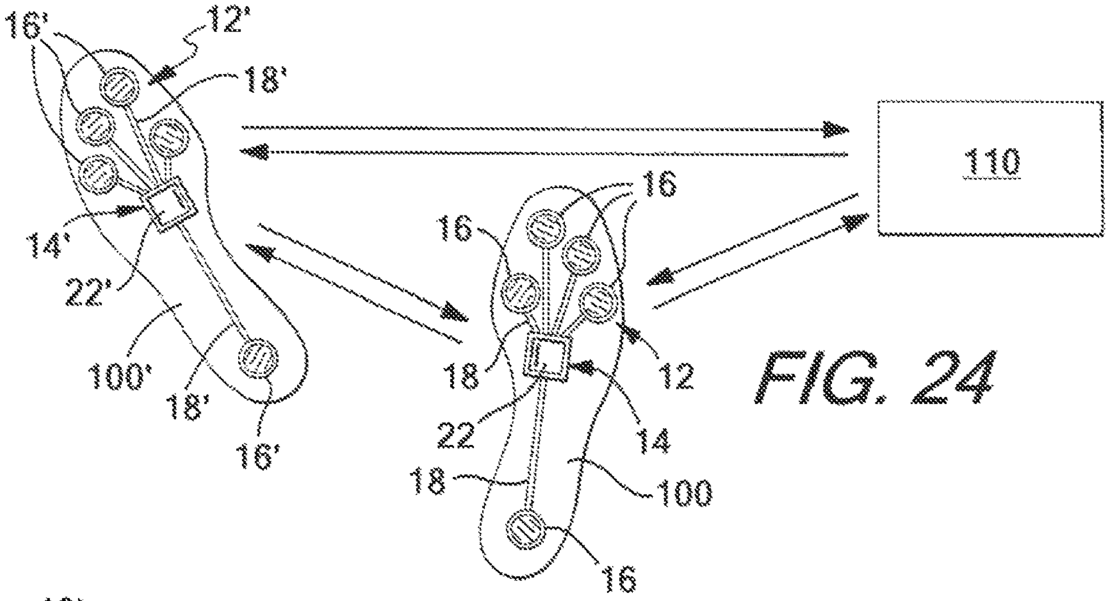
FIG. 24 is a schematic diagram of a pair of shoes, each containing a sensor system, in a mesh communication mode with an external device.
Figure 25:
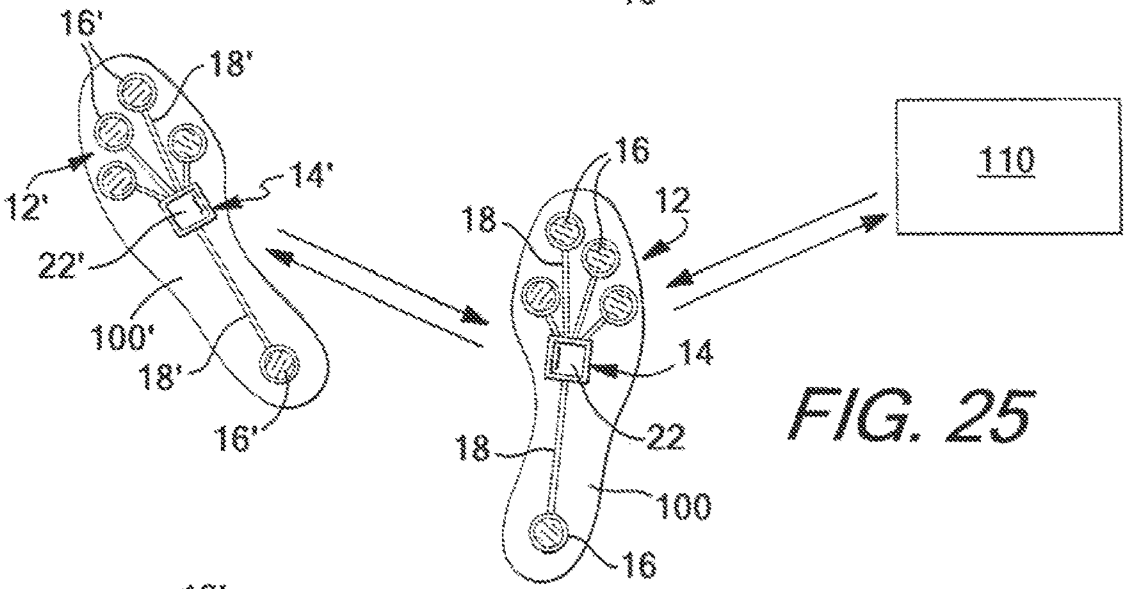
FIG. 25 is a schematic diagram of a pair of shoes, each containing a sensor system, in a "daisy chain" communication mode with an external device.
Figure 26:
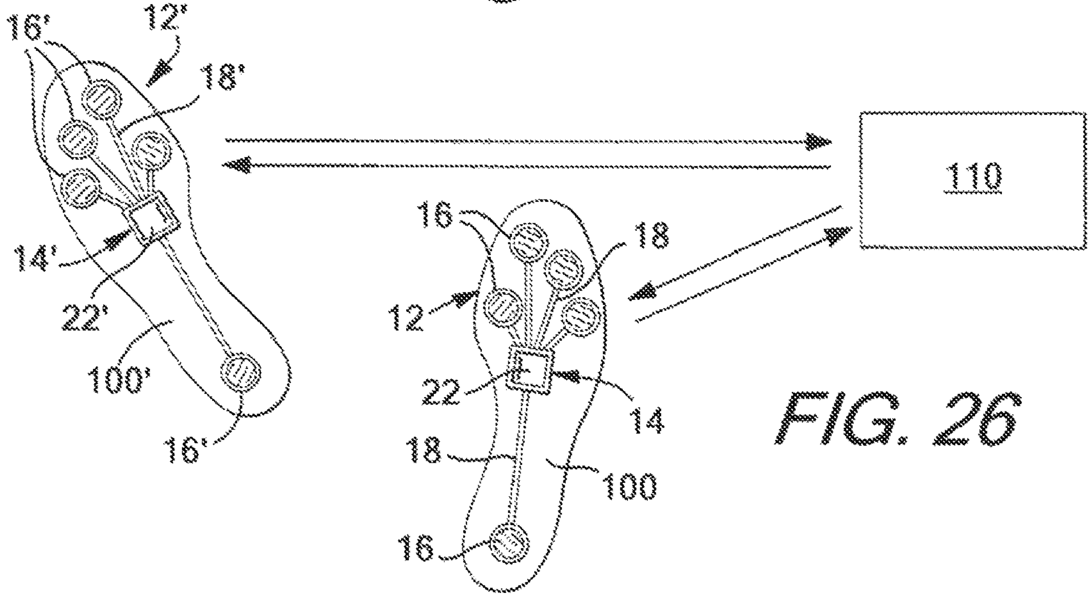
FIG. 26 is a schematic diagram of a pair of shoes, each containing a sensor system, in an independent communication mode with an external device.

A single article of footwear 100 containing the sensor system 12 as described herein can be used alone or in combination with a second article of footwear 100' having its own sensor system 12', such as a pair of shoes 100, 100' as illustrated in FIGS. 24-26. The sensor system 12' of the second shoe 100' generally contains one or more sensors 16' connected by sensor leads 18' to a port 14' in communication with an electronic module 22'. The second sensor system 12' of the second shoe 100' shown in FIGS. 24-26 has the same configuration as the sensor system 12 of the first shoe 100. However, in another embodiment, the shoes 100, 100' may have sensor systems 12, 12' having different configurations. The two shoes 100, 100' are both configured for communication with the external device 110, and in the embodiment illustrated, each of the shoes 100, 100' has an electronic module 22, 22' configured for communication with the external device 110. In another embodiment, both shoes 100, 100' may have ports 14, 14' configured for communication with the same electronic module 22. In this embodiment, at least one shoe 100, 100' may be configured for wireless communication with the module 22. FIGS. 24-26 illustrate various modes for communication between the modules 22, 22'.

FIG. 24 illustrates a "mesh" communication mode, where the modules 22, 22' are configured for communicating with each other, and are also configured for independent communication with the external device 110. FIG. 25 illustrates a "daisy chain" communication mode, where one module 22' communicates with the external device 110 through the other module 22. In other words, the second module 22' is configured to communicate signals (which may include data) to the first module 22, and the first module 22 is configured to communicate signals from both modules 22, 22' to the external device 110. Likewise, the external device communicates with the second module 22' through the first module 22, by sending signals to the first module 22, which communicates the signals to the second module 22'. In one embodiment, the modules 22, 22' can also communicate with each other for purposes other than transmitting signals to and from the external device 110. FIG. 26 illustrates an "independent" communication mode, where each module 22, 22' is configured for independent communication with the external device 110, and the modules 22, 22' are not configured for communication with each other. In other embodiments, the sensor systems 12, 12' may be configured for communication with each other and/or with the external device 110 in another manner.

As will be appreciated by one of skill in the art upon reading the present disclosure, various aspects described herein may be embodied as a method, a data processing system, or a computer program product. Accordingly, those aspects may take the form of an entirely hardware embodiment, an entirely software embodiment or an embodiment combining software and hardware aspects. Furthermore, such aspects may take the form of a computer program product stored by one or more tangible computer-readable storage media or storage devices having computer-readable program code, or instructions, embodied in or on the storage media. Any suitable tangible computer readable storage media may be utilized, including hard disks, CD-ROMs, optical storage devices, magnetic storage devices, and/or any combination thereof. In addition, various intangible signals representing data or events as described herein may be transferred between a source and a destination in the form of electromagnetic waves traveling through signal-conducting media such as metal wires, optical fibers, and/or wireless transmission media (e.g., air and/or space).

As described above, aspects of the present invention may be described in the general context of computer-executable instructions, such as program modules, being executed by a computer and/or a processor thereof. Generally, program modules include routines, programs, objects, components, data structures, etc. that perform particular tasks or implement particular abstract data types. Such a program module may be contained in a tangible, non-transitory computer-readable medium, as described above. Aspects of the present invention may also be practiced in distributed computing environments where tasks are performed by remote processing devices that are linked through a communications network. Program modules may be located in a memory, such as the memory 204 of the module 22 or memory 304 of the external device 110, or an external medium, such as game media 307, which may include both local and remote computer storage media including memory storage devices. It is understood that the module 22, the external device 110, and/or external media may include complementary program modules for use together, such as in a particular application. It is also understood that a single processor 202, 302 and single memory 204, 304 are shown and described in the module 22 and the external device 110 for sake of simplicity, and that the processor 202, 302 and memory 204, 304 may include a plurality of processors and/or memories respectively, and may comprise a system of processors and/or memories.

The sensor system described herein can be utilized in a variety of different applications and configurations including general athletic performance monitoring such as in fitness training or sport specific activity such as basketball. It is understood that additional sensors can be positioned at other locations on the footwear. The sensors in the sensor system can also be configured to sense specific lateral movements and athletic cutting movements. As discussed herein, data collected by the sensor system can be processed by the associated algorithms either in the electronic module, the mobile device or a remote site. It is contemplated that such data processing can be used to advise users regarding wear such that the user is advised when a new pair of shoes is needed. Such data could also be processed and used to advise a user of a particular type of shoe design that may be beneficial for the particular user. Finally, the data can be processed to aid in the custom design of footwear. While the sensor system is shown in footwear, the system can be used in other types of apparel.

The various embodiments of the sensor system described herein, as well as the articles of footwear, foot contacting members, inserts, and other structures incorporating the sensor system, provide benefits and advantages over existing technology. For example, many of the sensor embodiments described herein provide relatively low cost and durable options for sensor systems, so that a sensor system can be incorporated into articles of footwear with little added cost and good reliability. As a result, footwear can be manufactured with integral sensor systems regardless of whether the sensor systems are ultimately desired to be used by the consumer, without appreciably affecting price. Additionally, sole inserts with customized sensor systems can be inexpensively manufactured and distributed along with software designed to utilize the sensor systems, without appreciably affecting the cost of the software. As another example, the sensor system provides a wide range of functionality for a wide variety of applications, including gaming, fitness, athletic training and improvement, practical controls for computers and other devices, and many others described herein and recognizable to those skilled in the art. In one embodiment, third-party software developers can develop software configured to run using input from the sensor systems, including games and other programs. The ability of the sensor system to provide data in a universally readable format greatly expands the range of third party software and other applications for which the sensor system can be used. Additionally, in one embodiment, the sensor system can produce signals and data that permit accurate detection of applied forces, which provides greater utility and versatility. As a further example, the various sole inserts containing sensor systems, including liners, insoles, and other elements, permit interchangeability and customization of the sensor system for different applications. Other advantages are recognizable to those skilled in the art.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. The terms "first," "second," "top," "bottom," etc., as used herein, are intended for illustrative purposes only and do not limit the embodiments in any way. Additionally, the term "plurality," as used herein, indicates any number greater than one, either disjunctively or conjunctively, as necessary, up to an infinite number. Further, "Providing" an article or apparatus, as used herein, refers broadly to making the article available or accessible for future actions to be performed on the article, and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention and the scope of protection is only limited by the scope of the accompanying Claims.

What is claimed is:

1. An insert for use with an article of footwear, comprising:

an insert member configured to be inserted into a foot-receiving chamber of the article of footwear, the insert member having a top side and a bottom side, and further having a housing hole extending through the insert member from the top side to the bottom side, a first opening spaced from the housing hole, and a second opening spaced from the first opening and spaced from the housing hole, the first and second openings extending through the insert member from the top side to the bottom side;

a housing connected to the insert member and configured to receive an electronic module therein, the housing comprising:

- a tub positioned at least partially on the bottom side of the insert member and configured to receive the electronic module by insertion through the housing hole, the housing having a base wall and a plurality of side walls extending upward from the base wall;
- a flange connected to the tub and extending outward from the tub around at least a portion of the housing hole to cover at least a portion of the top side of the insert member;
- a first peg connected to the tub and the flange and extending from the flange downward through the first opening to the tub; and
- a second peg connected to the tub and the flange and extending from the flange downward through the second opening to the tub;

a port connected to the insert and having an interface accessible within the housing, wherein the port is configured for communication with the electronic module through the interface when the electronic module is received in the housing;

a plurality of force sensors connected to the insert member; and a plurality of conductive leads located on the insert and connecting the force sensors to the interface of the port.

2. The insert of claim 1, wherein the tub has a first receiver and a second receiver, and the first peg is received in the first receiver and the second peg is received in the second receiver.

3. The insert of claim 2, wherein the first peg is welded within the first receiver and the second peg is welded within the second receiver.

4. The insert of claim 1, wherein a portion of the insert member is sandwiched between the flange and the tub.

5. The insert of claim 1, further comprising a carrier connected to the tub and supporting a plurality of electrical contacts of the interface to be accessible within the housing.

6. The insert of claim 5, wherein the tub further comprises a first lateral slot, and the carrier is snugly received within the first lateral slot.

7. The insert of claim 6, wherein the tub further comprises a second lateral slot located behind the carrier, wherein the conductive leads are connected to the electrical contacts within the second lateral slot, and wherein a filler material is injected into the second lateral slot.

8. An insert for use with an article of footwear, comprising:

an insert member configured to be inserted into a foot-receiving chamber of the article of footwear, the insert member having a top side and a bottom side, and further having a first opening extending through the insert member from the top side to the bottom side;

a housing connected to the insert member and configured to receive an electronic module therein, the housing comprising:

a tub positioned at least partially on the bottom side of the insert member and configured to receive the electronic module;

a flange connected to the tub and extending outward around at least a portion of the tub to cover at least a portion of the top side of the insert member; and a first peg connected to the tub and the flange and extending from the flange downward through the first opening to the tub;

a port connected to the insert and having an interface accessible within the housing, wherein the port is configured for communication with the electronic module through the interface when the electronic module is received in the housing;

a plurality of force sensors connected to the insert member; and a plurality of conductive leads located on the insert and connecting the force sensors to the interface of the port.

9. The insert of claim 8, wherein the tub has a first receiver, and the first peg is received in the first receiver.

10. The insert of claim 9, wherein the insert member further comprises a second opening spaced from the first opening and extending through the insert member from the top side to the bottom side, and the housing further comprises a second peg connected to the tub and the flange and extending from the flange downward through the second opening to the tub, and wherein the tub has a second receiver, and the second peg is received in the second receiver.

11. The insert of claim 8, wherein a portion of the insert member is sandwiched between the flange and the tub.

12. The insert of claim 8, further comprising a carrier connected to the tub and supporting a plurality of electrical contacts of the interface to be accessible within the housing.

13. The insert of claim 12, wherein the tub further comprises a first lateral slot, and the carrier is snugly received within the first lateral slot, and the tub further comprises a second lateral slot located behind the carrier, wherein the conductive leads are connected to the electrical contacts within the second lateral slot, and wherein a filler material is injected into the second lateral slot.

14. An insert for use with an article of footwear, comprising:

an insert member configured to be inserted into a foot-receiving chamber of the article of footwear, the insert member having a top side and a bottom side, and further having a first opening and a second opening spaced from the first opening, the first and second openings extending through the insert member from the top side to the bottom side;

a housing connected to the insert member and configured to receive an electronic module therein, the housing comprising:

a base member positioned at least partially on the bottom side of the insert member;

a cover member positioned the top side of the insert member and connected to the base member, wherein the housing has a chamber configured for receiving the electronic module, the chamber being defined in part by the cover member and the base member;

a first peg connected to the base member and the cover member and extending from the cover member downward through the first opening to the base member; and a second peg connected to the base member and the cover member and extending from the cover member downward through the second opening to the base member;

a port connected to the insert and having an interface accessible within the housing, wherein the port is configured for communication with the electronic module through the interface when the electronic module is received in the housing;

a sensor system comprising a plurality of sensors connected to the insert member, the sensors being electrically connected to the interface of the port.

15. The insert of claim 14, wherein the base member has a first receiver and a second receiver, and the first peg is received in the first receiver and the second peg is received in the second receiver.

16. The insert of claim 15, wherein the first peg is welded within the first receiver and the second peg is welded within the second receiver.

17. The insert of claim 14, wherein a portion of the insert member is sandwiched between the cover member and the base member.

18. The insert of claim 14, wherein the insert further has a housing hole extending through the insert member from the top side to the bottom side and spaced from the first and second openings, and the housing is configured to be accessible through the housing hole for insertion and removal of the electronic module.

19. The insert of claim 18, wherein the cover member comprises a flange extending outward around a periphery of the housing hole and a depending wall extending downward from the flange and into the housing hole to engage the base member.

20. An assembly comprising:

an insert member configured to be engaged with a sole structure of an article of footwear, the insert member comprising at least one layer of a flexible film material and having a hole extending through a thickness of the insert member and a first opening and a second opening extending through the thickness of the insert member adjacent to the hole;

a plurality of sensors connected to the insert member, each of the plurality of sensors configured for detecting a force exerted on the respective sensor by a user's foot;

a housing connected to the insert member and received within the hole, the housing having a first peg extending through the first opening and a second peg extending through the second opening to connect the housing to the insert member, wherein the housing is configured for removably receiving an electronic module therein; and a port electronically connected to the plurality of sensors and comprising an interface having a plurality of electrical contacts configured to engage the electronic module when the electronic module is received within the housing to enable communication of data from the plurality of sensors to the electronic module.

21. The assembly of claim 20, wherein the housing further comprises:

a cover member configured to engage a top side of the insert member; and a base member configured to engage a bottom side of the insert member, wherein the first peg and the second peg extend from the cover member to the base member through the first opening and the second opening, respectively, to connect the cover member to the base member.

22. The assembly of claim 21, wherein the base member comprises a tub configured to receive the electronic module therein, and the cover member comprises a flange extending outward around at least a portion of a periphery of the tub.

23. The assembly of claim 22, wherein the cover member further comprises a depending wall extending downward from the flange and into the hole to engage the tub.

24. The assembly of claim 21, wherein one of the cover member and the base member has a first receiver and a second receiver, and the other of the cover member and the base member has the first peg and the second peg thereon, and wherein the first peg and the second peg are received in the first receiver and the second receiver to connect the cover member to the base member.

25. The assembly of claim 21, further comprising a plurality of conductive leads connected to the insert member and electronically connecting the plurality of sensors to the electrical contacts of the interface, wherein the insert member comprises a strip of the flexible film material extending into the hole, wherein the conductive leads extend onto the strip to form an electronic connection with the electrical contacts of the interface, and wherein the strip extends between the cover member and the base member.

* * * * *